United States Patent
Holman et al.

(10) Patent No.: US 10,121,218 B2
(45) Date of Patent: Nov. 6, 2018

(54) SUBSTRATE STRUCTURE INJECTION TREATMENT SYSTEM AND METHOD FOR INGESTIBLE PRODUCT SYSTEM AND METHOD

(75) Inventors: Paul Holman, Seattle, WA (US); Royce A. Levien, Lexington, MA (US); Mark A. Malamud, Seattle, WA (US); Neal Stephenson, Seattle, WA (US); Christopher Charles Young, Seattle, WA (US)

(73) Assignee: Elwha LLC, Bellevue, WA (US)

( * ) Notice: Subject to any disclaimer, the term of this patent is extended or adjusted under 35 U.S.C. 154(b) by 1065 days.

(21) Appl. No.: 13/528,331

(22) Filed: Jun. 20, 2012

(65) Prior Publication Data

US 2013/0330448 A1 Dec. 12, 2013

Related U.S. Application Data

(63) Continuation-in-part of application No. 13/494,536, filed on Jun. 12, 2012, and a continuation-in-part of
(Continued)

(51) Int. Cl.
*G06Q 50/22* (2018.01)
*A23P 10/00* (2016.01)
(Continued)

(52) U.S. Cl.
CPC .............. *G06Q 50/22* (2013.01); *A23P 10/00* (2016.08); *A23P 20/20* (2016.08); *G06F 19/00* (2013.01)

(58) Field of Classification Search
CPC ........ G06F 19/28; G06Q 10/10; G07F 13/065
See application file for complete search history.

(56) References Cited

U.S. PATENT DOCUMENTS 22,225 A 12/1858 Berry
88,023 A 3/1869 Estell
(Continued)

FOREIGN PATENT DOCUMENTS

EP 1 469 431 B1 9/2009
NL 2003661 C 4/2011
(Continued)

OTHER PUBLICATIONS

"Easy Delft Blue Eggs"; The Sweet Adventures of Sugarbelle Blog; Mar. 25, 2012; pp. 1-7; located at: www.sweetsugarbelle.com/2012/03/simple-delft-blue-easier-egg-cookies.
(Continued)

*Primary Examiner* — Timothy R Waggoner

(57) ABSTRACT

A computationally implemented system and method that is designed to, but is not limited to: electronically directing control of at least partial treatment of the one or more portions of the one or more ingestible substrate structures according to the treatment instructional information regarding the one or more subsequent injection operations including at least one or more injections of one or more materials into the one or more portions of the one or more ingestible substrate structures to form at least in part the one or more selected ingestible products subsequent to and based at least in part upon the electronically receiving the user status information and the electronically receiving the selection information at least in part identifying the one or more selected ingestible products. In addition to the foregoing, other method aspects are described in the claims, drawings, and text forming a part of the present disclosure.

47 Claims, 85 Drawing Sheets

Related U.S. Application Data application No. 13/494,654, filed on Jun. 12, 2012, and a continuation of application No. 13/528,298, filed on Jun. 20, 2012.

(51) Int. Cl.
  *A23P 20/20* (2016.01)
  *G06F 19/00* (2018.01)

(56) References Cited

U.S. PATENT DOCUMENTS

| | | |
|---|---|---|
| 116,634 A | 7/1871 | Schwerin |
| 260,918 A | 7/1882 | Yule et al. |
| 249,129 A | 2/1884 | Heffernan |
| 303,972 A | 8/1884 | Barton et al. |
| 1,570,405 A | 1/1926 | Salerno |
| 3,040,935 A | 6/1962 | Lopata |
| 3,702,583 A | 11/1972 | Rullman |
| 3,859,904 A | 1/1975 | Carriazo |
| 4,076,846 A | 2/1978 | Nakatsuka et al. |
| 4,127,232 A | 11/1978 | Gagliardo et al. |
| 4,135,077 A | 1/1979 | Wills |
| 4,293,296 A | 10/1981 | Caiello et al. |
| 4,452,132 A * | 6/1984 | Miller .................... A47J 27/04 126/369 |
| 4,634,597 A | 1/1987 | Spiel et al. |
| 4,666,204 A | 5/1987 | Reinholtz |
| 4,681,000 A | 7/1987 | Wolters |
| 4,723,614 A | 2/1988 | Lahti |
| 4,796,182 A | 1/1989 | Duboff |
| 4,797,818 A | 1/1989 | Cotter |
| 4,974,747 A | 12/1990 | Ahlstrom |
| 5,121,677 A | 6/1992 | Le Claire et al. |
| 5,132,914 A | 7/1992 | Cahlander et al. |
| 5,176,922 A | 1/1993 | Balsano et al. |
| 5,197,376 A | 3/1993 | Bird et al. |
| 5,228,382 A | 7/1993 | Hayashi et al. |
| 5,261,150 A | 11/1993 | Grube et al. |
| 5,408,443 A | 4/1995 | Weinberger |
| 5,417,989 A | 5/1995 | Atwood et al. |
| 5,511,594 A | 4/1996 | Brennan et al. |
| 5,522,309 A | 6/1996 | Mizobuchi et al. |
| 5,522,310 A | 6/1996 | Black, Sr. et al. |
| 5,540,943 A | 7/1996 | Naramura |
| 5,583,129 A | 12/1996 | Spona et al. |
| 5,598,947 A | 2/1997 | Smith |
| 5,615,778 A | 4/1997 | Kaiser et al. |
| 5,697,043 A | 12/1997 | Baskaran et al. |
| 5,731,020 A | 3/1998 | Russo |
| 5,736,940 A | 4/1998 | Burgener |
| 5,762,971 A | 6/1998 | Schirmer |
| 5,820,906 A | 10/1998 | Akesson et al. |
| 6,032,574 A | 3/2000 | Brayton et al. |
| 6,048,191 A | 4/2000 | Beltrami |
| 6,105,818 A | 8/2000 | Speranza |
| 6,112,182 A | 8/2000 | Akers et al. |
| 6,137,686 A | 10/2000 | Saye |
| 6,194,017 B1 | 2/2001 | Woodward et al. |
| 6,200,125 B1 | 3/2001 | Akutagawa |
| 6,202,923 B1 | 3/2001 | Boyer et al. |
| 6,236,974 B1 | 5/2001 | Kolawa et al. |
| 6,245,556 B1 | 6/2001 | Sako et al. |
| 6,251,456 B1 | 6/2001 | Maul et al. |
| 6,268,004 B1 | 7/2001 | Hayashi |
| 6,280,784 B1 | 8/2001 | Yang et al. |
| 6,280,785 B1 | 8/2001 | Yang et al. |
| 6,280,786 B1 | 8/2001 | Williams et al. |
| 6,317,686 B1 | 11/2001 | Ran |
| 6,359,239 B1 | 3/2002 | Missler et al. |
| 6,376,000 B1 | 4/2002 | Waters |
| 6,415,555 B1 | 7/2002 | Montague |
| 6,490,870 B1 | 12/2002 | Efremkine |
| 6,618,062 B1 | 9/2003 | Brown et al. |
| 6,622,064 B2 | 9/2003 | Bartholomew et al. |
| 6,637,432 B2 | 10/2003 | Wakefield et al. |
| 6,644,359 B1 | 11/2003 | Wertheim |
| 6,646,659 B1 | 11/2003 | Brown et al. |
| 6,658,990 B1 * | 12/2003 | Henning ................ A23B 4/285 99/352 |
| 6,660,317 B1 | 12/2003 | Akutagawa |
| 6,660,982 B2 | 12/2003 | Thorneywork |
| 6,711,460 B1 | 3/2004 | Reese |
| 6,802,433 B2 | 10/2004 | Leykin et al. |
| 6,841,185 B2 * | 1/2005 | Sargent ................... A23F 5/465 426/443 |
| 6,843,166 B1 | 1/2005 | Li |
| 6,859,215 B1 | 2/2005 | Brown et al. |
| 6,865,261 B1 | 3/2005 | Rao et al. |
| 6,998,087 B1 | 2/2006 | Hanson et al. |
| 7,006,893 B2 | 2/2006 | Hart et al. |
| 7,027,996 B2 | 4/2006 | Levinson |
| 7,054,909 B1 | 5/2006 | Ohkubo et al. |
| 7,080,597 B2 | 7/2006 | Ando |
| 7,098,794 B2 | 8/2006 | Lindsay et al. |
| 7,110,964 B2 | 9/2006 | Tengler et al. |
| 7,183,518 B2 | 2/2007 | Near et al. |
| 7,187,960 B2 | 3/2007 | Abreu |
| 7,188,082 B2 | 3/2007 | Keane et al. |
| 7,200,644 B1 | 4/2007 | Flanagan |
| 7,231,917 B2 | 6/2007 | Frederiksen |
| 7,243,789 B2 | 7/2007 | Discko, Jr. |
| 7,281,468 B2 | 10/2007 | Frem |
| 7,286,258 B2 | 10/2007 | Schnoebelen et al. |
| 7,295,889 B2 * | 11/2007 | Lahteenmaki .......... A61J 3/002 700/233 |
| 7,299,982 B2 | 11/2007 | Kreiner et al. |
| 7,319,780 B2 | 1/2008 | Fedorovskaya et al. |
| 7,343,174 B2 | 3/2008 | Suryanarayana et al. |
| 7,364,068 B1 | 4/2008 | Strubbe et al. |
| 7,392,193 B2 | 6/2008 | Mault |
| 7,395,134 B2 | 7/2008 | Bartholomew et al. |
| 7,415,375 B2 | 8/2008 | Shakman et al. |
| 7,451,015 B2 | 11/2008 | Mazur et al. |
| 7,457,685 B2 | 11/2008 | D'Silva |
| 7,555,360 B1 | 6/2009 | Green et al. |
| 7,571,586 B1 | 8/2009 | Morales |
| 7,625,198 B2 | 12/2009 | Lipson et al. |
| 7,630,790 B2 | 12/2009 | Handfield et al. |
| 7,680,690 B1 | 3/2010 | Catalano |
| 7,698,566 B1 | 4/2010 | Stone |
| 7,747,345 B2 | 6/2010 | Ohmura et al. |
| 7,762,181 B2 * | 7/2010 | Boland .................... A47J 31/40 99/321 |
| 7,783,379 B2 | 8/2010 | Beane et al. |
| 7,818,089 B2 | 10/2010 | Hanna et al. |
| 7,842,323 B1 | 11/2010 | White |
| 7,858,136 B2 * | 12/2010 | Park ......................... C12G 3/04 426/11 |
| 7,884,953 B1 | 2/2011 | Willcocks et al. |
| 7,961,916 B2 | 6/2011 | Wang et al. |
| 7,974,873 B2 | 7/2011 | Simmons et al. |
| 8,007,847 B2 | 8/2011 | Biderman et al. |
| 8,027,748 B2 | 9/2011 | Handfield et al. |
| 8,085,135 B2 | 12/2011 | Cohen Alloro et al. |
| 8,173,186 B2 | 5/2012 | Kuwabara et al. |
| 8,190,447 B2 | 5/2012 | Hungerford et al. |
| 8,204,757 B2 | 6/2012 | Carlson et al. |
| 8,249,946 B2 | 8/2012 | Froseth et al. |
| 8,306,655 B2 | 11/2012 | Newman |
| 8,321,364 B1 | 11/2012 | Gharpure et al. |
| 8,370,176 B2 | 2/2013 | Vespasiani |
| 8,412,369 B2 | 4/2013 | Ames, II et al. |
| 8,412,588 B2 | 4/2013 | Bodell et al. |
| 8,504,440 B1 | 8/2013 | Kolawa et al. |
| 8,521,326 B1 | 8/2013 | Holtje |
| 8,583,511 B2 | 11/2013 | Hendrickson |
| 8,594,838 B2 | 11/2013 | Selker et al. |
| 8,594,935 B2 | 11/2013 | Cioffi et al. |
| 8,688,277 B2 | 4/2014 | Studor et al. |
| 8,744,618 B2 * | 6/2014 | Peters .................. B67D 1/0041 700/236 |
| 8,793,588 B2 | 7/2014 | DiPietro |
| 8,846,122 B2 * | 9/2014 | Rumbaut ............. A23G 1/0069 426/285 |

(56) References Cited

U.S. PATENT DOCUMENTS

| | | |
|---|---|---|
| 9,165,117 B2 | 10/2015 | Teller et al. |
| 9,240,028 B2 | 1/2016 | Holman et al. |
| 9,703,928 B2 | 7/2017 | Mochizuki et al. |
| 9,744,721 B2 | 8/2017 | Klaber |
| 2001/0005830 A1 | 6/2001 | Kuroyanagi |
| 2001/0028308 A1 | 10/2001 | De La Huerga |
| 2001/0036495 A1 | 11/2001 | Ganan-Calvo |
| 2002/0029149 A1 | 3/2002 | Nishina |
| 2002/0035503 A1 | 3/2002 | Matsumoto |
| 2002/0042726 A1 | 4/2002 | Mayaud |
| 2002/0049652 A1 | 4/2002 | Moore et al. |
| 2002/0050526 A1 | 5/2002 | Swartz et al. |
| 2002/0055878 A1 | 5/2002 | Burton et al. |
| 2002/0069097 A1 | 6/2002 | Conrath |
| 2002/0081356 A1 | 6/2002 | Bebiak et al. |
| 2002/0116634 A1 | 8/2002 | Okubo |
| 2002/0138201 A1 | 9/2002 | Greensides |
| 2002/0156682 A1 | 10/2002 | DiPietro |
| 2002/0165787 A1 | 11/2002 | Bates et al. |
| 2002/0192572 A1 | 12/2002 | Lau |
| 2003/0017248 A1 | 1/2003 | Gray |
| 2003/0024946 A1 | 2/2003 | Severino |
| 2003/0050854 A1 | 3/2003 | Showghi et al. |
| 2003/0051606 A1 | 3/2003 | Cusenza et al. |
| 2003/0069745 A1 | 4/2003 | Zenko |
| 2003/0071806 A1 | 4/2003 | Annand |
| 2003/0079612 A1 | 5/2003 | Con |
| 2003/0099157 A1 | 5/2003 | Quine |
| 2003/0105555 A1 | 6/2003 | Lunak et al. |
| 2003/0121929 A1 | 7/2003 | Liff et al. |
| 2003/0125836 A1 | 7/2003 | Chirnomas |
| 2003/0125963 A1 | 7/2003 | Haken |
| 2003/0125986 A1 | 7/2003 | Collosi |
| 2003/0185948 A1 | 10/2003 | Garwood |
| 2003/0197005 A1 | 10/2003 | Huegerich et al. |
| 2003/0208113 A1 | 11/2003 | Mault et al. |
| 2003/0208409 A1 | 11/2003 | Mault |
| 2003/0219527 A1 | 11/2003 | Sasaki et al. |
| 2003/0236682 A1 | 12/2003 | Heyer |
| 2003/0236706 A1 | 12/2003 | Weiss |
| 2004/0015403 A1 | 1/2004 | Moskowitz et al. |
| 2004/0025701 A1* | 2/2004 | Colston ............... A47J 31/3628 99/279 |
| 2004/0044469 A1 | 3/2004 | Bender et al. |
| 2004/0044489 A1 | 3/2004 | Jones et al. |
| 2004/0045579 A1 | 3/2004 | Miki et al. |
| 2004/0049407 A1 | 3/2004 | Rosenberg |
| 2004/0054554 A1 | 3/2004 | Barts et al. |
| 2004/0073448 A1 | 4/2004 | Barts et al. |
| 2004/0073449 A1 | 4/2004 | Yang |
| 2004/0091843 A1 | 5/2004 | Albro et al. |
| 2004/0093265 A1 | 5/2004 | Ramchandani et al. |
| 2004/0093268 A1 | 5/2004 | Ramchandani et al. |
| 2004/0103033 A1 | 5/2004 | Reade et al. |
| 2004/0117205 A1 | 6/2004 | Reardan et al. |
| 2004/0131659 A1 | 7/2004 | Gibson et al. |
| 2004/0143503 A1 | 7/2004 | Suthar |
| 2004/0151820 A1 | 8/2004 | Harris |
| 2004/0158350 A1 | 8/2004 | Ostergaard et al. |
| 2004/0158499 A1 | 8/2004 | Dev et al. |
| 2004/0172169 A1 | 9/2004 | Wright, IV et al. |
| 2004/0183796 A1 | 9/2004 | Velde et al. |
| 2004/0193325 A1 | 9/2004 | Bonderud et al. |
| 2004/0193495 A1 | 9/2004 | Kim |
| 2004/0214597 A1 | 10/2004 | Suryanarayana et al. |
| 2004/0226775 A1 | 11/2004 | Takatama et al. |
| 2004/0238555 A1* | 12/2004 | Parks ...................... G07F 9/105 221/80 |
| 2004/0246819 A1 | 12/2004 | Quine |
| 2004/0250842 A1 | 12/2004 | Adams et al. |
| 2004/0263319 A1 | 12/2004 | Huomo |
| 2005/0023710 A1 | 2/2005 | Brodkin et al. |
| 2005/0038719 A1 | 2/2005 | Young et al. |
| 2005/0048461 A1 | 3/2005 | Lahteenmaki |
| 2005/0059849 A1 | 3/2005 | Liu |
| 2005/0060063 A1 | 3/2005 | Reichelt et al. |
| 2005/0065640 A1 | 3/2005 | Mallett et al. |
| 2005/0079257 A1 | 4/2005 | Neto |
| 2005/0080520 A1 | 4/2005 | Kline et al. |
| 2005/0080650 A1 | 4/2005 | Noel |
| 2005/0090425 A1 | 4/2005 | Reardan et al. |
| 2005/0098169 A1 | 5/2005 | Frederiksen |
| 2005/0113968 A1 | 5/2005 | Williams et al. |
| 2005/0114149 A1 | 5/2005 | Rodriguez et al. |
| 2005/0131738 A1 | 6/2005 | Morris |
| 2005/0157148 A1 | 7/2005 | Baker et al. |
| 2005/0160052 A1 | 7/2005 | Schneider et al. |
| 2005/0171663 A1 | 8/2005 | Mittelsteadt et al. |
| 2005/0193901 A1 | 9/2005 | Buehler |
| 2005/0209915 A1 | 9/2005 | Saluccio |
| 2005/0226975 A1 | 10/2005 | Drouillard |
| 2005/0230472 A1 | 10/2005 | Chang |
| 2005/0233011 A1 | 10/2005 | Beavers |
| 2005/0241497 A1 | 11/2005 | Cantu |
| 2005/0251289 A1 | 11/2005 | Bonney et al. |
| 2005/0267811 A1 | 12/2005 | Almblad |
| 2005/0280544 A1 | 12/2005 | Mishelevich |
| 2006/0015289 A1 | 1/2006 | Shakman et al. |
| 2006/0053184 A1 | 3/2006 | Grana |
| 2006/0064037 A1 | 3/2006 | Shalon et al. |
| 2006/0081653 A1 | 4/2006 | Boland et al. |
| 2006/0108415 A1 | 5/2006 | Thomas et al. |
| 2006/0111976 A1 | 5/2006 | Pompushko |
| 2006/0147581 A1 | 7/2006 | Svendsen et al. |
| 2006/0161453 A1 | 7/2006 | Kost et al. |
| 2006/0178943 A1 | 8/2006 | Rollinson et al. |
| 2006/0182240 A1 | 8/2006 | Schelberg, Jr. et al. |
| 2006/0191885 A1 | 8/2006 | Near et al. |
| 2006/0224419 A1 | 10/2006 | Servizio et al. |
| 2006/0237523 A1 | 10/2006 | Carlson et al. |
| 2006/0259188 A1 | 11/2006 | Berg |
| 2006/0260601 A1 | 11/2006 | Schedeler et al. |
| 2006/0263501 A1 | 11/2006 | Oghafua et al. |
| 2006/0277066 A1 | 12/2006 | Hungerford et al. |
| 2006/0278093 A1 | 12/2006 | Biderman et al. |
| 2006/0286218 A1 | 12/2006 | Salzman |
| 2007/0027432 A1 | 2/2007 | Radford et al. |
| 2007/0037567 A1 | 2/2007 | Ungless et al. |
| 2007/0038476 A1 | 2/2007 | Sternlicht |
| 2007/0038727 A1 | 2/2007 | Bailey et al. |
| 2007/0048407 A1 | 3/2007 | Collins et al. |
| 2007/0055550 A1 | 3/2007 | Courtney et al. |
| 2007/0055694 A1 | 3/2007 | Ruge et al. |
| 2007/0057039 A1 | 3/2007 | Carlson et al. |
| 2007/0061170 A1 | 3/2007 | Lorsch |
| 2007/0061209 A1 | 3/2007 | Jackson |
| 2007/0062156 A1 | 3/2007 | Kim |
| 2007/0083494 A1 | 4/2007 | Carlson et al. |
| 2007/0088624 A1 | 4/2007 | Vaughn et al. |
| 2007/0092614 A1 | 4/2007 | Waldock |
| 2007/0150371 A1 | 6/2007 | Gangji |
| 2007/0150375 A1 | 6/2007 | Yang |
| 2007/0151984 A1 | 7/2007 | Baker et al. |
| 2007/0168205 A1 | 7/2007 | Carlson et al. |
| 2007/0170049 A1 | 7/2007 | Mansur |
| 2007/0170195 A1 | 7/2007 | Segiet et al. |
| 2007/0183633 A1 | 8/2007 | Hoffmann |
| 2007/0185615 A1 | 8/2007 | Bossi et al. |
| 2007/0185785 A1 | 8/2007 | Carlson et al. |
| 2007/0191689 A1 | 8/2007 | Elitok |
| 2007/0192715 A1 | 8/2007 | Kataria et al. |
| 2007/0208454 A1 | 9/2007 | Forrester et al. |
| 2007/0231435 A1 | 10/2007 | Ream et al. |
| 2007/0260487 A1 | 11/2007 | Bartfeld et al. |
| 2007/0267441 A1 | 11/2007 | van Opstal et al. |
| 2007/0271001 A1 | 11/2007 | Ratnakar |
| 2007/0275690 A1 | 11/2007 | Hunter et al. |
| 2007/0292573 A1 | 12/2007 | Smith |
| 2007/0294129 A1 | 12/2007 | Froseth et al. |
| 2008/0059226 A1 | 3/2008 | Melker et al. |
| 2008/0077440 A1 | 3/2008 | Doron |
| 2008/0084450 A1 | 4/2008 | Silverbrook |
| 2008/0114678 A1 | 5/2008 | Bennett et al. |
| 2008/0124433 A1 | 5/2008 | Yelden et al. |

(56) References Cited

U.S. PATENT DOCUMENTS

| | | |
|---|---|---|
| 2008/0125897 A1 | 5/2008 | DiGianfilippo et al. |
| 2008/0126220 A1 | 5/2008 | Baril et al. |
| 2008/0126985 A1 | 5/2008 | Baril et al. |
| 2008/0141315 A1 | 6/2008 | Ogilvie |
| 2008/0162181 A1 | 7/2008 | Ben-Haim et al. |
| 2008/0163762 A1 | 7/2008 | Weiss |
| 2008/0171967 A1 | 7/2008 | Blomquist et al. |
| 2008/0172261 A1 | 7/2008 | Albertson et al. |
| 2008/0173711 A1 | 7/2008 | Handfield et al. |
| 2008/0189143 A1 | 8/2008 | Wurster |
| 2008/0195247 A1 | 8/2008 | Mallett et al. |
| 2008/0224823 A1 | 9/2008 | Lawson et al. |
| 2008/0249859 A1 | 10/2008 | Angell et al. |
| 2008/0249865 A1 | 10/2008 | Angell et al. |
| 2008/0260918 A1 | 10/2008 | Lai et al. |
| 2008/0272138 A1 | 11/2008 | Ross et al. |
| 2008/0281915 A1 | 11/2008 | Elad et al. |
| 2008/0288287 A1 | 11/2008 | Stanners |
| 2008/0314918 A1 | 12/2008 | Nuriely |
| 2009/0012433 A1 | 1/2009 | Fernstrom et al. |
| 2009/0029016 A1 | 1/2009 | Pfister et al. |
| 2009/0043176 A1 | 2/2009 | Nakajima et al. |
| 2009/0087819 A1 | 4/2009 | Adachi et al. |
| 2009/0094033 A1 | 4/2009 | Mazer et al. |
| 2009/0099944 A1 | 4/2009 | Robinson et al. |
| 2009/0105875 A1 | 4/2009 | Wiles |
| 2009/0106313 A1 | 4/2009 | Boldyga |
| 2009/0106316 A1 | 4/2009 | Kubono et al. |
| 2009/0106826 A1 | 4/2009 | Palestrant |
| 2009/0112683 A1 | 4/2009 | Hamilton, II et al. |
| 2009/0112754 A1 | 4/2009 | Seifert et al. |
| 2009/0112782 A1 | 4/2009 | Cross et al. |
| 2009/0130449 A1 | 5/2009 | El-Siblani |
| 2009/0132379 A1 | 5/2009 | Baril et al. |
| 2009/0142223 A1 | 6/2009 | Hyde et al. |
| 2009/0149717 A1 | 6/2009 | Brauer et al. |
| 2009/0161907 A1 | 6/2009 | Healey et al. |
| 2009/0164897 A1 | 6/2009 | Amer-Yahia et al. |
| 2009/0167553 A1 | 7/2009 | Hong et al. |
| 2009/0192898 A1 | 7/2009 | Baril |
| 2009/0198547 A1 | 8/2009 | Sudak |
| 2009/0199105 A1 | 8/2009 | Kamada et al. |
| 2009/0209240 A1 | 8/2009 | Mahowald |
| 2009/0218363 A1 | 9/2009 | Terzini |
| 2009/0234712 A1 | 9/2009 | Kolawa et al. |
| 2009/0236333 A1 | 9/2009 | Ben-Shmuel et al. |
| 2009/0236334 A1 | 9/2009 | Ben-Shmuel et al. |
| 2009/0236335 A1 | 9/2009 | Ben-Shmuel et al. |
| 2009/0242620 A1 | 10/2009 | Sahuguet |
| 2009/0254531 A1 | 10/2009 | Walker et al. |
| 2009/0259559 A1 | 10/2009 | Carroll et al. |
| 2009/0259688 A1 | 10/2009 | Do et al. |
| 2009/0261175 A1 | 10/2009 | Kauppinen et al. |
| 2009/0267895 A1 | 10/2009 | Bunch |
| 2009/0271004 A1 | 10/2009 | Zecchin et al. |
| 2009/0294521 A1 | 12/2009 | de la Huerga |
| 2009/0295569 A1 | 12/2009 | Corwin et al. |
| 2009/0295575 A1 | 12/2009 | Kennedy |
| 2009/0297668 A1 | 12/2009 | Cantu |
| 2009/0299645 A1 | 12/2009 | Colby et al. |
| 2009/0307139 A1 | 12/2009 | Mardikar et al. |
| 2009/0313125 A1 | 12/2009 | Roh et al. |
| 2009/0317519 A1 | 12/2009 | Lavie et al. |
| 2009/0326516 A1 | 12/2009 | Bangera et al. |
| 2010/0017296 A1 | 1/2010 | Spignesi, Jr. et al. |
| 2010/0038416 A1 | 2/2010 | Canora |
| 2010/0038594 A1 | 2/2010 | Bohlig et al. |
| 2010/0042427 A1 | 2/2010 | Graham et al. |
| 2010/0043834 A1 | 2/2010 | Scheringer |
| 2010/0045705 A1 | 2/2010 | Vertegaal et al. |
| 2010/0047410 A1 | 2/2010 | Lichtenstein |
| 2010/0052900 A1 | 3/2010 | Covannon et al. |
| 2010/0055257 A1 | 3/2010 | Hervig |
| 2010/0062169 A1 | 3/2010 | Pierre |
| 2010/0063889 A1 | 3/2010 | Proctor, Jr. et al. |
| 2010/0087155 A1 | 4/2010 | Dubost |
| 2010/0097180 A1 | 4/2010 | Cardullo |
| 2010/0100237 A1 | 4/2010 | Ratnakar |
| 2010/0106523 A1 | 4/2010 | Kalamas |
| 2010/0106607 A1 | 4/2010 | Riddiford et al. |
| 2010/0121156 A1 | 5/2010 | Yoo |
| 2010/0121669 A1 | 5/2010 | Madigan |
| 2010/0121722 A1 | 5/2010 | Vawter |
| 2010/0125362 A1 | 5/2010 | Canora et al. |
| 2010/0136666 A1 | 6/2010 | Kobayashi et al. |
| 2010/0139992 A1 | 6/2010 | Delia et al. |
| 2010/0145506 A1 | 6/2010 | Waugh et al. |
| 2010/0160745 A1 | 6/2010 | Hills et al. |
| 2010/0161345 A1 | 6/2010 | Cain et al. |
| 2010/0161600 A1 | 6/2010 | Higgins et al. |
| 2010/0167648 A1 | 7/2010 | Doutriaux |
| 2010/0181374 A1 | 7/2010 | Martis et al. |
| 2010/0189842 A1 | 7/2010 | Toren |
| 2010/0204676 A1 | 8/2010 | Cardullo |
| 2010/0206765 A1 | 8/2010 | Fonte |
| 2010/0235201 A1 | 9/2010 | McEvoy |
| 2010/0250384 A1 | 9/2010 | Bhargava |
| 2010/0256993 A1 | 10/2010 | Vespasiani |
| 2010/0259719 A1 | 10/2010 | Sabeta |
| 2010/0268378 A1 | 10/2010 | Sharpley |
| 2010/0268380 A1 | 10/2010 | Waugh et al. |
| 2010/0268792 A1 | 10/2010 | Butler et al. |
| 2010/0275625 A1 | 11/2010 | Lowenstein |
| 2010/0286632 A1 | 11/2010 | Dos Santos |
| 2010/0291515 A1 | 11/2010 | Pinnisi et al. |
| 2010/0292998 A1 | 11/2010 | Bodlaender et al. |
| 2010/0299158 A1 | 11/2010 | Siegel |
| 2010/0303972 A1 | 12/2010 | Srivastava |
| 2010/0305974 A1 | 12/2010 | Patch et al. |
| 2010/0310737 A1 | 12/2010 | Someya et al. |
| 2010/0312143 A1 | 12/2010 | Kim |
| 2010/0312385 A1 | 12/2010 | Deuber |
| 2010/0312601 A1 | 12/2010 | Lin |
| 2010/0320189 A1 | 12/2010 | Buchheit |
| 2010/0328099 A1 | 12/2010 | Wachman et al. |
| 2010/0332140 A1 | 12/2010 | Joyce et al. |
| 2010/0332250 A1 | 12/2010 | Simpson et al. |
| 2011/0000923 A1 | 1/2011 | Morales |
| 2011/0004624 A1 | 1/2011 | Bansai et al. |
| 2011/0009715 A1 | 1/2011 | O'Reilly et al. |
| 2011/0022225 A1* | 1/2011 | Rothschild ............ B67D 1/0041 700/233 |
| 2011/0022298 A1 | 1/2011 | Kronberg |
| 2011/0027432 A1 | 2/2011 | Loeser |
| 2011/0031236 A1 | 2/2011 | Ben-Shmuel et al. |
| 2011/0035338 A1 | 2/2011 | Kagan et al. |
| 2011/0040660 A1 | 2/2011 | Allison et al. |
| 2011/0054678 A1 | 3/2011 | Thompson |
| 2011/0055044 A1 | 3/2011 | Wiedl |
| 2011/0060457 A1 | 3/2011 | De Vrught et al. |
| 2011/0076349 A1 | 3/2011 | Yoshihara et al. |
| 2011/0080457 A1 | 4/2011 | Nagamine et al. |
| 2011/0087076 A1 | 4/2011 | Brynelsen et al. |
| 2011/0124996 A1 | 5/2011 | Reinke et al. |
| 2011/0133005 A1 | 6/2011 | Chesack |
| 2011/0160902 A1 | 6/2011 | Postins |
| 2011/0166881 A1 | 7/2011 | Brazzo et al. |
| 2011/0173062 A1 | 7/2011 | Chen et al. |
| 2011/0180441 A1 | 7/2011 | Bach |
| 2011/0186624 A1 | 8/2011 | Wagner et al. |
| 2011/0208617 A1 | 8/2011 | Weiland |
| 2011/0218839 A1 | 9/2011 | Shamaiengar |
| 2011/0231212 A1 | 9/2011 | Hurley et al. |
| 2011/0231266 A1 | 9/2011 | Baril |
| 2011/0282712 A1 | 11/2011 | Amos et al. |
| 2011/0289572 A1 | 11/2011 | Skeel et al. |
| 2011/0300270 A1 | 12/2011 | Koppens |
| 2011/0307316 A1 | 12/2011 | Peters et al. |
| 2011/0313867 A9 | 12/2011 | Silver |
| 2011/0318717 A1 | 12/2011 | Adamowicz |
| 2011/0320037 A1 | 12/2011 | Frugone |
| 2012/0004770 A1 | 1/2012 | Ooyen et al. |
| 2012/0016745 A1 | 1/2012 | Hendrickson |
| 2012/0016754 A1 | 1/2012 | Jackson |

(56) References Cited

U.S. PATENT DOCUMENTS

| | | |
|---|---|---|
| 2012/0036046 A1 | 2/2012 | Anderson et al. |
| 2012/0041770 A1 | 2/2012 | Philippe |
| 2012/0041778 A1 | 2/2012 | Kraft |
| 2012/0088023 A1 | 4/2012 | Begun |
| 2012/0088212 A1 | 4/2012 | Knaan |
| 2012/0089249 A1 | 4/2012 | Rosenblum |
| 2012/0101914 A1 | 4/2012 | Kumar et al. |
| 2012/0131619 A1 | 5/2012 | Ogilvie |
| 2012/0136731 A1 | 5/2012 | Kidron et al. |
| 2012/0137325 A1 | 5/2012 | Ogilvie |
| 2012/0152125 A1 | 6/2012 | Yoakim et al. |
| 2012/0156337 A1 | 6/2012 | Studor et al. |
| 2012/0168985 A1 | 7/2012 | Kläber |
| 2012/0173271 A1 | 7/2012 | Omidi |
| 2012/0179665 A1 | 7/2012 | Baarman et al. |
| 2012/0196011 A1 | 8/2012 | Felix |
| 2012/0214140 A1 | 8/2012 | Brynelsen et al. |
| 2012/0232484 A1 | 9/2012 | Blomquist |
| 2012/0233002 A1 | 9/2012 | Abujbara |
| 2012/0246004 A1 | 9/2012 | Book et al. |
| 2012/0251688 A1 | 10/2012 | Zimmerman et al. |
| 2012/0251689 A1 | 10/2012 | Batchelder |
| 2012/0258216 A1 | 10/2012 | Wessels |
| 2012/0262039 A1 | 10/2012 | Daugbjerg et al. |
| 2012/0268259 A1 | 10/2012 | Igel et al. |
| 2012/0284126 A1 | 11/2012 | Giraud et al. |
| 2012/0290412 A1 | 11/2012 | Marovets |
| 2012/0303425 A1 | 11/2012 | Katzin et al. |
| 2012/0310760 A1 | 12/2012 | Phillips et al. |
| 2012/0323208 A1 | 12/2012 | Bochenko et al. |
| 2012/0323707 A1 | 12/2012 | Urban |
| 2013/0006415 A1 | 1/2013 | Paydar et al. |
| 2013/0011529 A1 | 1/2013 | Belzowski et al. |
| 2013/0018356 A1 | 1/2013 | Prince et al. |
| 2013/0034633 A1 | 2/2013 | von Hasseln |
| 2013/0048023 A1 | 2/2013 | Holman et al. |
| 2013/0048037 A1 | 2/2013 | Holman et al. |
| 2013/0089642 A1 | 4/2013 | Lipson et al. |
| 2013/0092033 A1 | 4/2013 | Murphy et al. |
| 2013/0151268 A1 | 6/2013 | Fletcher |
| 2013/0158705 A1 | 6/2013 | Levy et al. |
| 2013/0171304 A1 | 7/2013 | Huntley |
| 2013/0189405 A1 | 7/2013 | Filliol et al. |
| 2013/0196035 A1 | 8/2013 | Passet et al. |
| 2013/0238118 A1 | 9/2013 | Haas |
| 2013/0273217 A1 | 10/2013 | Minvielle |
| 2013/0304529 A1 | 11/2013 | Phalake et al. |
| 2014/0013962 A1 | 1/2014 | Lipton et al. |
| 2014/0050811 A1 | 2/2014 | Lipton et al. |
| 2014/0236759 A1 | 8/2014 | Mirabile |
| 2014/0304055 A1 | 10/2014 | Faith |
| 2015/0151050 A1 | 6/2015 | Estes |
| 2015/0216201 A1 | 8/2015 | Bruckner et al. |
| 2015/0296865 A1 | 10/2015 | Holman et al. |
| 2015/0302375 A1 | 10/2015 | Holman et al. |

FOREIGN PATENT DOCUMENTS

| | | |
|---|---|---|
| WO | WO 03/056493 A1 | 7/2003 |
| WO | WO 2006/095212 A1 | 9/2006 |

OTHER PUBLICATIONS

Fiore et al; "Effects of Imagery Copy and Product Samples on Responses Toward the Product"; Journal of Interactive Marketing; bearing a date of Spring 2001; pp. 36-46; vol. 15, No. 2.

"Airline Tickets and Airline Reservations from American Airlines"; AA.com; 1 page; retrieved from the interne wayback machine on Oct. 27, 2011; located at http://web.archieve.org/web.20101027131457/http://www.aa.com.

American Society of Hospital Pharmacists; "ASHP Technical Assistance Bulleting on Compounding Nonsterile Products in Pharmacies"; Am. J. Hosp. Pharm.; bearing a date of 1994, approved Apr. 27, 1994; pp. 73-79; vol. 51, No. 1441-8; American Society of Hospital Pharmacists, Inc.

McDonald's; sample restaurant menu; Feb. 10, 2014; 1 page; located at: http://www.burgerbusiness.com/wp-content/uploads/McD_Calor. . . . .

"Scientists create 'inhalable' food?"; bearing a date of Aug. 29, 2012; snapshot taken Apr. 12, 2009; available at http://web.archive.org/web/20090412131937/http://chowhound.chow.com/topics/611174.

"Transdermal Nutrient Delivery System"; U.S. Army Soldier and Biological Chemical Command; snapshot taken Jul. 21, 2004; available at http://web.archive.org/web/20040721134210 http://archives.tproc.org/www.sbccom.army.mil/products/food/tdnds.pdf.

Williams, N.T.; "Medication administration through enteral feeding tubes"; Am J Health Syst Pharm.; bearing a date of Dec. 15, 2008; 2 pages (abstract only); vol. 65, No. 24; located at http://www.ncbi.nlm.nih.gov/pubmed/19052281.

U.S. Appl. No. 13/494,536, Holman et al.
U.S. Appl. No. 13/494,654, Holman et al.
U.S. Appl. No. 13/528,298, Holman et al.
U.S. Appl. No. 15/535,855, Holman et al.
U.S. Appl. No. 13/535,902, Holman et al.
U.S. Appl. No. 13/548,633, Holman et al.
U.S. Appl. No. 13/548,671, Holman et al.
U.S. Appl. No. 13/554,194, Holman et al.
U.S. Appl. No. 13/554,237, Holman et al.
U.S. Appl. No. 13/560,447, Holman et al.

"3D food printing"; PharmacyEscrow.com; printed on Apr. 4, 2012; 2 pages.

Blain, Loz; "Cornucopia: Digital Gastronomy—could 3D printing be the next revolution in cooking?"; Gizmag; Jan. 14, 2010; 4 pages.

Broomfield, Mark; "The Future of Food Printing"; Fab@Home; Aug. 20, 2009; 1 page.

Coelho, Marcelo; "Cornucopia"; printed on Apr. 4, 2012; 1 page; located at fluid.media.mut.edu.

Cohen et al.; "Hydrocolloid Printing: A Novel Platform for Customized Food Production"; Twentieth Annual International Solid Freeform Fabrication Symposium, Austin, Texas; bearing a date of 2009; cover page and pp. 807-818.

Fawkes, Piers; "3D Food Printing", PSFK; Jan. 17, 2008; 8 pages.

Flatley, Joseph L.; "Ikea's kitchen of the future: 3D food printing, mood lighting, virtual Gordon Ramsay"; Engadget; printed on Apr. 4, 2012; 4 pages; AOL Inc.

McKendrick, Joe; "3D food 'printing': coming to a kitchen near you"; Smartplanet; Dec. 27, 2010; 6 pages; located at www.smartplanet.com/business/blog/business-brains.

Periard et al.; "Printing Food"; Cornell University; printed on Apr. 6, 2012; 11 pages; located at www.creativemachines.cornell.edu/papers/SFF07_Periard2.pdf.

"Printed Meats!"; Fabbaloo; Aug. 23, 2010; 5 pages; Fabbaloo.

U.S. Appl. No. 13/560,477, Holman et al.
U.S. Appl. No. 13/590,774, Holman et al.
U.S. Appl. No. 13/590,799, Holman et al.
U.S. Appl. No. 13/596,469, Holman et al.
U.S. Appl. No. 13/596,499, Holman et al.

"Prototypes and Concept Designs for a Digital Gastronomy"; Cornucopia; printed on Apr. 4, 2012; 5 pages.

Sandhana, Lakshmi; "The printed future of Christmas dinner"; BBC News Technology; Dec. 24, 2010; 4 pages; MMXI.

Seth, Radhika; "Printing My Food by The Molecule"; Yanko Design; Mar. 2, 2010; 7 pages.

Seth, Radhika; "Surreal Food Is Real and Printed"; Yanko Design; Aug. 26, 2009; 6 pages.

"The CandyFab 6000"; Evil Mad Scientist Laboratories; bearing a date of 2011; 7 pages; Evil Mad Scientist Laboratories.

"Welcome to the CandyFabProject"; CandyFab.org; Jan. 22, 2011; 3 pages; The CandyFab Project.

Indiana State Excise Police; "Alcohol Laws"; snapshot taken Oct. 22, 2010; pp. 1-2; located at http://web.archive.org/web/20101222202431/http://www.in.gov/atc/isep/2384.htm.

Valuevapor.com; "Starter Kits"; printed on Sep. 22, 2014; pp. 1-2; located at http://web.archive.org/web/20100610083606/http://www.valuevapor.com/VV/store/index.php?main_page=index&cPath=10.

(56) References Cited

OTHER PUBLICATIONS

McDonagh-Philp, Deana; "Using Focus Groups to Support New Product Development"; Institution of Engineering Designers Journal; Sep. 2000; pp. 1-6.
Shimmura et al.; "Analysis of Eating Behavior in Restaurants Based on Leftover Food"; 2010; pp. 956-960; IEEE.
"Toddlers at the Table: Avoiding Power Straggles," located at https://web.archive.org/web/20101012173406/http://kidshealth.org/parent/nutrition_center/staying_fit/toddler_meals.html; KidsHealth; 2010; pp. 1-2; The Nemours Foundation.
Connors et al.; "Using a Visual Plate Waste Study to Monitor Menu Performance"; Journal of the American Dietetic Association; 2004; pp. 94-96; vol. 104; American Dietetic Association.
Poulter, Sean; "Medicine vending machines that dispense prescriptions 24 hours a day go on trial"; bearing a date of Jun. 22, 2010; created on Nov. 27, 2017; pp. 1-5; located at http://www.dailymail.co.uk/health/article-1288434/Medicine-vending-machine-dispense-prescriptions-pharmacist-launched.html.

\* cited by examiner

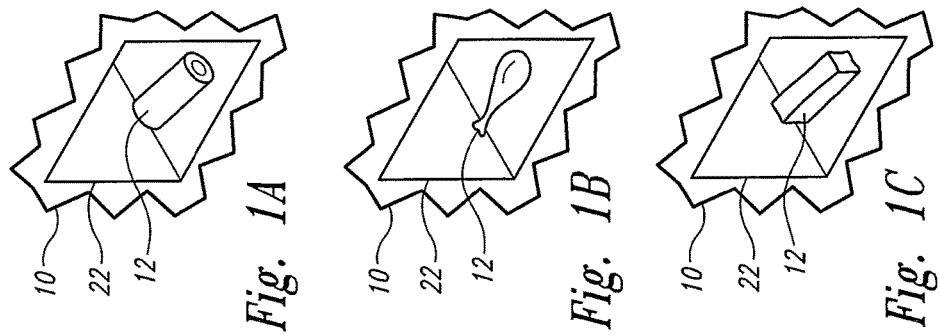
Fig. 1A  Fig. 1B  Fig. 1C
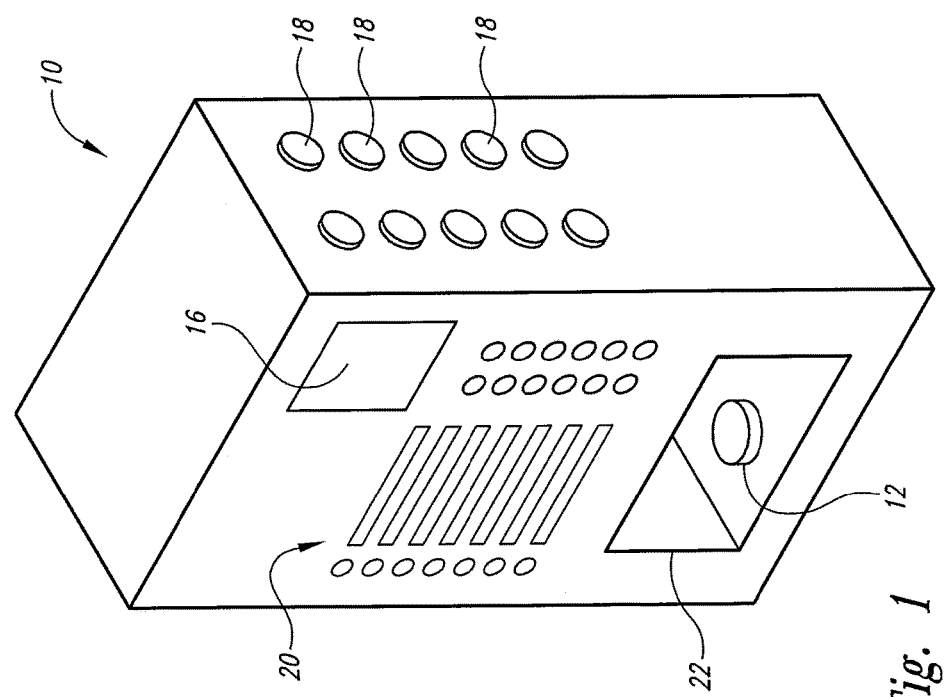
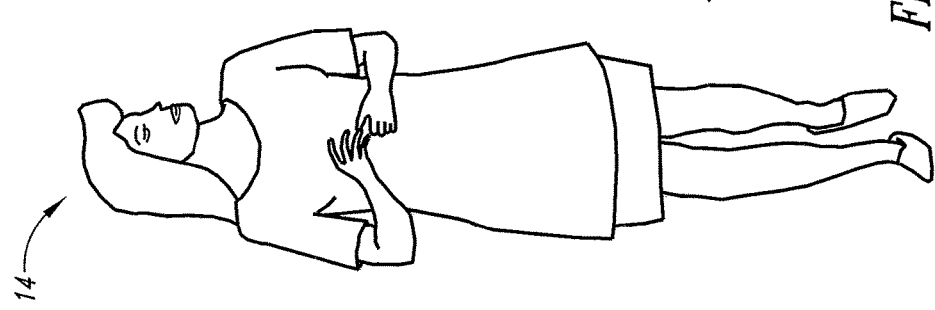
Fig. 1

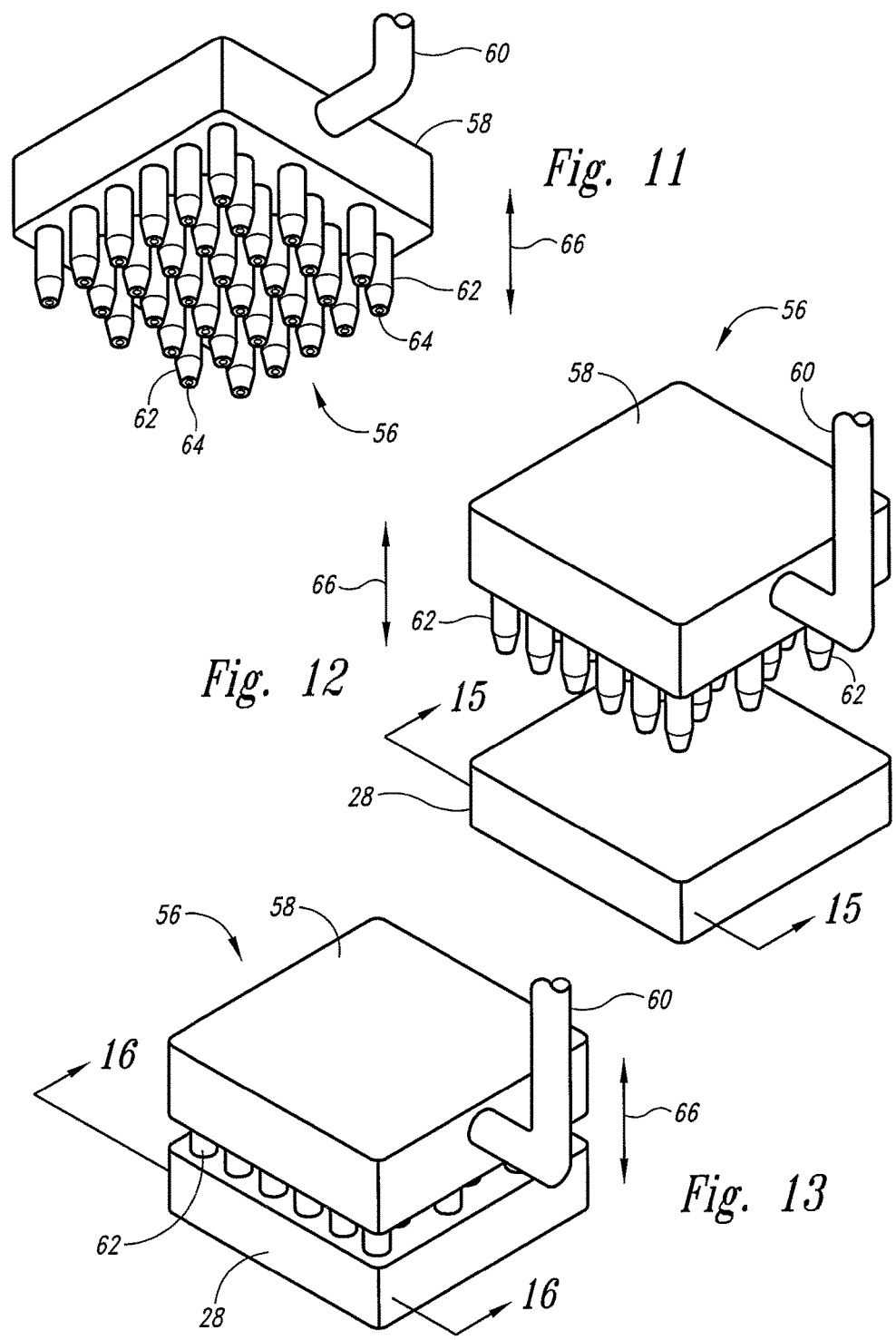

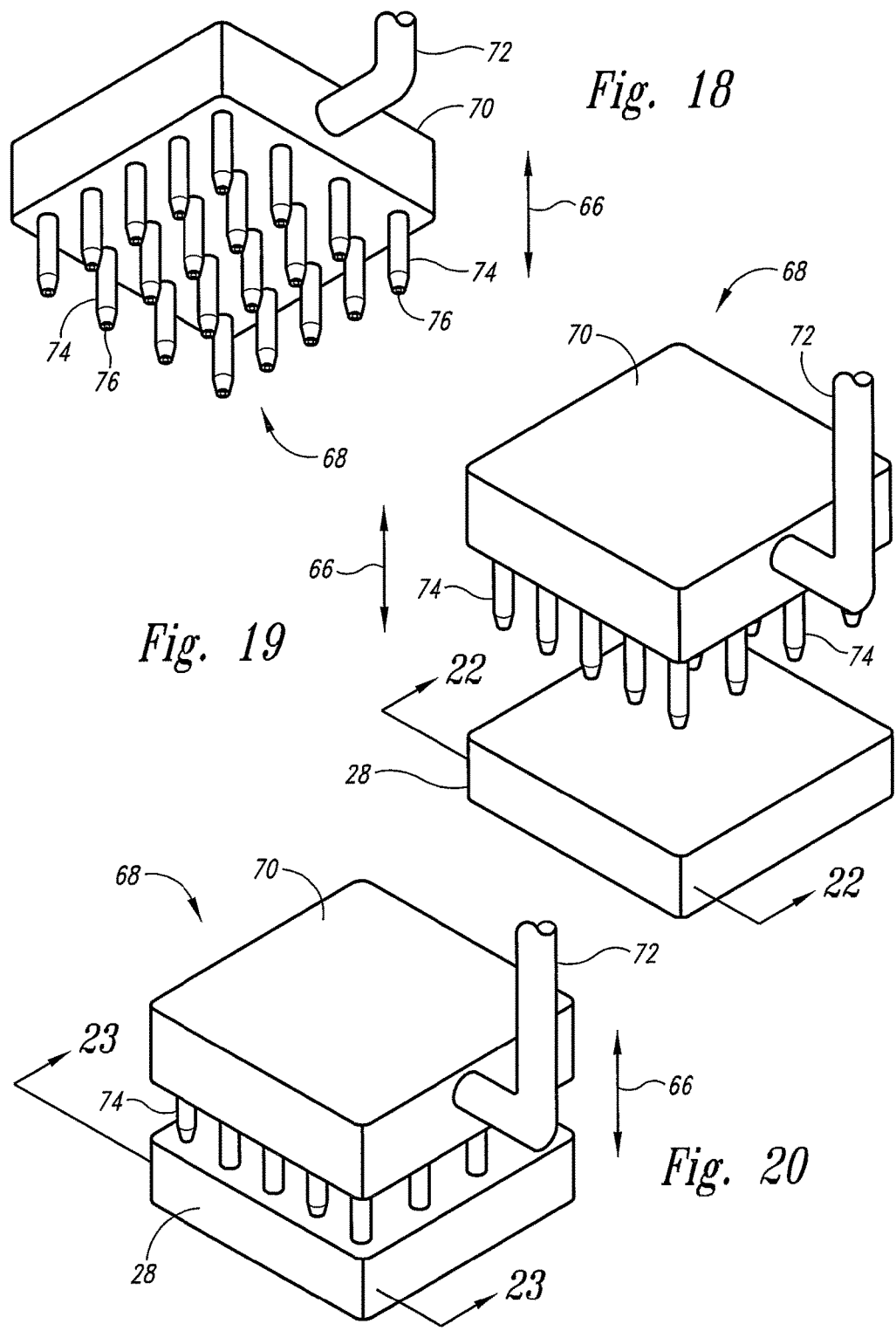

*Fig. 45*

| 10 ingestible product preparation system | | | |
|---|---|---|---|
| e12 controlling treatment elec circ arrange | | | |
| e1201 direct treatment circuits elec circ arrange | e1202 direct treatment network elec circ arrange | e1203 direct treatment adjacent elec circ arrange | e1204 direct modify color elec circ arrange |
| e1205 direct modify surface elec circ arrange | e1206 direct modify oral elec circ arrange | e1207 direct modify sound elec circ arrange | e1208 direct modify structural elec circ arrange | e1209 direct modify olfactory elec circ arrange |
| e1210 direct modify shape elec circ arrange | e1211 direct modify psycho-sensory elec circ arrange | e1212 direct modify acidic elec circ arrange | e1213 direct modify basic elec circ arrange | e1214 direct modify carbohydrate elec circ arrange |
| e1215 direct modify protein elec circ arrange | e1216 direct modify fat elec circ arrange | e1217 direct modify non-nutritive elec circ arrange | e1218 direct substrate carbohydrate elec circ arrange | e1219 direct substrate fat elec circ arrange |

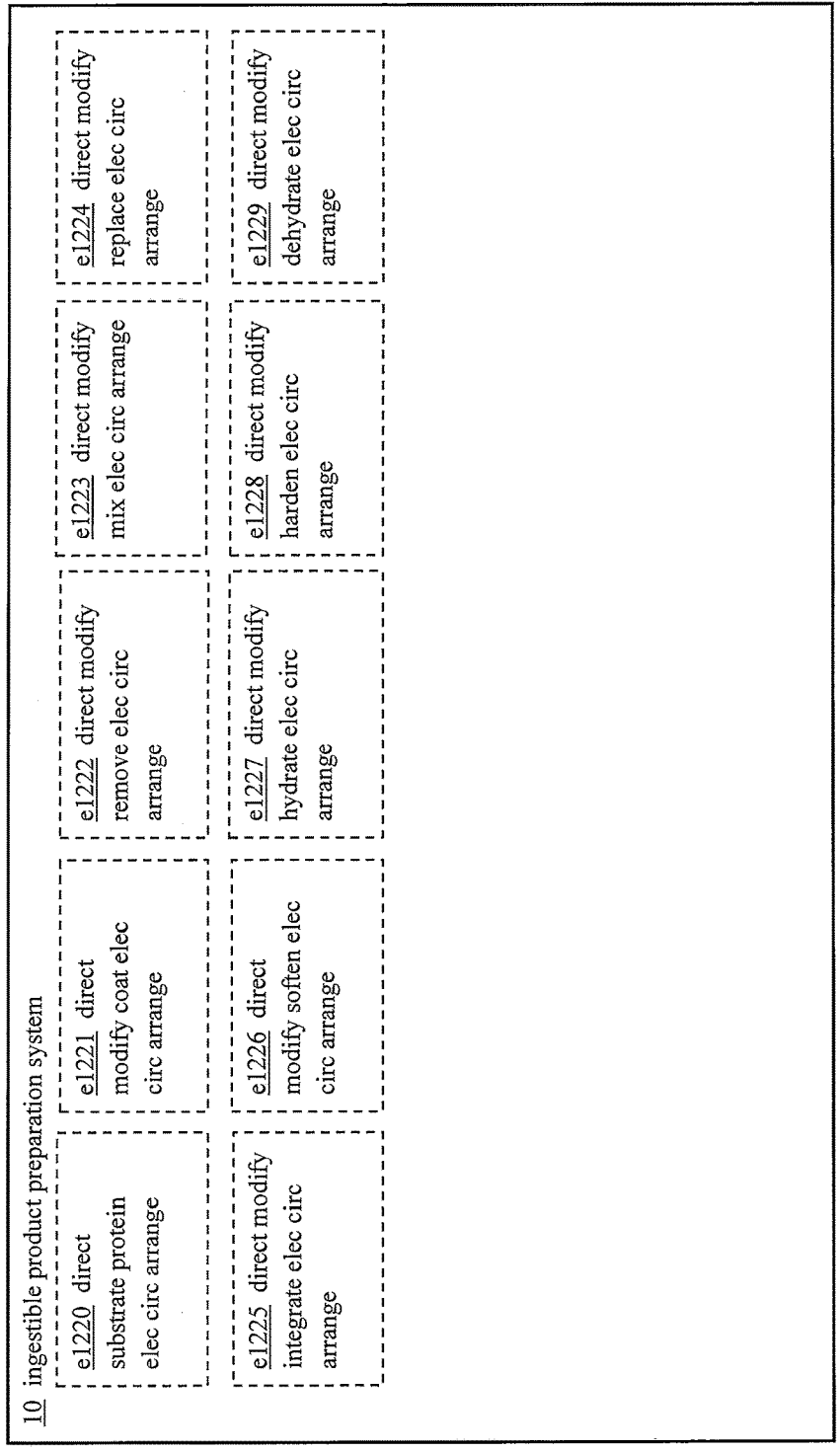

Fig. 65 o11 electronically receiving user status information regarding one or more particular individual living beings including one or more identifiers associated with the one or more particular individual living beings and electronically receiving selection information at least in part identifying one or more selected ingestible products being subject to ingestion by the one or more particular individual living beings, the selection information electronically received via electronically enabled input, the electronically receiving the user status information and the electronically receiving the selection information at least in part to electronically obtain treatment instructional information regarding one or more subsequent injection operations on one or more portions of one or more ingestible substrate structures o1110 electronically receiving the user status information regarding the one or more particular individual living beings wirelessly o1111 electronically receiving the user status information regarding the one or more particular individual living beings via one or more electronic keypad entries o1112 electronically receiving the user status information regarding the one or more particular individual living beings including the one or more identifiers associated with the one or more particular individual living beings as further associated with one or more restaurant meal orders

Fig. 93 o12

Start electronically directing control of at least partial treatment of the one or more portions of the one or more ingestible substrate structures according to the treatment instructional information regarding the one or more subsequent injection operations including at least one or more injections of one or more materials into the one or more portions of the one or more ingestible substrate structures to form at least in part the one or more selected ingestible products subsequent to and based at least in part upon the electronically receiving the user status information regarding the one or more particular individual living beings and the electronically receiving the selection information at least in part identifying the one or more selected ingestible products o1201 electronically directing control of the at least partial treatment of the one or more ingestible substrate structures according to the treatment instructional information regarding the one or more subsequent injection operations via at least in part one or more directly connected electrical circuits o1202 electronically directing control of the at least partial treatment of the one or more ingestible substrate structures according to the treatment instructional information regarding the one or more subsequent injection operations via at least in part electronic computer network communication o1203 electronically directing control of the at least partial treatment of the one or more ingestible substrate structures through electronic circuitry located substantially adjacent to electronic circuitry for the electronically receiving the user status information and the electronically receiving the selection information End

*Fig. 94* o12

Start → ⁀⁀ electronically directing control of at least partial treatment of the one or more portions of the one or more ingestible substrate structures according to the treatment instructional information regarding the one or more subsequent injection operations including at least one or more injections of one or more materials into the one or more portions of the one or more ingestible substrate structures to form at least in part the one or more selected ingestible products subsequent to and based at least in part upon the electronically receiving the user status information regarding the one or more particular individual living beings and the electronically receiving the selection information at least in part identifying the one or more selected ingestible products o1204 electronically directing control of the one or more injections of the one or more materials as one or more color modification materials into the one or more portions of the one or more ingestible substrate structures to modify one or more color properties of the one or more portions of the one or more ingestible substrate structures to form at least in part the one or more selected ingestible products o1205 electronically directing control of the one or more injections of the one or more materials as one or more surface texture modification materials into the one or more portions of the one or more ingestible substrate structures to modify one or more surface texture properties of the one or more portions of the one or more ingestible substrate structures to form at least in part the one or more selected ingestible products o1206 electronically directing control of the one or more injections of the one or more materials as one or more oral sensation modification materials into the one or more portions of the one or more ingestible substrate structures to modify one or more oral sensation properties of the one or more portions of the one or more ingestible substrate structures to form at least in part the one or more selected ingestible products End

*Fig. 95* o12 electronically directing control of at least partial treatment of the one or more portions of the one or more ingestible substrate structures according to the treatment instructional information regarding the one or more subsequent injection operations including at least one or more injections of one or more materials into the one or more portions of the one or more ingestible substrate structures to form at least in part the one or more selected ingestible products subsequent to and based at least in part upon the electronically receiving the user status information regarding the one or more particular individual living beings and the electronically receiving the selection information at least in part identifying the one or more selected ingestible products o1207 electronically directing control of the one or more injections of the one or more materials as one or more sound modification materials into the one or more portions of the one or more ingestible substrate structures to modify one or more sound properties of the one or more portions of the one or more ingestible substrate structures to form at least in part the one or more selected ingestible product o1208 electronically directing control of the one or more injections of the one or more materials as one or more structural texture modification materials into the one or more portions of the one or more ingestible substrate structures to modify one or more structural texture properties of the one or more portions of the one or more ingestible substrate structures to form at least in part the one or more selected ingestible products o1209 electronically directing control of the one or more injections of the one or more materials as one or more olfactory modification materials into the one or more portions of the one or more ingestible substrate structures to modify one or more olfactory properties of the one or more portions of the one or more ingestible substrate structures to form at least in part the one or more selected ingestible products

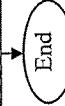

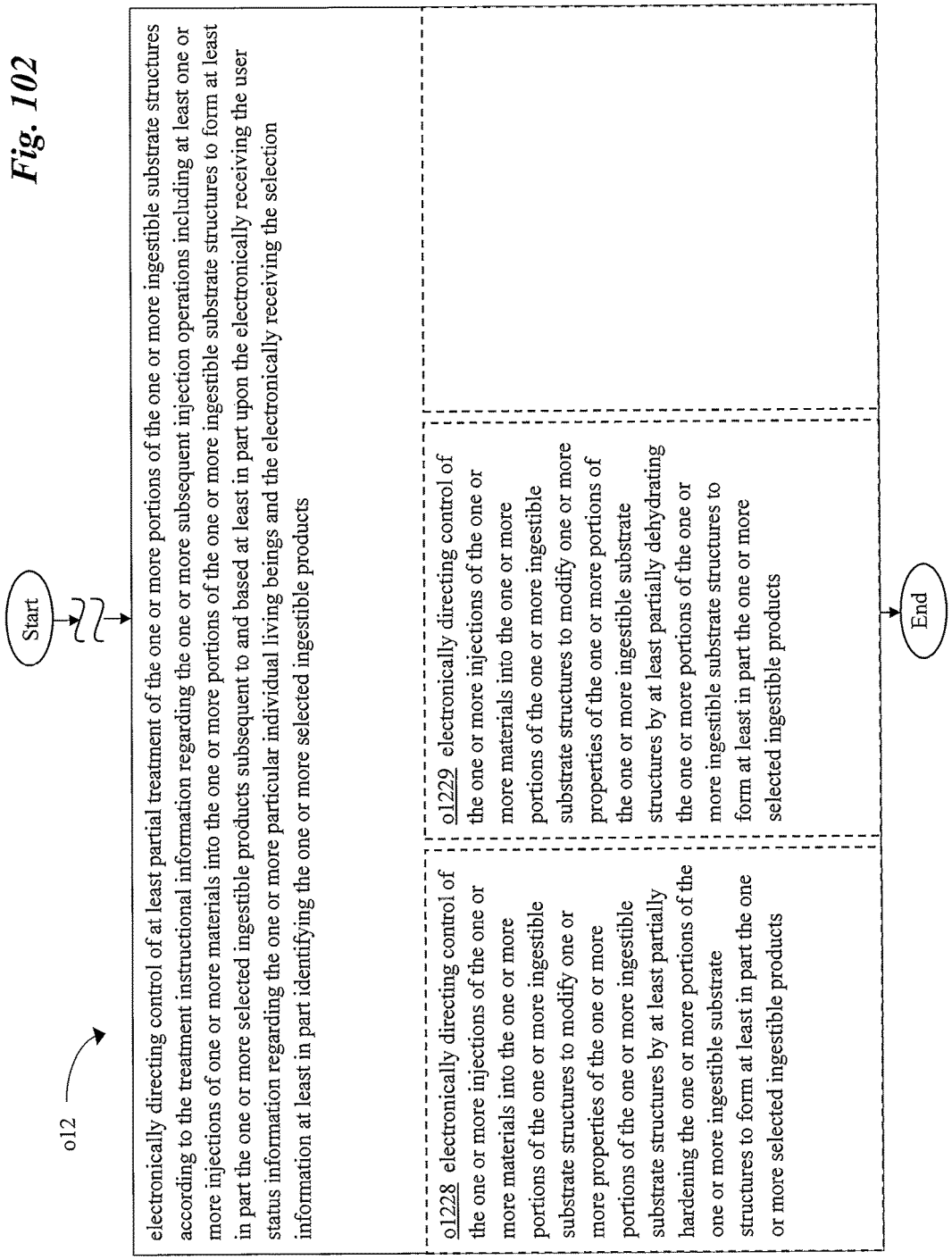

SUBSTRATE STRUCTURE INJECTION TREATMENT SYSTEM AND METHOD FOR INGESTIBLE PRODUCT SYSTEM AND METHOD

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC § 119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications is incorporated herein by reference to the extent such subject matter is not inconsistent herewith.

RELATED APPLICATIONS

For purposes of the USPTO extra-statutory requirements, the present application constitutes a continuation continuation-in-part of U.S. patent application Ser. No. 13/494,536, entitled SUBSTRATE STRUCTURE DEPOSITION TREATMENT SYSTEM AND METHOD FOR INGESTIBLE PRODUCT SYSTEM AND METHOD, naming Paul Holman, Royce A. Levien, Mark A. Malamud, Neal Stephenson and Christopher Charles Young as inventors, filed 12 Jun. 2012, which is currently co-pending or is an application of which a currently co-pending application is entitled to the benefit of the filing date.

For purposes of the USPTO extra-statutory requirements, the present application constitutes a continuation continuation-in-part of U.S. patent application Ser. No. 13/494,654, entitled SUBSTRATE STRUCTURE DEPOSITION TREATMENT SYSTEM AND METHOD FOR INGESTIBLE PRODUCT SYSTEM AND METHOD, naming Paul Holman, Royce A. Levien, Mark A. Malamud, Neal Stephenson and Christopher Charles Young as inventors, filed 12 Jun. 2012, which is currently co-pending or is an application of which a currently co-pending application is entitled to the benefit of the filing date.

For purposes of the USPTO extra-statutory requirements, the present application constitutes a continuation of U.S. patent application Ser. No. 13/528,298, entitled SUBSTRATE STRUCTURE INJECTION TREATMENT SYSTEM AND METHOD FOR INGESTIBLE PRODUCT SYSTEM AND METHOD, naming Paul Holman, Royce A. Levien, Mark A. Malamud, Neal Stephenson, and Christopher Charles Young as inventors, filed 20 Jun. 2012, which is currently co-pending or is an application of which a current co-pending application is entitled to the benefit of the filling date.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

SUMMARY

A computationally-implemented method includes, but is not limited to electronically receiving user status information regarding one or more particular individual living beings including one or more identifiers associated with the one or more particular individual living beings and electronically receiving selection information at least in part identifying one or more selected ingestible products being subject to ingestion by the one or more particular individual living beings, the selection information electronically received via electronically enabled input, the electronically receiving the user status information and the electronically receiving the selection information at least in part to electronically obtain treatment instructional information regarding one or more subsequent injection operations on one or more portions of one or more ingestible substrate structures; and electronically directing control of at least partial treatment of the one or more portions of the one or more ingestible substrate structures according to the treatment instructional information regarding the one or more subsequent injection operations including at least one or more injections of one or more materials into the one or more portions of the one or more ingestible substrate structures to form at least in part the one or more selected ingestible products subsequent to and based at least in part upon the electronically receiving the user status information regarding the one or more particular individual living beings and the electronically receiving the selection information at least in part identifying the one or more selected ingestible products.

In one or more various aspects, related machines, compositions of matter, or manufactures of systems may include, but are not limited to, virtually any combination of hardware, software, and/or firmware configured to effect the herein-referenced method aspects depending upon the design choices of the system designer (limited to patentable subject matter under 35 USC 101).

A computationally-implemented system includes, but is not limited to: means for electronically receiving user status information regarding one or more particular individual living beings including one or more identifiers associated with the one or more particular individual living beings and electronically receiving selection information at least in part identifying one or more selected ingestible products being subject to ingestion by the one or more particular individual living beings, the selection information electronically received via electronically enabled input, the electronically receiving the user status information and the electronically receiving the selection information at least in part to electronically obtain treatment instructional information regarding one or more subsequent injection operations on one or more portions of one or more ingestible substrate structures; and means for electronically directing control of at least partial treatment of the one or more portions of the one or more ingestible substrate structures according to the treatment instructional information regarding the one or more subsequent injection operations including at least one or more injections of one or more materials into the one or more portions of the one or more ingestible substrate structures to form at least in part the one or more selected ingestible products subsequent to and based at least in part upon the electronically receiving the user status information regarding the one or more particular individual living beings and the electronically receiving the selection information at least in part identifying the one or more selected ingestible products. In addition to the foregoing, other system aspects are described in the claims, drawings, and text forming a part of the present disclosure.

A computationally-implemented system includes, but is not limited to a receiving information electrical circuitry arrangement for electronically receiving user status information regarding one or more particular individual living beings including one or more identifiers associated with the one or more particular individual living beings and electronically receiving selection information at least in part identifying one or more selected ingestible products being subject to ingestion by the one or more particular individual living beings, the selection information electronically received via electronically enabled input, the electronically receiving the user status information and the electronically receiving the selection information at least in part to electronically obtain treatment instructional information regarding one or more subsequent injection operations on one or more portions of one or more ingestible substrate structures; and a controlling treatment electrical circuitry arrangement for electronically directing control of at least partial treatment of the one or more portions of the one or more ingestible substrate structures according to the treatment instructional information regarding the one or more subsequent injection operations including at least one or more injections of one or more materials into the one or more portions of the one or more ingestible substrate structures to form at least in part the one or more selected ingestible products subsequent to and based at least in part upon the electronically receiving the user status information regarding the one or more particular individual living beings and the electronically receiving the selection information at least in part identifying the one or more selected ingestible products. In addition to the foregoing, other system aspects are described in the claims, drawings, and text forming a part of the present disclosure.

A system includes, but is not limited to a receiving information module configured to operate in accordance with electronically receiving user status information regarding one or more particular individual living beings including one or more identifiers associated with the one or more particular individual living beings and electronically receiving selection information at least in part identifying one or more selected ingestible products being subject to ingestion by the one or more particular individual living beings, the selection information electronically received via electronically enabled input, the electronically receiving the user status information and the electronically receiving the selection information at least in part to electronically obtain treatment instructional information regarding one or more subsequent injection operations on one or more portions of one or more ingestible substrate structures; and a controlling treatment module configured to operate in accordance with electronically directing control of at least partial treatment of the one or more portions of the one or more ingestible substrate structures according to the treatment instructional information regarding the one or more subsequent injection operations including at least one or more injections of one or more materials into the one or more portions of the one or more ingestible substrate structures to form at least in part the one or more selected ingestible products subsequent to and based at least in part upon the electronically receiving the user status information regarding the one or more particular individual living beings and the electronically receiving the selection information at least in part identifying the one or more selected ingestible products. In addition to the foregoing, other system aspects are described in the claims, drawings, and text forming a part of the present disclosure.

An article of manufacture including one or more non-transitory signal-bearing storage medium bearing one or more instructions for electronically receiving user status information regarding one or more particular individual living beings including one or more identifiers associated with the one or more particular individual living beings and electronically receiving selection information at least in part identifying one or more selected ingestible products being subject to ingestion by the one or more particular individual living beings, the selection information electronically received via electronically enabled input, the electronically receiving the user status information and the electronically receiving the selection information at least in part to electronically obtain treatment instructional information regarding one or more subsequent injection operations on one or more portions of one or more ingestible substrate structures; and one or more instructions for electronically directing control of at least partial treatment of the one or more portions of the one or more ingestible substrate structures according to the treatment instructional information regarding the one or more subsequent injection operations including at least one or more injections of one or more materials into the one or more portions of the one or more ingestible substrate structures to form at least in part the one or more selected ingestible products subsequent to and based at least in part upon the electronically receiving the user status information regarding the one or more particular individual living beings and the electronically receiving the selection information at least in part identifying the one or more selected ingestible products. In addition to the foregoing, other computer program product aspects are described in the claims, drawings, and text forming a part of the present disclosure.

A system including one or more computing devices; and one or more instructions when executed on the one or more computing devices cause the one or more computing devices to perform electronically receiving user status information regarding one or more particular individual living beings including one or more identifiers associated with the one or more particular individual living beings and electronically receiving selection information at least in part identifying one or more selected ingestible products being subject to ingestion by the one or more particular individual living beings, the selection information electronically received via electronically enabled input, the electronically receiving the user status information and the electronically receiving the selection information at least in part to electronically obtain treatment instructional information regarding one or more subsequent injection operations on one or more portions of one or more ingestible substrate structures; and electronically directing control of at least partial treatment of the one or more portions of the one or more ingestible substrate structures according to the treatment instructional information regarding the one or more subsequent injection operations including at least one or more injections of one or more materials into the one or more portions of the one or more ingestible substrate structures to form at least in part the one or more selected ingestible products subsequent to and based at least in part upon the electronically receiving the user status information regarding the one or more particular individual living beings and the electronically receiving the selection information at least in part identifying the one or more selected ingestible products. In addition to the foregoing, other computer program product aspects are described in the claims, drawings, and text forming a part of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 1 is a perspective view depicting a first application of a first exemplary implementation of an ingestible product preparation system.

FIG. 1A is a fragmentary view depicting a second application of the first exemplary implementation of the ingestible product preparation system of FIG. 1.

FIG. 1B is a fragmentary view depicting a third application of the first exemplary implementation of the ingestible product preparation system of FIG. 1.

FIG. 1C is a fragmentary view depicting a fourth application of the first exemplary implementation of the ingestible product preparation system of FIG. 1.

FIG. 11 is a perspective view of a first exemplary injection treatment assembly configured for one or more ingestible material needle injection operations including for one or more liquid injection implementations to provide ingestible substrate structure treatment capability for the ingestible product preparation system.

FIG. 12 is a perspective view of a fifth exemplary ingestible substrate structure implementation about to be treated by the first exemplary injection treatment assembly of FIG. 11.

FIG. 13 is a perspective view of the fifth exemplary ingestible substrate structure implementation being treated by the first exemplary injection treatment assembly of FIG. 11.

FIG. 18 is a perspective view of a second exemplary injection treatment assembly configured for one or more ingestible material needle injection operations including for one or more gas and/or steam injection implementations to provide ingestible substrate structure treatment capability for the ingestible product preparation system.

FIG. 19 is a perspective view of the fifth exemplary ingestible substrate structure implementation about to be treated by the second exemplary injection treatment assembly of FIG. 18.

FIG. 20 is a perspective view of the fifth exemplary ingestible substrate structure implementation being treated by the second exemplary injection treatment assembly of FIG. 18.

FIG. 45 is a block diagram depicting one or more exemplary electrical circuitry arrangements of the ingestible product preparation system 10 of FIG. 1.

FIG. 46 is a block diagram depicting one or more exemplary electrical circuitry arrangements of the ingestible product preparation system 10 of FIG. 1.

FIG. 65 is a high-level flowchart including exemplary implementations of operation O11 of FIG. 61.

FIG. 93 is a high-level flowchart including exemplary implementations of operation O12 of FIG. 61.

FIG. 94 is a high-level flowchart including exemplary implementations of operation O12 of FIG. 61.

FIG. 95 is a high-level flowchart including exemplary implementations of operation O12 of FIG. 61.

FIG. 102 is a high-level flowchart including exemplary implementations of operation O12 of FIG. 61.

DETAILED DESCRIPTION

Figure 2:
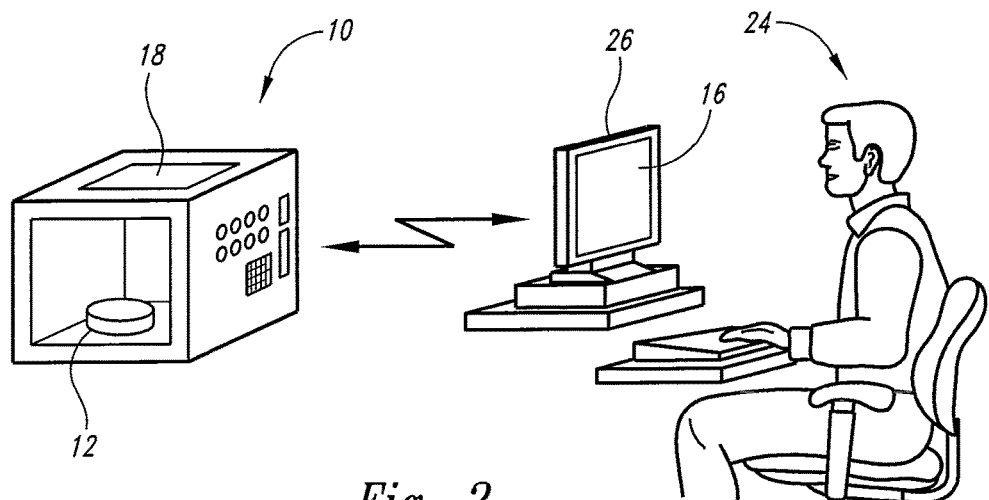
FIG. 2 is a perspective view depicting a first application of a second exemplary implementation of the ingestible product preparation system of FIG. 1.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Generally, automated and semi-automated machines to make, manufacture, fabricate, or otherwise prepare and/or dispense ingestible products to be ingested by living beings such as humans, animals, plants, etc. are known to a degree with interest existing for future development as well. Automated and semi-automated preparation of the ingestible products can incorporate all known forms of preparation of food and other ingestible products including but not limited to all known forms of energy addition to one or more ingredients of the ingestible products (such as through various forms of thermal heating or adding microwave, infrared, or ultrasonic energy), extracting energy from one or more ingredients of the ingestible products (such as through thermodynamic-cycle based cooling or peltier cooling), deposition methods (including deposition by layering or at the pixel level), and combinational methods (such as blending, mixing, ingredient injection, kneading, stirring, ultrasonic agitation, other agitational methods, etc.), etc.

Although ingestible products made, fabricated, or otherwise prepared and/or dispensed by semi-automated and automated machines are presently limited in scope to a degree, it is envisioned that with future development, this will change. Ingestible products can take many forms including, but not limited to, solids, semi-solids, liquids, gases, dispersions (such as true solutions, colloid dispersions, emulsions, foams, and gels) and vast combinations thereof. Time for final semi-automated and automated preparation may be reduced if ingestible substrate structures can be fabricated beforehand with modification, such as through deposition methods, done thereto near point of purchase or at other times near ingestion thereof.

Various methods of ingestion can include consumption methods and delivery methods such as oral, dermal, intranasal, transdermal, transmucosal, peroral, buccal, sublingual, ocular, rectal, injection, peg-tube, nasal, tear-duct, respiratory, inhalation, etc. as associated with ingestion by a particular individual living being of ingestible material dispensed or produced and selected under influence through selection information from the computer based social network service 46 through the ingestible product preparation system 10.

Figure 3:
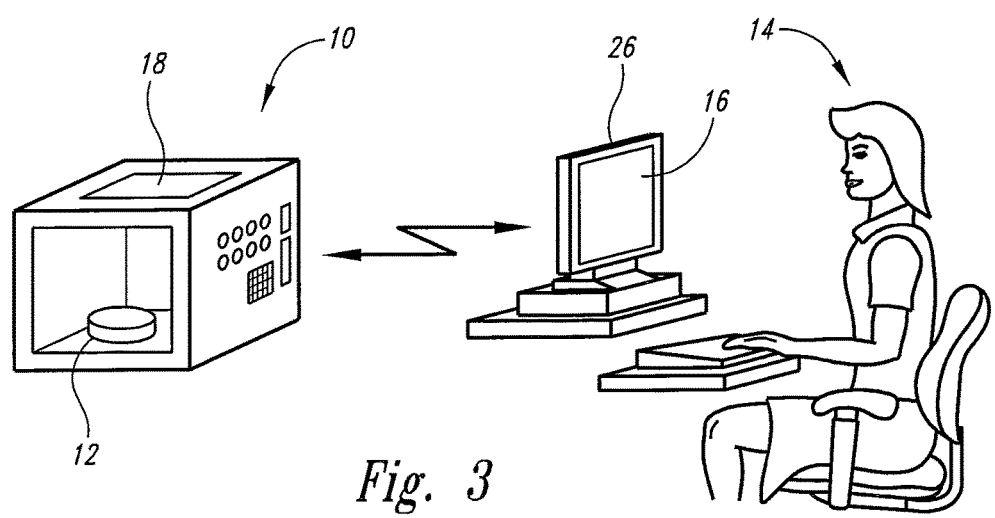
FIG. 3 is a perspective view depicting a second application of the second exemplary implementation of the ingestible product preparation system of FIG. 1.

As depicted in FIGS. 1-3, exemplary implementations of an ingestible product preparation system 10 are shown to prepare and dispense ingestible products 12 such as a liquid drink, hamburger, chicken dinner, or a snack bar (shown in dispensing area 22) to be consumed by a particular individual living being, such as a human being 14 (such as a user, etc.) shown. Exemplary implementations determine selection menus to be generated and outputted, for instance, on display 16 and selections or other information can be inputted through user interfaces, for instance, user input 20 or other types of user input.

For instance, input may be collected through active user input (e.g. keyboard, textual, audio, graphical user interface, etc.) or passive user input (e.g. image recognition of user behavior, refuse analysis of past dispensing such as quantity of wrappers, leftovers, audio analysis of collected unsolicited user comments, etc.). Selection menus can be generated that are unique to a particular individual living being, such as the human being 14, based upon such information as but not limited to identification of the individual and other information such as past selections, allergies, preferences, specials, holidays, location of preparation, location of dispensing, time of day, dislikes, recent ingestion, health goals, present illness, past illness, sports requirements, injuries, fads, hobbies, associated social organizations, etc. As further described these selection menus and other selection aspects can be influenced, guided, directed, or otherwise associated with factors that influence availability of ingredients used to prepare the ingestible products.

Other sorts of ingestible products can include but are not limited to sandwiches (FIG. 1A), full meals (FIG. 1B), food bars (FIG. 1C), meal replacements, snacks, plant and/or animal based products, nutraceuticals, pharmaceuticals, smoothies, etc. Just as the selection menus can be influenced by input from computer based social network services, the selection menus can also provide options for reporting to various computer based social networking services regarding use of the ingestible products including associates venues, parties, types of products involved, etc.

The ingestible product preparation system 10 and possibly smaller more portable versions such as unit 18 is further depicted in FIGS. 2 and 3 as communicating with the human being 14 an exemplary remotely located user or an exemplary advisor 24 (e.g. physician, nurse, nutritionist, health expert, sports coach, etc.) via a communication link (e.g. wireless or wired network or direct electronic communication, etc.) and display screen 16. The display screen 16 can include selection indicators configured to provide information described above by the users and advisors.

Selection menus can be furnished to suggest candidate ingestible products that once selected as selected ingestible products can be prepared and dispensed (in some implementations prepared such as from ingredient containers) and to provide other sorts of information discussed herein. The display screen 16 can display textual and graphic information such as including but not limited to menu screens allowing users to select various dispensing (including in some implementations preparation) options and information requests. Other implementations can include other devices and methods for information input and output including those further discussed below.

Figure 4:
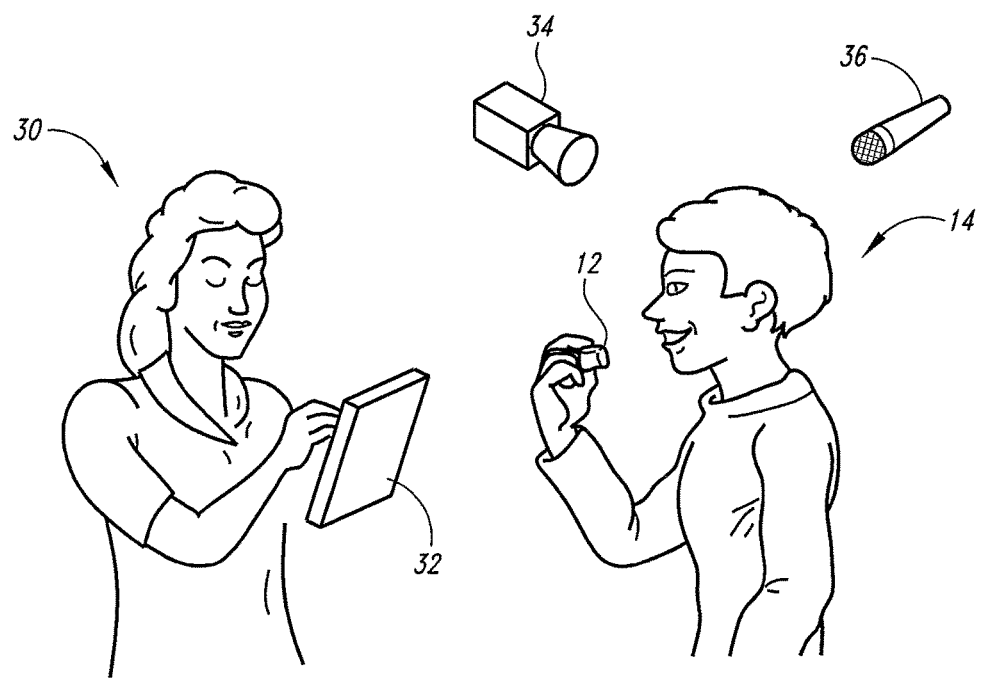
FIG. 4 is a perspective view depicting another location for placement of the ingestible product preparation system.
Figure 5:
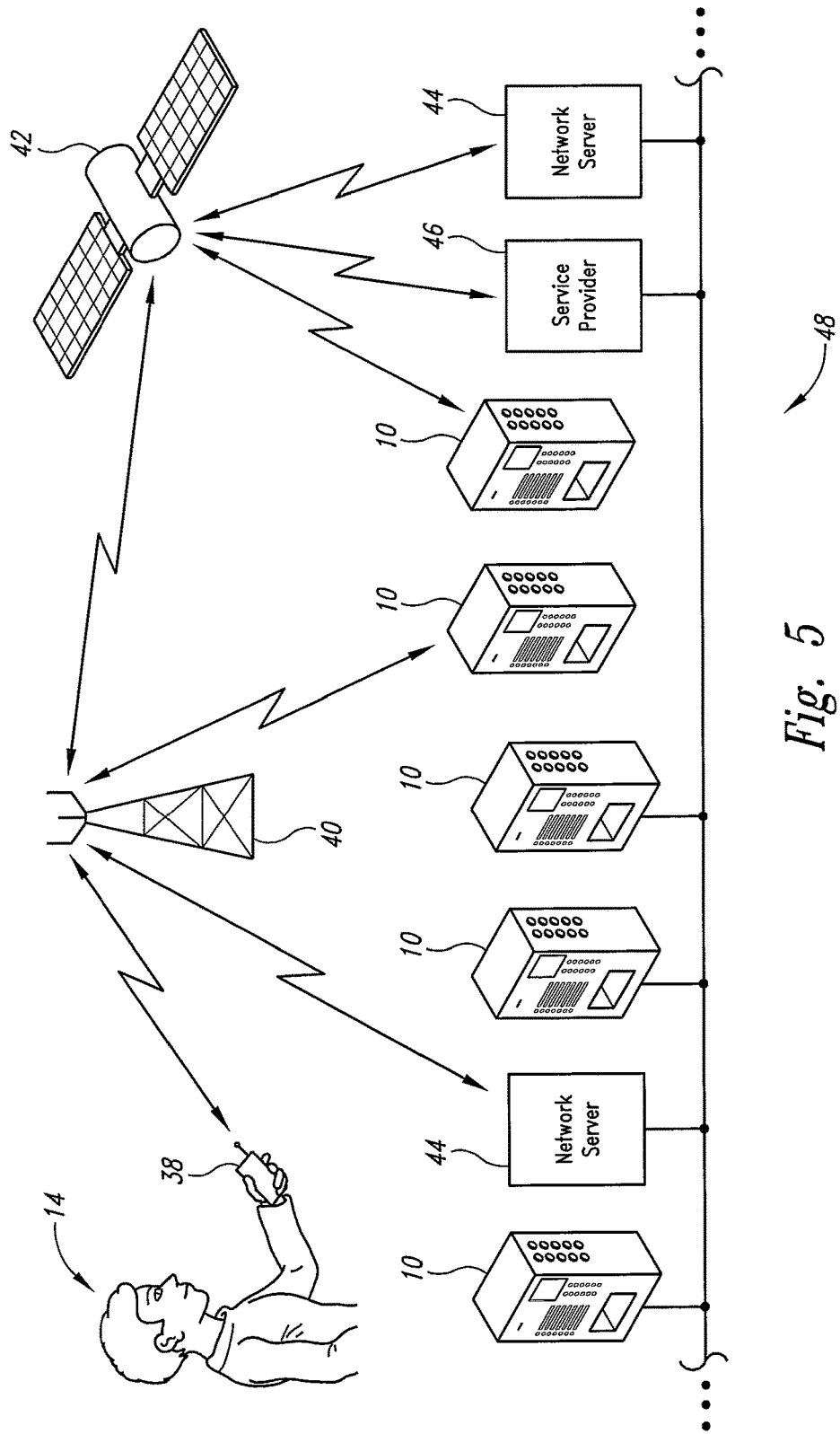
FIG. 5 is a perspective view depicting a communication network incorporating the ingestible product preparation system of FIG. 1.
Figure 6:
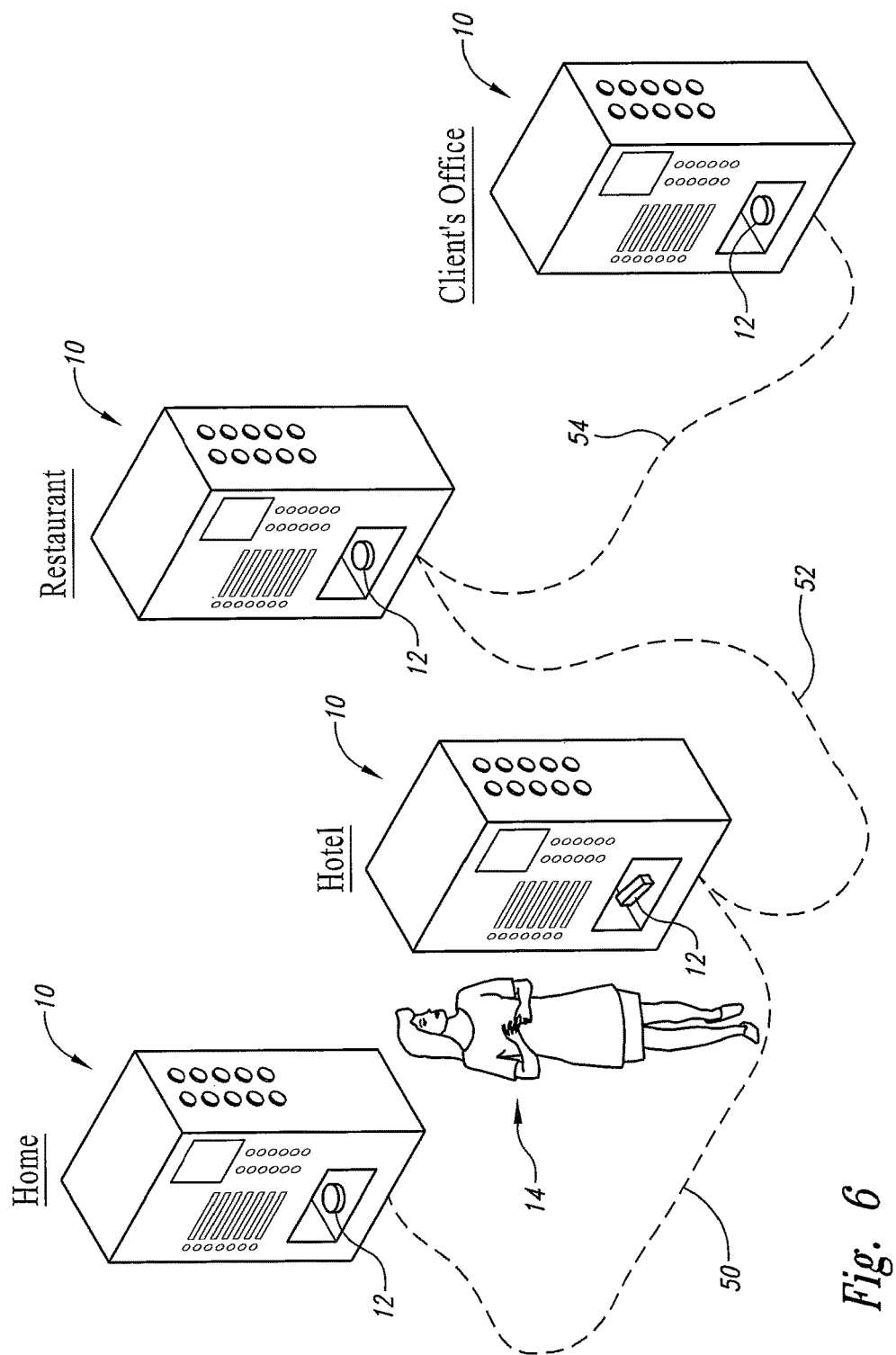
FIG. 6 is a perspective view depicting various locations for placement of the ingestible product preparation system of FIG. 1.

FIG. 4 is a perspective view depicting another location for placement of the ingestible product preparation system with the location including a wait staff 30, taking an order through input device 32 and having sensing devices such as camera 34 and microphone 36. FIG. 5 shows a schematic view of an exemplary communication network incorporating the ingestible product preparation system of FIG. 1 along with mobile device 38, base station 40, satellite 42, network server 44, and service provider 46. FIG. 6 is a perspective view depicting various locations for placement of the ingestible product preparation system of FIG. 1 along paths 50, 52, and 54.

Figure 7:
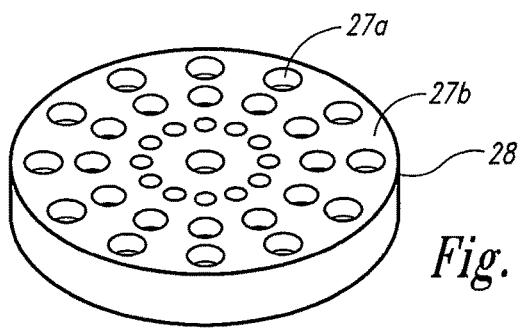
FIG. 7 is a perspective view of a first exemplary ingestible substrate implementation.

FIG. 7 is a perspective view of an exemplary implementation of an ingestible substrate structure 28 to be treated by one or more versions of the ingestible product preparation system. The ingestible substrate structure 28 is shown having an internal structural texture 27a and a surface texture 27b.

Figure 8:
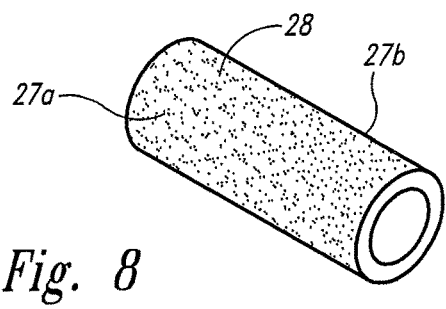
FIG. 8 is a perspective view of a second ingestible substrate implementation.
Figure 9:
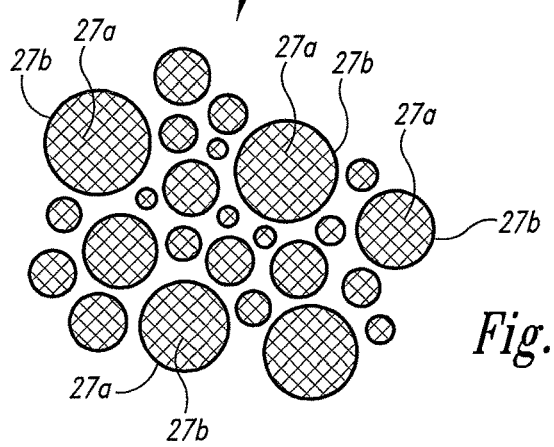
FIG. 9 is a perspective view of a third ingestible substrate implementation.
Figure 10:
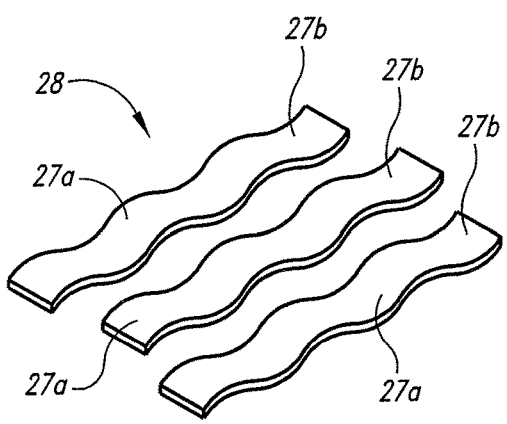
FIG. 10 is a perspective view of a fourth ingestible substrate implementation.

FIG. 8 is a perspective view of a second exemplary ingestible substrate structure 28. FIG. 9 is a perspective view of a third exemplary ingestible substrate structure 28. FIG. 10 is a perspective view of a fourth ingestible substrate structure 28.

FIG. 11 is a perspective view of a first exemplary injection treatment assembly 56 having base 58, injection material input 60, liquid injection needles 62 each with an orifice 64 shown with illustrative orientation arrow 66. The first assembly 56 is depicted as being configured for one or more ingestible material needle injection operations including for one or more liquid injection implementations to provide ingestible substrate structure treatment capability for the ingestible product preparation system.

FIG. 12 is a perspective view of a fifth exemplary ingestible substrate structure 28 about to be treated by the first exemplary injection treatment assembly of FIG. 11.

FIG. 13 is a perspective view of the fifth exemplary ingestible substrate structure 28 being treated by the first exemplary injection treatment assembly of FIG. 11.

Figure 14:
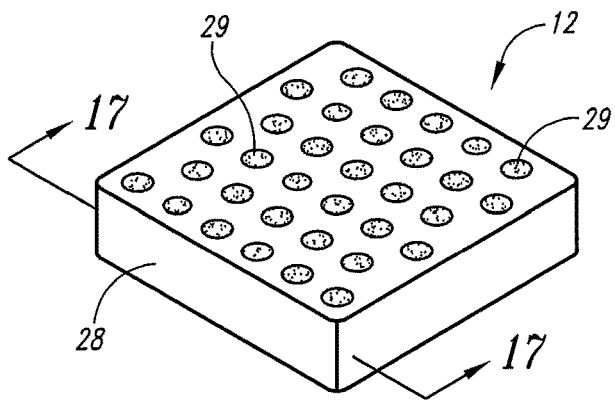
FIG. 14 is a perspective view of the fifth exemplary ingestible substrate structure having been treated by one or more versions of the ingestible product preparation system such as having the first exemplary injection treatment assembly of FIG. 11.

FIG. 14 is a perspective view of the fifth exemplary ingestible substrate structure 28 depicted as having injection treatment portions 29 containing injection material replacing, mixing with, removing, and/or etc. ingestible substrate structure material resulting from having been treated by one or more versions of the ingestible product preparation system such as having the first exemplary injection treatment assembly 56 of FIG. 11.

Figure 15:
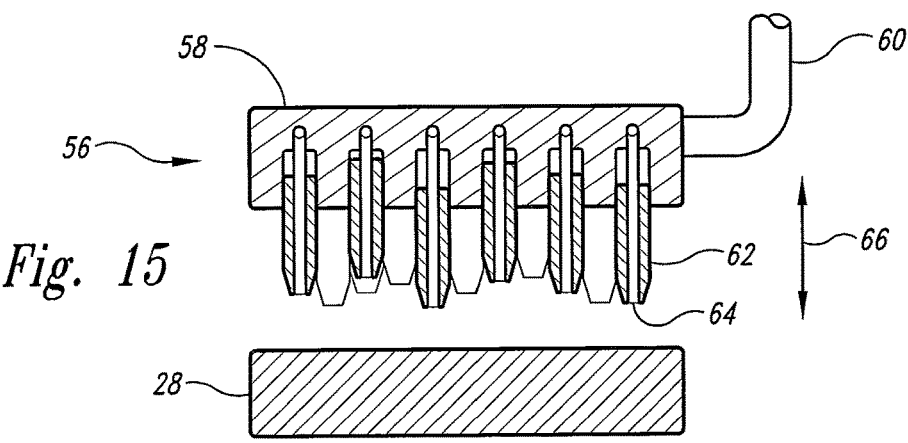
FIG. 15 is a cross-sectional view of the fifth exemplary ingestible substrate structure implementation about to be treated by the first exemplary injection treatment assembly of FIG. 11.

FIG. 15 is a cross-sectional view of the fifth exemplary ingestible substrate structure 28 about to be treated by the first exemplary injection treatment assembly 56 of FIG. 11.

Figure 16:
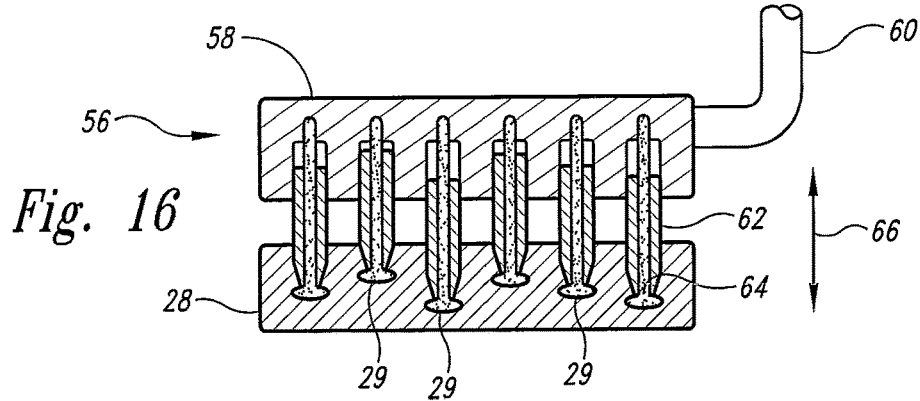
FIG. 16 is a cross-sectional view of the fifth exemplary ingestible substrate structure implementation being treated by the first exemplary injection treatment assembly of FIG. 11.

FIG. 16 is a cross-sectional view of the fifth exemplary ingestible substrate structure 28 being treated by the first exemplary injection treatment assembly 56 of FIG. 11.

Figure 17:
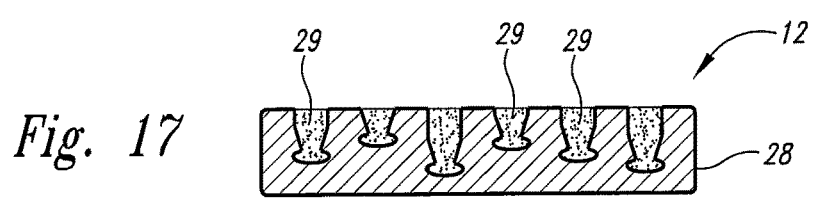
FIG. 17 is a cross-sectional view of the fifth exemplary ingestible substrate structure having been treated by one or more versions of the ingestible product preparation system such as having the first exemplary injection treatment assembly of FIG. 11.

FIG. 17 is a cross-sectional view of the fifth exemplary ingestible substrate structure 28 having been treated by one or more versions of the ingestible product preparation system such as having the first exemplary injection treatment assembly 56 of FIG. 11.

FIG. 18 is a perspective view of a second exemplary injection treatment assembly 68 having base 70, injection material input 72, gas and/or steam injection needles 74 each with an orifice 76 shown with illustrative orientation arrow 66. The second assembly 68 is depicted as being configured for one or more ingestible material needle injection operations including for one or more gas and/or steam injection implementations to provide ingestible substrate structure treatment capability for the ingestible product preparation system.

FIG. 19 is a perspective view of a fifth exemplary ingestible substrate structure 28 about to be treated by the second exemplary injection treatment assembly 68 of FIG. 18.

FIG. 20 is a perspective view of the fifth exemplary ingestible substrate structure 28 being treated by the second exemplary injection treatment assembly 68 of FIG. 18.

Figure 21:
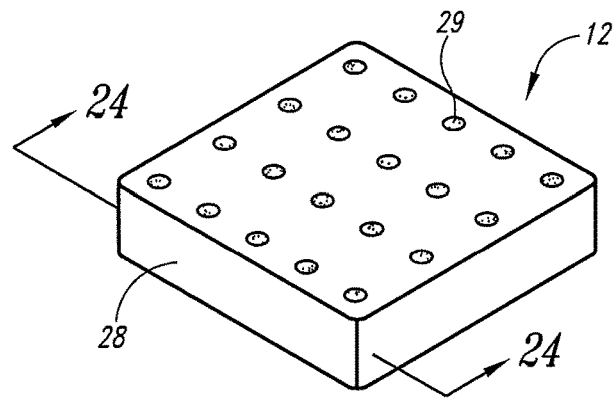
FIG. 21 is a perspective view of the fifth exemplary ingestible substrate structure having been treated by one or more versions of the ingestible product preparation system such as having the second exemplary injection treatment assembly of FIG. 18.

FIG. 21 is a perspective view of the fifth exemplary ingestible substrate structure 28 depicted as having injection treatment portions 29 containing injection material replacing, mixing with, removing, and/or etc. ingestible substrate structure material resulting from having been treated by one or more versions of the ingestible product preparation system such as having the second exemplary injection treatment assembly 68 of FIG. 18.

Figure 22:
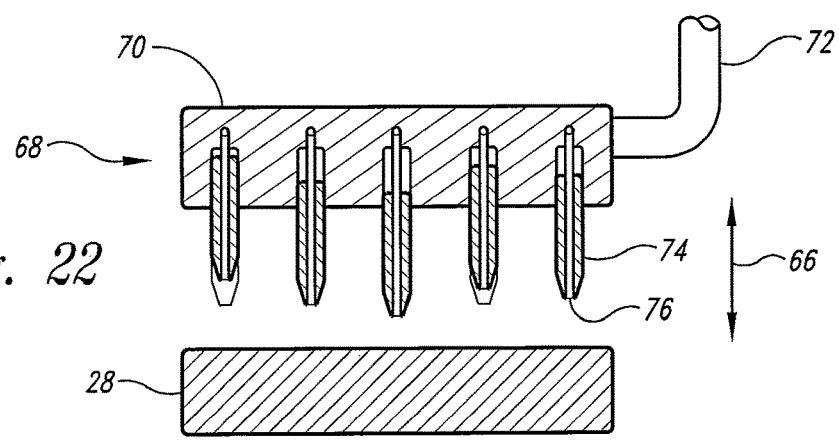
FIG. 22 is a cross-sectional view of the fifth exemplary ingestible substrate structure implementation about to be treated by the second exemplary injection treatment assembly of FIG. 18.

FIG. 22 is a cross-sectional view of the fifth exemplary ingestible substrate structure 28 about to be treated by the second exemplary injection treatment assembly 68 of FIG. 18.

Figure 23:
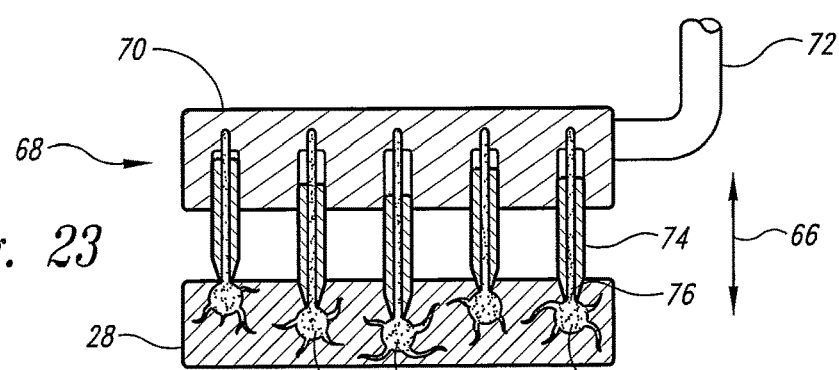
FIG. 23 is a cross-sectional view of the fifth exemplary ingestible substrate structure implementation being treated by the second exemplary injection treatment assembly of FIG. 18.

FIG. 23 is a cross-sectional view of the fifth exemplary ingestible substrate structure 28 being treated by the second exemplary injection treatment assembly 68 of FIG. 18.

Figure 24:
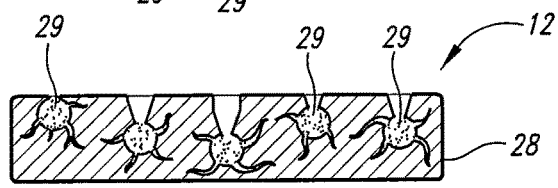
FIG. 24 is a cross-sectional view of the fifth exemplary ingestible substrate structure having been treated by one or more versions of the ingestible product preparation system such as having the second exemplary injection treatment assembly of FIG. 18.

FIG. 24 is a cross-sectional view of the fifth exemplary ingestible substrate structure 28 having been treated by one or more versions of the ingestible product preparation system such as having the second exemplary injection treatment assembly 68 of FIG. 18.

Figure 25:
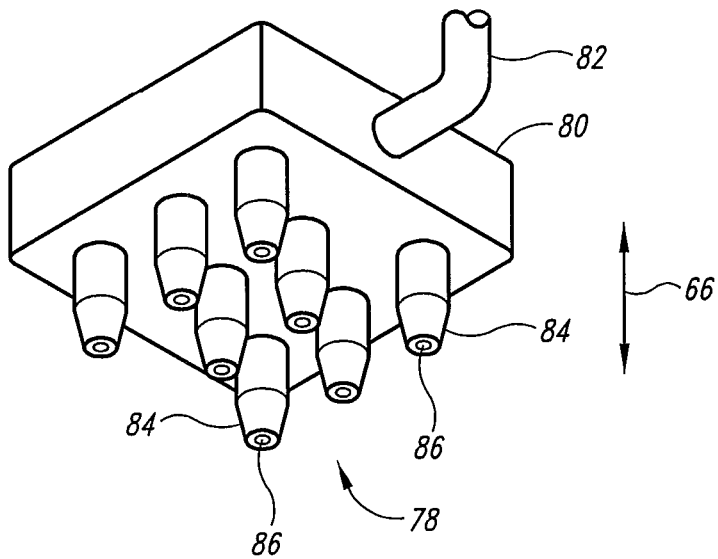
FIG. 25 is a perspective view of a third exemplary injection treatment assembly configured for one or more ingestible material jet injection operations including for one or more liquid injection implementations and/or gas injection implementations to provide ingestible substrate structure treatment capability for the ingestible product preparation system.

FIG. 25 is a perspective view of a third exemplary injection treatment assembly 78 having base 80, injection material input 82, fluid injection jets 84 each with an orifice 86 shown with illustrative orientation arrow 66. The third assembly 78 is depicted as being configured for one or more ingestible material jet injection operations including for one or more fluid injection implementations to provide ingestible substrate structure treatment capability for the ingestible product preparation system.

Figure 26:
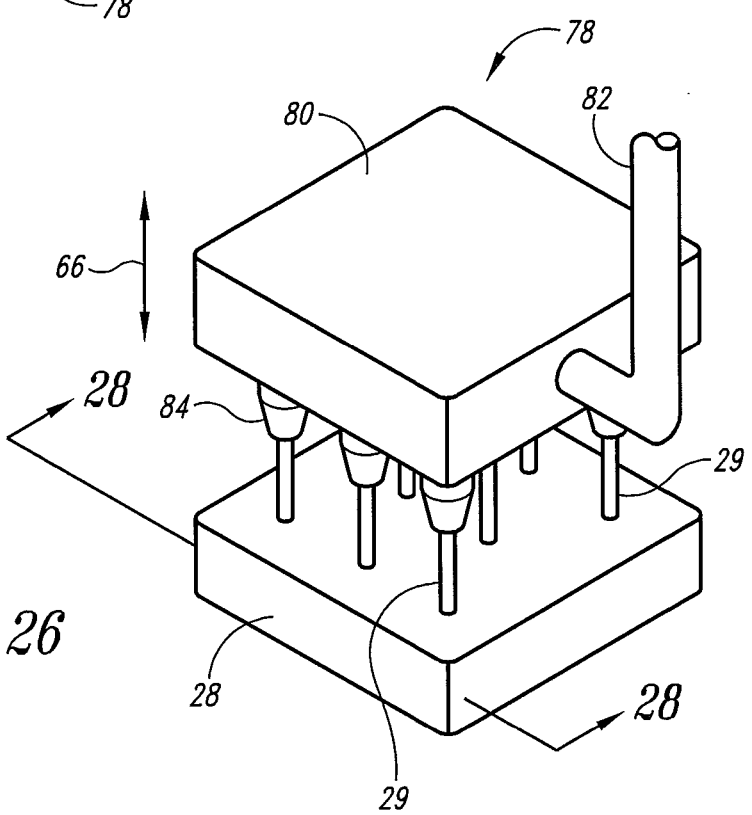
FIG. 26 is a perspective view of the fifth exemplary ingestible substrate structure implementation being treated by the third exemplary injection treatment assembly of FIG. 25.

FIG. 26 is a perspective view of the fifth exemplary ingestible substrate structure implementation 28 being treated by the third exemplary injection treatment assembly 78 of FIG. 25.

Figure 27:
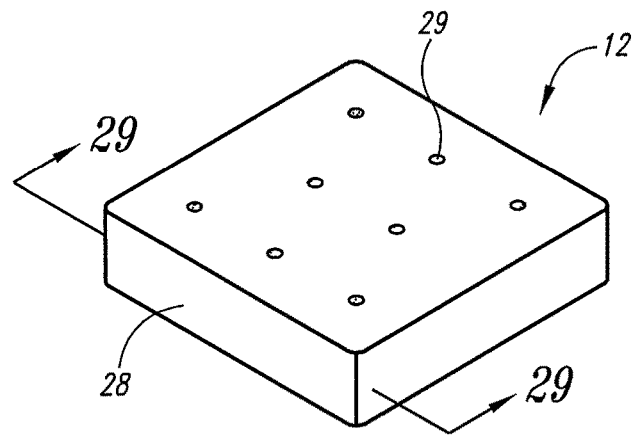
FIG. 27 is a perspective view of the fifth exemplary ingestible substrate structure having been treated by one or more versions of the ingestible product preparation system such as having the third exemplary injection treatment assembly of FIG. 25.

FIG. 27 is a perspective view of the fifth exemplary ingestible substrate structure 28 depicted as having injection treatment portions 29 containing injection material replacing, mixing with, removing, and/or etc. ingestible substrate structure material resulting from having been treated by one or more versions of the ingestible product preparation system such as having the third exemplary injection treatment assembly 78 of FIG. 25.

Figure 28:
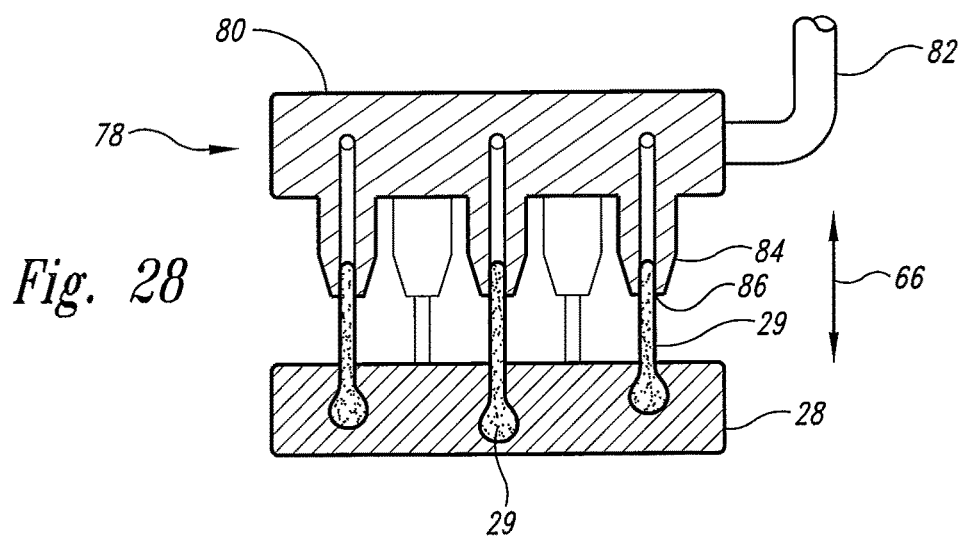
FIG. 28 is a cross-sectional view of the fifth exemplary ingestible substrate structure implementation being treated by the third exemplary injection treatment assembly of FIG. 25.

FIG. 28 is a cross-sectional view of the fifth exemplary ingestible substrate structure implementation 28 being treated by the third exemplary injection treatment assembly 78 of FIG. 25.

Figure 29:
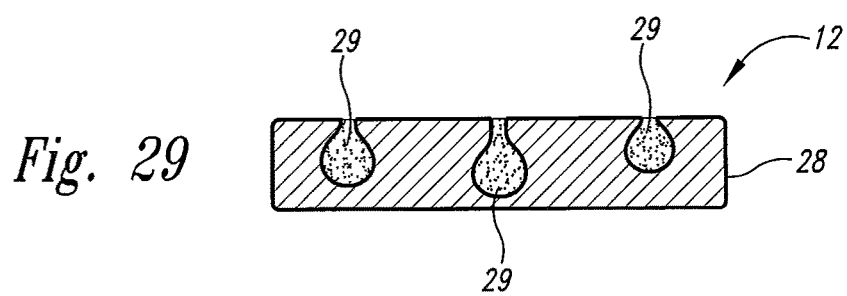
FIG. 29 is a cross-sectional view of the fifth exemplary ingestible substrate structure having been treated by one or more versions of the ingestible product preparation system such as having the third exemplary injection treatment assembly of FIG. 25.

FIG. 29 is a cross-sectional view of the fifth exemplary ingestible substrate structure 28 having been treated by one or more versions of the ingestible product preparation system such as having the third exemplary injection treatment assembly 78 of FIG. 25.

One or more of the ingestible substrate structures 28 and/or injection materials can be comprised from a wide variety of various ingestible materials. Some of these ingestible materials can include, but are not limited, one or more of the following:

Soy-based ingestible materials: such as for example textured vegetable protein (TVP), soy meat, tofu, tempeh or other ingestible materials through culturing and controlled fermentation processes, etc.

Corn-based ingestible materials: such as for example cornbread, unleavened; cornmeal, oil, water, salt: (combine and cook); corn tortilla masa harina (cornmeal treated with calcium hydroxide), water: (combine and cook), etc.

Rice-based ingestible materials: such as for example rice cake—rice (cooked), rice flour, water, sugar, salt: (combine and cook); rice cracker—rice, water, salt: (combine and cook) and/or—spread thin and cook rice again until crispy, etc.

Wheat-based ingestible materials such as for example wheat bread—unleavened, wheat flour, oil, water: (combine and cook); wheat cracker—wheat flour, salt, butter, baking soda, water: (combine and cook), etc.

Potato-based ingestible materials such as for example potato cake—potato (cooked), egg, salt: (combine and cook); potato cracker—potato (cooked), wheat flour, oats, oil: (combine and cook), etc.

Cassava-based ingestible materials such as for example cassava cake—cassava, milk, coconut cream, sugar, egg, egg white: (combine and cook), etc.

Sweet potato-based ingestible materials such as for example sweet potato bread—sweet potato (cooked), egg, oil, wheat flour, sugar, salt, baking soda, baking powder (combine and cook); sweet potato chip—potato, oil: (combine and cook), etc.

Sorghum-based ingestible materials such as for example sorghum cookie—sorghum, oil, sugar, baking soda, wheat flour, egg: (combine and cook); sorghum cake—sorghum, butter, cinnamon, wheat flour, vanilla, egg, baking soda, baking powder, salt, buttermilk: (combine and cook)—sorghum, butter, cinnamon, wheat flour, vanilla, egg, baking soda, baking powder, salt, buttermilk: (combine and cook), etc.

Yam-based ingestible materials such as for example yam cracker—yam (cooked), wheat flour, oats, oil (combine and cook); yam custard—yam (cooked), banana, milk, sugar, egg yolk, vanilla (combine and cook), etc.

Plantain-based ingestible materials such as for example plantain chip—plantain, oil, salt (combine and cook); plantain candied—plantain, butter, maple syrup, cinnamon (combine and cook), etc.

Legume-based ingestible materials such as for example adzuki, anasazi, black, black-eyed peas (cowpeas), broad, carob, chickpeas (garbanzo), edamame, fava, green, lentils, lima, lupins, mesquite, mung, navy, peanuts, peas, pinto, red kidney, soy, white, etc.

Grain-based ingestible materials such as for example amaranth, barley, buckwheat, durum, einkorn, emmer, fice, flax, fonio, kamut, kaniwa, maize, millet, oats, quinoa, rye, sorghum, spelt, teff, triticale, wild rice, wheat, etc.

Animal-based ingestible materials such as for example egg, meringue (whipped/foamed egg white), baked to hardened texture, yolk or white, etc.

Meat-based ingestible materials such as for example dehydrated (jerky), cured, cheese, hard, dry, creamed, string, melted, etc.

Other matter-based ingestible materials such as for example gelatin, pudding—custard, pureed fruit or vegetables, dehydrated and formed to shape, beverage—smoothie, etc.

Thinner-based ingestible materials such as for example oil, water, vinegar, etc.

Thickener-based ingestible materials such as for example starches, corn, arrowroot, kudzu, potato, rice, tapioca, wheat, etc.

Hydrocolloid-based ingestible materials such as for example agar, kappa carrageenan, lambda carrageenan, iota carrageenan, gelatin, high-acyl gellan, low-acyl gellan, guar gum, gum arabic, gum tragacanth, high methyl ester pectin, low methyl ester pectin, konjac gum, lucust bean gum, methylcellulose, hydroxypropyl methylcellulose, carboxy methylcellulose, microcrystalline cellulose, propylene glycol alginate, sodium alginate, xanthan gum, etc.

Surfactant emulsifier-based ingestible materials such as for example monoglyceride, diglyceride, sorbitan ester, polysorbate, propylene glycol esters, polyglycerol esters, phospholipids, gum arabic, etc.

Sugar-based ingestible materials such as for example monosaccharides, glucose (dextrose), fructose, galactose, disaccharides, sucrose, maltose, lactose, etc., sugar-based ingestible materials (common source) such as for example honey, sugar cane, sugar beet, etc. sweetener-based ingestible materials (natural) such as for example brazzein, curculin, erythritol, glycyrrhizin, glycerol, hydrogenated starch hydrolysates, inulin, isomalt, lactitol, luo han guo, mabinlin, maltitol, malto-oligosaccharide, mannitol, miraculin, monatin, monellin, osladin, pentadin, sorbitol, stevia, tagatose, thaumatin, xylitol, etc. sweetener-based ingestible materials (artificial) such as for example acesulfame potassium, aspartame, salt of aspartame-acesulfame, glucin, neohesperidin dihydrochalcone, neotame, saccharin, sucralose, etc.

Fat-based ingestible materials (plant) such as for example almond, avocado, beechnut, castor, cocoa butter, coconut, corn, cottonseed, grape seed, hazelnut, linseed, mustard, olive, palm, palm kernel, peanut, poppy seed, pumpkin seed, rapeseed, rice bran, safflower, soybean, sesame seed, sunflower seed, tea seed, walnut, etc. Fat-based ingestible materials (animal) such as for example milk, cow, milk, goat, chicken, cod liver, cow, egg yolk, fish, lard, pig, etc. Fat-based ingestible materials (forms) such as for example oil, milk, butter, lard, schmaltz, dripping, etc.

Binder-based ingestible materials (texture, forming, manipulation) such as for example egg albumen, semolina, rice gel, vital wheat gluten, saccharides, disaccharides, sucrose, lactose, polysaccharides, starches, cellulose, microcrystalline cellulose, cellulose esthers, hydroxypropyl, cellulose, sugar alcohols, xylitol, sorbitol, maltitol, protein, gelatin, synthetic, polymers, polyvinylpyrrolidone, polyethylene glycol, etc.

Coating-based ingestible materials such as those that generally, protect from deterioration by: moisture, light, air, other substances such as for example hydroxypropyl methylcellulose film coating, shellac, corn protein zein, gelatin, etc.

Disintegrant-based ingestible materials such as those that generally expand and dissolve when wet, causing material to break apart such as for example sodium starch glycolate, cross-linked polymers, crospovidone, croscamellose sodium, etc.

Filler-based ingestible materials such as those that generally increase volume of material for particular handling needs such as for example plant cellulose, dibasic calcium phosphate, fats and oils, lactose, sucrose, glucose, mannitol, sorbitol, calcium carbonate, magnesium stearate, etc.

Lubricant-based ingestible materials such as those that generally prevent ingredients from sticking together and from sticking to delivery devices such as for example talc, silica, fats and oils, stearin, magnesium stearate, stearic acid, etc.

Glidant-based ingestible materials such as those that generally are used to promote material flow by reducing interparticle friction and cohesion such as for example fumed silica, talc, magnesium carbonate, magnesium stearate, etc.

Sorbent-based ingestible materials such as those that generally are used for material-proofing by limiting fluid sorbing (fluid moving both directions, in or out of material) in a dry state.

Preservative-based ingestible materials such as for example antioxidants, vitamin A, vitamin E, vitamin C, retinyl palmitate, selenium, amino acids, cysteine, methionine, citric acid, sodium citrate, parabens, methyl paraben, propyl paraben, etc.

The one or more substrate structures 28 can be fabricated or otherwise made prior to final deposition treatment at point of sale or otherwise prior to final deposition treatment by a wide variety of methods such as, but not limited to one or more of the following exemplary processes such as for example heat processed, steamed, baked, boiled, cooked, heated, fried, grilled, radiated (microwave), roasted, pressure cooked, smoked, toasted, tempered, raw (untreated, unprocessed, uncooked), cooled, chilled, frozen, thawed, fluid, hydrated, reconstituted, solid, dehydrated, cured, evaporated, dried, salted, melted, thinned, fermented, preserved, heating, cooking, boiling, oxidation, use of sulfur dioxide, ozonation: use of ozone gas, or ozonated water, toxic inhibition, smoking, use of carbon dioxide, vinegar, alcohol, dehydration, osmotic inhibition, use of syrups, low temperature inactivation, freezing, ultra high water pressure, "cold" pasteurization, pickled, vinegar, pasteurized, ultra-pasteurization, uht (ultra high temperature) treated, sterilization by heating for 1-2 seconds at temperatures exceeding 135c (275f), washed, cleansed/cleaned, sterilized, bleached, irradiated, deionized, ionized, thickened, gelled, crystallized, agglomerated, condensed, concentrated, hydrogenated, extended/expanded, stretched, reduced, hydrolyzed, rendered, refined, semi-refined, mixed, blended, emulsified, homogenized, mechanically processed, filtered, centrifuged, chopped, granulated, ground, grated, kneaded, minced, diced, squeezed, pureed, powdered, extruded, conched such as grinding and warming (through mechanical friction), pressed, injected, packed, wrapped, canned, jarred, sealed, etc.

Figure 30:
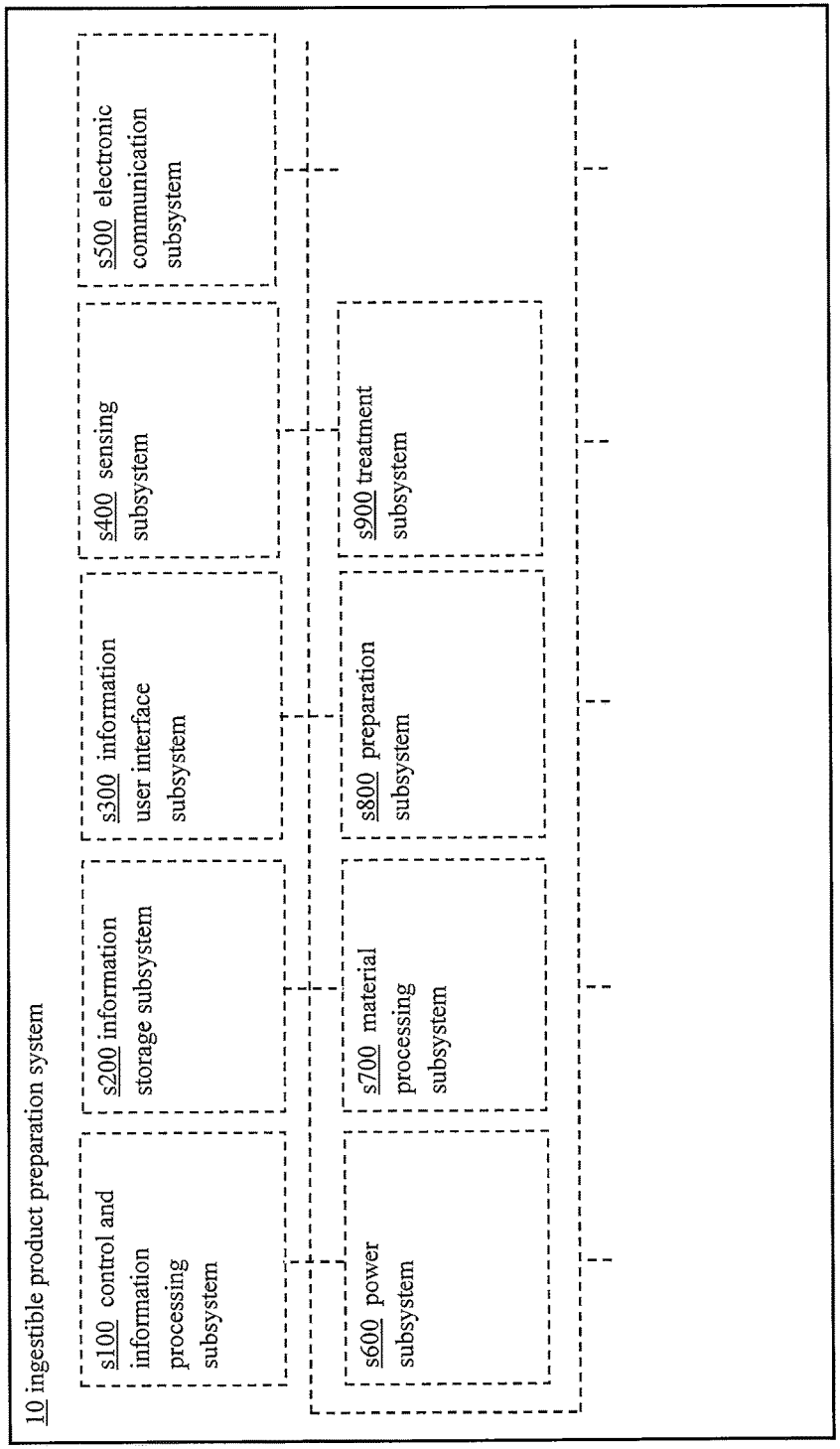
FIG. 30 is a block diagram depicting an exemplary implementation of the ingestible product preparation system 10 of FIG. 1 including exemplary subsystems.

An exemplary version of the ingestible product preparation system 10 is shown in FIG. 30 to optionally include various subsystems such as control and information processing subsystem s100, information storage subsystem s200, information user interface subsystem s300, sensing subsystem s400, electronic communication subsystem s500, power subsystem s600, material processing subsystem s700, preparation subsystem s800, treatment subsystem s900

Figure 31:
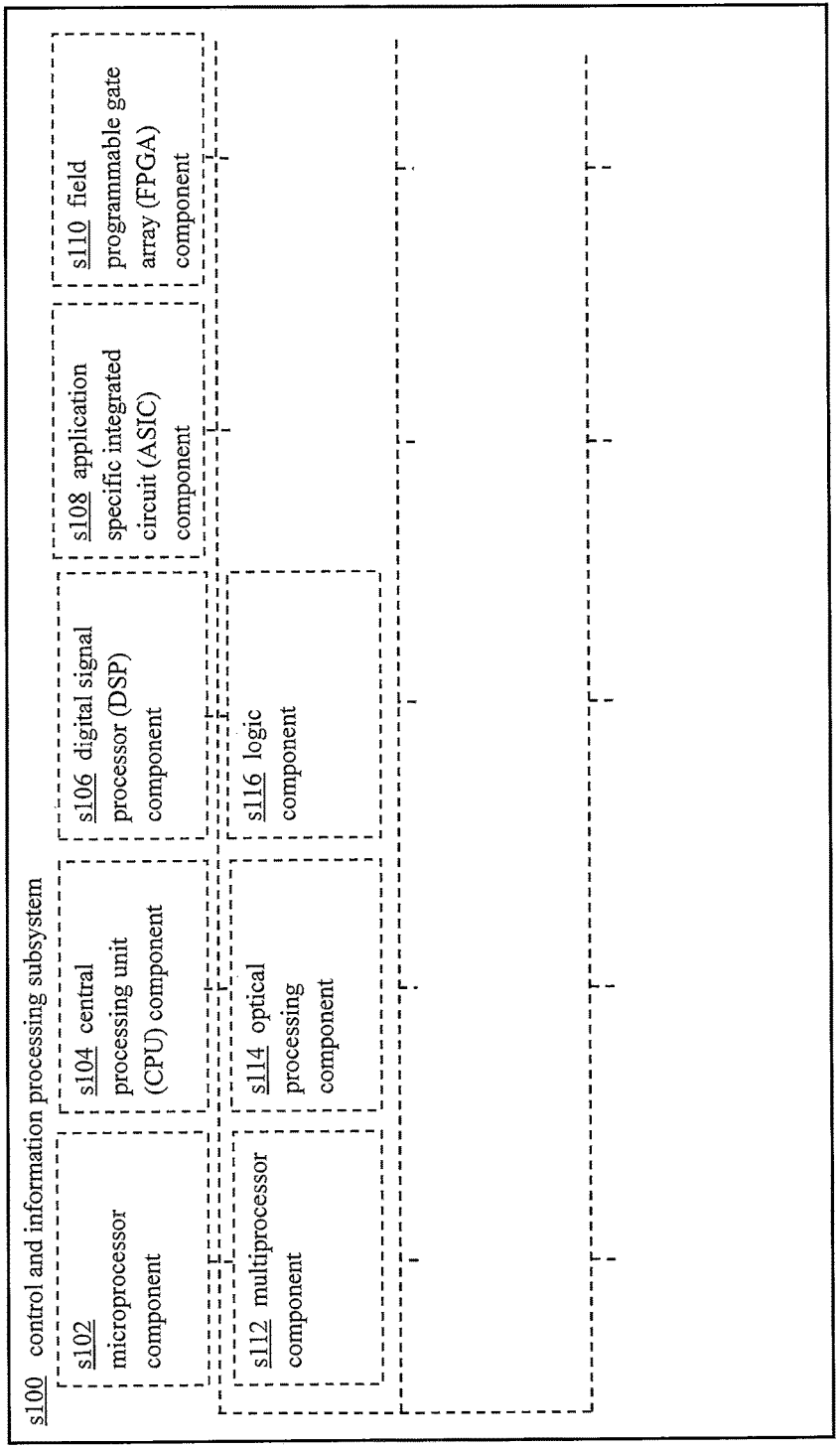
FIG. 31 is a block diagram depicting a control and information processing subsystem s100 of an exemplary implementation of the ingestible product preparation system 10 of FIG. 1.

An exemplary implementation of the control and information processing subsystem s100 is shown in FIG. 31 to optionally include various components such as microprocessor component s102, central processing unit (CPU) component s104, digital signal processor (DSP) component s106, application specific integrated circuit (ASIC) component s108, field programmable gate array (FPGA) component s110, multiprocessor component s112, optical processing component s114, and logic component s116.

Figure 32:
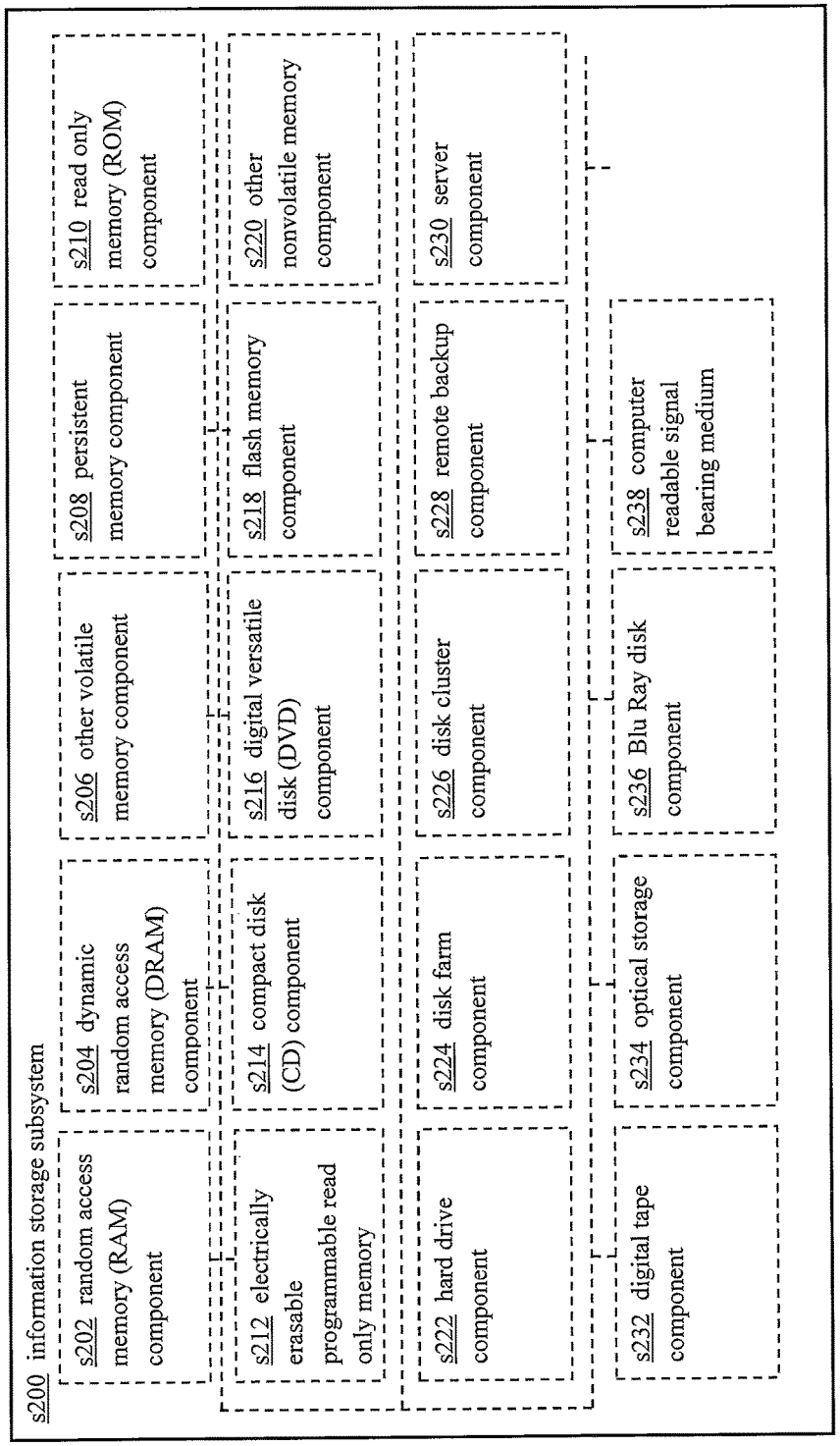
FIG. 32 is a block diagram depicting an information storage subsystem s200 of an exemplary implementation of the ingestible product preparation system 10 of FIG. 1.

An exemplary implementation of the information storage subsystem s200 is shown in FIG. 32 to optionally include various components such as random access memory (RAM) component s202, dynamic random access memory (DRAM) component s204, other volatile memory component s206, persistent memory component s208, read only memory (ROM) component s210, electrically erasable programmable read only memory (EEPROM) component s212, compact disk (CD) component s214, digital versatile disk (DVD) component s216, flash memory component s218, other nonvolatile memory component s220, hard drive component s222, disk farm component s224, disk cluster component s226, remote backup component s228, server component s230, digital tape component s232, optical storage component s234, Blu Ray disk component s236, and computer readable signal bearing medium s238.

Figure 33:
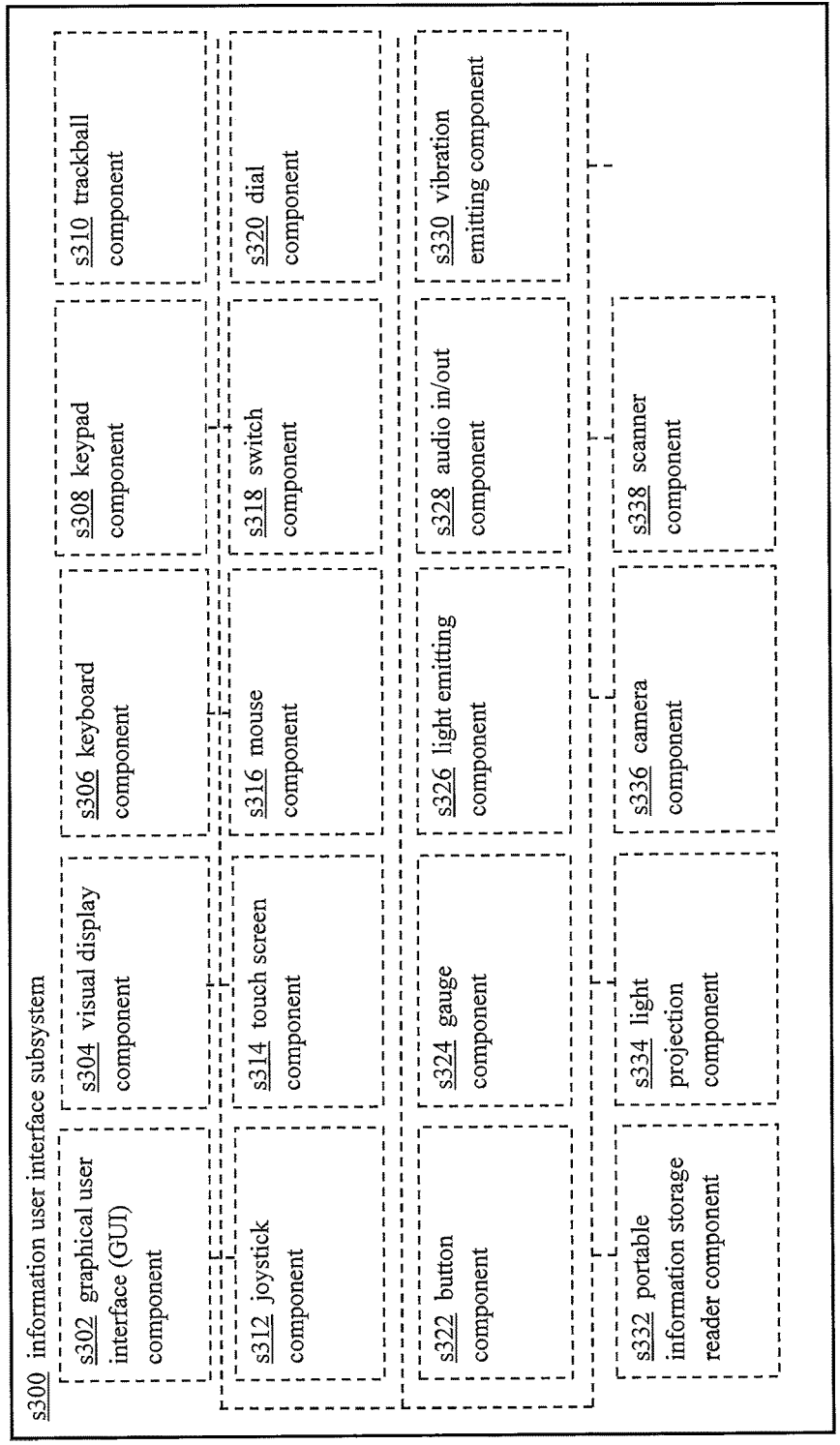
FIG. 33 is a block diagram depicting an information user interface subsystem s300 of an exemplary implementation of the ingestible product preparation system 10 of FIG. 1.

An exemplary implementation of the information user interface subsystem s300 is shown in FIG. 33 to optionally include various components such as graphical user interface (GUI) component s302, visual display component s304, keyboard component s306, keypad component s308, trackball component s310, joystick component s312, touch screen component s314, mouse component s316, switch component s318, dial component s320, button component s322, gauge component s324, light emitting component s326, audio in/out component s328, vibration emitting component s330, portable information storage reader component s332, light projection component s334, camera component s336, and scanner component s338.

Figure 34:
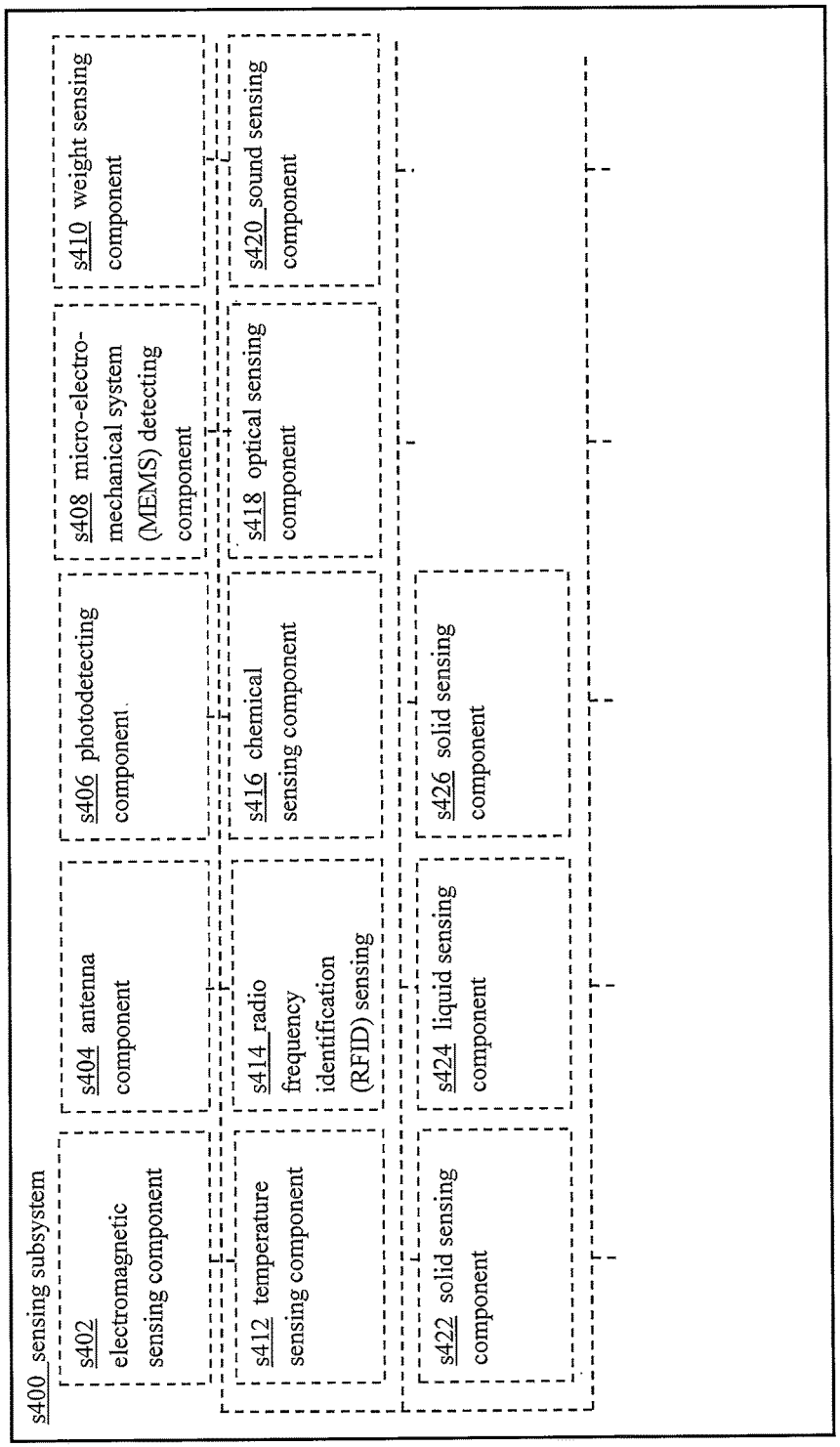
FIG. 34 is a block diagram depicting a sensing subsystem s400 of an exemplary implementation of the ingestible product preparation system 10 of FIG. 1.

An exemplary implementation of the sensing subsystem s400 is shown in FIG. 34 to optionally include various components such as electromagnetic sensing component s402, antenna component s404, photodetecting component s406, micro-electro-mechanical system (MEMS) detecting component s408, weight sensing component s410, temperature sensing component s412, radio frequency identification (RFID) sensing component s414, chemical sensing component s416, optical sensing component s418, sound sensing component s420, solid sensing component s422, liquid sensing component s424, and solid sensing component s426.

Figure 35:
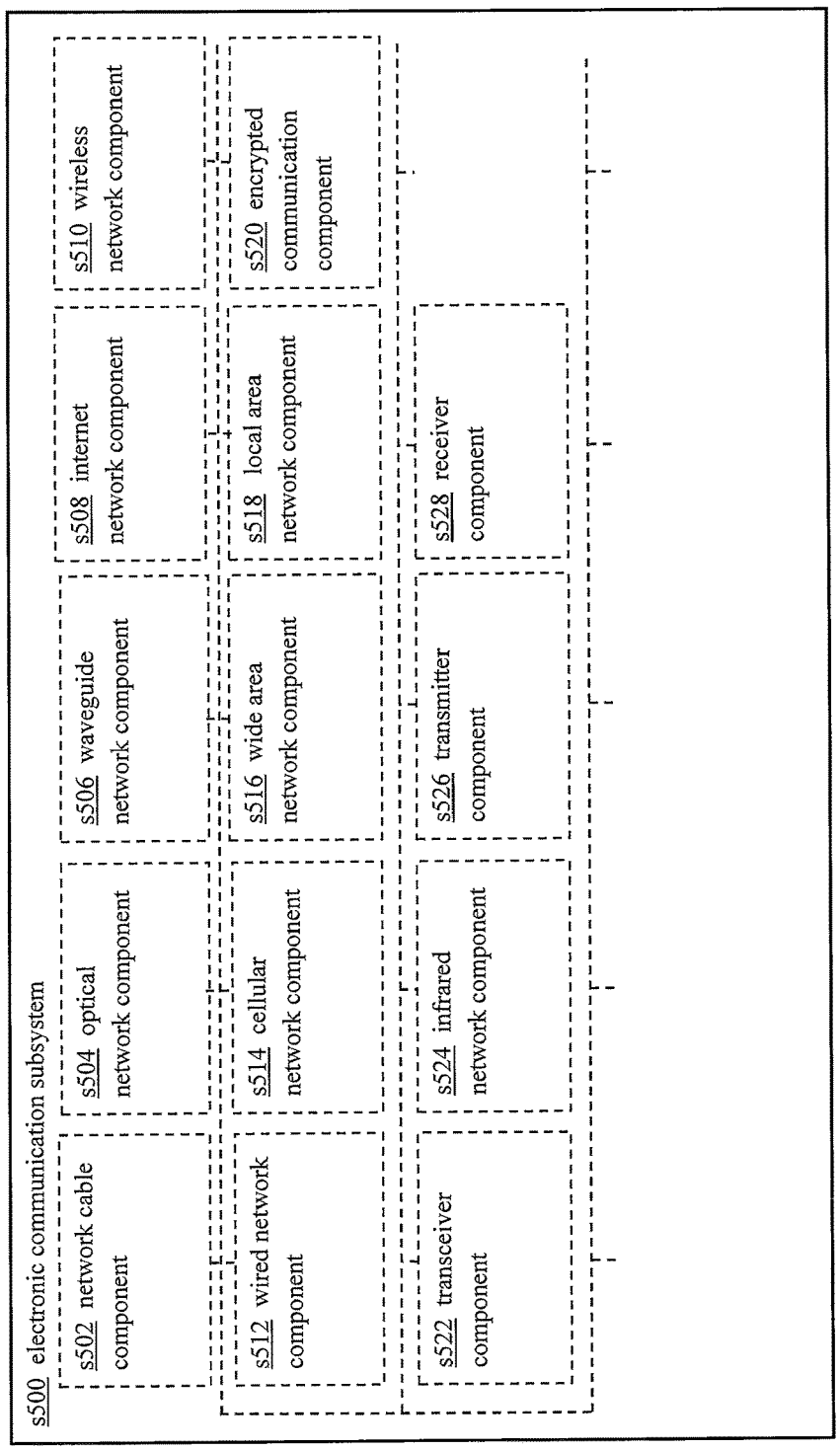
FIG. 35 is a block diagram depicting an electronic communication subsystem s500 of an exemplary implementation of the ingestible product preparation system 10 of FIG. 1.

An exemplary implementation of the electronic communication subsystem s500 is shown in FIG. 35 to optionally include various components such as network cable component s502, optical network component s504, waveguide network component s506, internet network component s508, wireless network component s510, wired network component s512, cellular network component s514, wide area network component s516, local area network component s518, encrypted communication component s520, transceiver component s522, infrared network component s524, transmitter component s526, and receiver component s528.

Figure 36:
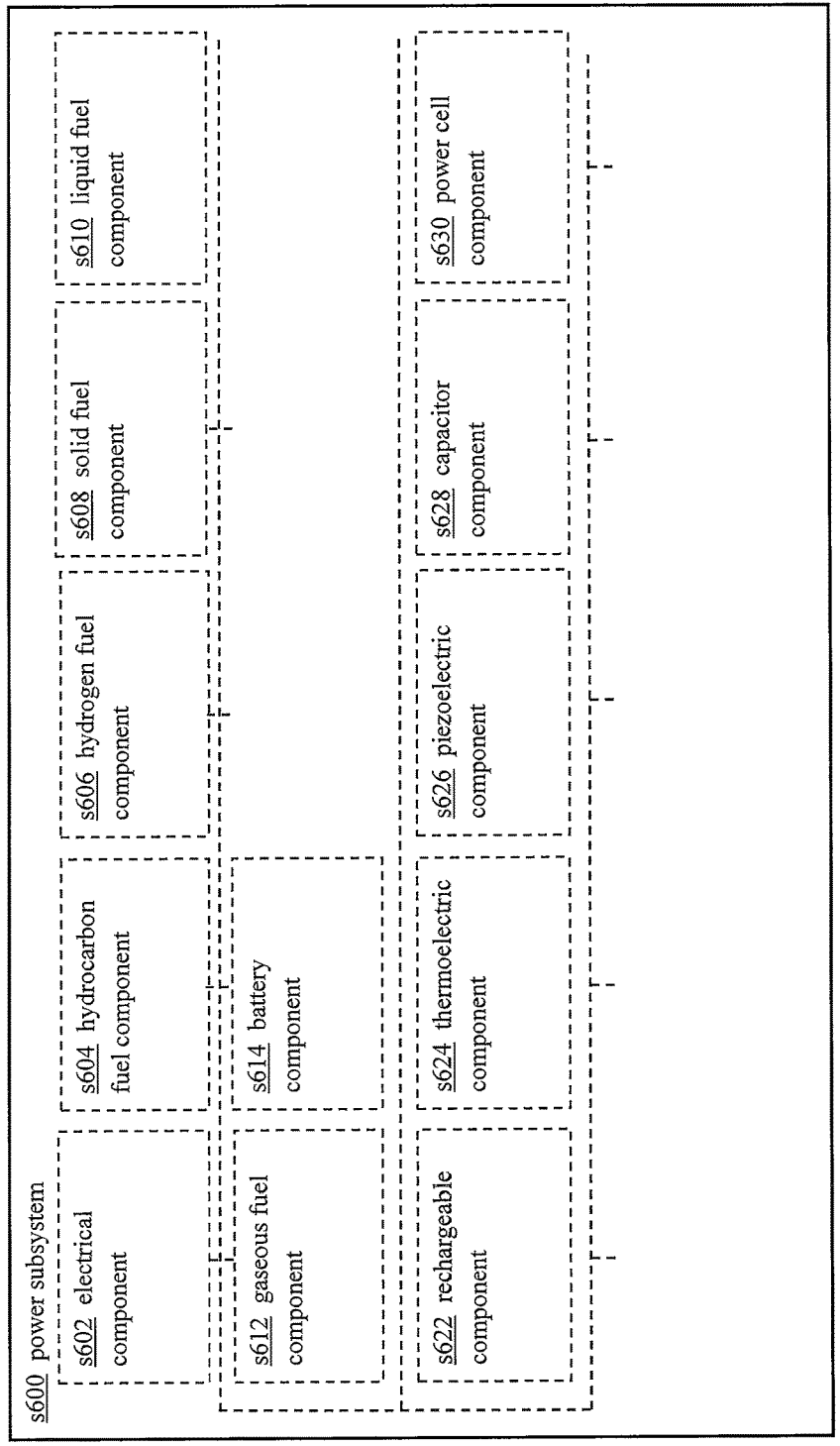
FIG. 36 is a block diagram depicting a power subsystem s600 of an exemplary implementation of the ingestible product preparation system 10 of FIG. 1.

An exemplary implementation of the power subsystem s600 is shown in FIG. 36 to optionally include various components such as electrical component s602, hydrocarbon fuel component s604, hydrogen fuel component s606, solid fuel component s608, liquid fuel component s610, gaseous fuel component s612, battery component s614, battery component s622, battery component s624, battery component s626, battery component s628, and power cell component s630.

Figure 37:
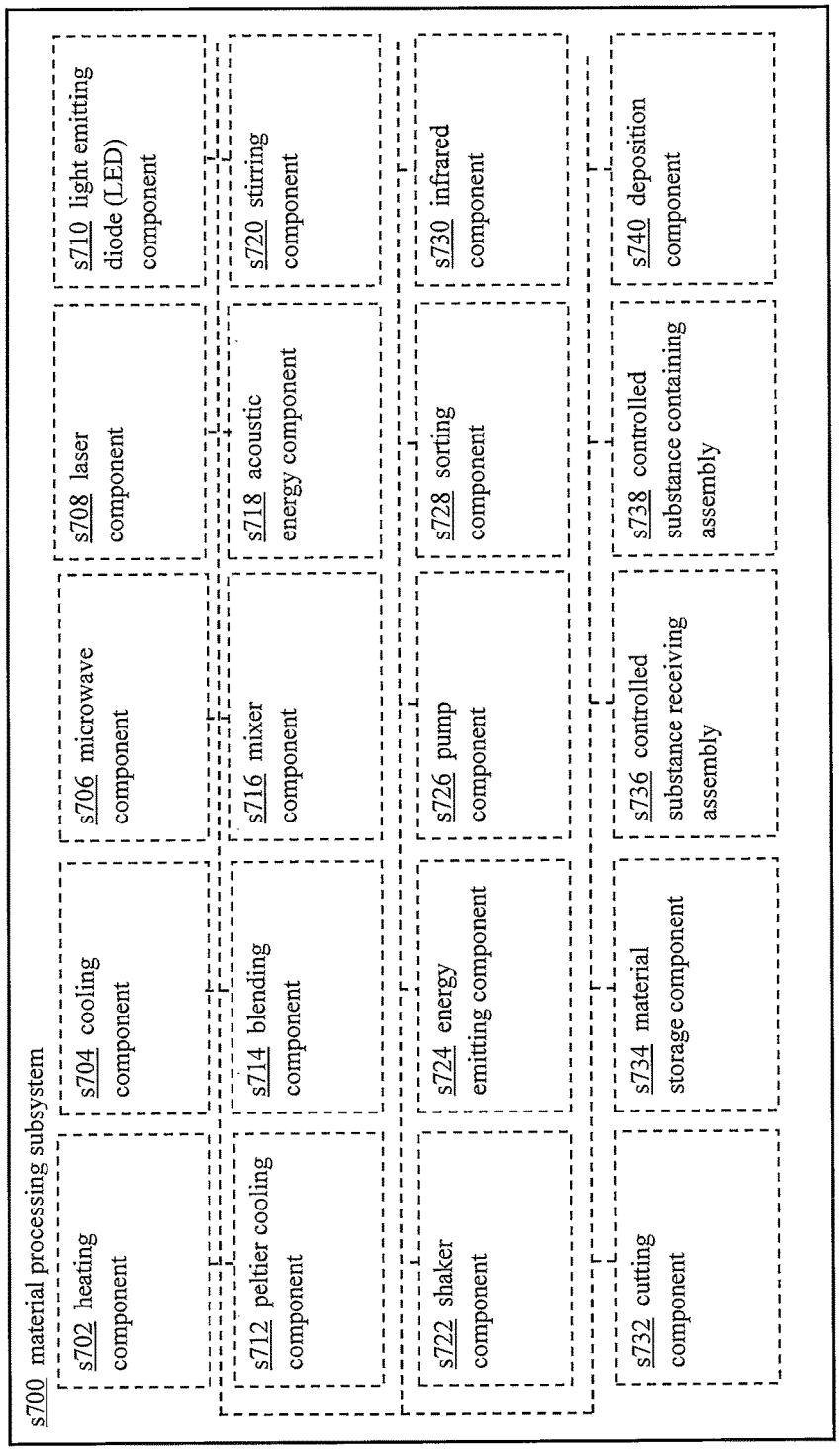
FIG. 37 is a block diagram depicting a material processing subsystem s700 of an exemplary implementation of the ingestible product preparation system 10 of FIG. 1.

An exemplary implementation of the material processing subsystem s700 is shown in FIG. 37 to optionally include various components such as heating component s702, cooling component s704, microwave component s706, laser component s708, light emitting diode (LED) component s710, peltier cooling component s712, blending component s714, mixer component s716, acoustic energy component s718, stirring component s720, shaker component s722, energy emitting component s724, pump component s726, sorting component s728, infrared component s730, cutting component s732, material storage component s734, controlled substance receiving assembly s736, controlled substance containing assembly s738, deposition component s740.

Figure 38:
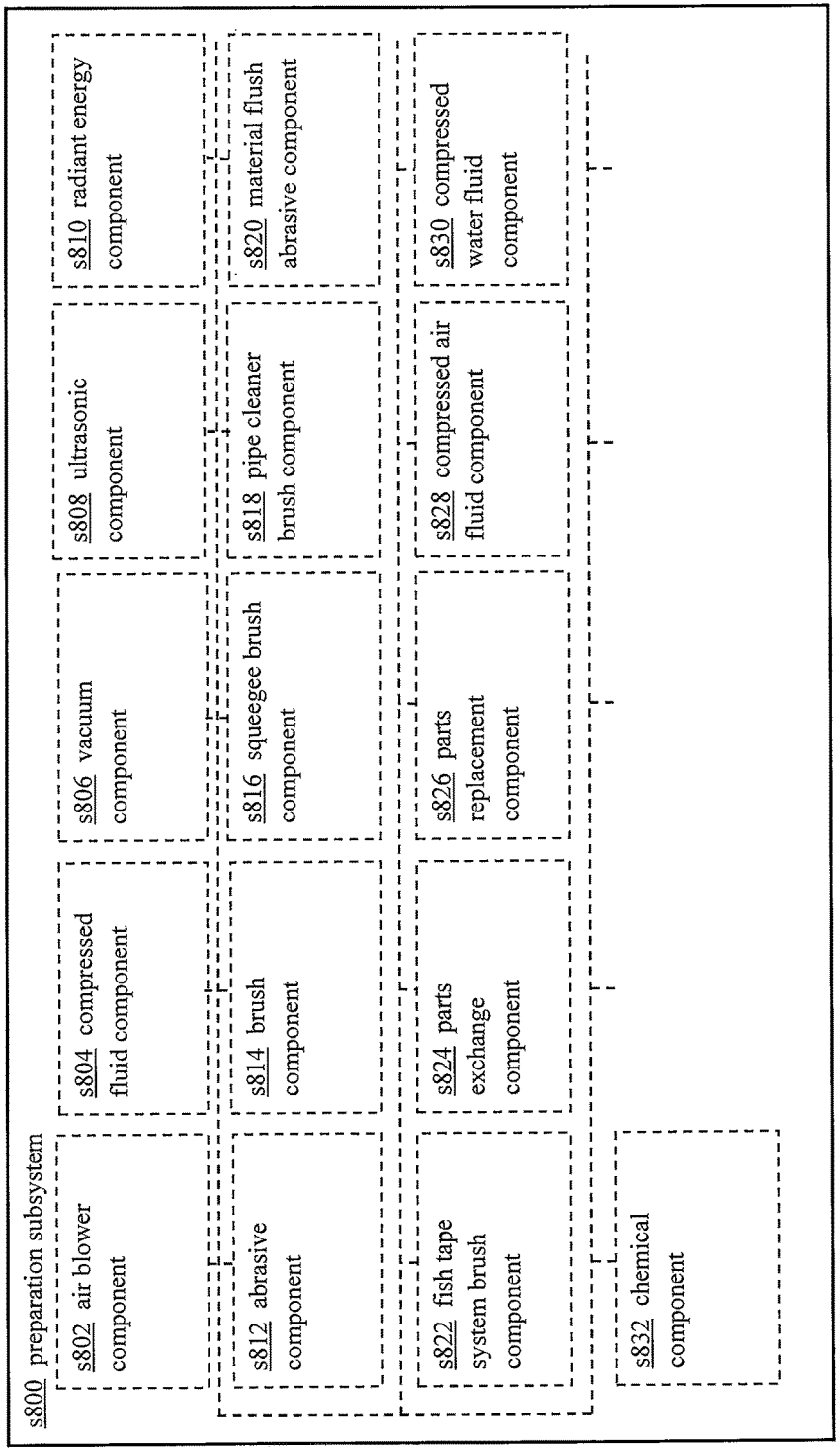
FIG. 38 is a block diagram depicting a preparation subsystem s800 of an exemplary implementation of the ingestible product preparation system 10 of FIG. 1.

An exemplary implementation of the preparation subsystem s800 is shown in FIG. 38 to optionally include various components such as air blower component s802, compressed fluid component s804, vacuum component s806, ultrasonic component s808, radiant energy component s810, abrasive component s812, brush component s814, squeegee brush component s816, pipe cleaner brush component s818, material flush abrasive component s820, fish tape system brush component s822, parts exchange component s824, parts replacement component s826, compressed air fluid component s828, compressed water fluid component s830, and chemical component s832.

Figure 39:
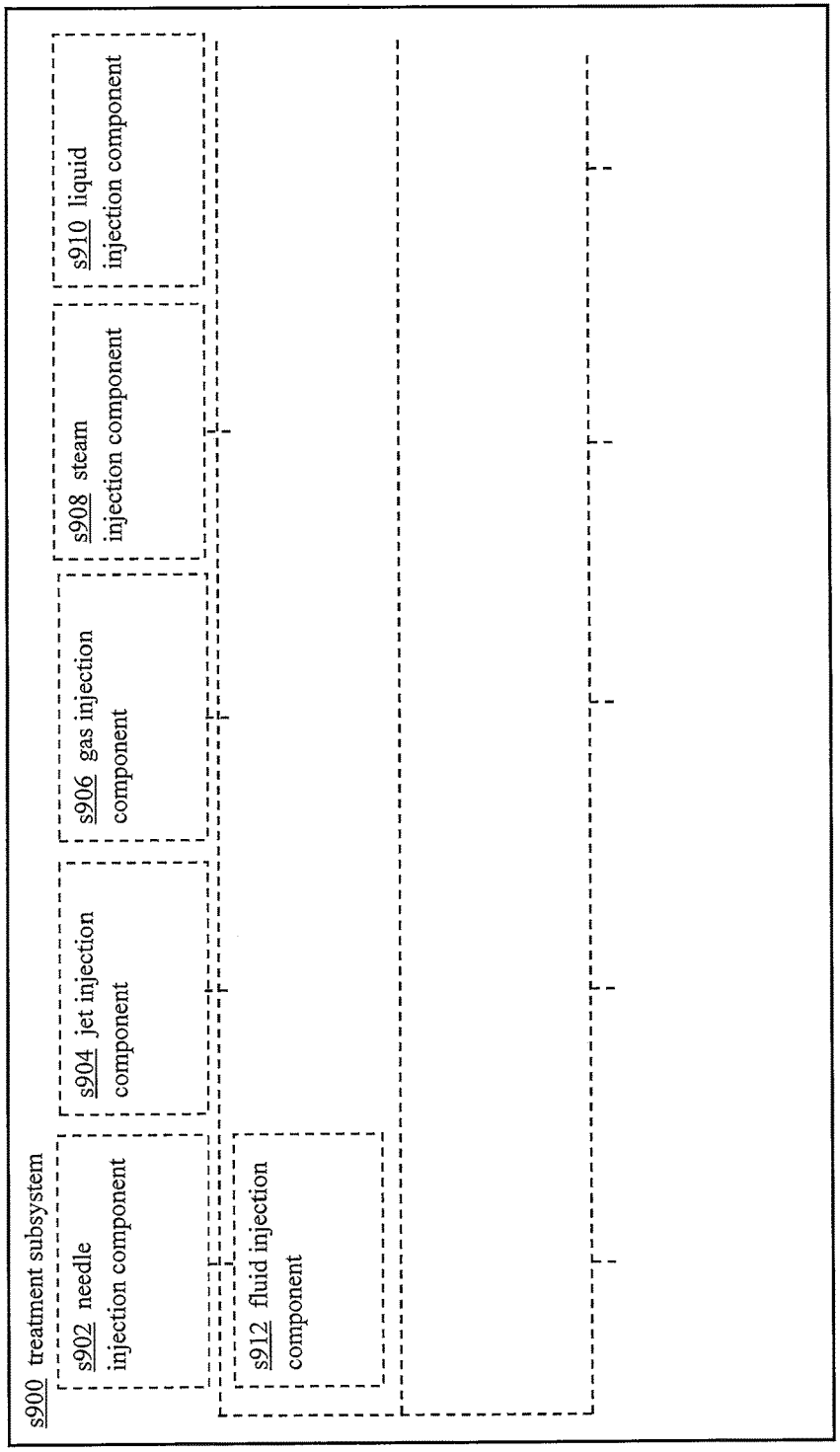
FIG. 39 is a block diagram depicting a treatment subsystem s900 of an exemplary implementation of the ingestible product preparation system 10 of FIG. 1.

An exemplary implementation of the treatment subsystem s900 is shown in FIG. 39 to optionally include various components such as needle injection component s902, jet injection component s904, gas injection component s906, steam injection component s908, liquid injection component s910, and fluid injection component s912.

Figure 40:
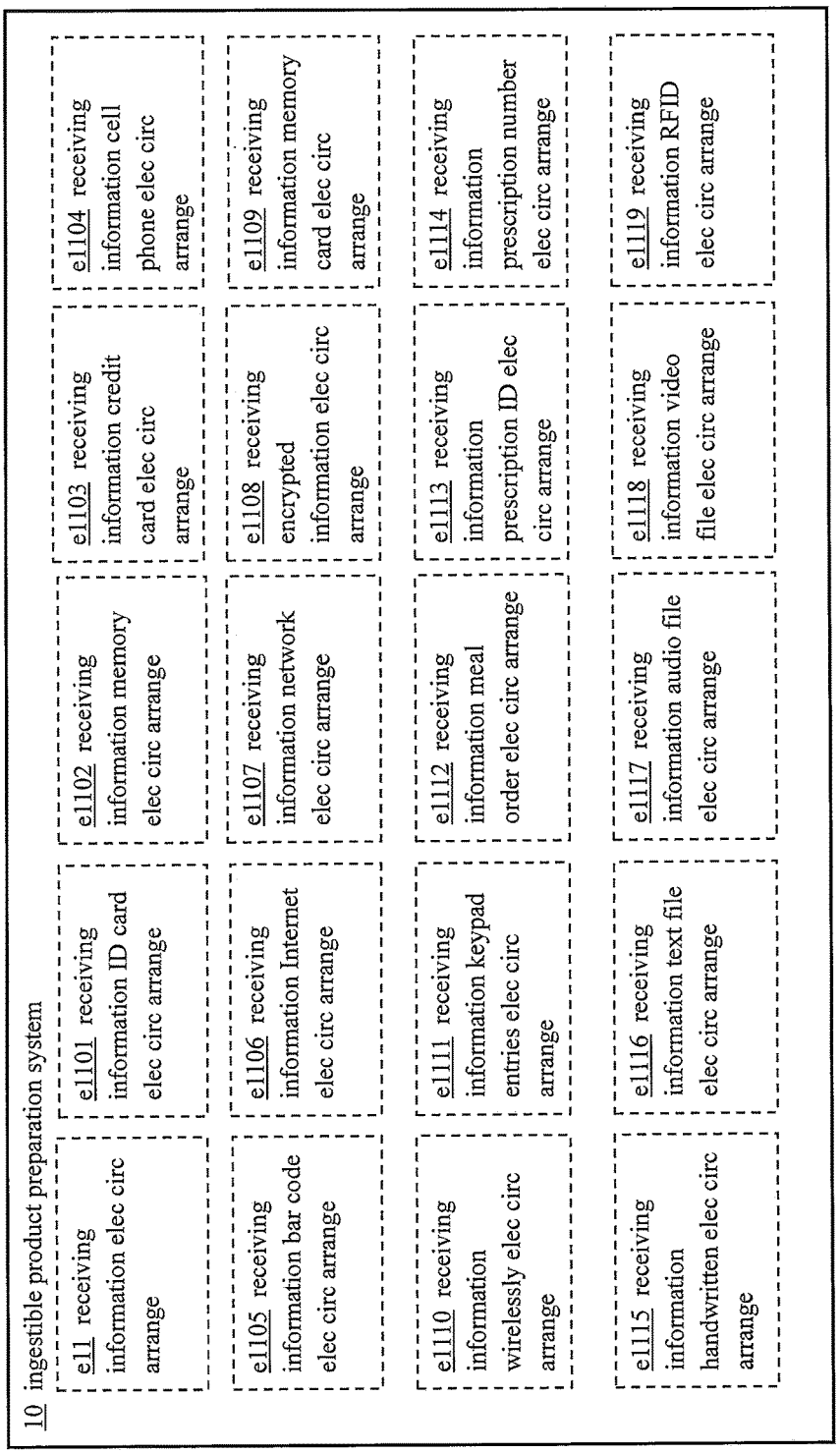
FIG. 40 is a block diagram depicting one or more exemplary electrical circuitry arrangements of the ingestible product preparation system 10 of FIG. 1.

Implementations involve different combinations (otherwise known as "electrical circuitry arrangements") of components from the subsystems of the ingestible product preparation system 10. Exemplary depictions of some of these electrical circuitry arrangements are shown in FIG. 40 to include receiving information electrical circuitry arrangement e11, receiving information ID card electrical circuitry arrangement e1101, receiving information memory electrical circuitry arrangement e1102, receiving information credit card electrical circuitry arrangement e1103, receiving information cell phone electrical circuitry arrangement e1104, receiving information bar code electrical circuitry arrangement e1105, receiving information Internet electrical circuitry arrangement e1106, receiving information network electrical circuitry arrangement e1107, receiving encrypted information electrical circuitry arrangement e1108, receiving information memory card electrical circuitry arrangement e1109, receiving information wirelessly electrical circuitry arrangement e1110, receiving information keypad entries electrical circuitry arrangement e1111, receiving information meal order electrical circuitry arrangement e1112, receiving information prescription ID electrical circuitry arrangement e1113, receiving information prescription number electrical circuitry arrangement e1114, receiving information handwritten electrical circuitry arrangement e1115, receiving information text file electrical circuitry arrangement e1116, receiving information audio file electrical circuitry arrangement e1117, receiving information video file electrical circuitry arrangement e1118, and receiving information RFID electrical circuitry arrangement e1119.

Figure 41:
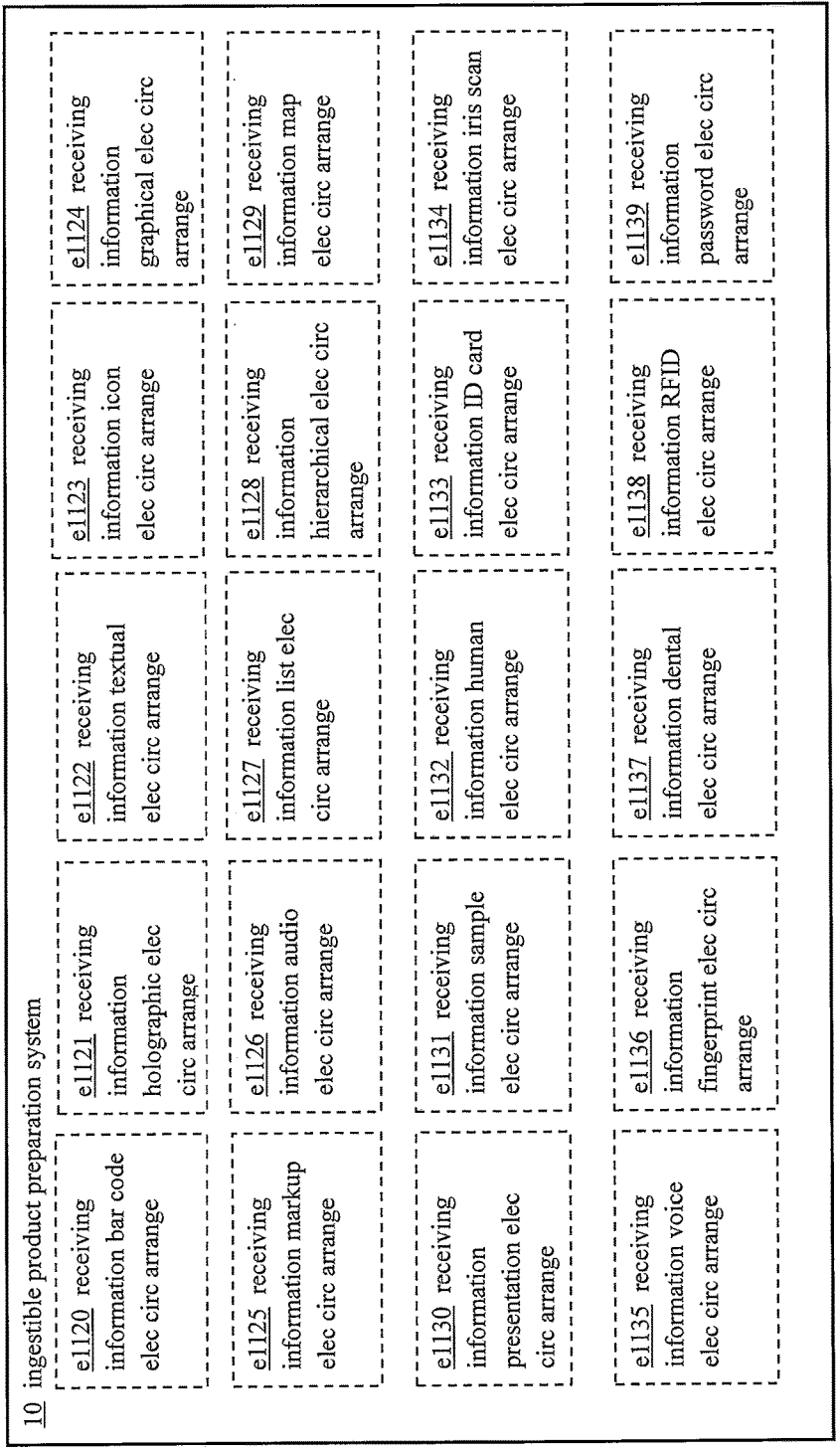
FIG. 41 is a block diagram depicting one or more exemplary electrical circuitry arrangements of the ingestible product preparation system 10 of FIG. 1.

Some of these electrical circuitry arrangements are depicted in FIG. 41 to include receiving information bar code electrical circuitry arrangement e1120, receiving information holographic electrical circuitry arrangement e1121, receiving information textual electrical circuitry arrangement e1122, receiving information icon electrical circuitry arrangement e1123, receiving information graphical electrical circuitry arrangement e1124, receiving information markup electrical circuitry arrangement e1125, receiving information audio electrical circuitry arrangement e1126, receiving information list electrical circuitry arrangement e1127, receiving information hierarchical electrical circuitry arrangement e1128, receiving information map electrical circuitry arrangement e1129, receiving information presentation electrical circuitry arrangement e1130, receiving information sample electrical circuitry arrangement e113, receiving information human electrical circuitry arrangement e1132, receiving information ID card electrical circuitry arrangement e1133, receiving information iris scan electrical circuitry arrangement e1134, receiving information voice electrical circuitry arrangement e1135, receiving information fingerprint electrical circuitry arrangement e1136, receiving information dental electrical circuitry arrangement e1137, receiving information RFID electrical circuitry arrangement e1138, and receiving information password electrical circuitry arrangement e1139.

Figure 42:
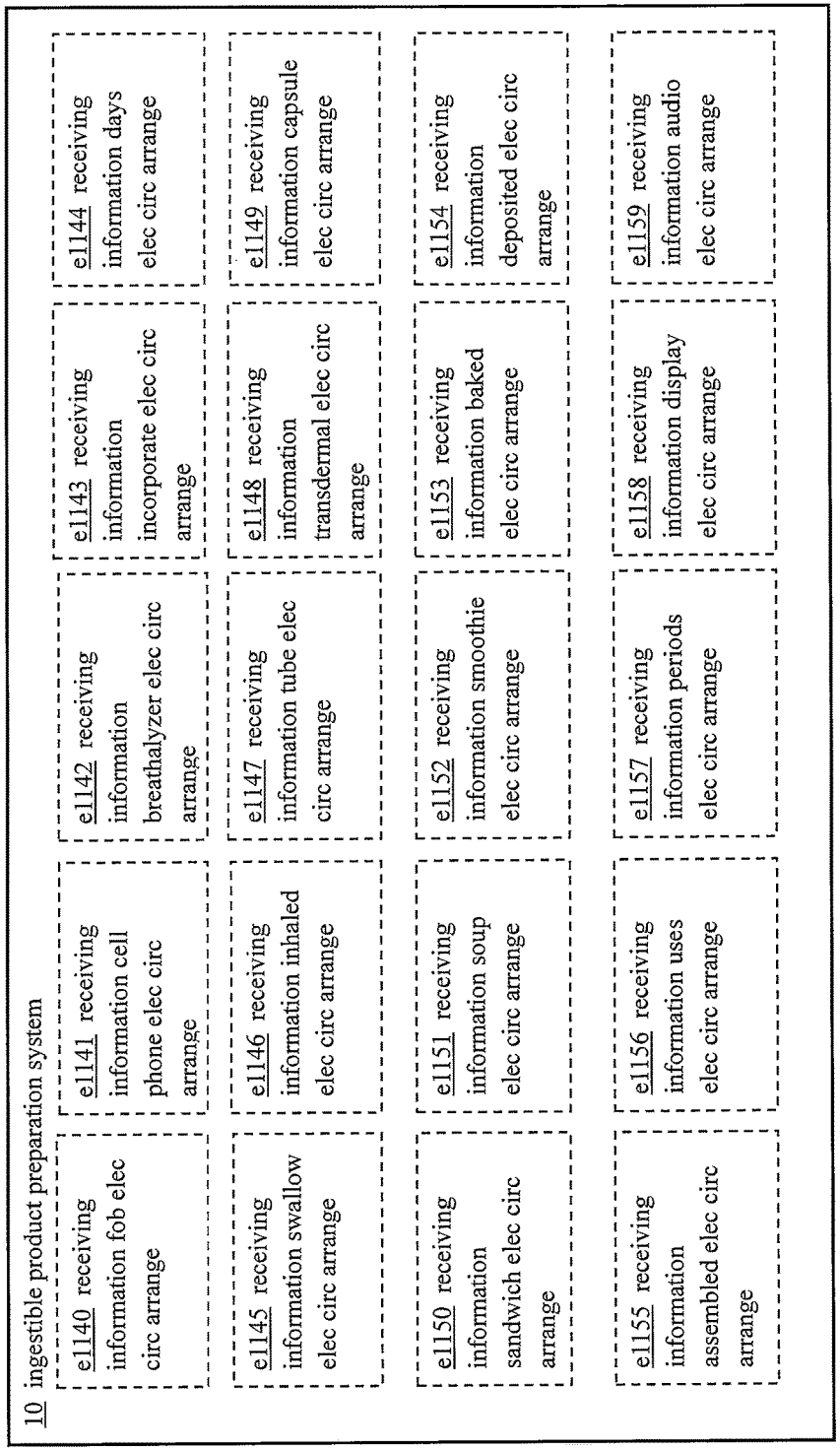
FIG. 42 is a block diagram depicting one or more exemplary electrical circuitry arrangements of the ingestible product preparation system 10 of FIG. 1.

Some of these electrical circuitry arrangements are depicted in FIG. 42 to include receiving information fob electrical circuitry arrangement e1140, receiving information cell phone electrical circuitry arrangement e1141, receiving information breathalyzer electrical circuitry arrangement e1142, receiving information incorporate electrical circuitry arrangement e1143, receiving information days electrical circuitry arrangement e1144, receiving information swallow electrical circuitry arrangement e1145, receiving information inhaled electrical circuitry arrangement e1146, receiving information tube electrical circuitry arrangement e1147, receiving information transdermal electrical circuitry arrangement e1148, receiving information capsule electrical circuitry arrangement e1149, receiving information sandwich electrical circuitry arrangement e1150, receiving information soup electrical circuitry arrangement e1151, receiving information smoothie electrical circuitry arrangement e1152, receiving information baked electrical circuitry arrangement e1153, receiving information deposited electrical circuitry arrangement e1154, receiving information assembled electrical circuitry arrangement e1155, receiving information uses electrical circuitry arrangement e1156, receiving information periods electrical circuitry arrangement e1157, receiving information display electrical circuitry arrangement e1158, and receiving information audio electrical circuitry arrangement e1159.

Figure 43:
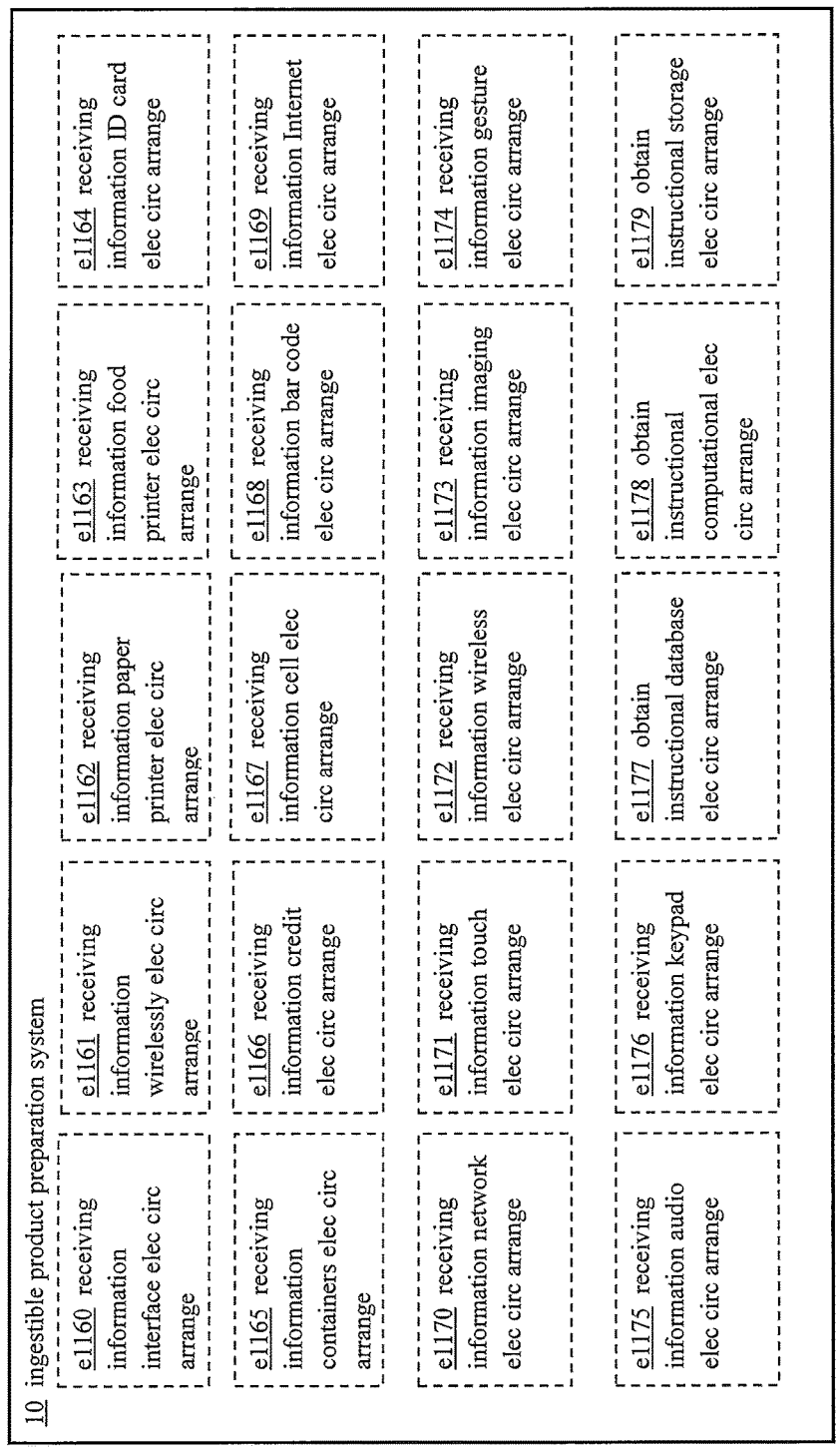
FIG. 43 is a block diagram depicting one or more exemplary electrical circuitry arrangements of the ingestible product preparation system 10 of FIG. 1.

Some of these electrical circuitry arrangements are depicted in FIG. 43 to include receiving information interface electrical circuitry arrangement e1160, receiving information wirelessly electrical circuitry arrangement e1161, receiving information paper printer electrical circuitry arrangement e1162, receiving information food printer electrical circuitry arrangement e1163, receiving information ID card electrical circuitry arrangement e1164, receiving information containers electrical circuitry arrangement e1165, and receiving information credit electrical circuitry arrangement e1166, receiving information cell electrical circuitry arrangement e1167, receiving information bar code electrical circuitry arrangement e1168, receiving information Internet electrical circuitry arrangement e1169, receiving information network electrical circuitry arrangement e1170, receiving information touch electrical circuitry arrangement e1171, receiving information wireless electrical circuitry arrangement e1172, receiving information imaging electrical circuitry arrangement e1173, receiving information gesture electrical circuitry arrangement e1174, receiving information audio electrical circuitry arrangement e1175, receiving information keypad electrical circuitry arrangement e1176, obtain instructional database electrical circuitry arrangement e1177, obtain instructional computational electrical circuitry arrangement e1178, and obtain instructional storage electrical circuitry arrangement e1179.

Figure 44:
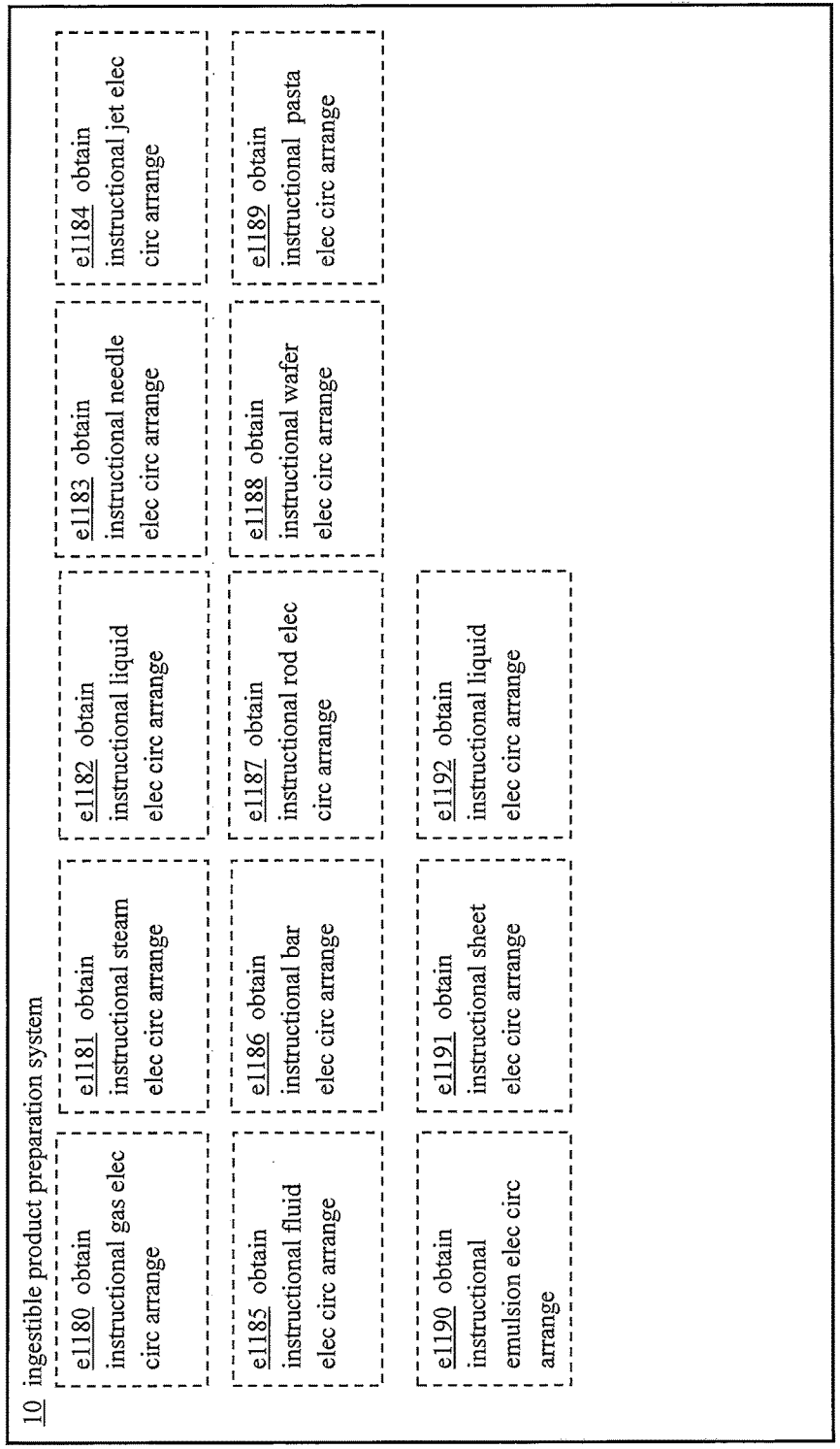
FIG. 44 is a block diagram depicting one or more exemplary electrical circuitry arrangements of the ingestible product preparation system 10 of FIG. 1.

Some of these electrical circuitry arrangements are depicted in FIG. 44 to include obtain instructional gas electrical circuitry arrangement e1180, obtain instructional steam electrical circuitry arrangement e1181, obtain instructional liquid electrical circuitry arrangement e1182, obtain instructional needle electrical circuitry arrangement e1183, obtain instructional jet electrical circuitry arrangement e1184, obtain instructional fluid electrical circuitry arrangement e1185, obtain instructional bar electrical circuitry arrangement e1186, obtain instructional rod electrical circuitry arrangement e1187, obtain instructional wafer electrical circuitry arrangement e1188, obtain instructional pasta electrical circuitry arrangement e1189, obtain instructional emulsion electrical circuitry arrangement e1190, obtain instructional sheet electrical circuitry arrangement e1191, and obtain instructional liquid electrical circuitry arrangement e1192.

Some of these electrical circuitry arrangements are depicted in FIG. 45 to include controlling treatment electrical circuitry arrangement e12, direct treatment circuits electrical circuitry arrangement e1201, direct treatment network electrical circuitry arrangement e1202, direct treatment adjacent electrical circuitry arrangement e1203, direct modify color electrical circuitry arrangement e1204, direct modify surface electrical circuitry arrangement e1205, direct modify oral electrical circuitry arrangement e1206, direct modify sound electrical circuitry arrangement e1207, direct modify structural electrical circuitry arrangement e1208, direct modify olfactory electrical circuitry arrangement e1209, direct modify shape electrical circuitry arrangement e1210, direct modify psycho-sensory electrical circuitry arrangement e1211, and direct modify acidic electrical circuitry arrangement e1212, direct modify basic electrical circuitry arrangement e1213, direct modify carbohydrate electrical circuitry arrangement e1214, direct modify protein electrical circuitry arrangement e1215, direct modify fat electrical circuitry arrangement e1216, direct modify non-nutritive electrical circuitry arrangement e1217, direct substrate carbohydrate electrical circuitry arrangement e1218, and direct substrate fat electrical circuitry arrangement e1219.

Some of these electrical circuitry arrangements are depicted in FIG. 46 to include direct substrate protein electrical circuitry arrangement e12, direct modify coat electrical circuitry arrangement e1221, direct modify remove electrical circuitry arrangement e1222, direct modify mix electrical circuitry arrangement e1223, direct modify replace electrical circuitry arrangement e1224, direct modify integrate electrical circuitry arrangement e1225, direct modify soften electrical circuitry arrangement e1226, direct modify hydrate electrical circuitry arrangement e1227, direct modify harden electrical circuitry arrangement e1228, and direct modify dehydrate electrical circuitry arrangement e1229.

In implementations one or more instructions are stored and/or otherwise borne in various subsystems, components, and/or accessories of the ingestible product preparation system 10 such as being borne in a non-transitory signal bearing medium of information storage subsystem s200. One or more exemplary instructions depicted in FIG. 47 as being borne in an exemplary version of a non-transitory signal bearing medium of information storage subsystem s200 include one or more receiving information instructions i11, one or more receiving information ID card instructions i1101, one or more receiving information memory instructions i1102, one or more receiving information credit card instructions i1103, one or more receiving information cell phone instructions i1104, one or more receiving information bar code instructions i1105, one or more receiving information Internet instructions i1106, one or more receiving information network instructions i1107, one or more receiving encrypted information instructions i1108, one or more receiving information memory card instructions i1109, one or more receiving information wirelessly instructions i1110, one or more receiving information keypad entries instructions i1111, one or more receiving information meal order instructions i1112, one or more receiving information prescription ID instructions i1113, one or more receiving information prescription number instructions i1114, one or more receiving information handwritten instructions i1115, one or more receiving information text file instructions i1116, one or more receiving information audio file instructions i1117, one or more receiving information video file instructions i1118, and one or more receiving information RFID instructions i1119.

Figure 48:
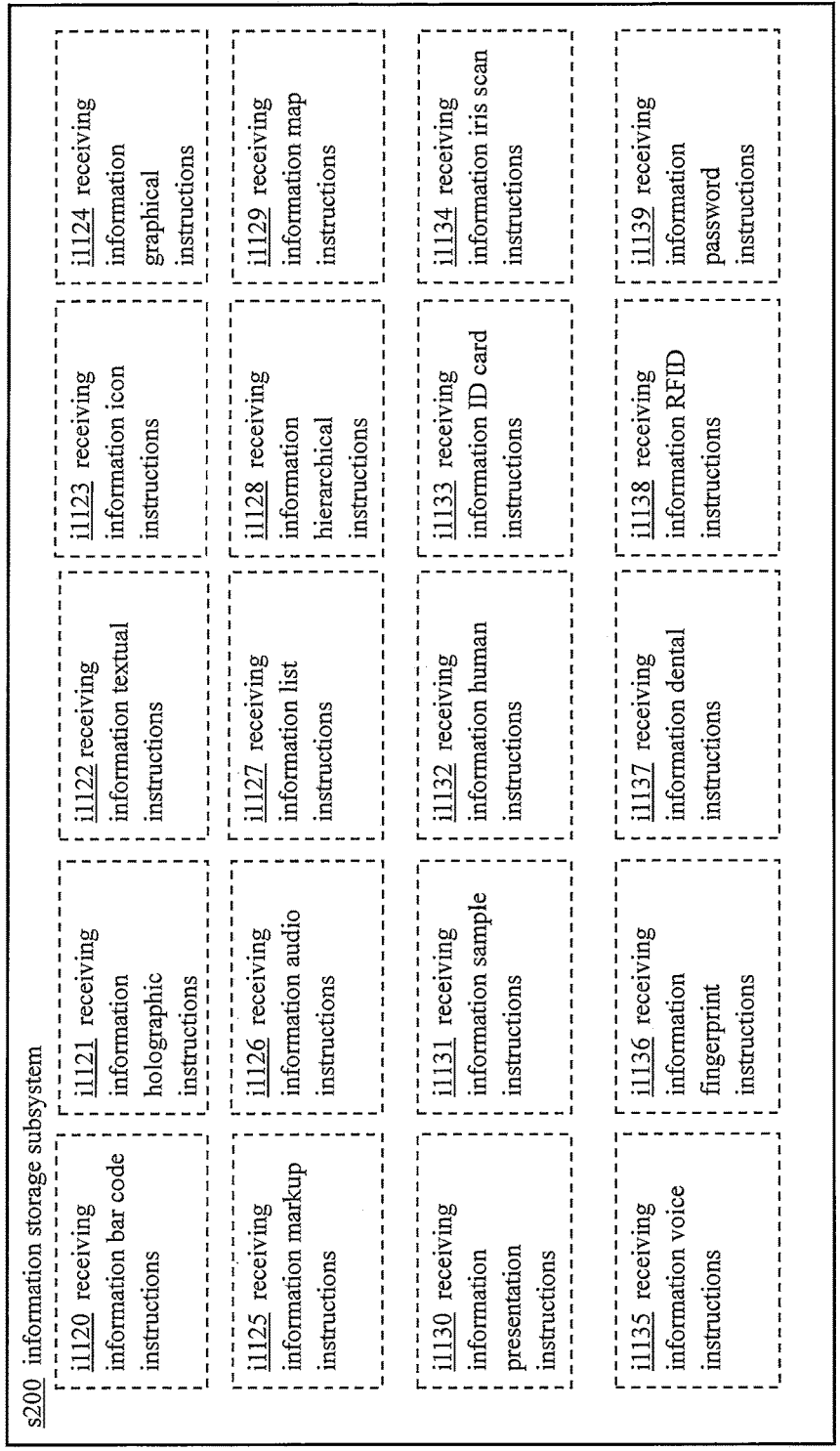
FIG. 48 is a block diagram depicting one or more exemplary instructions of the information storage subsystem s200 of the ingestible product preparation system 10 of FIG. 1.

One or more exemplary instructions depicted in FIG. 48 as being borne in an exemplary version of a non-transitory signal bearing medium of information storage subsystem s200 include one or more receiving information bar code instructions i1120, one or more receiving information holographic instructions i1121, one or more receiving information textual instructions i1122, one or more receiving information icon instructions i1123, one or more receiving information graphical instructions i1124, one or more receiving information markup instructions i1125, one or more receiving information audio instructions i1126, one or more receiving information list instructions i1127, one or more receiving information hierarchical instructions i1128, one or more receiving information map instructions i1129, one or more receiving information presentation instructions i1130, one or more receiving information sample instructions i1131, one or more receiving information human instructions i1132, one or more receiving information ID card instructions i1133, one or more receiving information iris scan instructions i1134, one or more receiving information voice instructions i1135, one or more receiving information fingerprint instructions i1136, one or more receiving information dental instructions i1137, one or more receiving information RFID instructions i1138, and one or more receiving information password instructions i1139.

Figure 49:
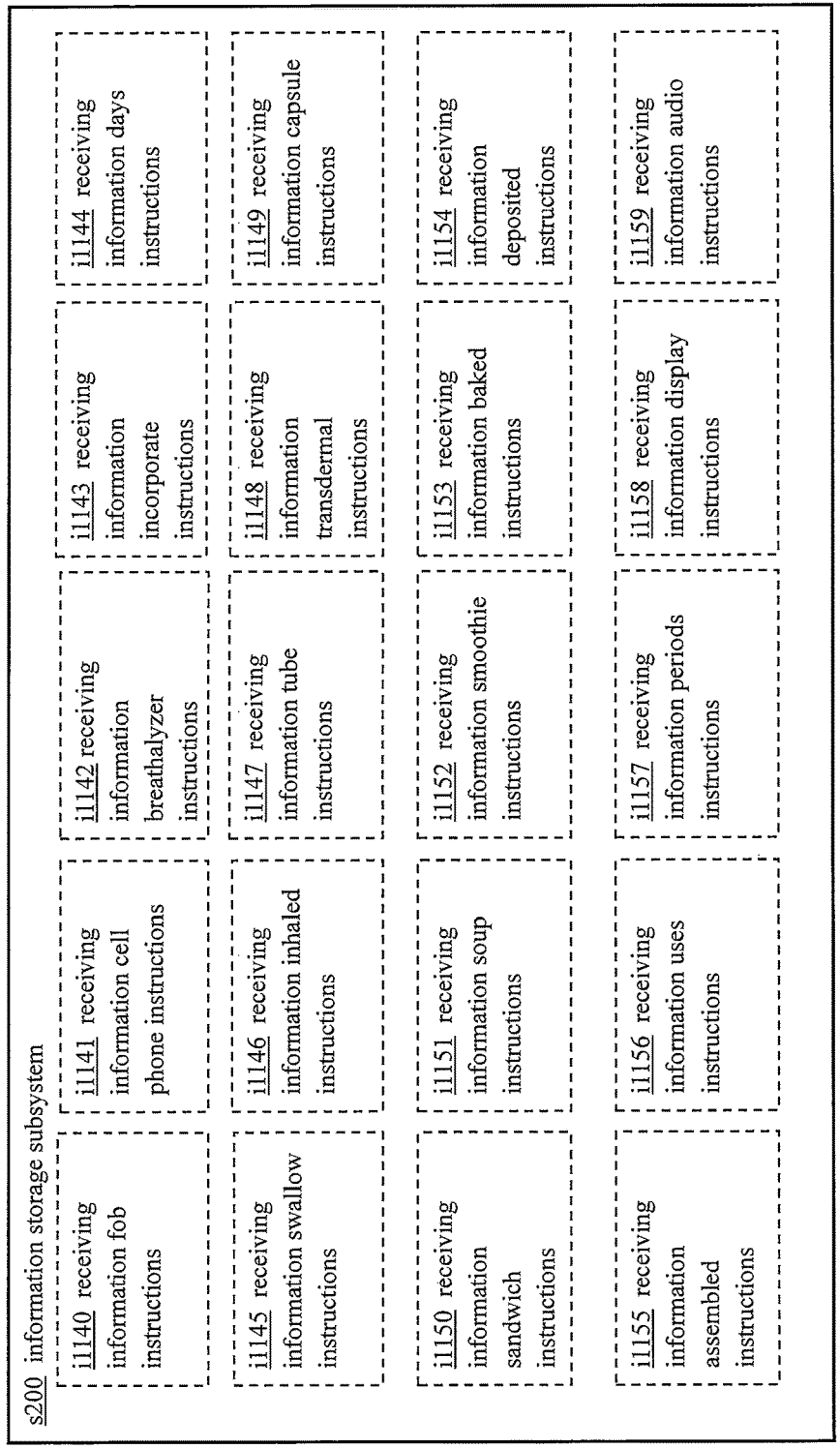
FIG. 49 is a block diagram depicting one or more exemplary instructions of the information storage subsystem s200 of the ingestible product preparation system 10 of FIG. 1.

One or more exemplary instructions depicted in FIG. 49 as being borne in an exemplary version of a non-transitory signal bearing medium of information storage subsystem s200 include one or more receiving information fob instructions i1140, one or more receiving information cell phone instructions i1141, one or more receiving information breathalyzer instructions i1142, one or more receiving information incorporate instructions i1143, one or more receiving information days instructions i1144, one or more receiving information swallow instructions i1145, one or more receiving information inhaled instructions i1146, one or more receiving information tube instructions i1147, one or more receiving information transdermal instructions i1148, one or more receiving information capsule instructions i1149, one or more receiving information sandwich instructions i1150, one or more receiving information soup instructions i1151, one or more receiving information smoothie instructions i1152, one or more receiving information baked instructions i1153, one or more receiving information deposited instructions i1154, one or more receiving information assembled instructions i1155, one or more receiving information uses instructions i1156, one or more receiving information periods instructions i1157, one or more receiving information display instructions i1158, and one or more receiving information audio instructions i1159.

Figure 50:
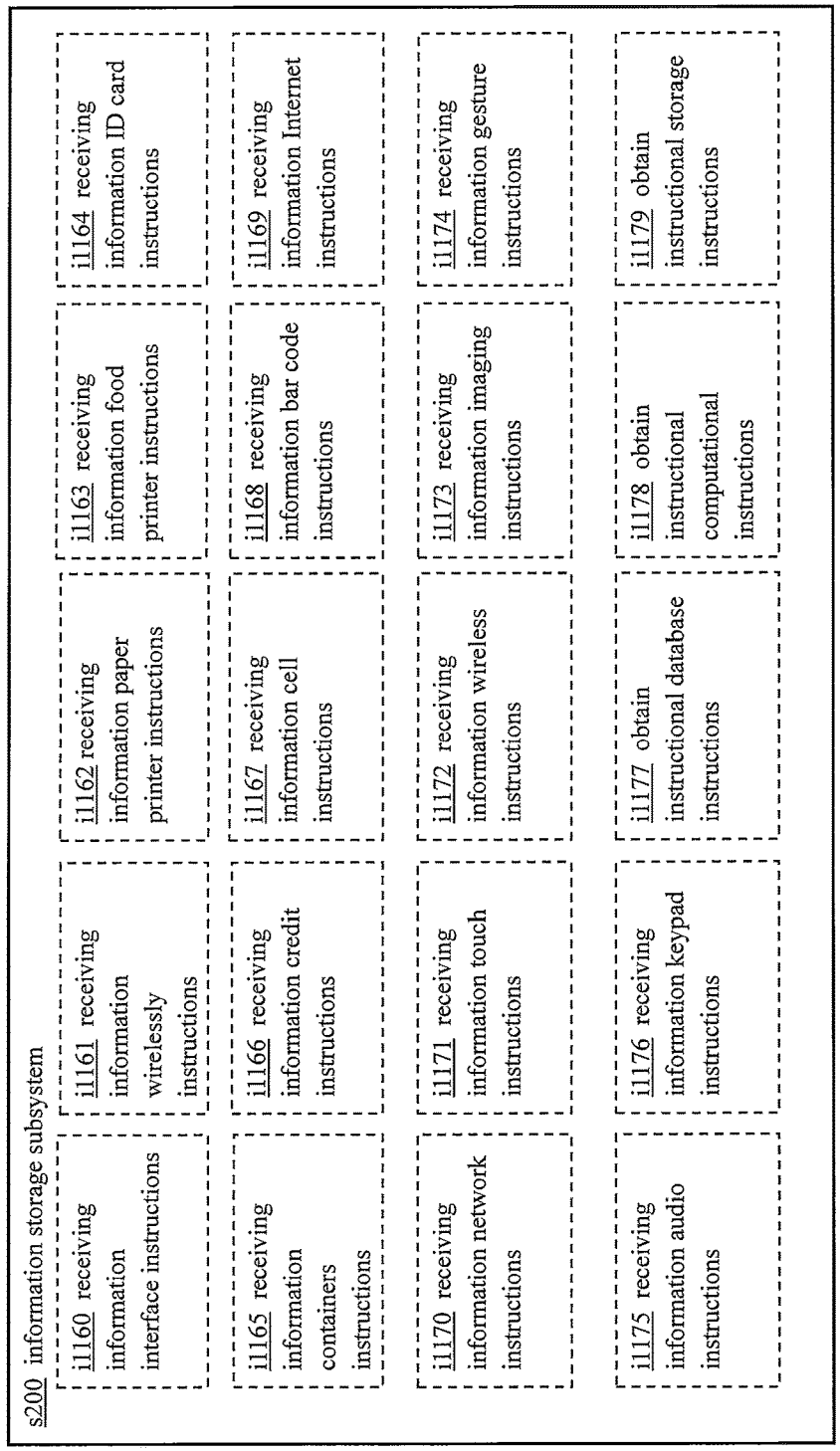
FIG. 50 is a block diagram depicting one or more exemplary instructions of the information storage subsystem s200 of the ingestible product preparation system 10 of FIG. 1.

One or more exemplary instructions depicted in FIG. 50 as being borne in an exemplary version of a non-transitory signal bearing medium of information storage subsystem s200 include one or more receiving information interface instructions i1160, one or more receiving information wirelessly instructions i1161, one or more receiving information paper printer instructions i1162, one or more receiving information food printer instructions i1163, one or more receiving information ID card instructions i1164, one or more receiving information containers instructions i1165, and one or more receiving information credit instructions i1166, one or more receiving information cell instructions i1167, one or more receiving information bar code instructions i1168, one or more receiving information Internet instructions i1169, one or more receiving information network instructions i1170, one or more receiving information touch instructions i1171, one or more receiving information wireless instructions i1172, one or more receiving information imaging instructions i1173, one or more receiving information gesture instructions i1174, one or more receiving information audio instructions i1175, one or more receiving information keypad instructions i1176, one or more obtain instructional database instructions i1177, one or more obtain instructional computational instructions i1178, and one or more obtain instructional storage instructions i1179.

Figure 51:
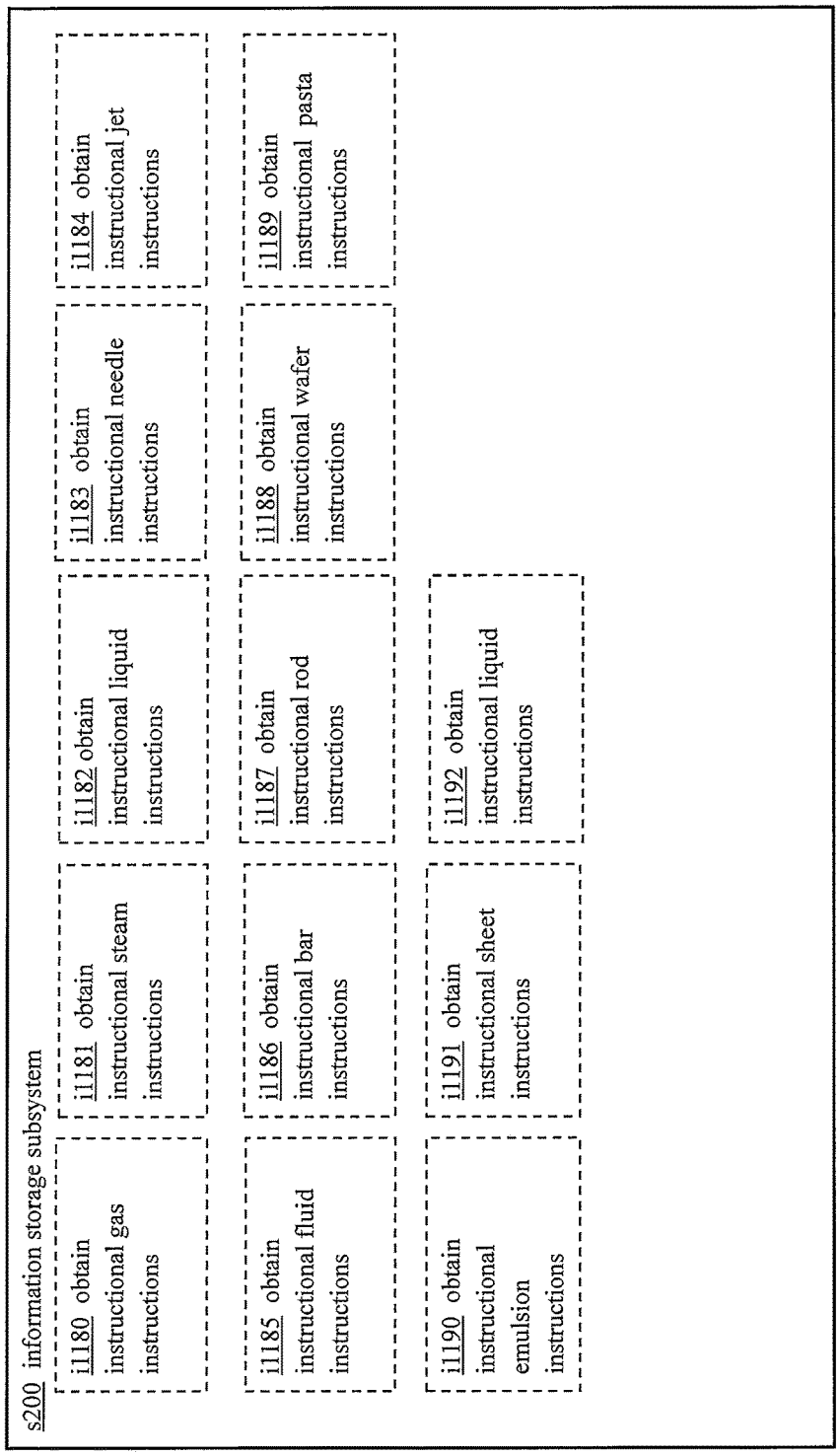
FIG. 51 is a block diagram depicting one or more exemplary instructions of the information storage subsystem s200 of the ingestible product preparation system 10 of FIG. 1.

One or more exemplary instructions depicted in FIG. 51 as being borne in an exemplary version of a non-transitory signal bearing medium of information storage subsystem s200 include one or more obtain instructional gas instructions i1180, one or more obtain instructional steam instructions i1181, one or more obtain instructional liquid instructions i1182, one or more obtain instructional needle instructions i1183, one or more obtain instructional jet instructions i1184, one or more obtain instructional fluid instructions i1185, one or more obtain instructional bar instructions i1186, one or more obtain instructional rod instructions i1187, one or more obtain instructional wafer instructions i1188, one or more obtain instructional pasta instructions i1189, one or more obtain instructional emulsion instructions i1190, one or more obtain instructional sheet instructions i1191, and one or more obtain instructional liquid instructions i1192.

Figure 52:
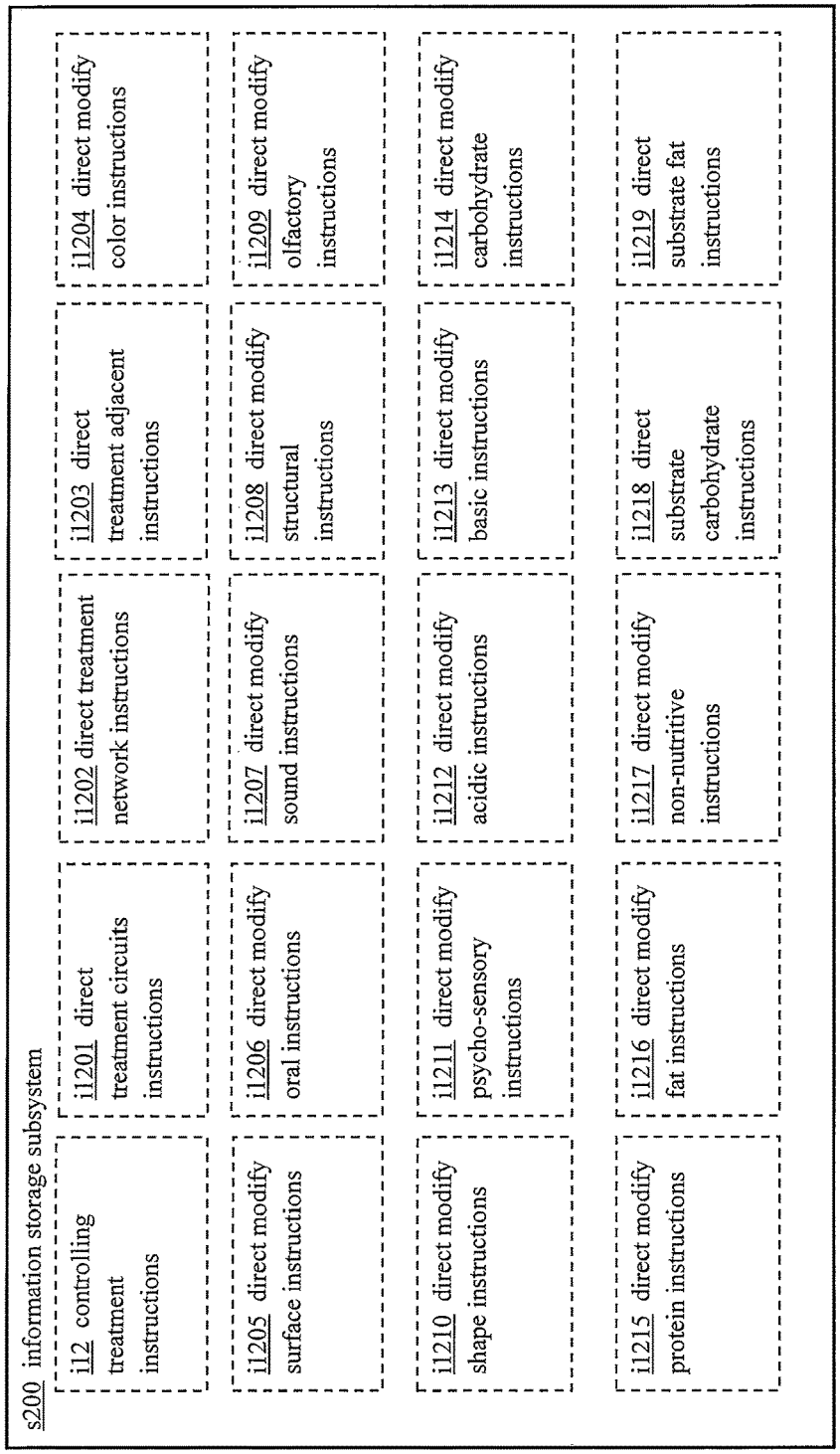
FIG. 52 is a block diagram depicting one or more exemplary instructions of the information storage subsystem s200 of the ingestible product preparation system 10 of FIG. 1.

One or more exemplary instructions depicted in FIG. 52 as being borne in an exemplary version of a non-transitory signal bearing medium of information storage subsystem s200 include one or more controlling treatment instructions i12, one or more direct treatment circuits instructions i1201, one or more direct treatment network instructions i1202, one or more direct treatment adjacent instructions i1203, one or more direct modify color instructions i1204, one or more direct modify surface instructions i1205, one or more direct modify oral instructions i1206, one or more direct modify sound instructions i1207, one or more direct modify structural instructions i1208, one or more direct modify olfactory instructions i1209, one or more direct modify shape instructions i1210, one or more direct modify psycho-sensory instructions i1211, one or more direct modify acidic instructions i1212, one or more direct modify basic instructions i1213, one or more direct modify carbohydrate instructions i1214, one or more direct modify protein instructions i1215, one or more direct modify fat instructions i1216, one or more direct modify non-nutritive instructions i1217, one or more direct substrate carbohydrate instructions i1218, and one or more direct substrate fat instructions i1219.

One or more exemplary instructions depicted in FIG. 52 as being borne in an exemplary version of a non-transitory signal bearing medium of information storage subsystem s200 include one or more direct substrate protein instructions i1220, one or more direct modify coat instructions i1221, one or more direct modify remove instructions i1222, one or more direct modify mix instructions i1223, one or more direct modify replace instructions i1224, one or more direct modify integrate instructions i1225, one or more direct modify soften instructions i1226, one or more direct modify hydrate instructions i1227, one or more direct modify harden instructions i1228, and one or more direct modify dehydrate instructions i1229.

Figure 54:
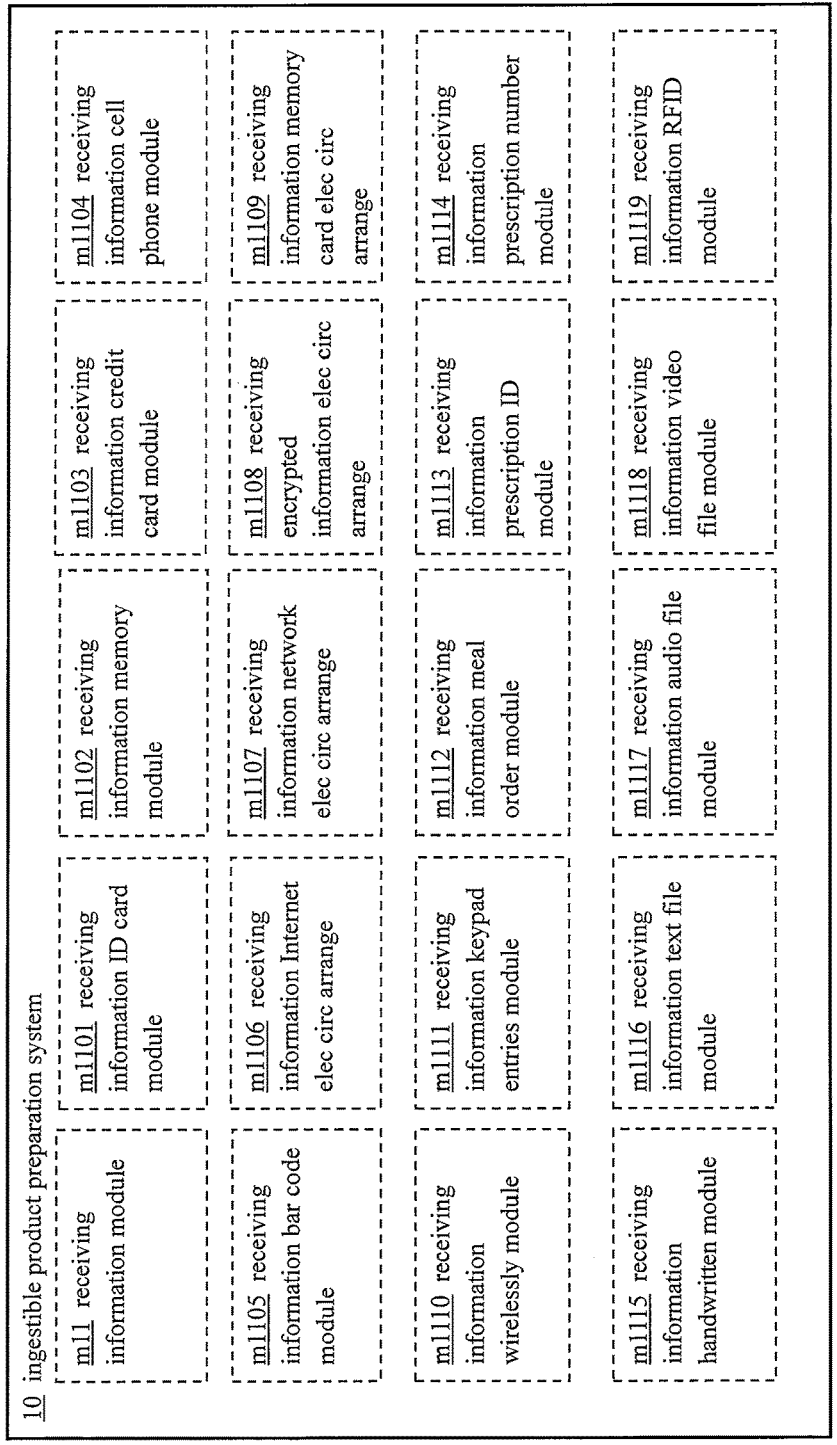
FIG. 54 is a block diagram depicting one or more exemplary modules of the ingestible product preparation system 10 of FIG. 1.

Implementations of modules involve different combinations (limited to patentable subject matter under 35 U.S.C. 101) of one or more aspects from one or more of the electrical circuitry arrangements and/or one or more aspects from one or more of the instructions of the ingestible product preparation system 10. Exemplary depictions of some of these modules are shown in FIG. 54 to include receiving information module m11, receiving information ID card module m1101, receiving information memory module m1102, receiving information credit card module m1103, receiving information cell phone module m1104, receiving information bar code module m1105, receiving information Internet module m1106, receiving information network module m1107, receiving encrypted information module m1108, receiving information memory card module m1109, receiving information wirelessly module m1110, receiving information keypad entries module m1111, receiving information meal order module m1112, receiving information prescription ID module m1113, receiving information prescription number module m1114, receiving information handwritten module m1115, receiving information text file module m1116, receiving information audio file module m1117, receiving information video file module m1118, and receiving information RFID module m1119.

Figure 55:
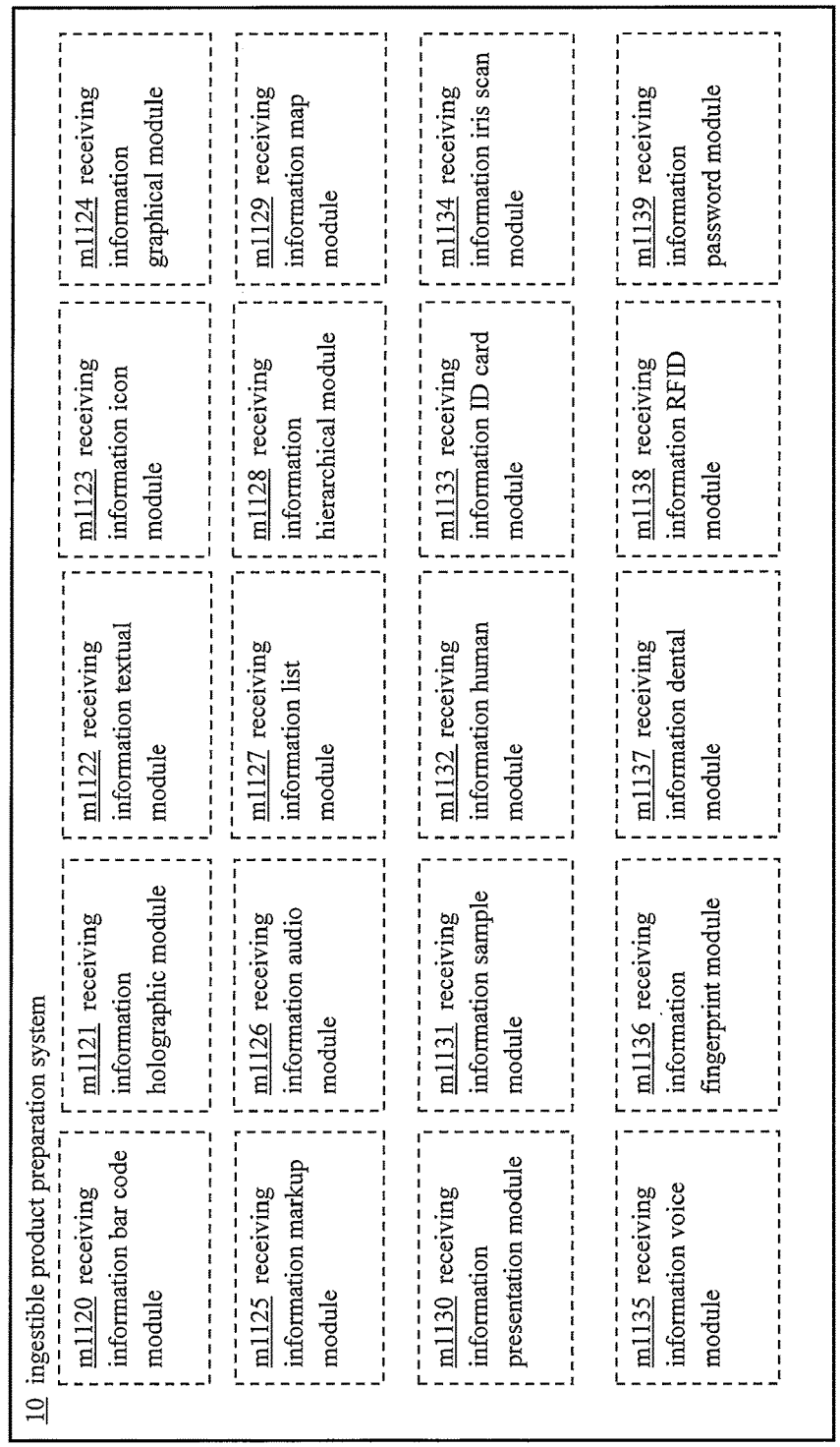
FIG. 55 is a block diagram depicting one or more exemplary modules of the ingestible product preparation system 10 of FIG. 1.

Some of these modules are depicted in FIG. 55 to include receiving information bar code module m1120, receiving information holographic module m1121, receiving information textual module m1122, receiving information icon module m1123, receiving information graphical module m1124, receiving information markup module m1125, receiving information audio module m1126, receiving information list module m1127, receiving information hierarchical module m1128, receiving information map module m1129, receiving information presentation module m1130, receiving information sample module m113, receiving information human module m1132, receiving information ID card module m1133, receiving information iris scan module m1134, receiving information voice module m1135, receiving information fingerprint module m1136, receiving information dental module m1137, receiving information RFID module m1138, and receiving information password module m1139.

Figure 56:
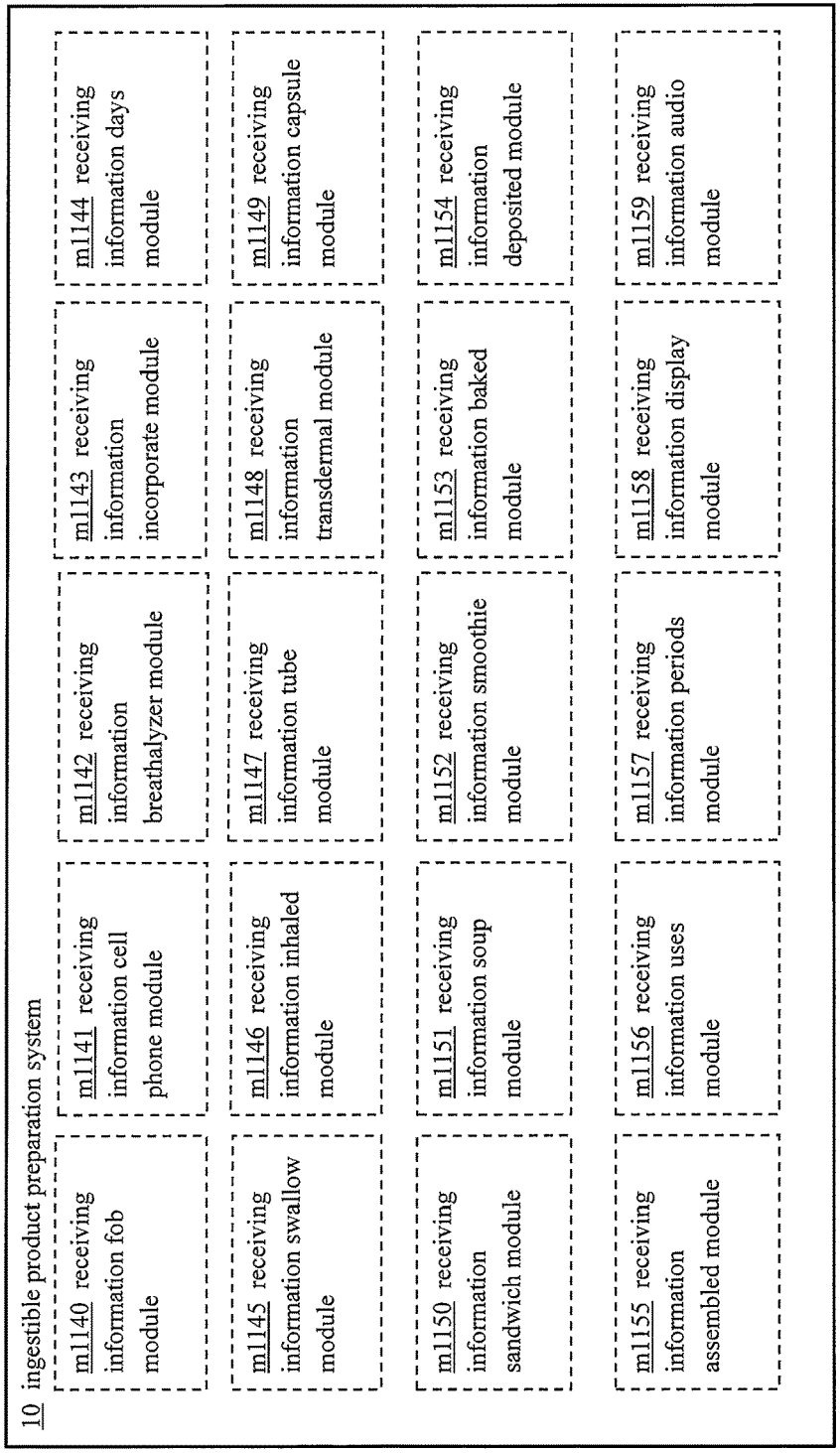
FIG. 56 is a block diagram depicting one or more exemplary modules of the ingestible product preparation system 10 of FIG. 1.

Some of these modules are depicted in FIG. 56 to include receiving information fob module m1140, receiving information cell phone module m1141, receiving information breathalyzer module m1142, receiving information incorporate module m1143, receiving information days module m1144, receiving information swallow module m1145, receiving information inhaled module m1146, receiving information tube module m1147, receiving information transdermal module m1148, receiving information capsule module m1149, receiving information sandwich module m1150, receiving information soup module m1151, receiving information smoothie module m1152, receiving information baked module m1153, receiving information deposited module m1154, receiving information assembled module m1155, receiving information uses module m1156, receiving information periods module m1157, receiving information display module m1158, and receiving information audio module m1159.

Figure 57:
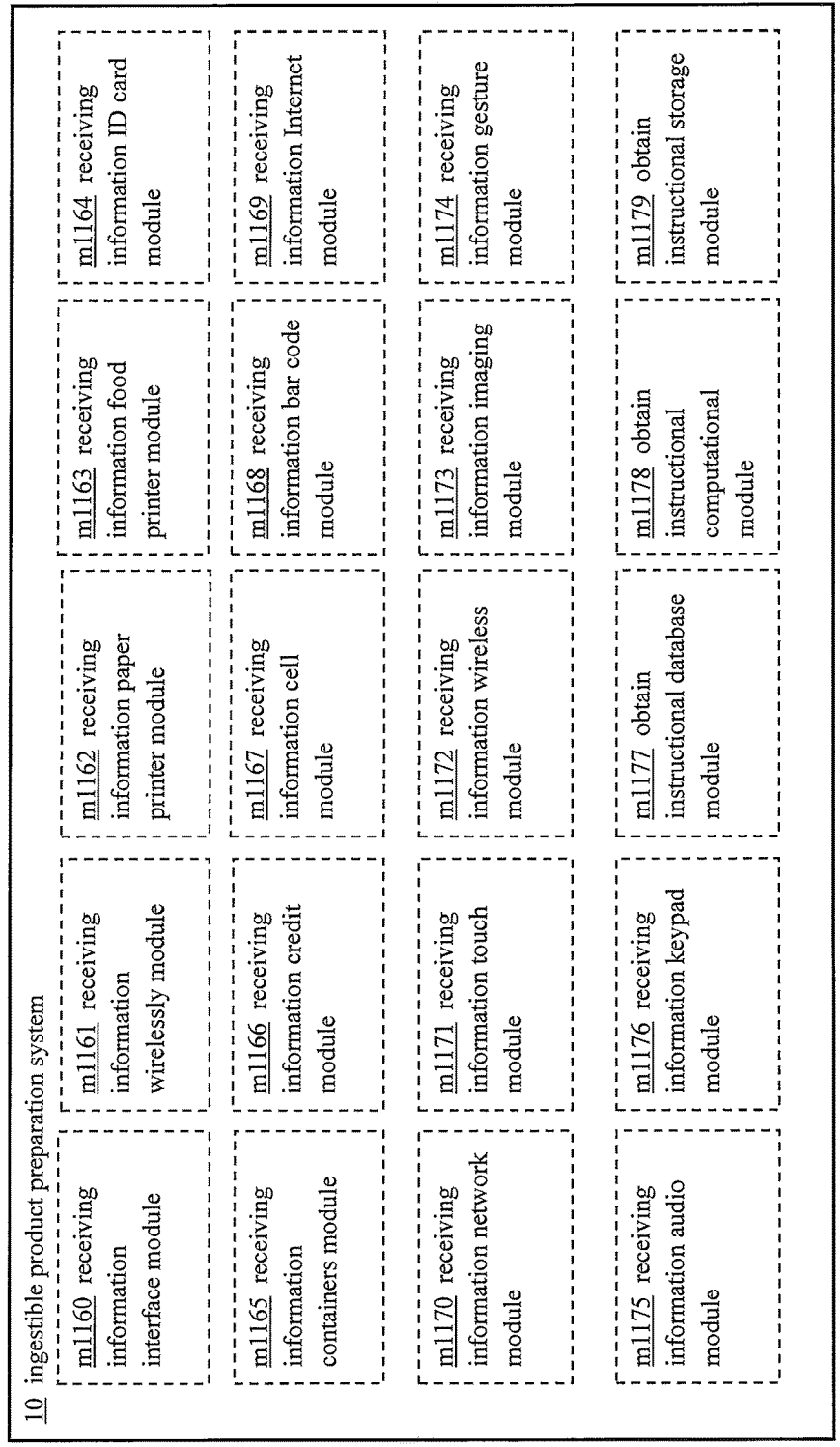
FIG. 57 is a block diagram depicting one or more exemplary modules of the ingestible product preparation system 10 of FIG. 1.

Some of these modules are depicted in FIG. 57 to include receiving information interface module m1160, receiving information wirelessly module m1161, receiving information paper printer module m1162, receiving information food printer module m1163, receiving information ID card module m1164, receiving information containers module m1165, and receiving information credit module m1166, receiving information cell module m1167, receiving information bar code module m1168, receiving information Internet module m1169, receiving information network module m1170, receiving information touch module m1171, receiving information wireless module m1172, receiving information imaging module m1173, receiving information gesture module m1174, receiving information audio module m1175, receiving information keypad module m1176, obtain instructional database module m1177, obtain instructional computational module m1178, and obtain instructional storage module m1179.

Figure 58:
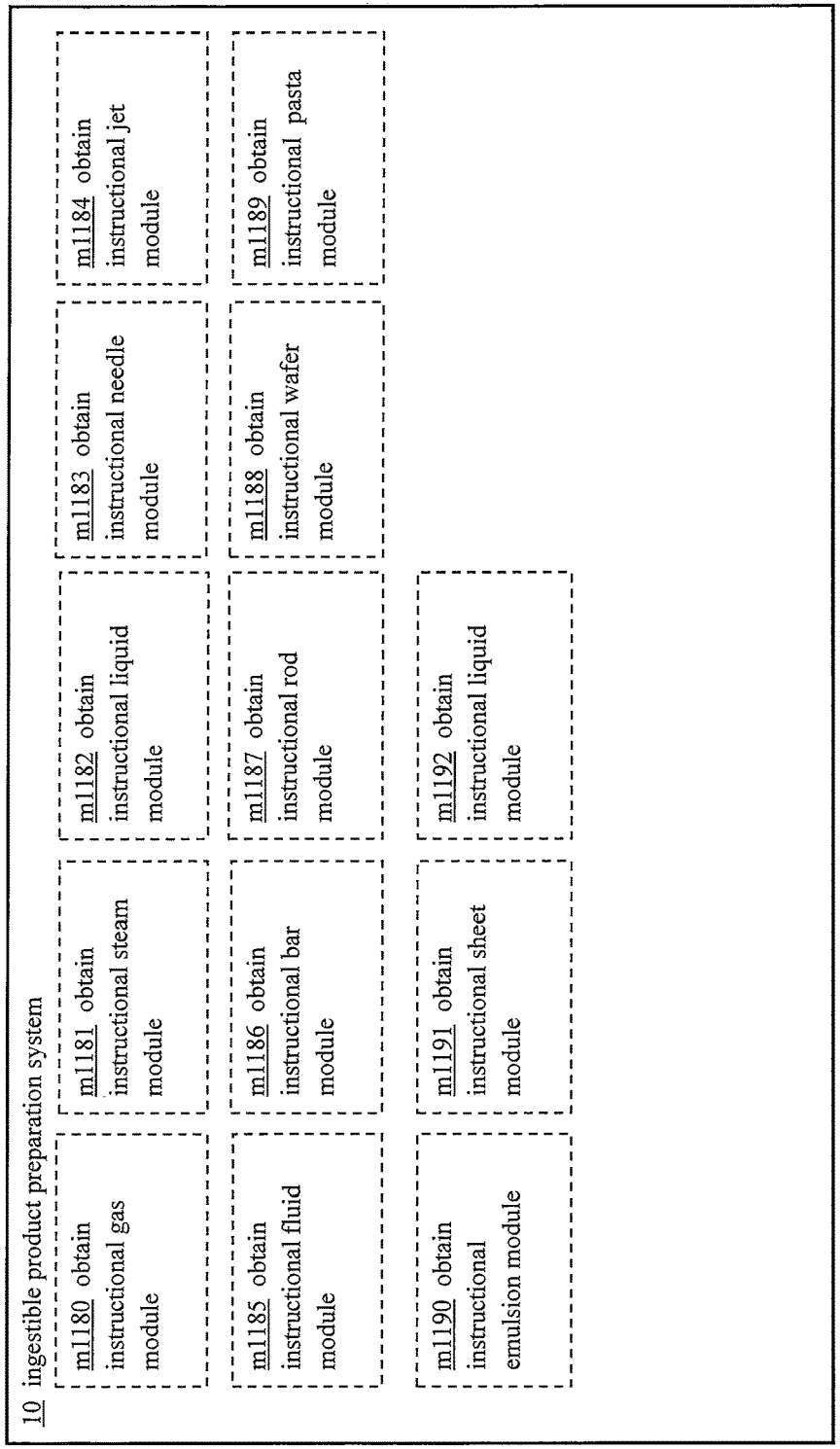
FIG. 58 is a block diagram depicting one or more exemplary modules of the ingestible product preparation system 10 of FIG. 1.

Some of these modules are depicted in FIG. 58 to include obtain instructional gas module m1180, obtain instructional steam module m1181, obtain instructional liquid module m1182, obtain instructional needle module m1183, obtain instructional jet module m1184, obtain instructional fluid module m1185, obtain instructional bar module m1186, obtain instructional rod module m1187, obtain instructional wafer module m1188, obtain instructional pasta module m1189, obtain instructional emulsion module m1190, obtain instructional sheet module m1191, and obtain instructional liquid module m1192.

Figure 59:
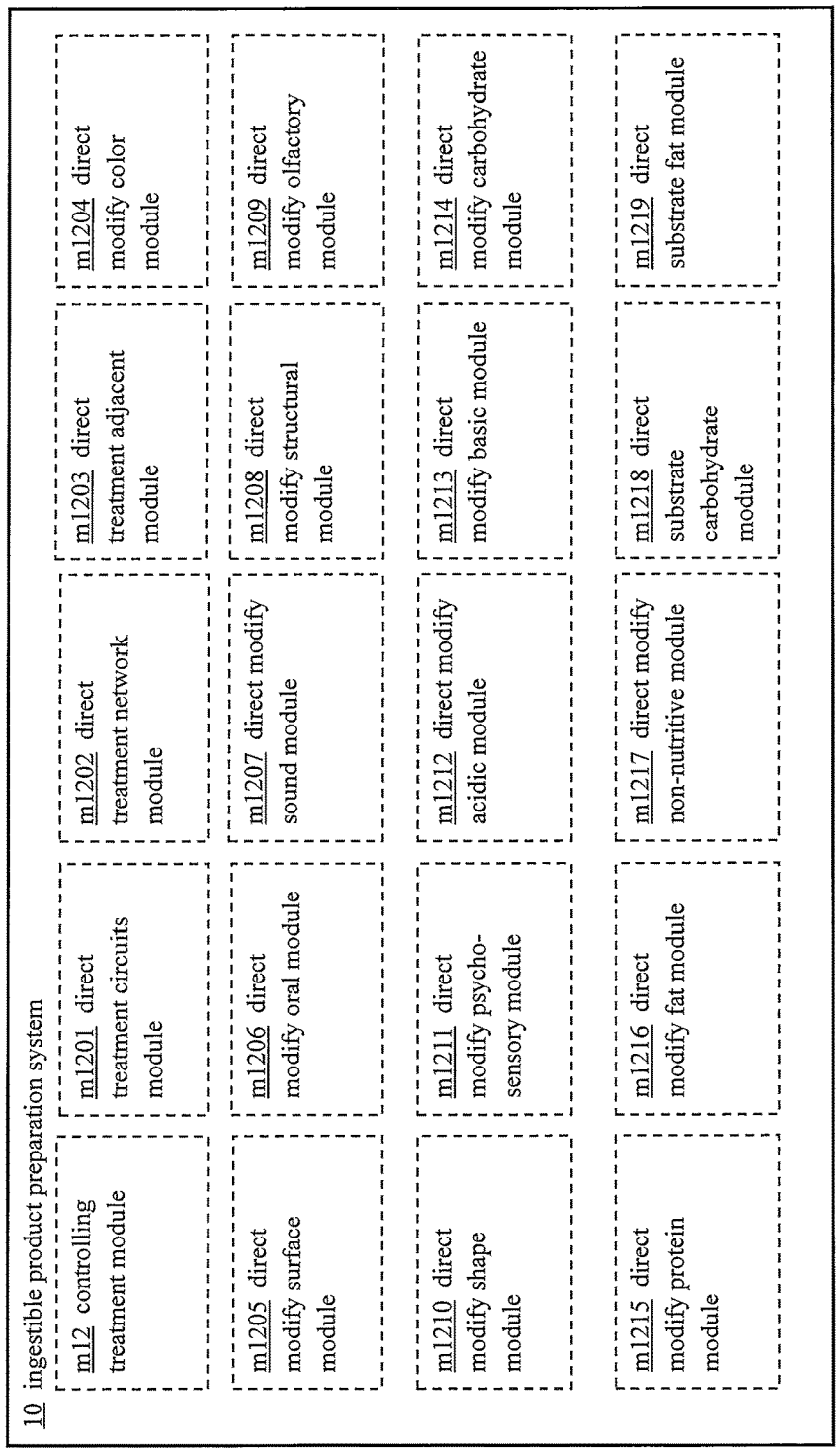
FIG. 59 is a block diagram depicting one or more exemplary modules of the ingestible product preparation system 10 of FIG. 1.

Some of these modules are depicted in FIG. 59 to include controlling treatment module m12, direct treatment circuits module m1201, direct treatment network module m1202, direct treatment adjacent module m1203, direct modify color module m1204, direct modify surface module m1205, direct modify oral module m1206, direct modify sound module m1207, direct modify structural module m1208, direct modify olfactory module m1209, direct modify shape module m1210, direct modify psycho-sensory module m1211, and direct modify acidic module m1212, direct modify basic module m1213, direct modify carbohydrate module m1214, direct modify protein module m1215, direct modify fat module m1216, direct modify non-nutritive module m1217, direct substrate carbohydrate module m1218, and direct substrate fat module m1219.

Figure 60:
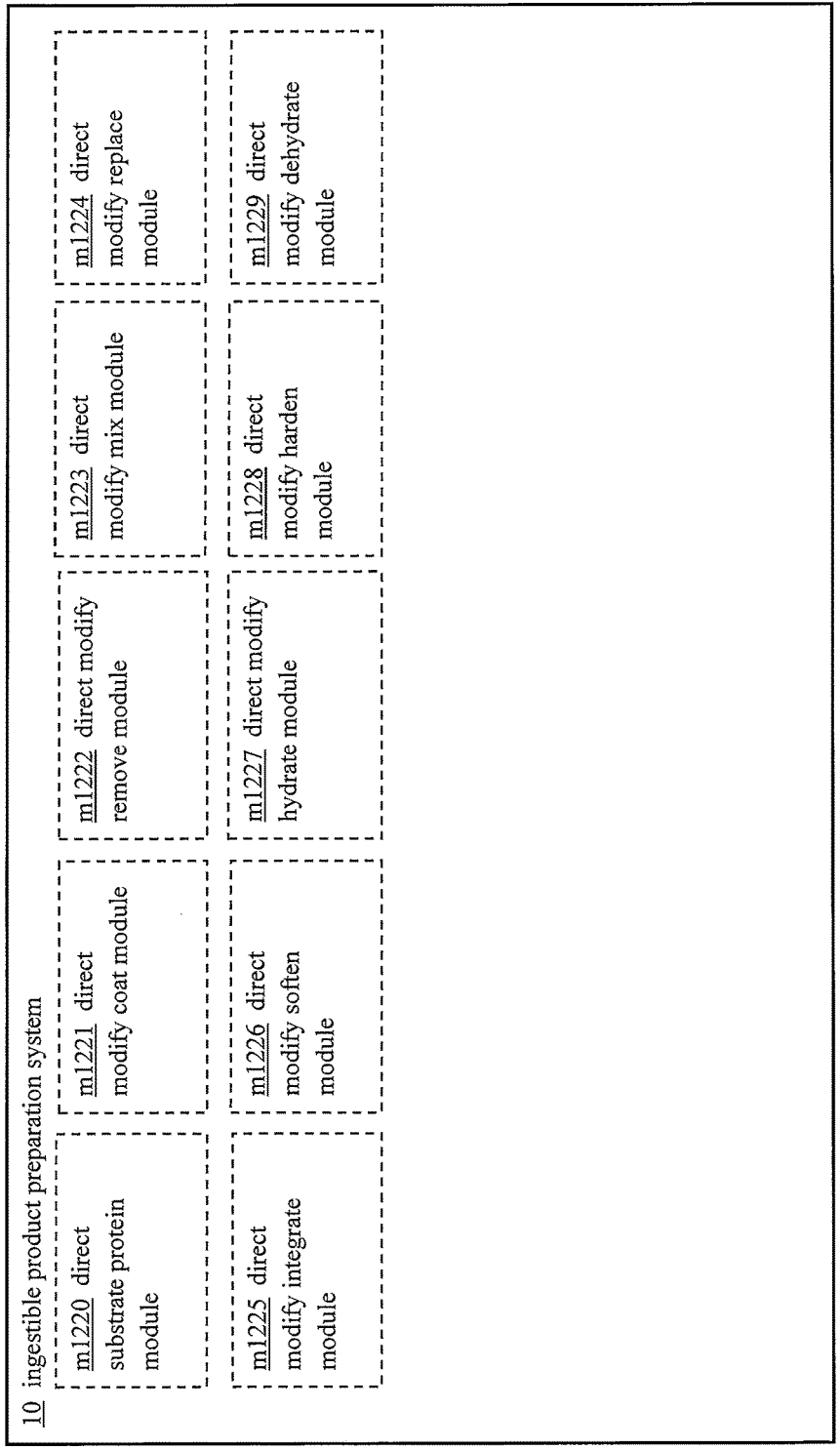
FIG. 60 is a block diagram depicting one or more exemplary modules of the ingestible product preparation system 10 of FIG. 1.

Some of these modules are depicted in FIG. 60 to include direct substrate protein module m12, direct modify coat module m1221, direct modify remove module m1222, direct modify mix module m1223, direct modify replace module m1224, direct modify integrate module m1225, direct modify soften module m1226, direct modify hydrate module m1227, direct modify harden module m1228, and direct modify dehydrate module m1229.

In some implementations, non-transitory signal-bearing medium of information storage subsystem s200 as articles of manufacture may store the one or more exemplary instructions. In some implementations, the non-transitory signal bearing medium may include a computer-readable medium. In some implementations, the non-transitory signal-bearing medium may include a recordable medium. In some implementations, the signal-bearing medium may include a communication medium.

The various subsystems and components of the ingestible product preparation system s10 such as the control and information processing subsystem s100, the information storage subsystem s200, the information user interface subsystems 300, the sensing subsystem s400 and the electronic communication subsystem s500 and their sub-components and the other exemplary entities depicted may be embodied by hardware, software and/or firmware (limited to patentable subject matter under 35 USC 101). For example, in some implementations of the ingestible product preparation system s10, aspects may be implemented with a processor (e.g., microprocessor, controller, and so forth) executing computer readable instructions (e.g., computer program product) stored in a storage medium (e.g., volatile or non-volatile memory) such as a signal-bearing medium. Alternatively, hardware such as application specific integrated circuit (ASIC) may be employed in order to implement such modules in some alternative implementations.

Figure 61:
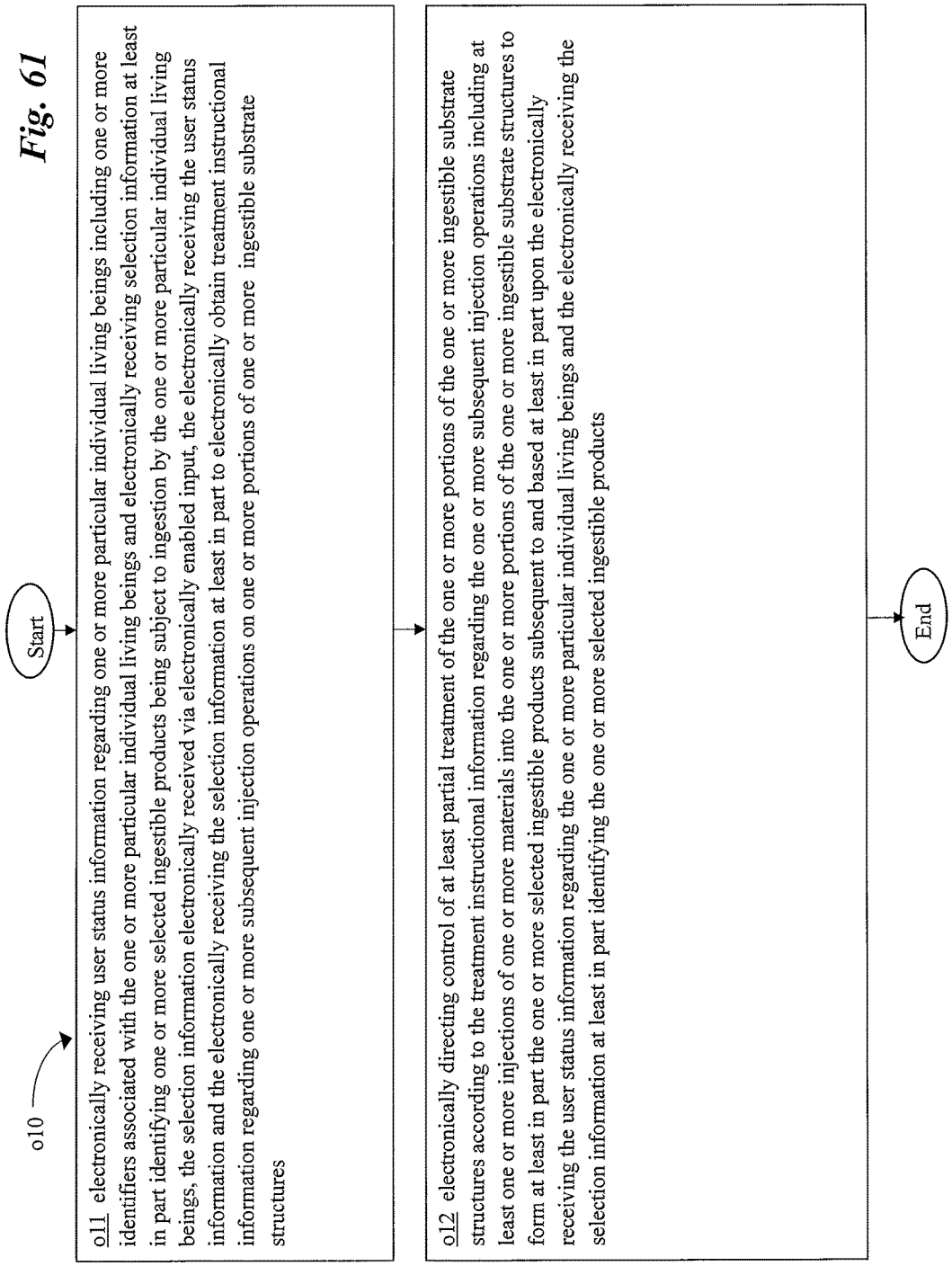
FIG. 61 is a high-level flowchart illustrating an operational flow o10 representing exemplary operations related to electronically receiving user status information regarding one or more particular individual living beings including one or more identifiers associated with the one or more particular individual living beings and electronically receiving selection information at least in part identifying one or more selected ingestible products being subject to ingestion by the one or more particular individual living beings, the selection information electronically received via electronically enabled input, the electronically receiving the user status information and the electronically receiving the selection information at least in part to electronically obtain treatment instructional information regarding one or more subsequent injection operations on one or more portions of one or more ingestible substrate structures, and electronically directing control of at least partial treatment of the one or more portions of the one or more ingestible substrate structures according to the treatment instructional information regarding the one or more subsequent injection operations including at least one or more injections of one or more materials into the one or more portions of the one or more ingestible substrate structures to form at least in part the one or more selected ingestible products subsequent to and based at least in part upon the electronically receiving the user status information regarding the one or more particular individual living beings and the electronically receiving the selection information at least in part identifying the one or more selected ingestible products at least associated with the depicted exemplary implementations of the system.

An operational flow o10 as shown in FIG. 61 represents example operations related to electronically receiving user status information regarding one or more particular individual living beings including one or more identifiers associated with the one or more particular individual living beings and electronically receiving selection information at least in part identifying one or more selected ingestible products being subject to ingestion by the one or more particular individual living beings, the selection information electronically received via electronically enabled input, the electronically receiving the user status information and the electronically receiving the selection information at least in part to electronically obtain treatment instructional information regarding one or more subsequent injection operations on one or more portions of one or more ingestible substrate structures and electronically directing control of at least partial treatment of the one or more portions of the one or more ingestible substrate structures according to the treatment instructional information regarding the one or more subsequent injection operations including at least one or more injections of one or more materials into the one or more portions of the one or more ingestible substrate structures to form at least in part the one or more selected ingestible products subsequent to and based at least in part upon the electronically receiving the user status information regarding the one or more particular individual living beings and the electronically receiving the selection information at least in part identifying the one or more selected ingestible products.

FIG. 61 and those figures that follow may have various examples of operational flows, and explanation may be provided with respect to the above-described examples of FIGS. 1-29 and/or with respect to other examples and contexts. Nonetheless, it should be understood that the operational flows may be executed in a number of other environments and contexts, and/or in modified versions of FIGS. 1-29. Furthermore, although the various operational flows are presented in the sequence(s) illustrated, it should be understood that the various operations may be performed in other orders than those which are illustrated, or may be performed concurrently.

In FIG. 61 and those figures that follow, various operations may be depicted in a box-within-a-box manner. Such depictions may indicate that an operation in an internal box may comprise an optional exemplary implementation of the operational step illustrated in one or more external boxes. However, it should be understood that internal box operations may be viewed as independent operations separate from any associated external boxes and may be performed in any sequence with respect to all other illustrated operations, or may be performed concurrently.

As shown in FIG. 61, the operational flow o10 proceeds to operation o11 for electronically receiving user status information regarding one or more particular individual living beings including one or more identifiers associated with the one or more particular individual living beings and electronically receiving selection information at least in part identifying one or more selected ingestible products being subject to ingestion by the one or more particular individual living beings, the selection information electronically received via electronically enabled input, the electronically receiving the user status information and the electronically receiving the selection information at least in part to electronically obtain treatment instructional information regarding one or more subsequent injection operations on one or more portions of one or more ingestible substrate structures. An exemplary version of a non-transitory signal bearing medium of information storage subsystem s200 is depicted as bearing one or more receiving information instructions i11 that when executed will direct performance of the operation o11. In an implementation, the one or more receiving information instructions i11 when executed direct electronically receiving (e.g. including the network cable component s502 carries information to the transceiver component s522, and/or etc.) user status information (e.g. including identification, characteristics, affiliations, and/or etc.) regarding one or more particular individual living beings (e.g. including one or more particular human beings, animals, and/or etc.) including one or more identifiers (e.g. including identification numbers, order numbers, passwords, biometric data such as voice prints, stored in information storage subsystem 200, and/or etc.) associated with the one or more particular individual living beings (e.g. including one or more humans, animals, and/or etc.) and electronically receiving (e.g. including through the receiver component s528, and/or etc.) selection information (e.g. including preferences, choices, and/or etc.) at least in part identifying (e.g. including textual descriptions, graphical representations, and/or etc.) one or more selected ingestible products (e.g. including sandwiches, snack bars, full course meals, and/or etc.) being subject to ingestion (e.g. including oral, dermal, nasal, and/or etc.) by the one or more particular individual living beings (e.g. including one or more humans, animals, and/or etc.), the selection information (e.g. including likes, dislikes, meal selection, and/or etc.) electronically received (e.g. including through the transceiver component s522, and/or etc.) via electronically enabled input (e.g. including voice, gesture, keypad, and/or etc.), the electronically receiving (e.g. including through transceiver component s522, and/or etc.) the user status information (e.g. including identification, associated location information, memberships, and/or etc.) and the electronically receiving (e.g. including through transceiver component s522, and/or etc.) the selection information (e.g. including ingestible materials desired, and/or etc.) at least in part to electronically obtain (e.g. including through data packets, and/or etc.) treatment instructional information (e.g. including methodology, preparation steps, and/or etc.) regarding one or more subsequent injection operations (e.g. including needle injection, jet injection, and/or etc.) on one or more portions of one or more ingestible substrate structures (e.g. including bars, sheets, and/or etc.). Furthermore, the receiving information electrical circuitry arrangement ("elec circ arrange") e11 when activated will perform the operation o1101. Also, the receiving information ID card module m1101, when executed and/or activated, will direct performance of and/or performs the operation o11. In an implementation, the receiving information electrical circuitry arrangement e11, when activated performs electronically receiving (e.g. including the network cable component s502 carries information to the transceiver component s522, and/or etc.) user status information (e.g. including identification, characteristics, affiliations, and/or etc.) regarding one or more particular individual living beings (e.g. including one or more particular human beings, animals, and/or etc.) including one or more identifiers (e.g. including identification numbers, order numbers, passwords, biometric data such as voice prints, stored in information storage subsystem 200, and/or etc.) associated with the one or more particular individual living beings (e.g. including one or more humans, animals, and/or etc.) and electronically receiving (e.g. including through the receiver component s528, and/or etc.) selection information (e.g. including preferences, choices, and/or etc.) at least in part identifying (e.g. including textual descriptions, graphical representations, and/or etc.) one or more selected ingestible products (e.g. including sandwiches, snack bars, full course meals, and/or etc.) being subject to ingestion (e.g. including oral, dermal, nasal, and/or etc.) by the one or more particular individual living beings (e.g. including one or more humans, animals, and/or etc.), the selection information (e.g. including likes, dislikes, meal selection, and/or etc.) electronically received (e.g. including through the transceiver component s522, and/or etc.) via electronically enabled input (e.g. including voice, gesture, keypad, and/or etc.), the electronically receiving (e.g. including through transceiver component s522, and/or etc.) the user status information (e.g. including identification, associated location information, memberships, and/or etc.) and the electronically receiving (e.g. including through transceiver component s522, and/or etc.) the selection information (e.g. including ingestible materials desired, and/or etc.) at least in part to electronically obtain (e.g. including through data packets, and/or etc.) treatment instructional information (e.g. including methodology, preparation steps, and/or etc.) regarding one or more subsequent injection operations (e.g. including needle injection, jet injection, and/or etc.) on one or more portions of one or more ingestible substrate structures (e.g. including bars, sheets, and/or etc.). Also, the receiving information module m11, when executed and/or activated, will direct performance of and/or perform the operation o11. In an implementation, the electronically receiving user status information regarding one or more particular individual living beings including one or more identifiers associated with the one or more particular individual living beings and electronically receiving selection information at least in part identifying one or more selected ingestible products being subject to ingestion by the one or more particular individual living beings, the selection information electronically received via electronically enabled input, the electronically receiving the user status information and the electronically receiving the selection information at least in part to electronically obtain treatment instructional information regarding one or more subsequent injection operations on one or more portions of one or more ingestible substrate structures is carried out by electronically receiving (e.g. including the network cable component s502 carries information to the transceiver component s522, and/or etc.) user status information (e.g. including identification, characteristics, affiliations, and/or etc.) regarding one or more particular individual living beings (e.g. including one or more particular human beings, animals, and/or etc.) including one or more identifiers (e.g. including identification numbers, order numbers, passwords, biometric data such as voice prints, stored in information storage subsystem 200, and/or etc.) associated with the one or more particular individual living beings (e.g. including one or more humans, animals, and/or etc.) and electronically receiving (e.g. including through the receiver component s528, and/or etc.) selection information (e.g. including preferences, choices, and/or etc.) at least in part identifying (e.g. including textual descriptions, graphical representations, and/or etc.) one or more selected ingestible products (e.g. including sandwiches, snack bars, full course meals, and/or etc.) being subject to ingestion (e.g. including oral, dermal, nasal, and/or etc.) by the one or more particular individual living beings (e.g. including one or more humans, animals, and/or etc.), the selection information (e.g. including likes, dislikes, meal selection, and/or etc.) electronically received (e.g. including through the transceiver component s522, and/or etc.) via electronically enabled input (e.g. including voice, gesture, keypad, and/or etc.), the electronically receiving (e.g. including through transceiver component s522, and/or etc.) the user status information (e.g. including identification, associated location information, memberships, and/or etc.) and the electronically receiving (e.g. including through transceiver component s522, and/or etc.) the selection information (e.g. including ingestible materials desired, and/or etc.) at least in part to electronically obtain (e.g. including through data packets, and/or etc.) treatment instructional information (e.g. including methodology, preparation steps, and/or etc.) regarding one or more subsequent injection operations (e.g. including needle injection, jet injection, and/or etc.) on one or more portions of one or more ingestible substrate structures (e.g. including bars, sheets, and/or etc.).

Figure 47:
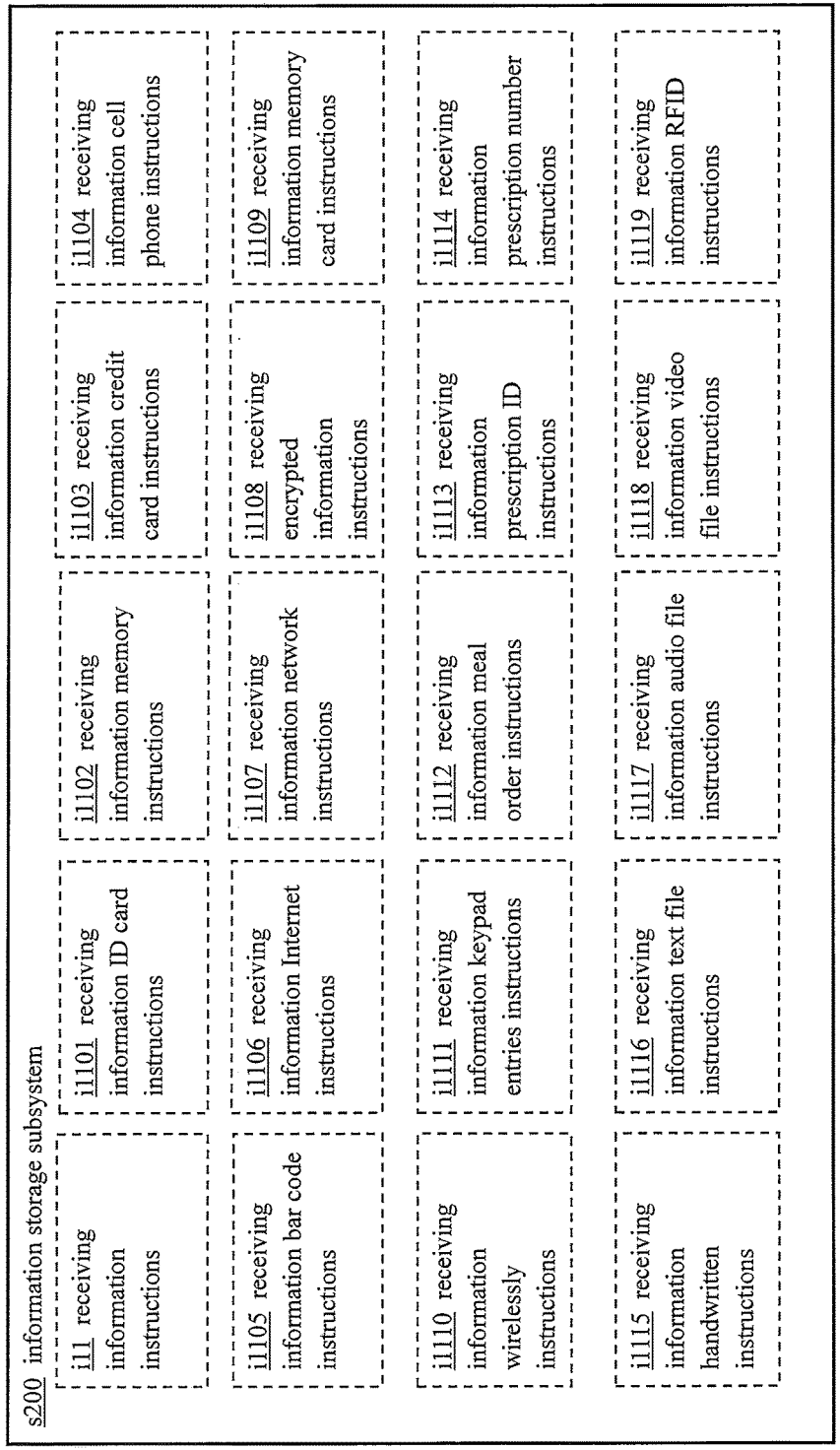
FIG. 47 is a block diagram depicting one or more exemplary instructions of the information storage subsystem s200 of the ingestible product preparation system 10 of FIG. 1.
Figure 62:
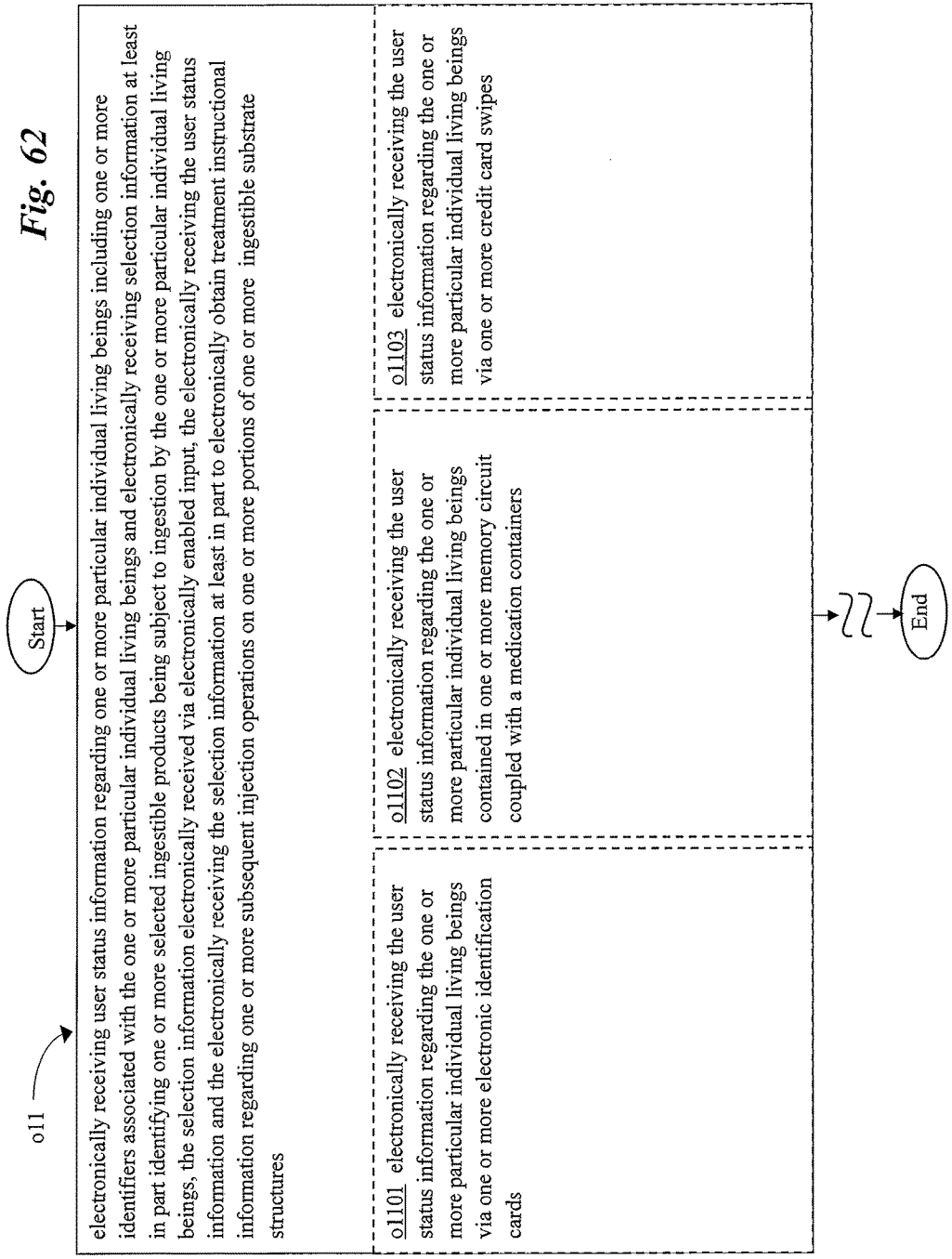
FIG. 62 is a high-level flowchart including exemplary implementations of operation O11 of FIG. 61.

In one or more implementations, as shown in FIG. 62, operation o11 includes an operation o1101 for electronically receiving the user status information regarding the one or more particular individual living beings via one or more electronic identification cards. Origination of an illustratively derived receiving information ID card component group can be accomplished through skilled in the art design choice selection of one or more of the above depicted components from one or more of the above depicted subsystems shown in FIG. 30. Components from the receiving information ID card component group can be used in implementing execution of the one or more receiving information ID card instructions i1101 of FIG. 47, can be used in performance of the receiving information ID card electrical circuitry arrangement e1101 of FIG. 40, and/or can be used in otherwise fulfillment of the operation o1101. An exemplary non-transitory signal bearing medium version of the information storage subsystem s200 is depicted in FIG. 47 as bearing the one or more receiving information ID card instructions i1101 that when executed will direct performance of the operation o1101. Furthermore, the receiving information ID card electrical circuitry arrangement ("elec circ arrange") e1101, when activated, will perform the operation o1101. Also, the receiving information ID card module m1101, when executed and/or activated, will direct performance of and/or perform the operation o1101. For instance, in one or more exemplary implementations, the one or more receiving information ID card instructions i1101, when executed, direct performance of the operation o1101 in the illustrative depiction as follows, and/or the receiving information ID card electrical circuitry arrangement e1101, when activated, performs the operation o1101 in the illustrative depiction as follows, and/or the receiving information ID card module m1101, when executed and/or activated, directs performance of and/or performs the operation o1101 in the illustrative depiction as follows, and/or the operation o1101 is otherwise carried out in the illustrative depiction as follows: electronically receiving the user status information regarding the one or more particular individual living beings via one or more electronic identification cards (e.g. including an implementation of the receiver component s528 is configured to electronically engage with a card having memory storage holding the user status information, and/or etc.).

In one or more implementations, as shown in FIG. 62, operation o11 includes an operation o1102 for electronically receiving the user status information regarding the one or more particular individual living beings contained in one or more memory circuit coupled with a medication containers. Origination of an illustratively derived receiving information memory component group can be accomplished through skilled in the art design choice selection of one or more of the above depicted components from one or more of the above depicted subsystems shown in FIG. 30. Components from the receiving information memory component group can be used in implementing execution of the one or more receiving information memory instructions i1102 of FIG. 47, can be used in performance of the receiving information memory electrical circuitry arrangement e1102 of FIG. 40, and/or can be used in otherwise fulfillment of the operation o1102. An exemplary non-transitory signal bearing medium version of the information storage subsystem s200 is depicted in FIG. 47 as bearing the one or more receiving information memory instructions i1102 that when executed will direct performance of the operation o1102. Furthermore, the receiving information memory electrical circuitry arrangement ("elec circ arrange") e1102, when activated, will perform the operation o1102. Also, the receiving information memory module m1102, when executed and/or activated, will direct performance of and/or perform the operation o1102. For instance, in one or more exemplary implementations, the one or more receiving information memory instructions i1102, when executed, direct performance of the operation o1102 in the illustrative depiction as follows, and/or the receiving information memory electrical circuitry arrangement e1102, when activated, performs the operation o1102 in the illustrative depiction as follows, and/or the receiving information memory module m1102, when executed and/or activated, directs performance of and/or performs the operation o1102 in the illustrative depiction as follows, and/or the operation o1102 is otherwise carried out in the illustrative depiction as follows: electronically receiving the user status information regarding the one or more particular individual living beings contained in one or more memory circuit (e.g. including RAM component s202, and/or etc.) coupled with a medication containers (e.g. including an implementation of the receiver component s528 is configured to electronically engage with a memory storage coupled with a medication container to receive the user status information in electronic form, and/or etc.).

In one or more implementations, as shown in FIG. 62, operation o11 includes an operation o1103 for electronically receiving the user status information regarding the one or more particular individual living beings via one or more credit card swipes. Origination of an illustratively derived receiving information credit card component group can be accomplished through skilled in the art design choice selection of one or more of the above depicted components from one or more of the above depicted subsystems shown in FIG. 30. Components from the receiving information credit card component group can be used in implementing execution of the one or more receiving information credit card instructions i1103 of FIG. 47, can be used in performance of the receiving information credit card electrical circuitry arrangement e1103 of FIG. 40, and/or can be used in otherwise fulfillment of the operation o1103. An exemplary non-transitory signal bearing medium version of the information storage subsystem s200 is depicted in FIG. 47 as bearing the one or more receiving information credit card instructions i1103 that when executed will direct performance of the operation o1103. Furthermore, the receiving information credit card electrical circuitry arrangement ("elec circ arrange") e1103, when activated, will perform the operation o1103. Also, the receiving information credit card module m1103, when executed and/or activated, will direct performance of and/or perform the operation o1103. For instance, in one or more exemplary implementations, the one or more receiving information credit card instructions i1103, when executed, direct performance of the operation o1103 in the illustrative depiction as follows, and/or the receiving information credit card electrical circuitry arrangement e1103, when activated, performs the operation o1103 in the illustrative depiction as follows, and/or the receiving information credit card module m1103, when executed and/or activated, directs performance of and/or performs the operation o1103 in the illustrative depiction as follows, and/or the operation o1103 is otherwise carried out in the illustrative depiction as follows: electronically receiving the user status information regarding the one or more particular individual living beings via one or more credit card swipes (e.g. including an implementation of the receiver component s528 is configured to electronically engage with an electronic memory stripe integrated into a credit card to receive the user status information, and/or etc.).

Figure 63:
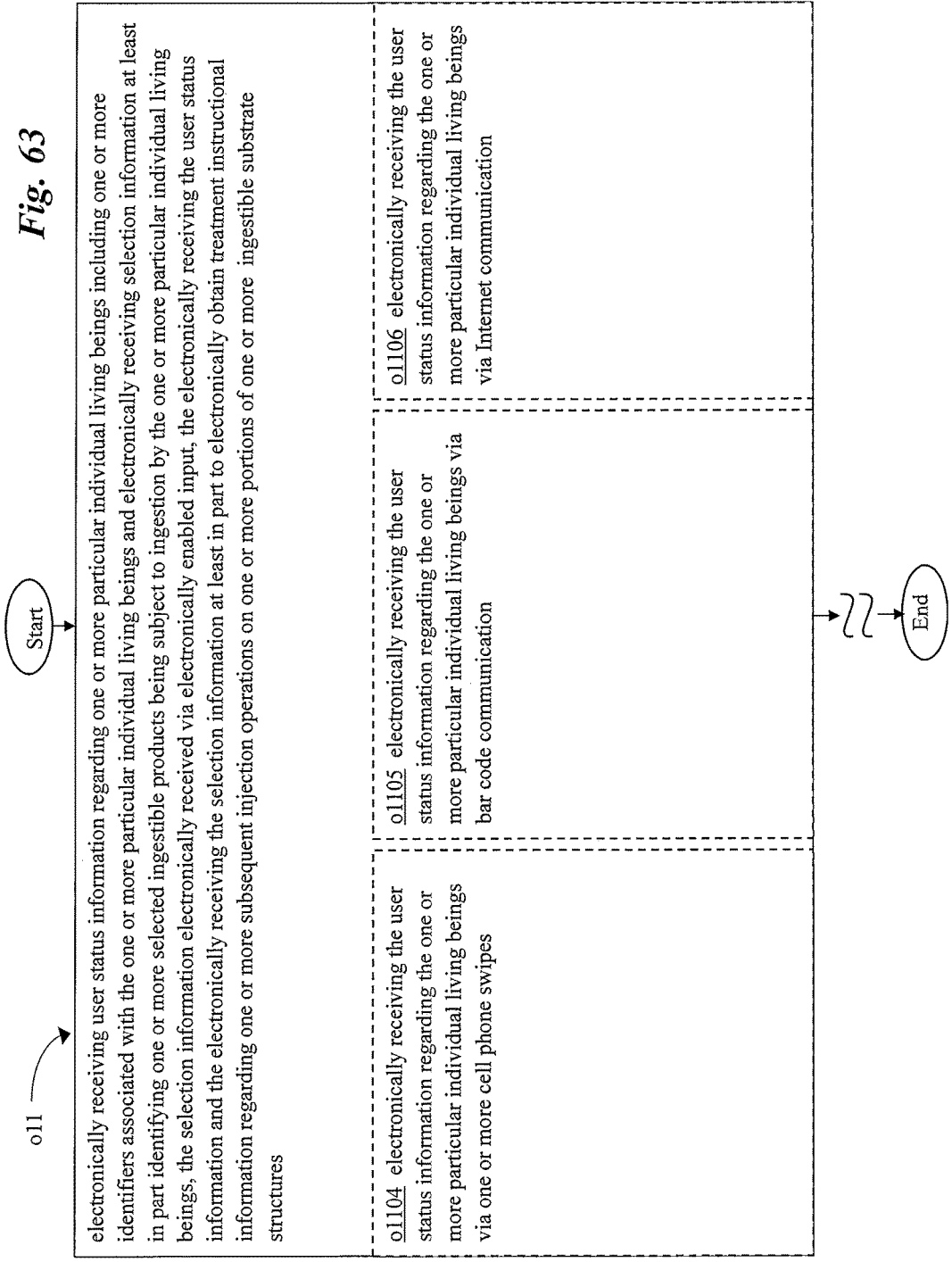
FIG. 63 is a high-level flowchart including exemplary implementations of operation O11 of FIG. 61.

In one or more implementations, as shown in FIG. 63, operation o11 includes an operation o1104 for electronically receiving the user status information regarding the one or more particular individual living beings via one or more cell phone swipes. Origination of an illustratively derived receiving information cell phone component group can be accomplished through skilled in the art design choice selection of one or more of the above depicted components from one or more of the above depicted subsystems shown in FIG. 30. Components from the receiving information cell phone component group can be used in implementing execution of the one or more receiving information cell phone instructions i1104 of FIG. 47, can be used in performance of the receiving information cell phone electrical circuitry arrangement e1104 of FIG. 40, and/or can be used in otherwise fulfillment of the operation o1104. An exemplary non-transitory signal bearing medium version of the information storage subsystem s200 is depicted in FIG. 47 as bearing the one or more receiving information cell phone instructions i1104 that when executed will direct performance of the operation o1104. Furthermore, the receiving information cell phone electrical circuitry arrangement ("elec circ arrange") e1104, when activated, will perform the operation o1104. Also, the receiving information cell phone module m1104, when executed and/or activated, will direct performance of and/or perform the operation o1104. For instance, in one or more exemplary implementations, the one or more receiving information cell phone instructions i1104, when executed, direct performance of the operation o1104 in the illustrative depiction as follows, and/or the receiving information cell phone electrical circuitry arrangement e1104, when activated, performs the operation o1104 in the illustrative depiction as follows, and/or the receiving information cell phone module m1104, when executed and/or activated, directs performance of and/or performs the operation o1104 in the illustrative depiction as follows, and/or the operation o1104 is otherwise carried out in the illustrative depiction as follows: electronically receiving the user status information regarding the one or more particular individual living beings via one or more cell phone swipes (e.g. including an implementation of the receiver component s528 is configured to electronically engage with an electronic memory component integrated into a cell phone to receive the user status information, and/or etc.).

In one or more implementations, as shown in FIG. 63, operation o11 includes an operation o1105 for electronically receiving the user status information regarding the one or more particular individual living beings via bar code communication. Origination of an illustratively derived receiving information bar code component group can be accomplished through skilled in the art design choice selection of one or more of the above depicted components from one or more of the above depicted subsystems shown in FIG. 30. Components from the receiving information bar code component group can be used in implementing execution of the one or more receiving information bar code instructions i1105 of FIG. 47, can be used in performance of the receiving information bar code electrical circuitry arrangement e1105 of FIG. 40, and/or can be used in otherwise fulfillment of the operation o1105. An exemplary non-transitory signal bearing medium version of the information storage subsystem s200 is depicted in FIG. 47 as bearing the one or more receiving information bar code instructions i1105 that when executed will direct performance of the operation o1105. Furthermore, the receiving information bar code electrical circuitry arrangement ("elec circ arrange") e1105, when activated, will perform the operation o1105. Also, the receiving information bar code module m1105, when executed and/or activated, will direct performance of and/or perform the operation o1105. For instance, in one or more exemplary implementations, the one or more receiving information bar code instructions i1105, when executed, direct performance of the operation o1105 in the illustrative depiction as follows, and/or the receiving information bar code electrical circuitry arrangement e1105, when activated, performs the operation o1105 in the illustrative depiction as follows, and/or the receiving information bar code module m1105, when executed and/or activated, directs performance of and/or performs the operation o1105 in the illustrative depiction as follows, and/or the operation o1105 is otherwise carried out in the illustrative depiction as follows: electronically receiving the user status information regarding the one or more particular individual living beings via bar code communication (e.g. including an implementation of the receiver component s528 is configured to electronically read a bar code label to receive the user status information, and/or etc.).

In one or more implementations, as shown in FIG. 63, operation o11 includes an operation o1106 for electronically receiving the user status information regarding the one or more particular individual living beings via Internet communication. Origination of an illustratively derived receiving information Internet component group can be accomplished through skilled in the art design choice selection of one or more of the above depicted components from one or more of the above depicted subsystems shown in FIG. 30. Components from the receiving information Internet component group can be used in implementing execution of the one or more receiving information Internet instructions i1106 of FIG. 47, can be used in performance of the receiving information Internet electrical circuitry arrangement e1106 of FIG. 40, and/or can be used in otherwise fulfillment of the operation o1106. An exemplary non-transitory signal bearing medium version of the information storage subsystem s200 is depicted in FIG. 47 as bearing the one or more receiving information Internet instructions i1106 that when executed will direct performance of the operation o1106. Furthermore, the receiving information Internet electrical circuitry arrangement ("elec circ arrange") e1106, when activated, will perform the operation o1106. Also, the receiving information Internet module m1106, when executed and/or activated, will direct performance of and/or perform the operation o1106. For instance, in one or more exemplary implementations, the one or more receiving information Internet instructions i1106, when executed, direct performance of the operation o1106 in the illustrative depiction as follows, and/or the receiving information Internet electrical circuitry arrangement e1106, when activated, performs the operation o1106 in the illustrative depiction as follows, and/or the receiving information Internet module m1106, when executed and/or activated, directs performance of and/or performs the operation o1106 in the illustrative depiction as follows, and/or the operation o1106 is otherwise carried out in the illustrative depiction as follows: electronically receiving the user status information regarding the one or more particular individual living beings via Internet communication (e.g. including an implementation of the receiver component s528 is configured to electronically receive through the internet network component s508 the user status information, and/or etc.).

Figure 64:
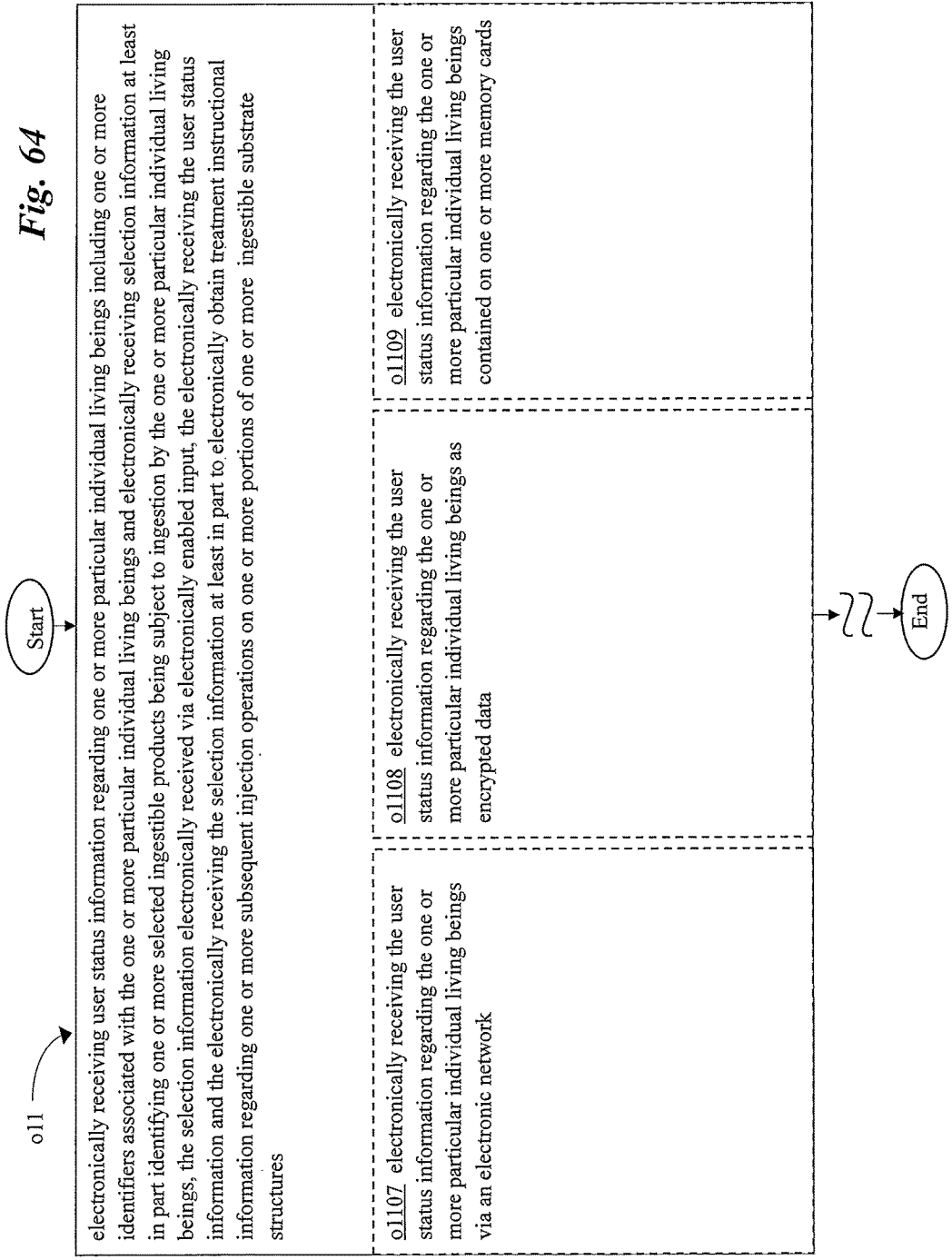
FIG. 64 is a high-level flowchart including exemplary implementations of operation O11 of FIG. 61.

In one or more implementations, as shown in FIG. 64, operation o11 includes an operation o1107 for electronically receiving the user status information regarding the one or more particular individual living beings via an electronic network. Origination of an illustratively derived receiving information network component group can be accomplished through skilled in the art design choice selection of one or more of the above depicted components from one or more of the above depicted subsystems shown in FIG. 30. Components from the receiving information network component group can be used in implementing execution of the one or more receiving information network instructions i1107 of FIG. 47, can be used in performance of the receiving information network electrical circuitry arrangement e1107 of FIG. 40, and/or can be used in otherwise fulfillment of the operation o1107. An exemplary non-transitory signal bearing medium version of the information storage subsystem s200 is depicted in FIG. 47 as bearing the one or more receiving information network instructions i1107 that when executed will direct performance of the operation o1107. Furthermore, the receiving information network electrical circuitry arrangement ("elec circ arrange") e1107, when activated, will perform the operation o1107. Also, the receiving information network module m1107, when executed and/or activated, will direct performance of and/or perform the operation o1107. For instance, in one or more exemplary implementations, the one or more receiving information network instructions i1107, when executed, direct performance of the operation o1107 in the illustrative depiction as follows, and/or the receiving information network electrical circuitry arrangement e1107, when activated, performs the operation o1107 in the illustrative depiction as follows, and/or the receiving information network module m1107, when executed and/or activated, directs performance of and/or performs the operation o1107 in the illustrative depiction as follows, and/or the operation o1107 is otherwise carried out in the illustrative depiction as follows: electronically receiving the user status information regarding the one or more particular individual living beings via an electronic network (e.g. including an implementation of the receiver component s528 is configured to electronically engage with the network cable component s502 to receive the user status information, and/or etc.).

In one or more implementations, as shown in FIG. 64, operation o11 includes an operation o1108 for electronically receiving the user status information regarding the one or more particular individual living beings as encrypted data. Origination of an illustratively derived receiving encrypted information component group can be accomplished through skilled in the art design choice selection of one or more of the above depicted components from one or more of the above depicted subsystems shown in FIG. 30. Components from the receiving encrypted information component group can be used in implementing execution of the one or more receiving encrypted information instructions i1108 of FIG. 47, can be used in performance of the receiving encrypted information electrical circuitry arrangement e1108 of FIG. 40, and/or can be used in otherwise fulfillment of the operation o1108. An exemplary non-transitory signal bearing medium version of the information storage subsystem s200 is depicted in FIG. 47 as bearing the one or more receiving encrypted information instructions i1108 that when executed will direct performance of the operation o1108. Furthermore, the receiving encrypted information electrical circuitry arrangement ("elec circ arrange") e1108, when activated, will perform the operation o1108. Also, the receiving encrypted information module m1108, when executed and/or activated, will direct performance of and/or perform the operation o1108. For instance, in one or more exemplary implementations, the one or more receiving encrypted information instructions i1108, when executed, direct performance of the operation o1108 in the illustrative depiction as follows, and/or the receiving encrypted information electrical circuitry arrangement e1108, when activated, performs the operation o1108 in the illustrative depiction as follows, and/or the receiving encrypted information module m1108, when executed and/or activated, directs performance of and/or performs the operation o1108 in the illustrative depiction as follows, and/or the operation o1108 is otherwise carried out in the illustrative depiction as follows: electronically receiving the user status information regarding the one or more particular individual living beings as encrypted data (e.g. including an implementation of the receiver component s528 is configured to electronically receive through the encrypted communication component s520 the user status information, and/or etc.).

In one or more implementations, as shown in FIG. 64, operation o11 includes an operation o1109 for electronically receiving the user status information regarding the one or more particular individual living beings contained on one or more memory cards. Origination of an illustratively derived receiving information memory card component group can be accomplished through skilled in the art design choice selection of one or more of the above depicted components from one or more of the above depicted subsystems shown in FIG. 30. Components from the receiving information memory card component group can be used in implementing execution of the one or more receiving information memory card instructions i1109 of FIG. 47, can be used in performance of the receiving information memory card electrical circuitry arrangement e1109 of FIG. 40, and/or can be used in otherwise fulfillment of the operation o1109. An exemplary non-transitory signal bearing medium version of the information storage subsystem s200 is depicted in FIG. 47 as bearing the one or more receiving information memory card instructions i1109 that when executed will direct performance of the operation o1109. Furthermore, the receiving information memory card electrical circuitry arrangement ("elec circ arrange") e1109, when activated, will perform the operation o1109. Also, the receiving information memory card module m1109, when executed and/or activated, will direct performance of and/or perform the operation o1109. For instance, in one or more exemplary implementations, the one or more receiving information memory card instructions i1109, when executed, direct performance of the operation o1109 in the illustrative depiction as follows, and/or the receiving information memory card electrical circuitry arrangement e1109, when activated, performs the operation o1109 in the illustrative depiction as follows, and/or the receiving information memory card module m1109, when executed and/or activated, directs performance of and/or performs the operation o1109 in the illustrative depiction as follows, and/or the operation o1109 is otherwise carried out in the illustrative depiction as follows: electronically receiving the user status information regarding the one or more particular individual living beings contained on one or more memory cards (e.g. including an implementation of the receiver component s528 is configured to electronically engage with an electronic memory card to receive the user status information, and/or etc.).

In one or more implementations, as shown in FIG. 65, operation o11 includes an operation o1110 for electronically receiving the user status information regarding the one or more particular individual living beings wirelessly. Origination of an illustratively derived receiving information wirelessly component group can be accomplished through skilled in the art design choice selection of one or more of the above depicted components from one or more of the above depicted subsystems shown in FIG. 30. Components from the receiving information wirelessly component group can be used in implementing execution of the one or more receiving information wirelessly instructions i1110 of FIG. 47, can be used in performance of the receiving information wirelessly electrical circuitry arrangement e1110 of FIG. 40, and/or can be used in otherwise fulfillment of the operation o1110. An exemplary non-transitory signal bearing medium version of the information storage subsystem s200 is depicted in FIG. 47 as bearing the one or more receiving information wirelessly instructions i1110 that when executed will direct performance of the operation o1110. Furthermore, the receiving information wirelessly electrical circuitry arrangement ("elec circ arrange") e1110, when activated, will perform the operation o1110. Also, the receiving information wirelessly module m1110, when executed and/or activated, will direct performance of and/or perform the operation o1110. For instance, in one or more exemplary implementations, the one or more receiving information wirelessly instructions i1110, when executed, direct performance of the operation o1110 in the illustrative depiction as follows, and/or the receiving information wirelessly electrical circuitry arrangement e1110, when activated, performs the operation o1110 in the illustrative depiction as follows, and/or the receiving information wirelessly module m1110, when executed and/or activated, directs performance of and/or performs the operation o1110 in the illustrative depiction as follows, and/or the operation o1110 is otherwise carried out in the illustrative depiction as follows: electronically receiving the user status information regarding the one or more particular individual living beings wirelessly (e.g. including an implementation of the receiver component s528 is configured to electronically receive through the wireless network component s512 the user status information, and/or etc.).

In one or more implementations, as shown in FIG. 65, operation o11 includes an operation o1111 for electronically receiving the user status information regarding the one or more particular individual living beings via one or more electronic keypad entries. Origination of an illustratively derived receiving information keypad entries component group can be accomplished through skilled in the art design choice selection of one or more of the above depicted components from one or more of the above depicted subsystems shown in FIG. 30. Components from the receiving information keypad entries component group can be used in implementing execution of the one or more receiving information keypad entries instructions i1111 of FIG. 47, can be used in performance of the receiving information keypad entries electrical circuitry arrangement e1111 of FIG. 40, and/or can be used in otherwise fulfillment of the operation o1111. An exemplary non-transitory signal bearing medium version of the information storage subsystem s200 is depicted in FIG. 47 as bearing the one or more receiving information keypad entries instructions i1111 that when executed will direct performance of the operation o1111. Furthermore, the receiving information keypad entries electrical circuitry arrangement ("elec circ arrange") e1111, when activated, will perform the operation o1111. Also, the receiving information keypad entries module m1111, when executed and/or activated, will direct performance of and/or perform the operation o1111. For instance, in one or more exemplary implementations, the one or more receiving information keypad entries instructions i1111, when executed, direct performance of the operation o1111 in the illustrative depiction as follows, and/or the receiving information keypad entries electrical circuitry arrangement e1111, when activated, performs the operation o1111 in the illustrative depiction as follows, and/or the receiving information keypad entries module m1111, when executed and/or activated, directs performance of and/or performs the operation o1111 in the illustrative depiction as follows, and/or the operation o1111 is otherwise carried out in the illustrative depiction as follows: electronically receiving the user status information regarding the one or more particular individual living beings via one or more electronic keypad entries (e.g. including an implementation of the receiver component s528 is configured to electronically engage with the keypad component s308 to receive the user status information as inputted by a user, and/or etc.).

In one or more implementations, as shown in FIG. 65, operation o11 includes an operation o1112 for electronically receiving the user status information regarding the one or more particular individual living beings including the one or more identifiers associated with the one or more particular individual living beings as further associated with one or more restaurant meal orders. Origination of an illustratively derived receiving information meal order component group can be accomplished through skilled in the art design choice selection of one or more of the above depicted components from one or more of the above depicted subsystems shown in FIG. 30. Components from the receiving information meal order component group can be used in implementing execution of the one or more receiving information meal order instructions i1112 of FIG. 47, can be used in performance of the receiving information meal order electrical circuitry arrangement e1112 of FIG. 40, and/or can be used in otherwise fulfillment of the operation o1112. An exemplary non-transitory signal bearing medium version of the information storage subsystem s200 is depicted in FIG. 47 as bearing the one or more receiving information meal order instructions i1112 that when executed will direct performance of the operation o1112. Furthermore, the receiving information meal order electrical circuitry arrangement ("elec circ arrange") e1112, when activated, will perform the operation o1112. Also, the receiving information meal order module m1112, when executed and/or activated, will direct performance of and/or perform the operation o1112. For instance, in one or more exemplary implementations, the one or more receiving information meal order instructions i1112, when executed, direct performance of the operation o1112 in the illustrative depiction as follows, and/or the receiving information meal order electrical circuitry arrangement e1112, when activated, performs the operation o1112 in the illustrative depiction as follows, and/or the receiving information meal order module m1112, when executed and/or activated, directs performance of and/or performs the operation o1112 in the illustrative depiction as follows, and/or the operation o1112 is otherwise carried out in the illustrative depiction as follows: electronically receiving the user status information regarding the one or more particular individual living beings including the one or more identifiers associated with the one or more particular individual living beings via one or more restaurant meal orders (e.g. including an implementation of the receiver component s528 is configured to electronically engage with the processor component s102 to receive the user status information including the one or more identifiers associated with the one or more particular individual living beings via a meal order electronically inputted by a wait staff person, and/or etc.).

Figure 66:
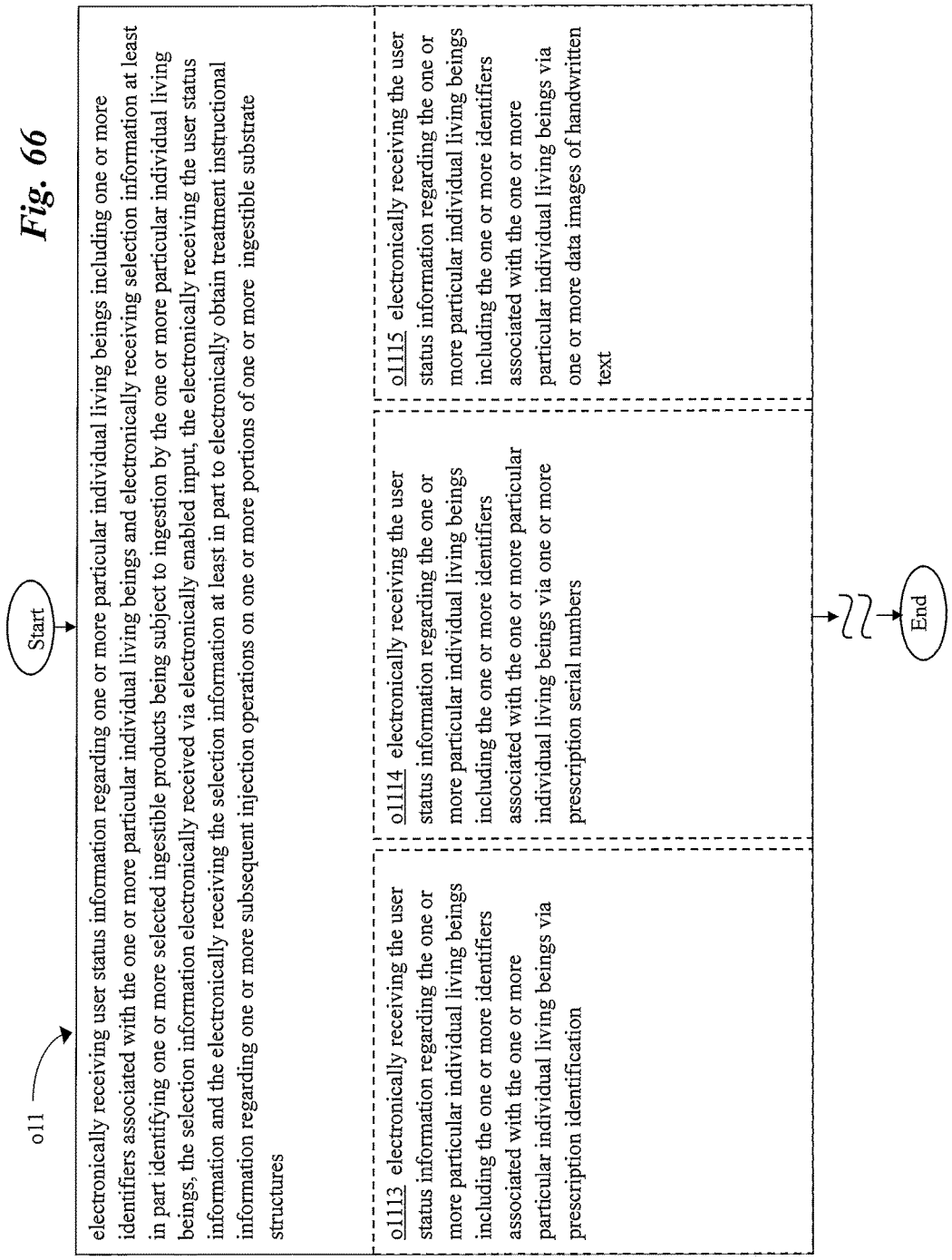
FIG. 66 is a high-level flowchart including exemplary implementations of operation O11 of FIG. 61.

In one or more implementations, as shown in FIG. 66, operation o11 includes an operation o1113 for electronically receiving the user status information regarding the one or more particular individual living beings including the one or more identifiers associated with the one or more particular individual living beings via prescription identification. Origination of an illustratively derived receiving information prescription ID component group can be accomplished through skilled in the art design choice selection of one or more of the above depicted components from one or more of the above depicted subsystems shown in FIG. 30. Components from the receiving information prescription ID component group can be used in implementing execution of the one or more receiving information prescription ID instructions i1113 of FIG. 47, can be used in performance of the receiving information prescription ID electrical circuitry arrangement e1113 of FIG. 40, and/or can be used in otherwise fulfillment of the operation o1113. An exemplary non-transitory signal bearing medium version of the information storage subsystem s200 is depicted in FIG. 47 as bearing the one or more receiving information prescription ID instructions i1113 that when executed will direct performance of the operation o1113. Furthermore, the receiving information prescription ID electrical circuitry arrangement ("elec circ arrange") e1113, when activated, will perform the operation o1113. Also, the receiving information prescription ID module m1113, when executed and/or activated, will direct performance of and/or perform the operation o1113. For instance, in one or more exemplary implementations, the one or more receiving information prescription ID instructions i1113, when executed, direct performance of the operation o1113 in the illustrative depiction as follows, and/or the receiving information prescription ID electrical circuitry arrangement e1113, when activated, performs the operation o1113 in the illustrative depiction as follows, and/or the receiving information prescription ID module m1113, when executed and/or activated, directs performance of and/or performs the operation o1113 in the illustrative depiction as follows, and/or the operation o1113 is otherwise carried out in the illustrative depiction as follows: electronically receiving the user status information regarding the one or more particular individual living beings including the one or more identifiers associated with the one or more particular individual living beings via prescription identification (e.g. including an implementation of the receiver component s528 is configured to electronically engage with the processor component s102 to receive the user status information including the one or more identifiers associated with the particular individual living being as determined by the processor component to include a prescription identification, and/or etc.).

In one or more implementations, as shown in FIG. 66, operation o11 includes an operation o1114 for electronically receiving the user status information regarding the one or more particular individual living beings including the one or more identifiers associated with the one or more particular individual living beings via one or more prescription serial numbers. Origination of an illustratively derived receiving information prescription number component group can be accomplished through skilled in the art design choice selection of one or more of the above depicted components from one or more of the above depicted subsystems shown in FIG. 30. Components from the receiving information prescription number component group can be used in implementing execution of the one or more receiving information prescription number instructions i1114 of FIG. 47, can be used in performance of the receiving information prescription number electrical circuitry arrangement e1114 of FIG. 40, and/or can be used in otherwise fulfillment of the operation o1114. An exemplary non-transitory signal bearing medium version of the information storage subsystem s200 is depicted in FIG. 47 as bearing the one or more receiving information prescription number instructions i1114 that when executed will direct performance of the operation o1114. Furthermore, the receiving information prescription number electrical circuitry arrangement ("elec circ arrange") e1114, when activated, will perform the operation o1114. Also, the receiving information prescription number module m1114, when executed and/or activated, will direct performance of and/or perform the operation o1114. For instance, in one or more exemplary implementations, the one or more receiving information prescription number instructions i1114, when executed, direct performance of the operation o1114 in the illustrative depiction as follows, and/or the receiving information prescription number electrical circuitry arrangement e1114, when activated, performs the operation o1114 in the illustrative depiction as follows, and/or the receiving information prescription number module m1114, when executed and/or activated, directs performance of and/or performs the operation o1114 in the illustrative depiction as follows, and/or the operation o1114 is otherwise carried out in the illustrative depiction as follows: electronically receiving the user status information regarding the one or more particular individual living beings including the one or more identifiers associated with the one or more particular individual living beings via one or more prescription serial numbers (e.g. including an implementation of the receiver component s528 is configured to electronically engage with the processor component s102 to receive the user status information including the one or more identifiers associated with the particular individual living being as determined by the processor component to include a prescription serial number, and/or etc.).

In one or more implementations, as shown in FIG. 66, operation o11 includes an operation o1115 for electronically receiving the user status information regarding the one or more particular individual living beings including the one or more identifiers associated with the one or more particular individual living beings via one or more data images of handwritten text. Origination of an illustratively derived receiving information handwritten component group can be accomplished through skilled in the art design choice selection of one or more of the above depicted components from one or more of the above depicted subsystems shown in FIG. 30. Components from the receiving information handwritten component group can be used in implementing execution of the one or more receiving information handwritten instructions i1115 of FIG. 47, can be used in performance of the receiving information handwritten electrical circuitry arrangement e1115 of FIG. 40, and/or can be used in otherwise fulfillment of the operation o1115. An exemplary non-transitory signal bearing medium version of the information storage subsystem s200 is depicted in FIG. 47 as bearing the one or more receiving information handwritten instructions i1115 that when executed will direct performance of the operation o1115. Furthermore, the receiving information handwritten electrical circuitry arrangement ("elec circ arrange") e1115, when activated, will perform the operation o1115. Also, the receiving information handwritten module m1115, when executed and/or activated, will direct performance of and/or perform the operation o1115. For instance, in one or more exemplary implementations, the one or more receiving information handwritten instructions i1115, when executed, direct performance of the operation o1115 in the illustrative depiction as follows, and/or the receiving information handwritten electrical circuitry arrangement e1115, when activated, performs the operation o1115 in the illustrative depiction as follows, and/or the receiving information handwritten module m1115, when executed and/or activated, directs performance of and/or performs the operation o1115 in the illustrative depiction as follows, and/or the operation o1115 is otherwise carried out in the illustrative depiction as follows: electronically receiving the user status information regarding the one or more particular individual living beings including the one or more identifiers associated with the one or more particular individual living beings via one or more data images of handwritten text (e.g. including an implementation of the receiver component s528 is configured to electronically engage with the processor component s102 to receive the user status information regarding the particular individual living being including the one or more identifiers associated with the particular individual living being as determined by the processor component through electronic handwriting analysis of the data image of the handwritten text, and/or etc.).

Figure 67:
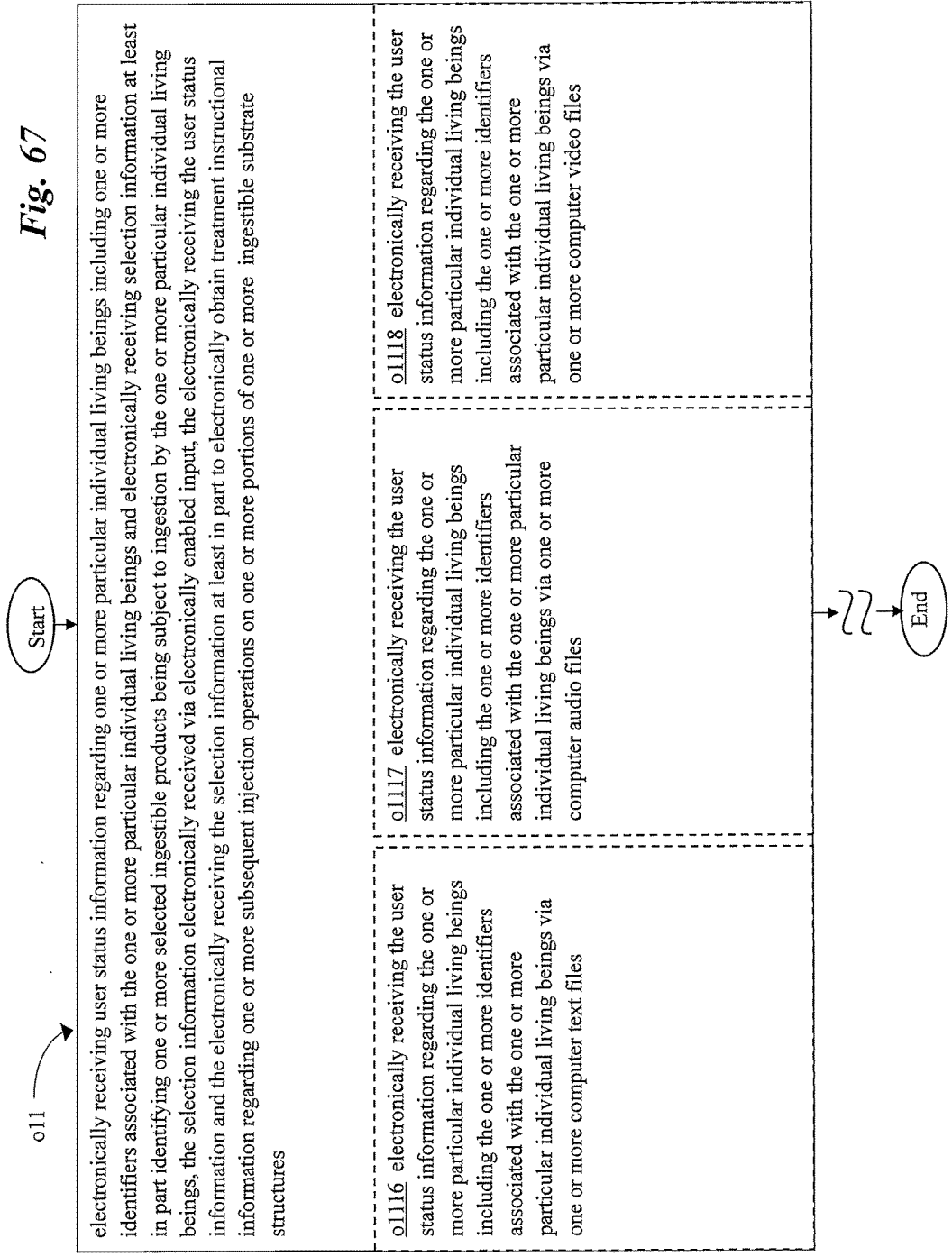
FIG. 67 is a high-level flowchart including exemplary implementations of operation O11 of FIG. 61.

In one or more implementations, as shown in FIG. 67, operation o11 includes an operation o1116 for electronically receiving the user status information regarding the one or more particular individual living beings including the one or more identifiers associated with the one or more particular individual living beings via one or more computer text files. Origination of an illustratively derived receiving information text file component group can be accomplished through skilled in the art design choice selection of one or more of the above depicted components from one or more of the above depicted subsystems shown in FIG. 30. Components from the receiving information text file component group can be used in implementing execution of the one or more receiving information text file instructions i1116 of FIG. 47, can be used in performance of the receiving information text file electrical circuitry arrangement e1116 of FIG. 40, and/or can be used in otherwise fulfillment of the operation o1116. An exemplary non-transitory signal bearing medium version of the information storage subsystem s200 is depicted in FIG. 47 as bearing the one or more receiving information text file instructions i1116 that when executed will direct performance of the operation o1116. Furthermore, the receiving information text file electrical circuitry arrangement ("elec circ arrange") e1116, when activated, will perform the operation o1116. Also, the receiving information text file module m1116, when executed and/or activated, will direct performance of and/or perform the operation o1116. For instance, in one or more exemplary implementations, the one or more receiving information text file instructions i1116, when executed, direct performance of the operation o1116 in the illustrative depiction as follows, and/or the receiving information text file electrical circuitry arrangement e1116, when activated, performs the operation o1116 in the illustrative depiction as follows, and/or the receiving information text file module m1116, when executed and/or activated, directs performance of and/or performs the operation o1116 in the illustrative depiction as follows, and/or the operation o1116 is otherwise carried out in the illustrative depiction as follows: electronically receiving the user status information regarding the one or more particular individual living beings including the one or more identifiers associated with the one or more particular individual living beings via one or more computer text files (e.g. including an implementation of the receiver component s528 is configured to electronically engage with the processor component s102 to receive the user status information including the one or more identifiers associated with the particular individual living being as determined by the processor component through electronic reading of the computer text file, and/or etc.).

In one or more implementations, as shown in FIG. 67, operation o11 includes an operation o1117 for electronically receiving the user status information regarding the one or more particular individual living beings including the one or more identifiers associated with the one or more particular individual living beings via one or more computer audio files. Origination of an illustratively derived receiving information audio file component group can be accomplished through skilled in the art design choice selection of one or more of the above depicted components from one or more of the above depicted subsystems shown in FIG. 30. Components from the receiving information audio file component group can be used in implementing execution of the one or more receiving information audio file instructions i1117 of FIG. 47, can be used in performance of the receiving information audio file electrical circuitry arrangement e1117 of FIG. 40, and/or can be used in otherwise fulfillment of the operation o1117. An exemplary non-transitory signal bearing medium version of the information storage subsystem s200 is depicted in FIG. 47 as bearing the one or more receiving information audio file instructions i1117 that when executed will direct performance of the operation o1117. Furthermore, the receiving information audio file electrical circuitry arrangement ("elec circ arrange") e1117, when activated, will perform the operation o1117. Also, the receiving information audio file module m1117, when executed and/or activated, will direct performance of and/or perform the operation o1117. For instance, in one or more exemplary implementations, the one or more receiving information audio file instructions i1117, when executed, direct performance of the operation o1117 in the illustrative depiction as follows, and/or the receiving information audio file electrical circuitry arrangement e1117, when activated, performs the operation o1117 in the illustrative depiction as follows, and/or the receiving information audio file module m1117, when executed and/or activated, directs performance of and/or performs the operation o1117 in the illustrative depiction as follows, and/or the operation o1117 is otherwise carried out in the illustrative depiction as follows: electronically receiving the user status information regarding the one or more particular individual living beings including the one or more identifiers associated with the one or more particular individual living beings via one or more computer audio files (e.g. including an implementation of the receiver component s528 is configured to electronically engage with the processor component s102 to receive the user status information including the one or more identifiers associated with the particular individual living being as determined by the processor component through electronic reading of the computer audio file, and/or etc.).

In one or more implementations, as shown in FIG. 67, operation o11 includes an operation o1118 for electronically receiving the user status information regarding the one or more particular individual living beings including the one or more identifiers associated with the one or more particular individual living beings via one or more computer video files. Origination of an illustratively derived receiving information video file component group can be accomplished through skilled in the art design choice selection of one or more of the above depicted components from one or more of the above depicted subsystems shown in FIG. 30. Components from the receiving information video file component group can be used in implementing execution of the one or more receiving information video file instructions i1118 of FIG. 47, can be used in performance of the receiving information video file electrical circuitry arrangement e1118 of FIG. 40, and/or can be used in otherwise fulfillment of the operation o1118. An exemplary non-transitory signal bearing medium version of the information storage subsystem s200 is depicted in FIG. 47 as bearing the one or more receiving information video file instructions i1118 that when executed will direct performance of the operation o1118. Furthermore, the receiving information video file electrical circuitry arrangement ("elec circ arrange") e1118, when activated, will perform the operation o1118. Also, the receiving information video file module m1118, when executed and/or activated, will direct performance of and/or perform the operation o1118. For instance, in one or more exemplary implementations, the one or more receiving information video file instructions i1118, when executed, direct performance of the operation o1118 in the illustrative depiction as follows, and/or the receiving information video file electrical circuitry arrangement e1118, when activated, performs the operation o1118 in the illustrative depiction as follows, and/or the receiving information video file module m1118, when executed and/or activated, directs performance of and/or performs the operation o1118 in the illustrative depiction as follows, and/or the operation o1118 is otherwise carried out in the illustrative depiction as follows: electronically receiving the user status information regarding the one or more particular individual living beings including the one or more particular individual living beings via one or more computer video files (e.g. including an implementation of the receiver component s528 is configured to electronically engage with the processor component s102 to receive the user status information including the one or more identifiers associated with the particular individual living being as determined by the processor component through electronic reading of the computer video file, and/or etc.).

Figure 68:
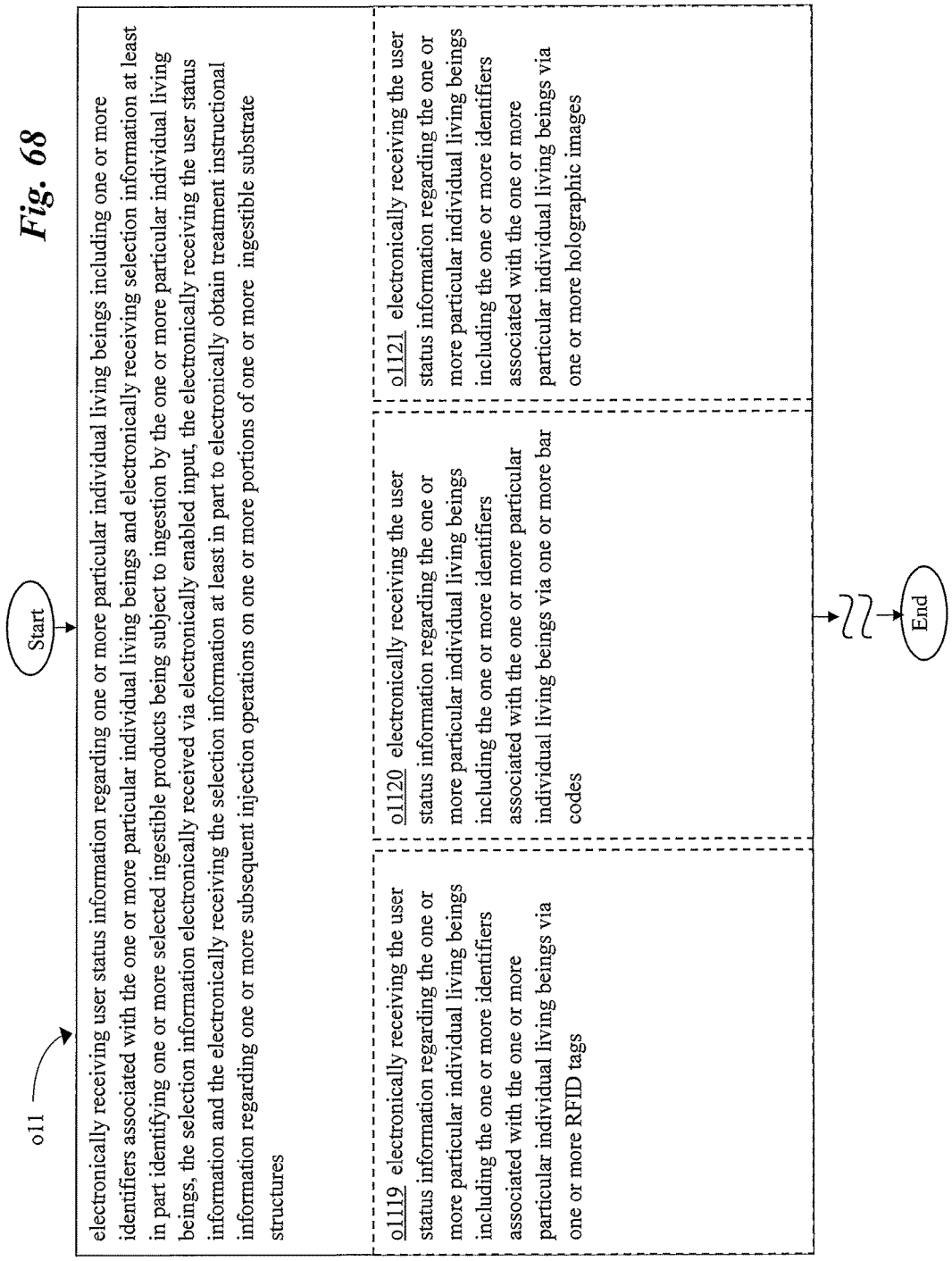
FIG. 68 is a high-level flowchart including exemplary implementations of operation O11 of FIG. 61.

In one or more implementations, as shown in FIG. 68, operation o11 includes an operation o1119 for electronically receiving the user status information regarding the one or more particular individual living beings including the one or more identifiers associated with the one or more particular individual living beings via one or more RFID tags. Origination of an illustratively derived receiving information RFID component group can be accomplished through skilled in the art design choice selection of one or more of the above depicted components from one or more of the above depicted subsystems shown in FIG. 30. Components from the receiving information RFID component group can be used in implementing execution of the one or more receiving information RFID instructions i1119 of FIG. 47, can be used in performance of the receiving information RFID electrical circuitry arrangement e1119 of FIG. 40, and/or can be used in otherwise fulfillment of the operation o1119. An exemplary non-transitory signal bearing medium version of the information storage subsystem s200 is depicted in FIG. 47 as bearing the one or more receiving information RFID instructions i1119 that when executed will direct performance of the operation o1119. Furthermore, the receiving information RFID electrical circuitry arrangement ("elec circ arrange") e1119, when activated, will perform the operation o1119. Also, the receiving information RFID module m1119, when executed and/or activated, will direct performance of and/or perform the operation o1119. For instance, in one or more exemplary implementations, the one or more receiving information RFID instructions i1119, when executed, direct performance of the operation o1119 in the illustrative depiction as follows, and/or the receiving information RFID electrical circuitry arrangement e1119, when activated, performs the operation o1119 in the illustrative depiction as follows, and/or the receiving information RFID module m1119, when executed and/or activated, directs performance of and/or performs the operation o1119 in the illustrative depiction as follows, and/or the operation o1119 is otherwise carried out in the illustrative depiction as follows: electronically receiving the user status information regarding the one or more particular individual living beings including the one or more identifiers associated with the one or more particular individual living beings via one or more RFID tags (e.g. including an implementation of the receiver component s528 is configured to electronically engage with the processor component s102 to receive the user status information including the one or more identifiers associated with the particular individual living being as determined by the processor component through electronic reading be the radio frequency identification (RFID) sensing component s414 of the RFID tag, and/or etc.).

In one or more implementations, as shown in FIG. 68, operation o11 includes an operation o1120 for electronically receiving the user status information regarding the one or more particular individual living beings including the one or more identifiers associated with the one or more particular individual living beings via one or more bar codes. Origination of an illustratively derived receiving information bar code component group can be accomplished through skilled in the art design choice selection of one or more of the above depicted components from one or more of the above depicted subsystems shown in FIG. 30. Components from the receiving information bar code component group can be used in implementing execution of the one or more receiving information bar code instructions i1120 of FIG. 48, can be used in performance of the receiving information bar code electrical circuitry arrangement e1120 of FIG. 41, and/or can be used in otherwise fulfillment of the operation o1120. An exemplary non-transitory signal bearing medium version of the information storage subsystem s200 is depicted in FIG. 48 as bearing the one or more receiving information bar code instructions i1120 that when executed will direct performance of the operation o1120. Furthermore, the receiving information bar code electrical circuitry arrangement ("elec circ arrange") e1120, when activated, will perform the operation o1120. Also, the receiving information bar code module m1120, when executed and/or activated, will direct performance of and/or perform the operation o1120. For instance, in one or more exemplary implementations, the one or more receiving information bar code instructions i1120, when executed, direct performance of the operation o1120 in the illustrative depiction as follows, and/or the receiving information bar code electrical circuitry arrangement e1120, when activated, performs the operation o1120 in the illustrative depiction as follows, and/or the receiving information bar code module m1120, when executed and/or activated, directs performance of and/or performs the operation o1120 in the illustrative depiction as follows, and/or the operation o1120 is otherwise carried out in the illustrative depiction as follows: electronically receiving the user status information regarding the one or more particular individual living beings including the one or more identifiers associated with the one or more particular individual living beings via one or more bar codes (e.g. including an implementation of the receiver component s528 is configured to electronically engage with the processor component s102 to receive the user status information including the one or more identifiers associated with the particular individual living being as determined by the processor component through electronic reading of the bar code, and/or etc.).

In one or more implementations, as shown in FIG. 68, operation o11 includes an operation o1121 for electronically receiving the user status information regarding the one or more particular individual living beings including the one or more identifiers associated with the one or more particular individual living beings via one or more holographic images. Origination of an illustratively derived receiving information holographic component group can be accomplished through skilled in the art design choice selection of one or more of the above depicted components from one or more of the above depicted subsystems shown in FIG. 30. Components from the receiving information holographic component group can be used in implementing execution of the one or more receiving information holographic instructions i1121 of FIG. 48, can be used in performance of the receiving information holographic electrical circuitry arrangement e1121 of FIG. 41, and/or can be used in otherwise fulfillment of the operation o1121. An exemplary non-transitory signal bearing medium version of the information storage subsystem s200 is depicted in FIG. 48 as bearing the one or more receiving information holographic instructions i1121 that when executed will direct performance of the operation o1121. Furthermore, the receiving information holographic electrical circuitry arrangement ("elec circ arrange") e1121, when activated, will perform the operation o1121. Also, the receiving information holographic module m1121, when executed and/or activated, will direct performance of and/or perform the operation o1121. For instance, in one or more exemplary implementations, the one or more receiving information holographic instructions i1121, when executed, direct performance of the operation o1121 in the illustrative depiction as follows, and/or the receiving information holographic electrical circuitry arrangement e1121, when activated, performs the operation o1121 in the illustrative depiction as follows, and/or the receiving information holographic module m1121, when executed and/or activated, directs performance of and/or performs the operation o1121 in the illustrative depiction as follows, and/or the operation o1121 is otherwise carried out in the illustrative depiction as follows: electronically receiving the user status information regarding the one or more particular individual living beings including the one or more identifiers associated with the one or more particular individual living beings via one or more holographic images (e.g. including an implementation of the receiver component s528 is configured to electronically engage with the processor component s102 to receive the user status information including the one or more identifiers associated with the particular individual living being as determined by the processor component through electronic reading of the holographic image, and/or etc.).

Figure 69:
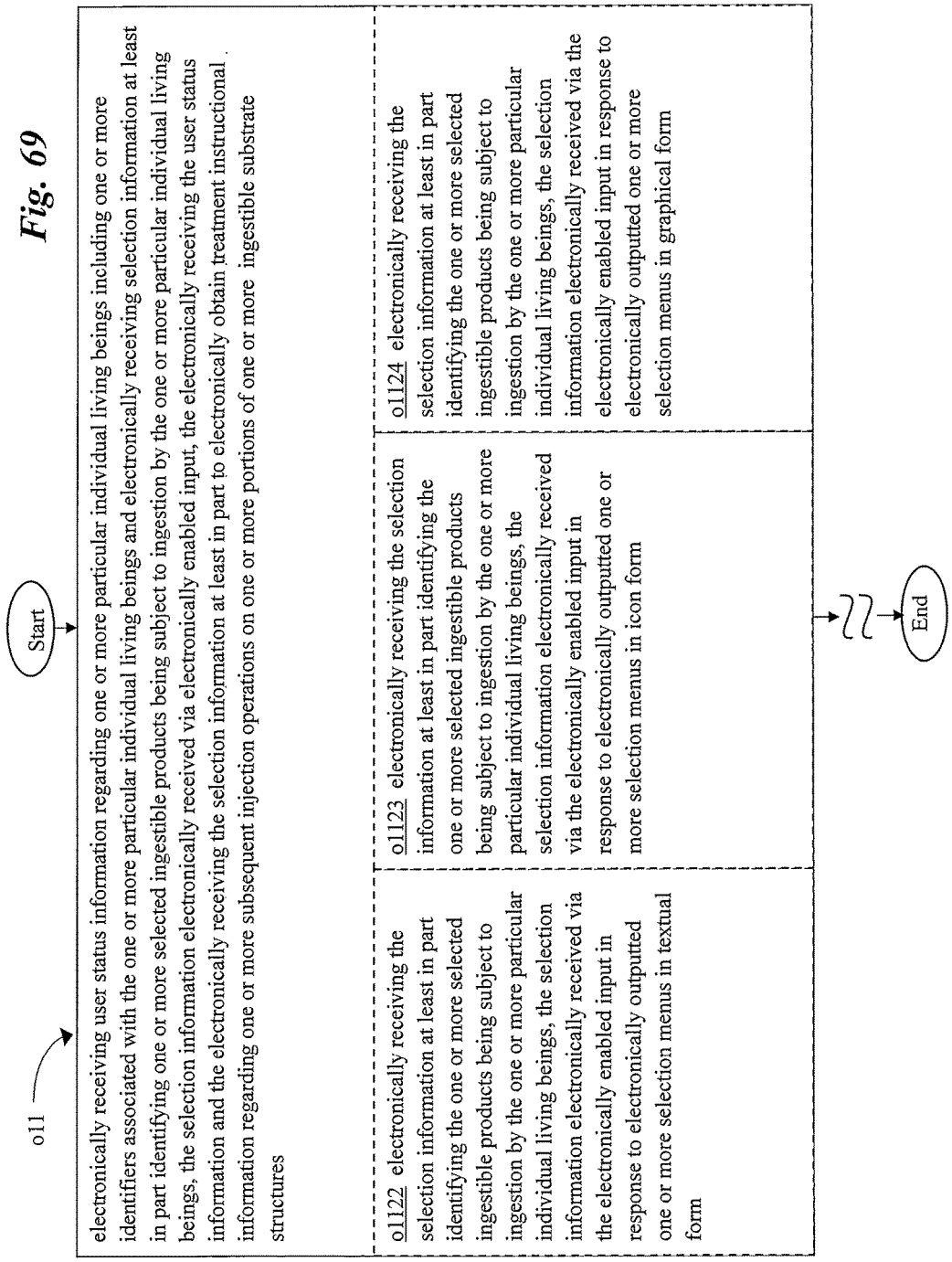
FIG. 69 is a high-level flowchart including exemplary implementations of operation O11 of FIG. 61.

In one or more implementations, as shown in FIG. 69, operation o11 includes an operation o1122 for electronically receiving the selection information at least in part identifying the one or more selected ingestible products being subject to ingestion by the one or more particular individual living beings, the selection information electronically received via the electronically enabled input in response to electronically outputted one or more selection menus in textual form. Origination of an illustratively derived receiving information textual component group can be accomplished through skilled in the art design choice selection of one or more of the above depicted components from one or more of the above depicted subsystems shown in FIG. 30. Components from the receiving information textual component group can be used in implementing execution of the one or more receiving information textual instructions i1122 of FIG. 48, can be used in performance of the receiving information textual electrical circuitry arrangement e1122 of FIG. 41, and/or can be used in otherwise fulfillment of the operation o1122. An exemplary non-transitory signal bearing medium version of the information storage subsystem s200 is depicted in FIG. 48 as bearing the one or more receiving information textual instructions i1122 that when executed will direct performance of the operation o1122. Furthermore, the receiving information textual electrical circuitry arrangement ("elec circ arrange") e1122, when activated, will perform the operation o1122. Also, the receiving information textual module m1122, when executed and/or activated, will direct performance of and/or perform the operation o1122. For instance, in one or more exemplary implementations, the one or more receiving information textual instructions i1122, when executed, direct performance of the operation o1122 in the illustrative depiction as follows, and/or the receiving information textual electrical circuitry arrangement e1122, when activated, performs the operation o1122 in the illustrative depiction as follows, and/or the receiving information textual module m1122, when executed and/or activated, directs performance of and/or performs the operation o1122 in the illustrative depiction as follows, and/or the operation o1122 is otherwise carried out in the illustrative depiction as follows: electronically receiving the selection information at least in part identifying the one or more selected ingestible products being subject to ingestion by the one or more particular individual living beings, the selection information electronically received via the electronically enabled input in response to the electronically outputted one or more selection menus in textual form (e.g. including an implementation of the receiver component s528 is configured to electronically engage with the processor component s102 to receive the user status information including the one or more identifiers associated with the particular individual living being for the processor component to at least in part electronically generate, based at least in part upon the user status information regarding the particular individual living being, such as based on associated allergies, one or more selection menus in textual form, such as a menu containing textual one or more descriptions of possible ingestible product to select from, and/or etc.).

In one or more implementations, as shown in FIG. 69, operation o11 includes an operation o1123 for electronically receiving the selection information at least in part identifying the one or more selected ingestible products being subject to ingestion by the one or more particular individual living beings, the selection information electronically received via the electronically enabled input in response to electronically outputted one or more selection menus in icon form. Origination of an illustratively derived receiving information icon component group can be accomplished through skilled in the art design choice selection of one or more of the above depicted components from one or more of the above depicted subsystems shown in FIG. 30. Components from the receiving information icon component group can be used in implementing execution of the one or more receiving information icon instructions i1123 of FIG. 48, can be used in performance of the receiving information icon electrical circuitry arrangement e1123 of FIG. 41, and/or can be used in otherwise fulfillment of the operation o1123. An exemplary non-transitory signal bearing medium version of the information storage subsystem s200 is depicted in FIG. 48 as bearing the one or more receiving information icon instructions i1123 that when executed will direct performance of the operation o1123. Furthermore, the receiving information icon electrical circuitry arrangement ("elec circ arrange") e1123, when activated, will perform the operation o1123. Also, the receiving information icon module m1123, when executed and/or activated, will direct performance of and/or perform the operation o1123. For instance, in one or more exemplary implementations, the one or more receiving information icon instructions i1123, when executed, direct performance of the operation o1123 in the illustrative depiction as follows, and/or the receiving information icon electrical circuitry arrangement e1123, when activated, performs the operation o1123 in the illustrative depiction as follows, and/or the receiving information icon module m1123, when executed and/or activated, directs performance of and/or performs the operation o1123 in the illustrative depiction as follows, and/or the operation o1123 is otherwise carried out in the illustrative depiction as follows: electronically receiving the selection information at least in part identifying the one or more selected ingestible products being subject to ingestion by the one or more particular individual living beings, the selection information electronically received via the electronically enabled input in response to the electronically outputted one or more selection menus in icon form (e.g. including an implementation of the receiver component s528 is configured to electronically engage with the processor component s102 to receive the user status information including the one or more identifiers associated with the particular individual living being for the processor component to at least in part electronically generate, based at least in part upon the user status information regarding the particular individual living being, such as based on associated previous meals, one or more selection menus in icon form, such as a menu containing iconic one or more descriptions of possible ingestible product to select from, and/or etc.).

In one or more implementations, as shown in FIG. 69, operation o11 includes an operation o1124 for electronically receiving the selection information at least in part identifying the one or more selected ingestible products being subject to ingestion by the one or more particular individual living beings, the selection information electronically received via the electronically enabled input in response to electronically outputted one or more selection menus in graphical form. Origination of an illustratively derived receiving information graphical component group can be accomplished through skilled in the art design choice selection of one or more of the above depicted components from one or more of the above depicted subsystems shown in FIG. 30. Components from the receiving information graphical component group can be used in implementing execution of the one or more receiving information graphical instructions i1124 of FIG. 48, can be used in performance of the receiving information graphical electrical circuitry arrangement e1124 of FIG. 41, and/or can be used in otherwise fulfillment of the operation o1124. An exemplary non-transitory signal bearing medium version of the information storage subsystem s200 is depicted in FIG. 48 as bearing the one or more receiving information graphical instructions i1124 that when executed will direct performance of the operation o1124. Furthermore, the receiving information graphical electrical circuitry arrangement ("elec circ arrange") e1124, when activated, will perform the operation o1124. Also, the receiving information graphical module m1124, when executed and/or activated, will direct performance of and/or perform the operation o1124. For instance, in one or more exemplary implementations, the one or more receiving information graphical instructions i1124, when executed, direct performance of the operation o1124 in the illustrative depiction as follows, and/or the receiving information graphical electrical circuitry arrangement e1124, when activated, performs the operation o1124 in the illustrative depiction as follows, and/or the receiving information graphical module m1124, when executed and/or activated, directs performance of and/or performs the operation o1124 in the illustrative depiction as follows, and/or the operation o1124 is otherwise carried out in the illustrative depiction as follows: electronically receiving the selection information at least in part identifying the one or more selected ingestible products being subject to ingestion by the one or more particular individual living beings, the selection information electronically received via the electronically enabled input in response to the electronically outputted one or more selection menus in graphical form (e.g. including an implementation of the receiver component s528 is configured to electronically engage with the processor component s102 to receive the user status information including the one or more identifiers associated with the particular individual living being for the processor component to at least in part electronically generate, based at least in part upon the user status information regarding the particular individual living being, such as based on associated favorite foods as observed and recorded in a database, one or more selection menus in graphical form, such as a menu containing graphical one or more descriptions of possible ingestible product to select from, and/or etc.).

Figure 70:
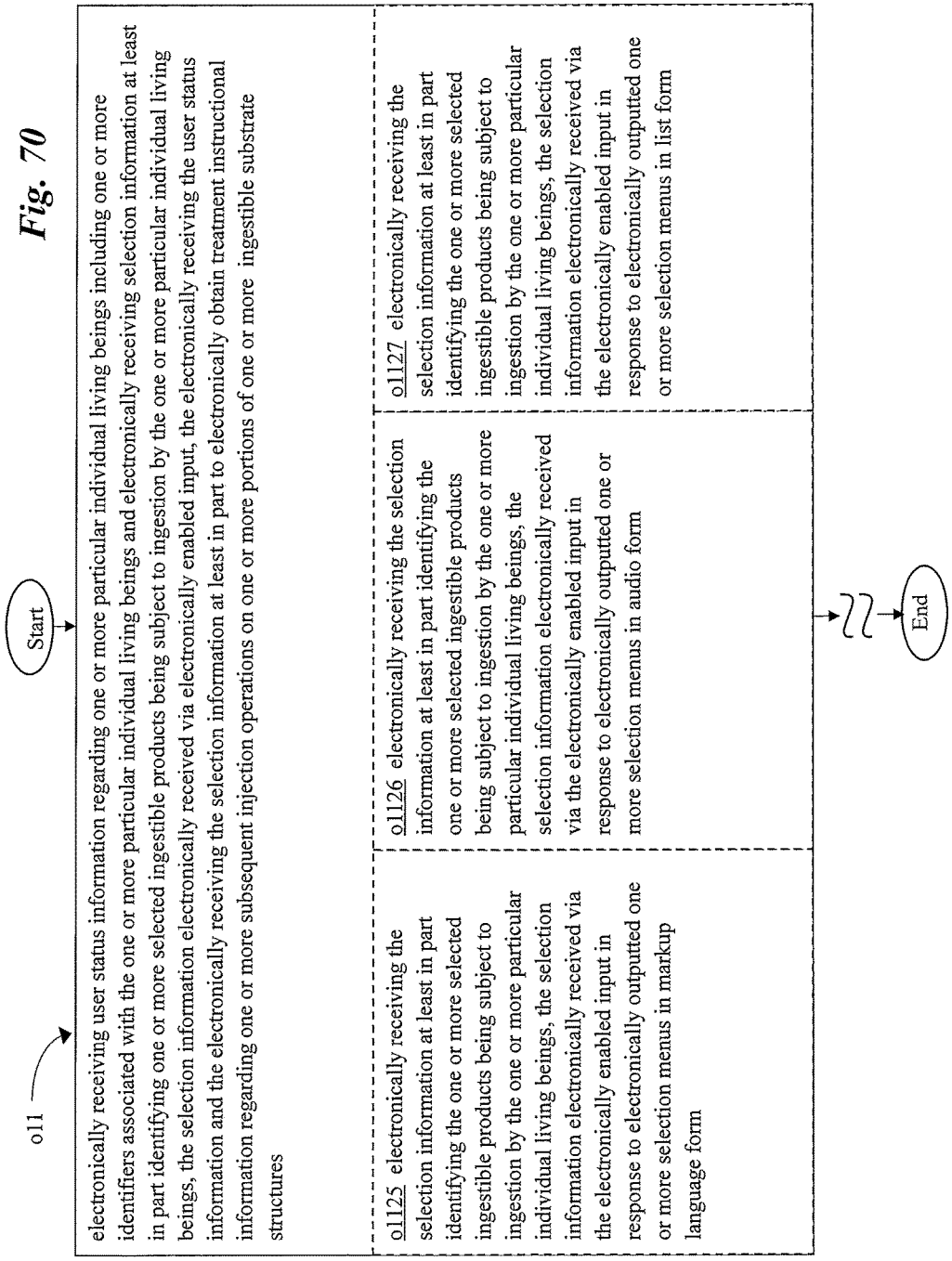
FIG. 70 is a high-level flowchart including exemplary implementations of operation O11 of FIG. 61.

In one or more implementations, as shown in FIG. 70, operation o11 includes an operation o1125 for electronically receiving the selection information at least in part identifying the one or more selected ingestible products being subject to ingestion by the one or more particular individual living beings, the selection information electronically received via the electronically enabled input in response to electronically outputted one or more selection menus in markup language form. Origination of an illustratively derived receiving information markup component group can be accomplished through skilled in the art design choice selection of one or more of the above depicted components from one or more of the above depicted subsystems shown in FIG. 30. Components from the receiving information markup component group can be used in implementing execution of the one or more receiving information markup instructions i1125 of FIG. 48, can be used in performance of the receiving information markup electrical circuitry arrangement e1125 of FIG. 41, and/or can be used in otherwise fulfillment of the operation o1125. An exemplary non-transitory signal bearing medium version of the information storage subsystem s200 is depicted in FIG. 48 as bearing the one or more receiving information markup instructions i1125 that when executed will direct performance of the operation o1125. Furthermore, the receiving information markup electrical circuitry arrangement ("elec circ arrange") e1125, when activated, will perform the operation o1125. Also, the receiving information markup module m1125, when executed and/or activated, will direct performance of and/or perform the operation o1125. For instance, in one or more exemplary implementations, the one or more receiving information markup instructions i1125, when executed, direct performance of the operation o1125 in the illustrative depiction as follows, and/or the receiving information markup electrical circuitry arrangement e1125, when activated, performs the operation o1125 in the illustrative depiction as follows, and/or the receiving information markup module m1125, when executed and/or activated, directs performance of and/or performs the operation o1125 in the illustrative depiction as follows, and/or the operation o1125 is otherwise carried out in the illustrative depiction as follows: electronically receiving the selection information at least in part identifying the one or more selected ingestible products being subject to ingestion by the one or more particular individual living beings, the selection information electronically received via the electronically enabled input in response to the electronically outputted one or more selection menus in markup language form (e.g. including an implementation of the receiver component s528 is configured to electronically engage with the processor component s102 to receive the user status information including the one or more identifiers associated with the particular individual living being for the processor component to at least in part electronically generate, based at least in part upon the user status information regarding the particular individual living being, such as based on associated health building goals, one or more selection menus in markup language form, such as a menu containing markup language one or more descriptions of possible ingestible product to select from, and/or etc.).

In one or more implementations, as shown in FIG. 70, operation o11 includes an operation o1126 for electronically receiving the selection information at least in part identifying the one or more selected ingestible products being subject to ingestion by the one or more particular individual living beings, the selection information electronically received via the electronically enabled input in response to electronically outputted one or more selection menus in audio form. Origination of an illustratively derived receiving information audio component group can be accomplished through skilled in the art design choice selection of one or more of the above depicted components from one or more of the above depicted subsystems shown in FIG. 30. Components from the receiving information audio component group can be used in implementing execution of the one or more receiving information audio instructions i1126 of FIG. 48, can be used in performance of the receiving information audio electrical circuitry arrangement e1126 of FIG. 41, and/or can be used in otherwise fulfillment of the operation o1126. An exemplary non-transitory signal bearing medium version of the information storage subsystem s200 is depicted in FIG. 48 as bearing the one or more receiving information audio instructions i1126 that when executed will direct performance of the operation o1126. Furthermore, the receiving information audio electrical circuitry arrangement ("elec circ arrange") e1126, when activated, will perform the operation o1126. Also, the receiving information audio module m1126, when executed and/or activated, will direct performance of and/or perform the operation o1126. For instance, in one or more exemplary implementations, the one or more receiving information audio instructions i1126, when executed, direct performance of the operation o1126 in the illustrative depiction as follows, and/or the receiving information audio electrical circuitry arrangement e1126, when activated, performs the operation o1126 in the illustrative depiction as follows, and/or the receiving information audio module m1126, when executed and/or activated, directs performance of and/or performs the operation o1126 in the illustrative depiction as follows, and/or the operation o1126 is otherwise carried out in the illustrative depiction as follows: electronically receiving the selection information at least in part identifying the one or more selected ingestible products being subject to ingestion by the one or more particular individual living beings, the selection information electronically received via the electronically enabled input in response to the electronically outputted one or more selection menus in audio form (e.g. including an implementation of the receiver component s528 is configured to electronically engage with the processor component s102 to receive the user status information including the one or more identifiers associated with the particular individual living being for the processor component to at least in part electronically generate, based at least in part upon the user status information regarding the particular individual living being, such as based on associated disease mitigating measures, one or more selection menus in audio form, such as a menu containing audio one or more descriptions of possible ingestible product to select from, and/or etc.).

In one or more implementations, as shown in FIG. 70, operation o11 includes an operation o1127 for electronically receiving the selection information at least in part identifying the one or more selected ingestible products being subject to ingestion by the one or more particular individual living beings, the selection information electronically received via the electronically enabled input in response to electronically outputted one or more selection menus in list form. Origination of an illustratively derived receiving information list component group can be accomplished through skilled in the art design choice selection of one or more of the above depicted components from one or more of the above depicted subsystems shown in FIG. 30. Components from the receiving information list component group can be used in implementing execution of the one or more receiving information list instructions i1127 of FIG. 48, can be used in performance of the receiving information list electrical circuitry arrangement e1127 of FIG. 41, and/or can be used in otherwise fulfillment of the operation o1127. An exemplary non-transitory signal bearing medium version of the information storage subsystem s200 is depicted in FIG. 48 as bearing the one or more receiving information list instructions i1127 that when executed will direct performance of the operation o1127. Furthermore, the receiving information list electrical circuitry arrangement ("elec circ arrange") e1127, when activated, will perform the operation o1127. Also, the receiving information list module m1127, when executed and/or activated, will direct performance of and/or perform the operation o1127. For instance, in one or more exemplary implementations, the one or more receiving information list instructions i1127, when executed, direct performance of the operation o1127 in the illustrative depiction as follows, and/or the receiving information list electrical circuitry arrangement e1127, when activated, performs the operation o1127 in the illustrative depiction as follows, and/or the receiving information list module m1127, when executed and/or activated, directs performance of and/or performs the operation o1127 in the illustrative depiction as follows, and/or the operation o1127 is otherwise carried out in the illustrative depiction as follows: electronically receiving the selection information at least in part identifying the one or more selected ingestible products being subject to ingestion by the one or more particular individual living beings, the selection information electronically received via the electronically enabled input in response to the electronically outputted one or more selection menus in list form (e.g. including an implementation of the receiver component s528 is configured to electronically engage with the processor component s102 to receive the user status information including the one or more identifiers associated with the particular individual living being for the processor component to at least in part electronically generate, based at least in part upon the user status information regarding the particular individual living being, such as based on associated dislikes, one or more selection menus in list form, such as a menu containing listed one or more descriptions of possible ingestible product to select from, and/or etc.).

Figure 71:
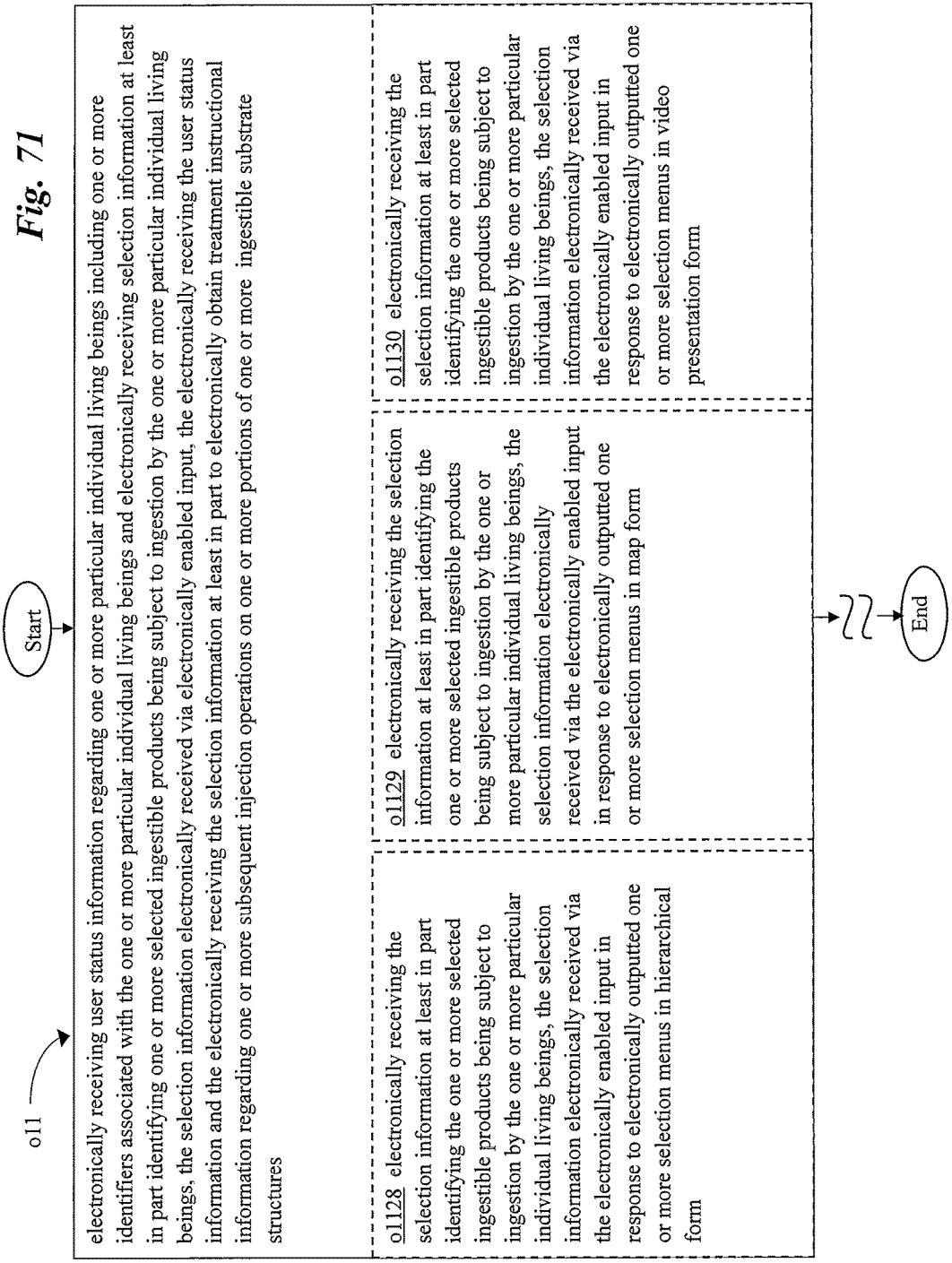
FIG. 71 is a high-level flowchart including exemplary implementations of operation O11 of FIG. 61.

In one or more implementations, as shown in FIG. 71, operation o11 includes an operation o1128 for electronically receiving the selection information at least in part identifying the one or more selected ingestible products being subject to ingestion by the one or more particular individual living beings, the selection information electronically received via the electronically enabled input in response to electronically outputted one or more selection menus in hierarchical form. Origination of an illustratively derived receiving information hierarchical component group can be accomplished through skilled in the art design choice selection of one or more of the above depicted components from one or more of the above depicted subsystems shown in FIG. 30. Components from the receiving information hierarchical component group can be used in implementing execution of the one or more receiving information hierarchical instructions i1128 of FIG. 48, can be used in performance of the receiving information hierarchical electrical circuitry arrangement e1128 of FIG. 41, and/or can be used in otherwise fulfillment of the operation o1128. An exemplary non-transitory signal bearing medium version of the information storage subsystem s200 is depicted in FIG. 48 as bearing the one or more receiving information hierarchical instructions i1128 that when executed will direct performance of the operation o1128. Furthermore, the receiving information hierarchical electrical circuitry arrangement ("elec circ arrange") e1128, when activated, will perform the operation o1128. Also, the receiving information hierarchical module m1128, when executed and/or activated, will direct performance of and/or perform the operation o1128. For instance, in one or more exemplary implementations, the one or more receiving information hierarchical instructions i1128, when executed, direct performance of the operation o1128 in the illustrative depiction as follows, and/or the receiving information hierarchical electrical circuitry arrangement e1128, when activated, performs the operation o1128 in the illustrative depiction as follows, and/or the receiving information hierarchical module m1128, when executed and/or activated, directs performance of and/or performs the operation o1128 in the illustrative depiction as follows, and/or the operation o1128 is otherwise carried out in the illustrative depiction as follows: electronically receiving the selection information at least in part identifying the one or more selected ingestible products being subject to ingestion by the one or more particular individual living beings, the selection information electronically received via the electronically enabled input in response to the electronically outputted one or more selection menus in hierarchical form (e.g. including an implementation of the receiver component s528 is configured to electronically engage with the processor component s102 to receive the user status information including the one or more identifiers associated with the particular individual living being for the processor component to at least in part electronically generate, based at least in part upon the user status information regarding the particular individual living being, such as based on associated past purchases, one or more selection menus in hierarchical form, such as a menu containing hierarchical one or more descriptions of possible ingestible product to select from, and/or etc.).

In one or more implementations, as shown in FIG. 71, operation o11 includes an operation o1129 for electronically receiving the selection information at least in part identifying the one or more selected ingestible products being subject to ingestion by the one or more particular individual living beings, the selection information electronically received via the electronically enabled input in response to electronically outputted one or more selection menus in map form. Origination of an illustratively derived receiving information map component group can be accomplished through skilled in the art design choice selection of one or more of the above depicted components from one or more of the above depicted subsystems shown in FIG. 30. Components from the receiving information map component group can be used in implementing execution of the one or more receiving information map instructions i1129 of FIG. 48, can be used in performance of the receiving information map electrical circuitry arrangement e1129 of FIG. 41, and/or can be used in otherwise fulfillment of the operation o1129. An exemplary non-transitory signal bearing medium version of the information storage subsystem s200 is depicted in FIG. 48 as bearing the one or more receiving information map instructions i1129 that when executed will direct performance of the operation o1129. Furthermore, the receiving information map electrical circuitry arrangement ("elec circ arrange") e1129, when activated, will perform the operation o1129. Also, the receiving information map module m1129, when executed and/or activated, will direct performance of and/or perform the operation o1129. For instance, in one or more exemplary implementations, the one or more receiving information map instructions i1129, when executed, direct performance of the operation o1129 in the illustrative depiction as follows, and/or the receiving information map electrical circuitry arrangement e1129, when activated, performs the operation o1129 in the illustrative depiction as follows, and/or the receiving information map module m1129, when executed and/or activated, directs performance of and/or performs the operation o1129 in the illustrative depiction as follows, and/or the operation o1129 is otherwise carried out in the illustrative depiction as follows: electronically receiving the selection information at least in part identifying the one or more selected ingestible products being subject to ingestion by the one or more particular individual living beings, the selection information electronically received via the electronically enabled input in response to the electronically outputted one or more selection menus in map form (e.g. including an implementation of the receiver component s528 is configured to electronically engage with the processor component s102 to receive the user status information including the one or more identifiers associated with the particular individual living being for the processor component to at least in part electronically generate, based at least in part upon the user status information regarding the particular individual living being, such as based on associated food preferences determined from use history stored in one or more distributed databases, one or more selection menus in map form, such as a menu having arrangements resembling one or more maps containing one or more selections and one or more descriptions of possible ingestible product to select from, and/or etc.).

In one or more implementations, as shown in FIG. 71, operation o11 includes an operation o1130 for electronically receiving the selection information at least in part identifying the one or more selected ingestible products being subject to ingestion by the one or more particular individual living beings, the selection information electronically received via the electronically enabled input in response to electronically outputted one or more selection menus in video presentation form. Origination of an illustratively derived receiving information presentation component group can be accomplished through skilled in the art design choice selection of one or more of the above depicted components from one or more of the above depicted subsystems shown in FIG. 30. Components from the receiving information presentation component group can be used in implementing execution of the one or more receiving information presentation instructions i1130 of FIG. 48, can be used in performance of the receiving information presentation electrical circuitry arrangement e1130 of FIG. 41, and/or can be used in otherwise fulfillment of the operation o1130. An exemplary non-transitory signal bearing medium version of the information storage subsystem s200 is depicted in FIG. 48 as bearing the one or more receiving information presentation instructions i1130 that when executed will direct performance of the operation o1130. Furthermore, the receiving information presentation electrical circuitry arrangement ("elec circ arrange") e1130, when activated, will perform the operation o1130. Also, the receiving information presentation module m1130, when executed and/or activated, will direct performance of and/or perform the operation o1130. For instance, in one or more exemplary implementations, the one or more receiving information presentation instructions i1130, when executed, direct performance of the operation o1130 in the illustrative depiction as follows, and/or the receiving information presentation electrical circuitry arrangement e1130, when activated, performs the operation o1130 in the illustrative depiction as follows, and/or the receiving information presentation module m1130, when executed and/or activated, directs performance of and/or performs the operation o1130 in the illustrative depiction as follows, and/or the operation o1130 is otherwise carried out in the illustrative depiction as follows: electronically receiving the selection information at least in part identifying the one or more selected ingestible products being subject to ingestion by the one or more particular individual living beings, the selection information electronically received via the electronically enabled input in response to the electronically outputted one or more selection menus in video presentation form (e.g. including an implementation of the receiver component s528 is configured to electronically engage with the processor component s102 to receive the user status information including the one or more identifiers associated with the particular individual living being for the processor component to at least in part electronically generate, based at least in part upon the user status information regarding the particular individual living being, such as based on associated one or more prescriptions, one or more selection menus in video presentation form, such as a menu containing one or more video presentations having one or more descriptions of possible ingestible product to select from, and/or etc.).

Figure 72:
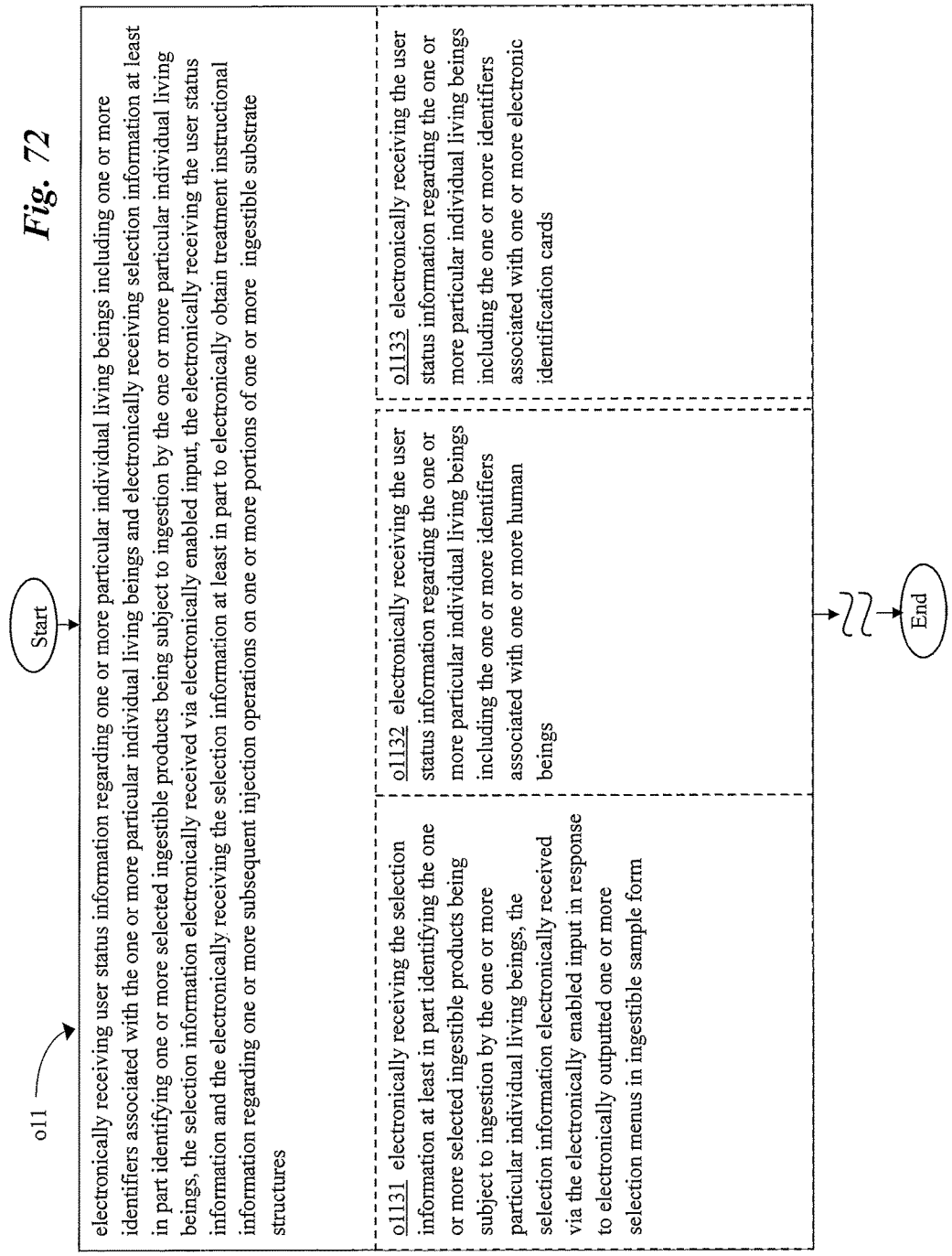
FIG. 72 is a high-level flowchart including exemplary implementations of operation O11 of FIG. 61.

In one or more implementations, as shown in FIG. 72, operation o11 includes an operation o1131 for electronically receiving the selection information at least in part identifying the one or more selected ingestible products being subject to ingestion by the one or more particular individual living beings, the selection information electronically received via the electronically enabled input in response to electronically outputted one or more selection menus in ingestible sample form. Origination of an illustratively derived receiving information sample component group can be accomplished through skilled in the art design choice selection of one or more of the above depicted components from one or more of the above depicted subsystems shown in FIG. 30. Components from the receiving information sample component group can be used in implementing execution of the one or more receiving information sample instructions i1131 of FIG. 48, can be used in performance of the receiving information sample electrical circuitry arrangement e1131 of FIG. 41, and/or can be used in otherwise fulfillment of the operation o1131. An exemplary non-transitory signal bearing medium version of the information storage subsystem s200 is depicted in FIG. 48 as bearing the one or more receiving information sample instructions i1131 that when executed will direct performance of the operation o1131. Furthermore, the receiving information sample electrical circuitry arrangement ("elec circ arrange") e1131, when activated, will perform the operation o1131. Also, the receiving information sample module m1131, when executed and/or activated, will direct performance of and/or perform the operation o1131. For instance, in one or more exemplary implementations, the one or more receiving information sample instructions i1131, when executed, direct performance of the operation o1131 in the illustrative depiction as follows, and/or the receiving information sample electrical circuitry arrangement e1131, when activated, performs the operation o1131 in the illustrative depiction as follows, and/or the receiving information sample module m1131, when executed and/or activated, directs performance of and/or performs the operation o1131 in the illustrative depiction as follows, and/or the operation o1131 is otherwise carried out in the illustrative depiction as follows: electronically receiving the selection information at least in part identifying the one or more selected ingestible products being subject to ingestion by the one or more particular individual living beings, the selection information electronically received via the electronically enabled input in response to the electronically outputted one or more selection menus in ingestible sample form (e.g. including an implementation of the receiver component s528 is configured to electronically engage with the processor component s102 to receive the user status information including the one or more identifiers associated with the particular individual living being for the processor component to at least in part electronically generate, based at least in part upon the user status information regarding the particular individual living being, such as based on associated one or more holidays stored in one or more databases, one or more selection menus in ingestible sample form, such as a menu containing ingestible samples that are either stored or produced in real time to serve as or otherwise complement one or more descriptions of possible ingestible product to select from, and/or etc.).

In one or more implementations, as shown in FIG. 72, operation o11 includes an operation o1132 for electronically receiving the user status information regarding the one or more particular individual living beings including the one or more identifiers associated with one or more human beings. Origination of an illustratively derived receiving information human component group can be accomplished through skilled in the art design choice selection of one or more of the above depicted components from one or more of the above depicted subsystems shown in FIG. 30. Components from the receiving information human component group can be used in implementing execution of the one or more receiving information human instructions i1132 of FIG. 48, can be used in performance of the receiving information human electrical circuitry arrangement e1132 of FIG. 41, and/or can be used in otherwise fulfillment of the operation o1132. An exemplary non-transitory signal bearing medium version of the information storage subsystem s200 is depicted in FIG. 48 as bearing the one or more receiving information human instructions i1132 that when executed will direct performance of the operation o1132. Furthermore, the receiving information human electrical circuitry arrangement ("elec circ arrange") e1132, when activated, will perform the operation o1132. Also, the receiving information human module m1132, when executed and/or activated, will direct performance of and/or perform the operation o1132. For instance, in one or more exemplary implementations, the one or more receiving information human instructions i1132, when executed, direct performance of the operation o1132 in the illustrative depiction as follows, and/or the receiving information human electrical circuitry arrangement e1132, when activated, performs the operation o1132 in the illustrative depiction as follows, and/or the receiving information human module m1132, when executed and/or activated, directs performance of and/or performs the operation o1132 in the illustrative depiction as follows, and/or the operation o1132 is otherwise carried out in the illustrative depiction as follows: electronically receiving the user status information regarding the one or more particular individual living beings including the one or more identifiers associated with one or more human beings (e.g. including an implementation of the receiver component s528 is configured to electronically engage with the processor component s102 to receive the user status information regarding the particular individual living being including one or more identifiers as determined by the processor component to be identifying a human being, and/or etc.).

In one or more implementations, as shown in FIG. 72, operation o11 includes an operation o1133 for electronically receiving the user status information regarding the one or more particular individual living beings including the one or more identifiers associated with one or more electronic identification cards. Origination of an illustratively derived receiving information ID card component group can be accomplished through skilled in the art design choice selection of one or more of the above depicted components from one or more of the above depicted subsystems shown in FIG. 30. Components from the receiving information ID card component group can be used in implementing execution of the one or more receiving information ID card instructions i1133 of FIG. 48, can be used in performance of the receiving information ID card electrical circuitry arrangement e1133 of FIG. 41, and/or can be used in otherwise fulfillment of the operation o1133. An exemplary non-transitory signal bearing medium version of the information storage subsystem s200 is depicted in FIG. 48 as bearing the one or more receiving information ID card instructions i1133 that when executed will direct performance of the operation o1133. Furthermore, the receiving information ID card electrical circuitry arrangement ("elec circ arrange") e1133, when activated, will perform the operation o1133.

Also, the receiving information ID card module m1133, when executed and/or activated, will direct performance of and/or perform the operation o1133. For instance, in one or more exemplary implementations, the one or more receiving information ID card instructions i1133, when executed, direct performance of the operation o1133 in the illustrative depiction as follows, and/or the receiving information ID card electrical circuitry arrangement e1133, when activated, performs the operation o1133 in the illustrative depiction as follows, and/or the receiving information ID card module m1133, when executed and/or activated, directs performance of and/or performs the operation o1133 in the illustrative depiction as follows, and/or the operation o1133 is otherwise carried out in the illustrative depiction as follows: electronically receiving the user status information regarding the one or more particular individual living beings including the one or more identifiers associated with one or more electronic identification cards (e.g. including an implementation of the receiver component s528 is configured to electronically engage with the processor component s102 to receive the user status information regarding the particular individual living being including one or more identifiers as determined by the processor component to be identifying a living being through the electronic identification card, and/or etc.).

Figure 73:
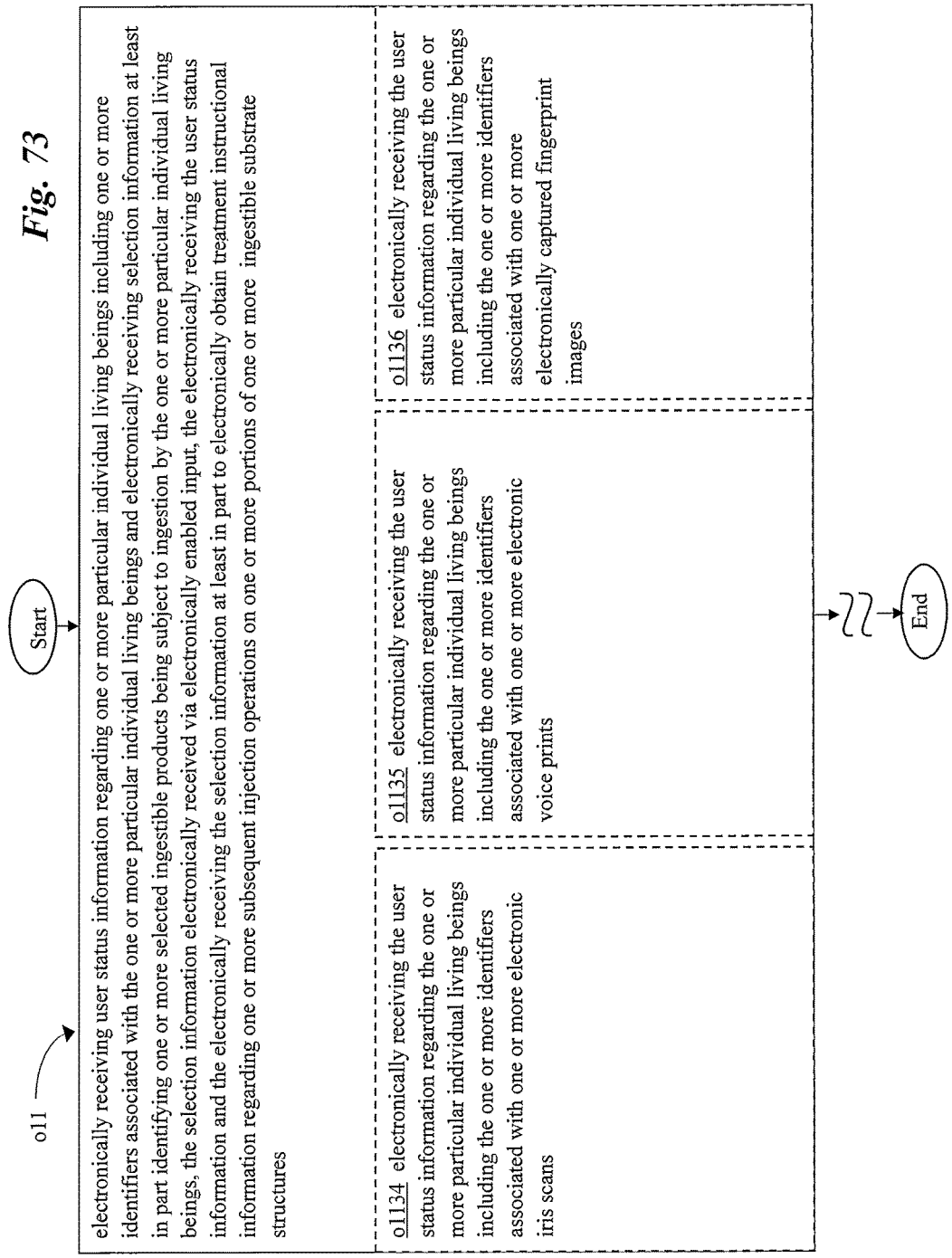
FIG. 73 is a high-level flowchart including exemplary implementations of operation O11 of FIG. 61.

In one or more implementations, as shown in FIG. 73, operation o11 includes an operation o1134 for electronically receiving the user status information regarding the one or more particular individual living beings including the one or more identifiers associated with one or more electronic iris scans. Origination of an illustratively derived receiving information iris scan component group can be accomplished through skilled in the art design choice selection of one or more of the above depicted components from one or more of the above depicted subsystems shown in FIG. 30. Components from the receiving information iris scan component group can be used in implementing execution of the one or more receiving information iris scan instructions i1134 of FIG. 48, can be used in performance of the receiving information iris scan electrical circuitry arrangement e1134 of FIG. 41, and/or can be used in otherwise fulfillment of the operation o1134. An exemplary non-transitory signal bearing medium version of the information storage subsystem s200 is depicted in FIG. 48 as bearing the one or more receiving information iris scan instructions i1134 that when executed will direct performance of the operation o1134. Furthermore, the receiving information iris scan electrical circuitry arrangement ("elec circ arrange") e1134, when activated, will perform the operation o1134. Also, the receiving information iris scan module m1134, when executed and/or activated, will direct performance of and/or perform the operation o1134. For instance, in one or more exemplary implementations, the one or more receiving information iris scan instructions i1134, when executed, direct performance of the operation o1134 in the illustrative depiction as follows, and/or the receiving information iris scan electrical circuitry arrangement e1134, when activated, performs the operation o1134 in the illustrative depiction as follows, and/or the receiving information iris scan module m1134, when executed and/or activated, directs performance of and/or performs the operation o1134 in the illustrative depiction as follows, and/or the operation o1134 is otherwise carried out in the illustrative depiction as follows: electronically receiving the user status information regarding the one or more particular individual living beings including the one or more identifiers associated with one or more electronic iris scans (e.g. including an implementation of the receiver component s528 is configured to electronically engage with the processor component s102 to receive the user status information regarding the particular individual living being including one or more identifiers as determined by the processor component to be identifying the living being through the electronic iris scan, and/or etc.).

In one or more implementations, as shown in FIG. 73, operation o11 includes an operation o1135 for electronically receiving the user status information regarding the one or more particular individual living beings including the one or more identifiers associated with one or more electronic voice prints. Origination of an illustratively derived receiving information voice component group can be accomplished through skilled in the art design choice selection of one or more of the above depicted components from one or more of the above depicted subsystems shown in FIG. 30. Components from the receiving information voice component group can be used in implementing execution of the one or more receiving information voice instructions i1135 of FIG. 48, can be used in performance of the receiving information voice electrical circuitry arrangement e1135 of FIG. 41, and/or can be used in otherwise fulfillment of the operation o1135. An exemplary non-transitory signal bearing medium version of the information storage subsystem s200 is depicted in FIG. 48 as bearing the one or more receiving information voice instructions i1135 that when executed will direct performance of the operation o1135. Furthermore, the receiving information voice electrical circuitry arrangement ("elec circ arrange") e1135, when activated, will perform the operation o1135. Also, the receiving information voice module m1135, when executed and/or activated, will direct performance of and/or perform the operation o1135. For instance, in one or more exemplary implementations, the one or more receiving information voice instructions i1135, when executed, direct performance of the operation o1135 in the illustrative depiction as follows, and/or the receiving information voice electrical circuitry arrangement e1135, when activated, performs the operation o1135 in the illustrative depiction as follows, and/or the receiving information voice module m1135, when executed and/or activated, directs performance of and/or performs the operation o1135 in the illustrative depiction as follows, and/or the operation o1135 is otherwise carried out in the illustrative depiction as follows: electronically receiving the user status information regarding the one or more particular individual living beings including the one or more identifiers associated with one or more electronic voice prints (e.g. including an implementation of the receiver component s528 is configured to electronically engage with the processor component s102 to receive the user status information regarding the particular individual living being including one or more identifiers as determined by the processor component to be identifying the living being through the electronic voice print, and/or etc.).

In one or more implementations, as shown in FIG. 73, operation o11 includes an operation o1136 for electronically receiving the user status information regarding the one or more particular individual living beings including the one or more identifiers associated with one or more electronically captured fingerprint images. Origination of an illustratively derived receiving information fingerprint component group can be accomplished through skilled in the art design choice selection of one or more of the above depicted components from one or more of the above depicted subsystems shown in FIG. 30. Components from the receiving information fingerprint component group can be used in implementing execution of the one or more receiving information fingerprint instructions i1136 of FIG. 48, can be used in performance of the receiving information fingerprint electrical circuitry arrangement e1136 of FIG. 41, and/or can be used in otherwise fulfillment of the operation o1136. An exemplary non-transitory signal bearing medium version of the information storage subsystem s200 is depicted in FIG. 48 as bearing the one or more receiving information fingerprint instructions i1136 that when executed will direct performance of the operation o1136. Furthermore, the receiving information fingerprint electrical circuitry arrangement ("elec circ arrange") e1136, when activated, will perform the operation o1136. Also, the receiving information fingerprint module m1136, when executed and/or activated, will direct performance of and/or perform the operation o1136. For instance, in one or more exemplary implementations, the one or more receiving information fingerprint instructions i1136, when executed, direct performance of the operation o1136 in the illustrative depiction as follows, and/or the receiving information fingerprint electrical circuitry arrangement e1136, when activated, performs the operation o1136 in the illustrative depiction as follows, and/or the receiving information fingerprint module m1136, when executed and/or activated, directs performance of and/or performs the operation o1136 in the illustrative depiction as follows, and/or the operation o1136 is otherwise carried out in the illustrative depiction as follows: electronically receiving the user status information regarding the one or more particular individual living beings including the one or more identifiers associated with one or more electronically captured fingerprint images (e.g. including an implementation of the receiver component s528 is configured to electronically engage with the processor component s102 to receive the user status information regarding the particular individual living being including one or more identifiers as determined by the processor component to be identifying the living being through the electronically captured fingerprint image, and/or etc.).

Figure 74:
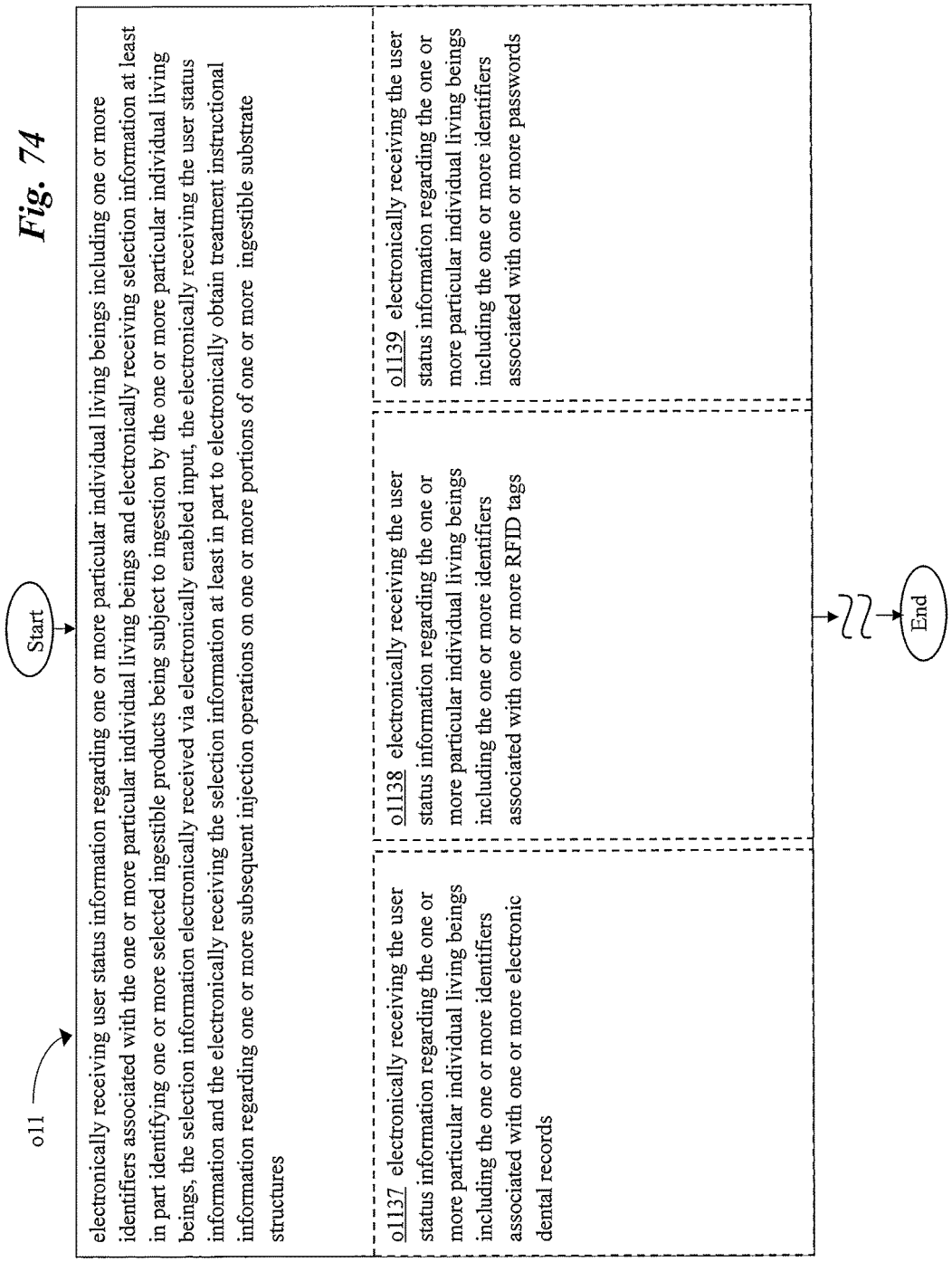
FIG. 74 is a high-level flowchart including exemplary implementations of operation O11 of FIG. 61.

In one or more implementations, as shown in FIG. 74, operation o11 includes an operation o1137 for electronically receiving the user status information regarding the one or more particular individual living beings including the one or more identifiers associated with one or more electronic dental records. Origination of an illustratively derived receiving information dental component group can be accomplished through skilled in the art design choice selection of one or more of the above depicted components from one or more of the above depicted subsystems shown in FIG. 30. Components from the receiving information dental component group can be used in implementing execution of the one or more receiving information dental instructions i1137 of FIG. 48, can be used in performance of the receiving information dental electrical circuitry arrangement e1137 of FIG. 41, and/or can be used in otherwise fulfillment of the operation o1137. An exemplary non-transitory signal bearing medium version of the information storage subsystem s200 is depicted in FIG. 48 as bearing the one or more receiving information dental instructions i1137 that when executed will direct performance of the operation o1137. Furthermore, the receiving information dental electrical circuitry arrangement ("elec circ arrange") e1137, when activated, will perform the operation o1137. Also, the receiving information dental module m1137, when executed and/or activated, will direct performance of and/or perform the operation o1137. For instance, in one or more exemplary implementations, the one or more receiving information dental instructions i1137, when executed, direct performance of the operation o1137 in the illustrative depiction as follows, and/or the receiving information dental electrical circuitry arrangement e1137, when activated, performs the operation o1137 in the illustrative depiction as follows, and/or the receiving information dental module m1137, when executed and/or activated, directs performance of and/or performs the operation o1137 in the illustrative depiction as follows, and/or the operation o1137 is otherwise carried out in the illustrative depiction as follows: electronically receiving the user status information regarding the one or more particular individual living beings including the one or more identifiers associated with one or more electronic dental records (e.g. including an implementation of the receiver component s528 is configured to electronically engage with the processor component s102 to receive the user status information regarding the particular individual living being including one or more identifiers as determined by the processor component to be identifying the living being through the electronic dental records, and/or etc.).

In one or more implementations, as shown in FIG. 74, operation o11 includes an operation o1138 for electronically receiving the user status information regarding the one or more particular individual living beings including the one or more identifiers associated with one or more RFID tags. Origination of an illustratively derived receiving information RFID component group can be accomplished through skilled in the art design choice selection of one or more of the above depicted components from one or more of the above depicted subsystems shown in FIG. 30. Components from the receiving information RFID component group can be used in implementing execution of the one or more receiving information RFID instructions i1138 of FIG. 48, can be used in performance of the receiving information RFID electrical circuitry arrangement e1138 of FIG. 41, and/or can be used in otherwise fulfillment of the operation o1138. An exemplary non-transitory signal bearing medium version of the information storage subsystem s200 is depicted in FIG. 48 as bearing the one or more receiving information RFID instructions i1138 that when executed will direct performance of the operation o1138. Furthermore, the receiving information RFID electrical circuitry arrangement ("elec circ arrange") e1138, when activated, will perform the operation o1138. Also, the receiving information RFID module m1138, when executed and/or activated, will direct performance of and/or perform the operation o1138. For instance, in one or more exemplary implementations, the one or more receiving information RFID instructions i1138, when executed, direct performance of the operation o1138 in the illustrative depiction as follows, and/or the receiving information RFID electrical circuitry arrangement e1138, when activated, performs the operation o1138 in the illustrative depiction as follows, and/or the receiving information RFID module m1138, when executed and/or activated, directs performance of and/or performs the operation o1138 in the illustrative depiction as follows, and/or the operation o1138 is otherwise carried out in the illustrative depiction as follows: electronically receiving the user status information regarding the one or more particular individual living beings including the one or more identifiers associated with one or more RFID tags (e.g. including an implementation of the receiver component s528 is configured to electronically engage with the processor component s102 to receive the user status information regarding the particular individual living being including one or more identifiers as determined by the processor component to be identifying the living being through the RFID tag, and/or etc.).

In one or more implementations, as shown in FIG. 74, operation o11 includes an operation o1139 for electronically receiving the user status information regarding the one or more particular individual living beings including the one or more identifiers associated with one or more passwords. Origination of an illustratively derived receiving information password component group can be accomplished through skilled in the art design choice selection of one or more of the above depicted components from one or more of the above depicted subsystems shown in FIG. 30. Components from the receiving information password component group can be used in implementing execution of the one or more receiving information password instructions i1139 of FIG. 48, can be used in performance of the receiving information password electrical circuitry arrangement e1139 of FIG. 41, and/or can be used in otherwise fulfillment of the operation o1139. An exemplary non-transitory signal bearing medium version of the information storage subsystem s200 is depicted in FIG. 48 as bearing the one or more receiving information password instructions i1139 that when executed will direct performance of the operation o1139. Furthermore, the receiving information password electrical circuitry arrangement ("elec circ arrange") e1139, when activated, will perform the operation o1139. Also, the receiving information password module m1139, when executed and/or activated, will direct performance of and/or perform the operation o1139. For instance, in one or more exemplary implementations, the one or more receiving information password instructions i1139, when executed, direct performance of the operation o1139 in the illustrative depiction as follows, and/or the receiving information password electrical circuitry arrangement e1139, when activated, performs the operation o1139 in the illustrative depiction as follows, and/or the receiving information password module m1139, when executed and/or activated, directs performance of and/or performs the operation o1139 in the illustrative depiction as follows, and/or the operation o1139 is otherwise carried out in the illustrative depiction as follows: electronically receiving the user status information regarding the one or more particular individual living beings including the one or more identifiers associated with one or more passwords (e.g. including an implementation of the receiver component s528 is configured to electronically engage with the processor component s102 to receive the user status information regarding the particular individual living being including one or more identifiers as determined by the processor component to be identifying the living being through the password, and/or etc.).

Figure 75:
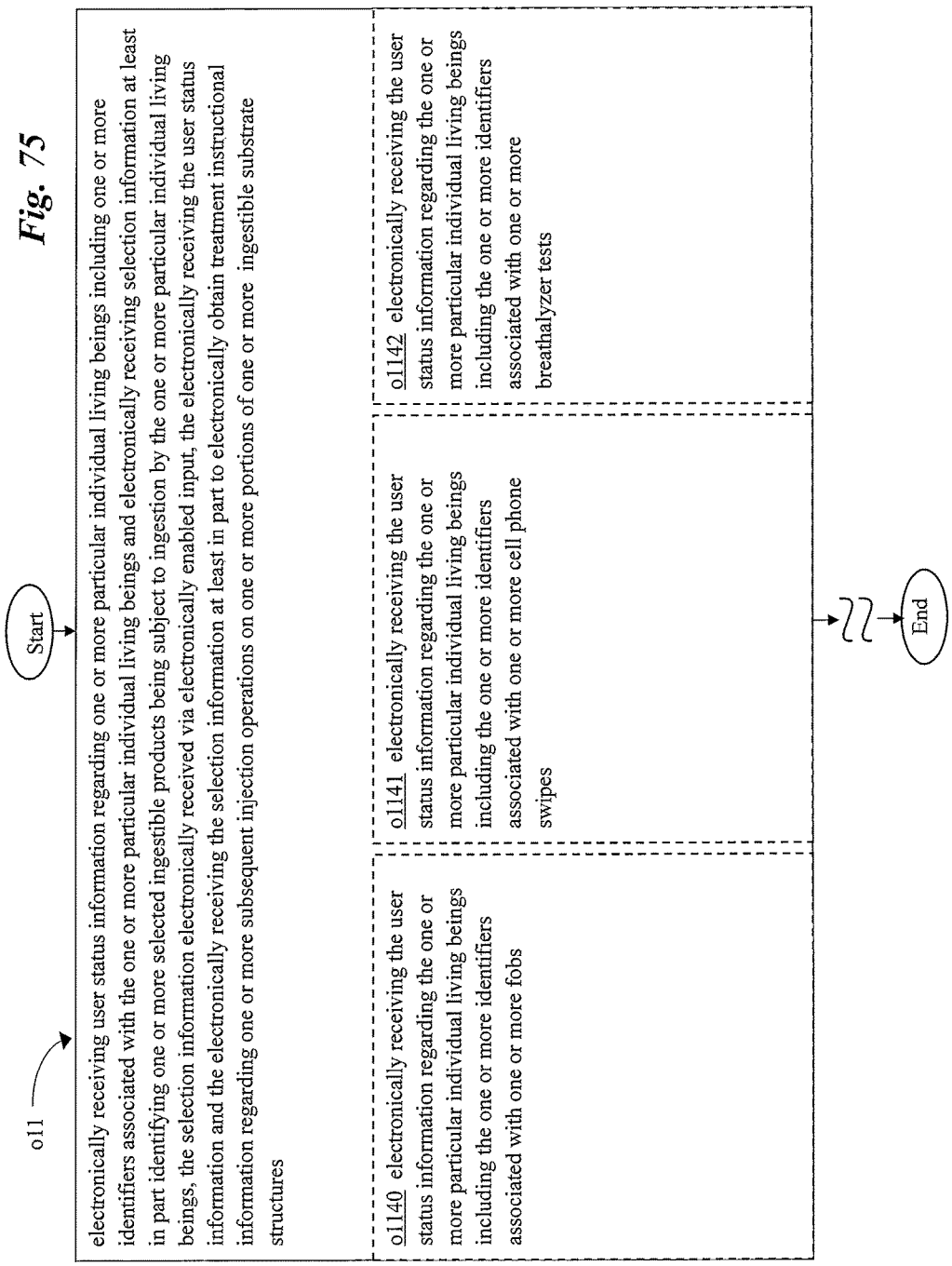
FIG. 75 is a high-level flowchart including exemplary implementations of operation O11 of FIG. 61.

In one or more implementations, as shown in FIG. 75, operation o11 includes an operation o1140 for electronically receiving the user status information regarding the one or more particular individual living beings including the one or more identifiers associated with one or more fobs. Origination of an illustratively derived receiving information fob component group can be accomplished through skilled in the art design choice selection of one or more of the above depicted components from one or more of the above depicted subsystems shown in FIG. 30. Components from the receiving information fob component group can be used in implementing execution of the one or more receiving information fob instructions i1140 of FIG. 49, can be used in performance of the receiving information fob electrical circuitry arrangement e1140 of FIG. 42, and/or can be used in otherwise fulfillment of the operation o1140. An exemplary non-transitory signal bearing medium version of the information storage subsystem s200 is depicted in FIG. 49 as bearing the one or more receiving information fob instructions i1140 that when executed will direct performance of the operation o1140. Furthermore, the receiving information fob electrical circuitry arrangement ("elec circ arrange") e1140, when activated, will perform the operation o1140. Also, the receiving information fob module m1140, when executed and/or activated, will direct performance of and/or perform the operation o1140. For instance, in one or more exemplary implementations, the one or more receiving information fob instructions i1140, when executed, direct performance of the operation o1140 in the illustrative depiction as follows, and/or the receiving information fob electrical circuitry arrangement e1140, when activated, performs the operation o1140 in the illustrative depiction as follows, and/or the receiving information fob module m1140, when executed and/or activated, directs performance of and/or performs the operation o1140 in the illustrative depiction as follows, and/or the operation o1140 is otherwise carried out in the illustrative depiction as follows: electronically receiving the user status information regarding the one or more particular individual living beings including the one or more identifiers associated with one or more fobs (e.g. including an implementation of the receiver component s528 is configured to electronically engage with the processor component s102 to receive the user status information regarding the particular individual living being including one or more identifiers as determined by the processor component to be identifying the living being through electronic data contained on the fob, and/or etc.).

In one or more implementations, as shown in FIG. 75, operation o11 includes an operation o1141 for electronically receiving the user status information regarding the one or more particular individual living beings including the one or more identifiers associated with one or more cell phone swipes. Origination of an illustratively derived receiving information cell phone component group can be accomplished through skilled in the art design choice selection of one or more of the above depicted components from one or more of the above depicted subsystems shown in FIG. 30. Components from the receiving information cell phone component group can be used in implementing execution of the one or more receiving information cell phone instructions i1141 of FIG. 49, can be used in performance of the receiving information cell phone electrical circuitry arrangement e1141 of FIG. 42, and/or can be used in otherwise fulfillment of the operation o1141. An exemplary non-transitory signal bearing medium version of the information storage subsystem s200 is depicted in FIG. 49 as bearing the one or more receiving information cell phone instructions i1141 that when executed will direct performance of the operation o1141. Furthermore, the receiving information cell phone electrical circuitry arrangement ("elec circ arrange") e1141, when activated, will perform the operation o1141. Also, the receiving information cell phone module m1141, when executed and/or activated, will direct performance of and/or perform the operation o1141. For instance, in one or more exemplary implementations, the one or more receiving information cell phone instructions i1141, when executed, direct performance of the operation o1141 in the illustrative depiction as follows, and/or the receiving information cell phone electrical circuitry arrangement e1141, when activated, performs the operation o1141 in the illustrative depiction as follows, and/or the receiving information cell phone module m1141, when executed and/or activated, directs performance of and/or performs the operation o1141 in the illustrative depiction as follows, and/or the operation o1141 is otherwise carried out in the illustrative depiction as follows: electronically receiving the user status information regarding the one or more particular individual living beings including the one or more identifiers associated with one or more cell phone swipes (e.g. including an implementation of the receiver component s528 is configured to electronically engage with the processor component s102 to receive the user status information regarding the particular individual living being including one or more identifiers as determined by the processor component to be identifying the living being through passing the cell phone in close proximity to the cell phone, and/or etc.).

In one or more implementations, as shown in FIG. 75, operation o11 includes an operation o1142 for electronically receiving the user status information regarding the one or more particular individual living beings including the one or more identifiers associated with one or more breathalyzer tests. Origination of an illustratively derived receiving information breathalyzer component group can be accomplished through skilled in the art design choice selection of one or more of the above depicted components from one or more of the above depicted subsystems shown in FIG. 30. Components from the receiving information breathalyzer component group can be used in implementing execution of the one or more receiving information breathalyzer instructions i1142 of FIG. 49, can be used in performance of the receiving information breathalyzer electrical circuitry arrangement e1142 of FIG. 42, and/or can be used in otherwise fulfillment of the operation o1142. An exemplary non-transitory signal bearing medium version of the information storage subsystem s200 is depicted in FIG. 49 as bearing the one or more receiving information breathalyzer instructions i1142 that when executed will direct performance of the operation o1142. Furthermore, the receiving information breathalyzer electrical circuitry arrangement ("elec circ arrange") e1142, when activated, will perform the operation o1142. Also, the receiving information breathalyzer module m1142, when executed and/or activated, will direct performance of and/or perform the operation o1142. For instance, in one or more exemplary implementations, the one or more receiving information breathalyzer instructions i1142, when executed, direct performance of the operation o1142 in the illustrative depiction as follows, and/or the receiving information breathalyzer electrical circuitry arrangement e1142, when activated, performs the operation o1142 in the illustrative depiction as follows, and/or the receiving information breathalyzer module m1142, when executed and/or activated, directs performance of and/or performs the operation o1142 in the illustrative depiction as follows, and/or the operation o1142 is otherwise carried out in the illustrative depiction as follows: electronically receiving the user status information regarding the one or more particular individual living beings including the one or more identifiers associated with one or more breathalyzer tests (e.g. including an implementation of the receiver component s528 is configured to electronically engage with the processor component s102 to receive the user status information regarding the particular individual living being including one or more identifiers as determined by the processor component to be identifying the living being through the breathalyzer test of the living being, and/or etc.).

Figure 76:
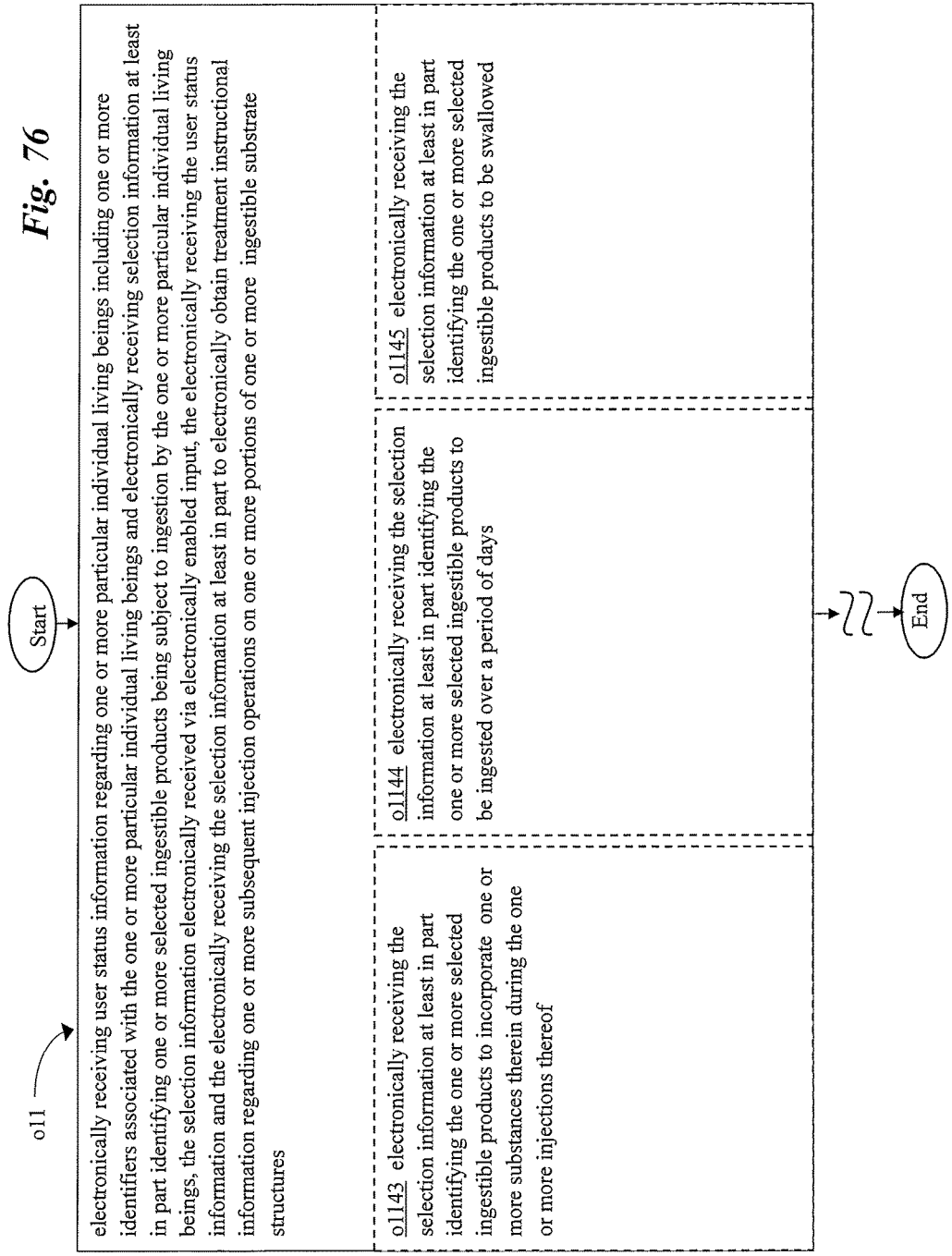
FIG. 76 is a high-level flowchart including exemplary implementations of operation O11 of FIG. 61.

In one or more implementations, as shown in FIG. 76, operation o11 includes an operation o1143 for electronically receiving the selection information at least in part identifying the one or more selected ingestible products to incorporate one or more substances therein during the one or more injections thereof. Origination of an illustratively derived receiving information incorporate component group can be accomplished through skilled in the art design choice selection of one or more of the above depicted components from one or more of the above depicted subsystems shown in FIG. 30. Components from the receiving information incorporate component group can be used in implementing execution of the one or more receiving information incorporate instructions i1143 of FIG. 49, can be used in performance of the receiving information incorporate electrical circuitry arrangement e1143 of FIG. 42, and/or can be used in otherwise fulfillment of the operation o1143. An exemplary non-transitory signal bearing medium version of the information storage subsystem s200 is depicted in FIG. 49 as bearing the one or more receiving information incorporate instructions i1143 that when executed will direct performance of the operation o1143. Furthermore, the receiving information incorporate electrical circuitry arrangement ("elec circ arrange") e1143, when activated, will perform the operation o1143. Also, the receiving information incorporate module m1143, when executed and/or activated, will direct performance of and/or perform the operation o1143. For instance, in one or more exemplary implementations, the one or more receiving information incorporate instructions i1143, when executed, direct performance of the operation o1143 in the illustrative depiction as follows, and/or the receiving information incorporate electrical circuitry arrangement e1143, when activated, performs the operation o1143 in the illustrative depiction as follows, and/or the receiving information incorporate module m1143, when executed and/or activated, directs performance of and/or performs the operation o1143 in the illustrative depiction as follows, and/or the operation o1143 is otherwise carried out in the illustrative depiction as follows: electronically receiving the selection information at least in part identifying the one or more selected ingestible products to incorporate one or more substances (e.g. including an implementation of the receiver component s528 is configured to electronically receive the selection information and to engage with the processor component s102 to at least in part electronically identify one or more selected ingestible products to incorporate one or more substances such as a sandwich to include the substance as an amino acid incorporated into the sandwich, and/or etc.) therein during the one or more injections thereof.

In one or more implementations, as shown in FIG. 76, operation o11 includes an operation o1144 for electronically receiving the selection information at least in part identifying the one or more selected ingestible products to be ingested over a period of days. Origination of an illustratively derived receiving information days component group can be accomplished through skilled in the art design choice selection of one or more of the above depicted components from one or more of the above depicted subsystems shown in FIG. 30. Components from the receiving information days component group can be used in implementing execution of the one or more receiving information days instructions i1144 of FIG. 49, can be used in performance of the receiving information days electrical circuitry arrangement e1144 of FIG. 42, and/or can be used in otherwise fulfillment of the operation o1144. An exemplary non-transitory signal bearing medium version of the information storage subsystem s200 is depicted in FIG. 49 as bearing the one or more receiving information days instructions i1144 that when executed will direct performance of the operation o1144. Furthermore, the receiving information days electrical circuitry arrangement ("elec circ arrange") e1144, when activated, will perform the operation o1144. Also, the receiving information days module m1144, when executed and/or activated, will direct performance of and/or perform the operation o1144. For instance, in one or more exemplary implementations, the one or more receiving information days instructions i1144, when executed, direct performance of the operation o1144 in the illustrative depiction as follows, and/or the receiving information days electrical circuitry arrangement e1144, when activated, performs the operation o1144 in the illustrative depiction as follows, and/or the receiving information days module m1144, when executed and/or activated, directs performance of and/or performs the operation o1144 in the illustrative depiction as follows, and/or the operation o1144 is otherwise carried out in the illustrative depiction as follows: electronically receiving the selection information at least in part identifying the one or more selected ingestible products to be ingested over a period of days (e.g. including an implementation of the receiver component s528 is configured to electronically receive the selection information and engage with the processor component s102 to at least in part electronically identify one or more selected ingestible products to be ingested over a period of days such as a smoothie to contain an activator that is designed to interact with a substance, such as a pharmaceutical agent that is encapsulated in pill form to be ingested over a period of days by a living being, such as a boy, at the same time that the smoothie is being ingested by the boy, and/or etc.).

In one or more implementations, as shown in FIG. 76, operation o11 includes an operation o1145 for electronically receiving the selection information at least in part identifying the one or more selected ingestible products to be swallowed. Origination of an illustratively derived receiving information swallow component group can be accomplished through skilled in the art design choice selection of one or more of the above depicted components from one or more of the above depicted subsystems shown in FIG. 30. Components from the receiving information swallow component group can be used in implementing execution of the one or more receiving information swallow instructions i1145 of FIG. 49, can be used in performance of the receiving information swallow electrical circuitry arrangement e1145 of FIG. 42, and/or can be used in otherwise fulfillment of the operation o1145. An exemplary non-transitory signal bearing medium version of the information storage subsystem s200 is depicted in FIG. 49 as bearing the one or more receiving information swallow instructions i1145 that when executed will direct performance of the operation o1145. Furthermore, the receiving information swallow electrical circuitry arrangement ("elec circ arrange") e1145, when activated, will perform the operation o1145. Also, the receiving information swallow module m1145, when executed and/or activated, will direct performance of and/or perform the operation o1145. For instance, in one or more exemplary implementations, the one or more receiving information swallow instructions i1145, when executed, direct performance of the operation o1145 in the illustrative depiction as follows, and/or the receiving information swallow electrical circuitry arrangement e1145, when activated, performs the operation o1145 in the illustrative depiction as follows, and/or the receiving information swallow module m1145, when executed and/or activated, directs performance of and/or performs the operation o1145 in the illustrative depiction as follows, and/or the operation o1145 is otherwise carried out in the illustrative depiction as follows: electronically receiving the selection information at least in part identifying the one or more selected ingestible products to be swallowed (e.g. including an implementation of the receiver component s528 is configured to electronically receive the selection information and engage with the processor component s102 to direct the material processing subsystem s700 to electronically identify the one or more selected ingestible products to be swallowed such as a snack bar, and/or etc.).

Figure 77:
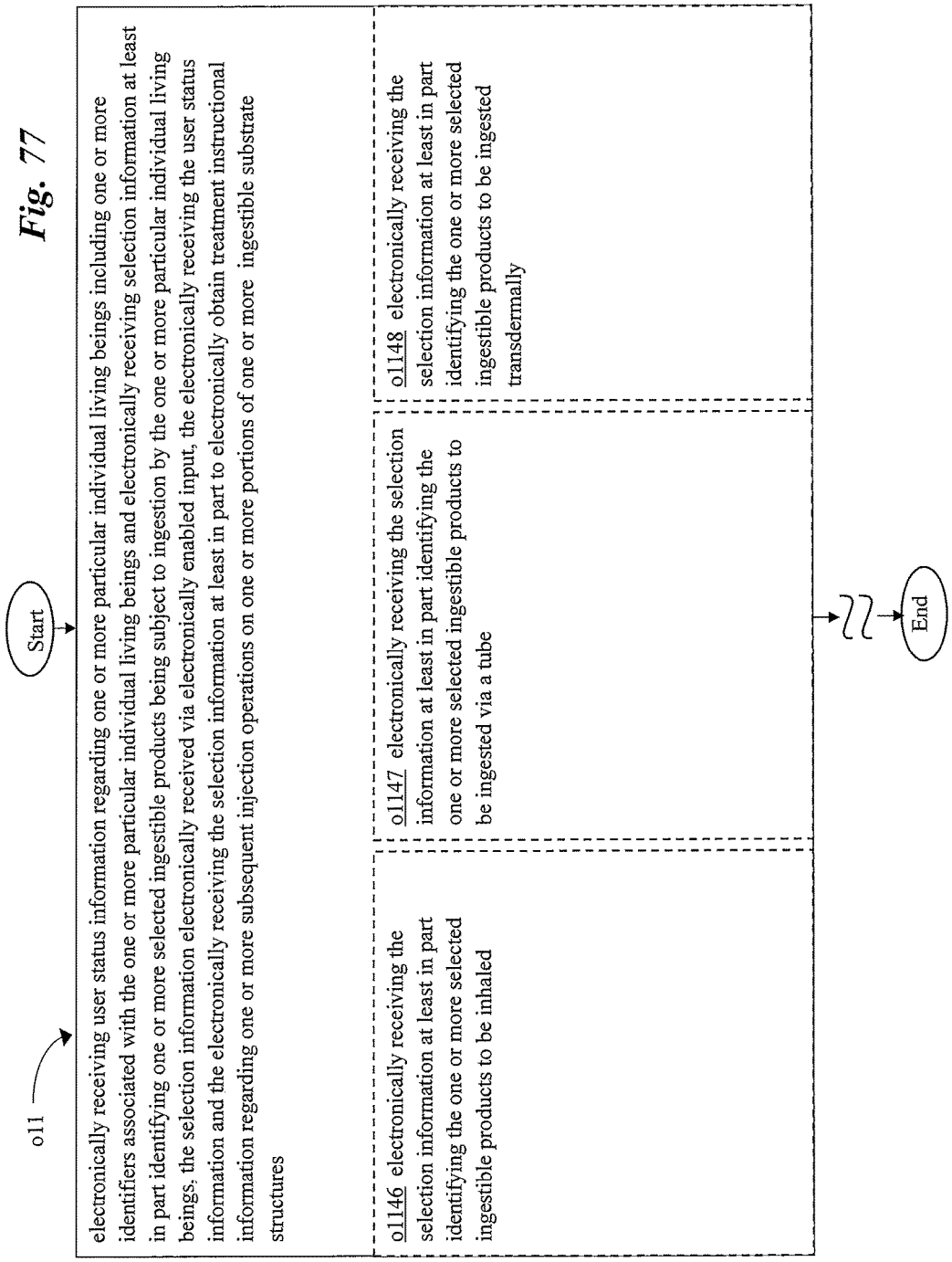
FIG. 77 is a high-level flowchart including exemplary implementations of operation O11 of FIG. 61.

In one or more implementations, as shown in FIG. 77, operation o11 includes an operation o1146 for electronically receiving the selection information at least in part identifying the one or more selected ingestible products to be inhaled. Origination of an illustratively derived receiving information inhaled component group can be accomplished through skilled in the art design choice selection of one or more of the above depicted components from one or more of the above depicted subsystems shown in FIG. 30. Components from the receiving information inhaled component group can be used in implementing execution of the one or more receiving information inhaled instructions i1146 of FIG. 49, can be used in performance of the receiving information inhaled electrical circuitry arrangement e1146 of FIG. 42, and/or can be used in otherwise fulfillment of the operation o1146. An exemplary non-transitory signal bearing medium version of the information storage subsystem s200 is depicted in FIG. 49 as bearing the one or more receiving information inhaled instructions i1146 that when executed will direct performance of the operation o1146. Furthermore, the receiving information inhaled electrical circuitry arrangement ("elec circ arrange") e1146, when activated, will perform the operation o1146. Also, the receiving information inhaled module m1146, when executed and/or activated, will direct performance of and/or perform the operation o1146. For instance, in one or more exemplary implementations, the one or more receiving information inhaled instructions i1146, when executed, direct performance of the operation o1146 in the illustrative depiction as follows, and/or the receiving information inhaled electrical circuitry arrangement e1146, when activated, performs the operation o1146 in the illustrative depiction as follows, and/or the receiving information inhaled module m1146, when executed and/or activated, directs performance of and/or performs the operation o1146 in the illustrative depiction as follows, and/or the operation o1146 is otherwise carried out in the illustrative depiction as follows: electronically receiving the selection information at least in part identifying the one or more selected ingestible products to be inhaled (e.g. including an implementation of the receiver component s528 is configured to electronically receive the selection information and engage with the processor component s102 to direct the material processing subsystem s700 to electronically identify the one or more selected ingestible products to be inhaled such as a medicament dispensed through a nebulizer, and/or etc.).

In one or more implementations, as shown in FIG. 77, operation o11 includes an operation o1147 for electronically receiving the selection information at least in part identifying the one or more selected ingestible products to be ingested via a tube. Origination of an illustratively derived receiving information tube component group can be accomplished through skilled in the art design choice selection of one or more of the above depicted components from one or more of the above depicted subsystems shown in FIG. 30. Components from the receiving information tube component group can be used in implementing execution of the one or more receiving information tube instructions i1147 of FIG. 49, can be used in performance of the receiving information tube electrical circuitry arrangement e1147 of FIG. 42, and/or can be used in otherwise fulfillment of the operation o1147. An exemplary non-transitory signal bearing medium version of the information storage subsystem s200 is depicted in FIG. 49 as bearing the one or more receiving information tube instructions i1147 that when executed will direct performance of the operation o1147. Furthermore, the receiving information tube electrical circuitry arrangement ("elec circ arrange") e1147, when activated, will perform the operation o1147. Also, the receiving information tube module m1147, when executed and/or activated, will direct performance of and/or perform the operation o1147. For instance, in one or more exemplary implementations, the one or more receiving information tube instructions i1147, when executed, direct performance of the operation o1147 in the illustrative depiction as follows, and/or the receiving information tube electrical circuitry arrangement e1147, when activated, performs the operation o1147 in the illustrative depiction as follows, and/or the receiving information tube module m1147, when executed and/or activated, directs performance of and/or performs the operation o1147 in the illustrative depiction as follows, and/or the operation o1147 is otherwise carried out in the illustrative depiction as follows: electronically receiving the selection information at least in part identifying the one or more selected ingestible products to be ingested via a tube (e.g. including an implementation of the receiver component s528 is configured to electronically receive the selection information and engage with the processor component s102 to direct the material processing subsystem s700 to electronically identify at least in part the one or more selected ingestible products to be ingested via a tube such as a liquid meal replacement, and/or etc.).

In one or more implementations, as shown in FIG. 77, operation o11 includes an operation o1148 for electronically receiving the selection information at least in part identifying the one or more selected ingestible products to be ingested transdermally. Origination of an illustratively derived receiving information transdermal component group can be accomplished through skilled in the art design choice selection of one or more of the above depicted components from one or more of the above depicted subsystems shown in FIG. 30. Components from the receiving information transdermal component group can be used in implementing execution of the one or more receiving information transdermal instructions i1148 of FIG. 49, can be used in performance of the receiving information transdermal electrical circuitry arrangement e1148 of FIG. 42, and/or can be used in otherwise fulfillment of the operation o1148. An exemplary non-transitory signal bearing medium version of the information storage subsystem s200 is depicted in FIG. 49 as bearing the one or more receiving information transdermal instructions i1148 that when executed will direct performance of the operation o1148. Furthermore, the receiving information transdermal electrical circuitry arrangement ("elec circ arrange") e1148, when activated, will perform the operation o1148. Also, the receiving information transdermal module m1148, when executed and/or activated, will direct performance of and/or perform the operation o1148. For instance, in one or more exemplary implementations, the one or more receiving information transdermal instructions i1148, when executed, direct performance of the operation o1148 in the illustrative depiction as follows, and/or the receiving information transdermal electrical circuitry arrangement e1148, when activated, performs the operation o1148 in the illustrative depiction as follows, and/or the receiving information transdermal module m1148, when executed and/or activated, directs performance of and/or performs the operation o1148 in the illustrative depiction as follows, and/or the operation o1148 is otherwise carried out in the illustrative depiction as follows: electronically receiving the selection information at least in part identifying the one or more selected ingestible products to be ingested transdermally (e.g. including an implementation of the receiver component s528 is configured to electronically receive the selection information and engage with the processor component s102 to direct the material processing subsystem s700 to at least in part electronically identify the one or more selected ingestible products to be ingested transdermally such as a cream, and/or etc.).

Figure 78:
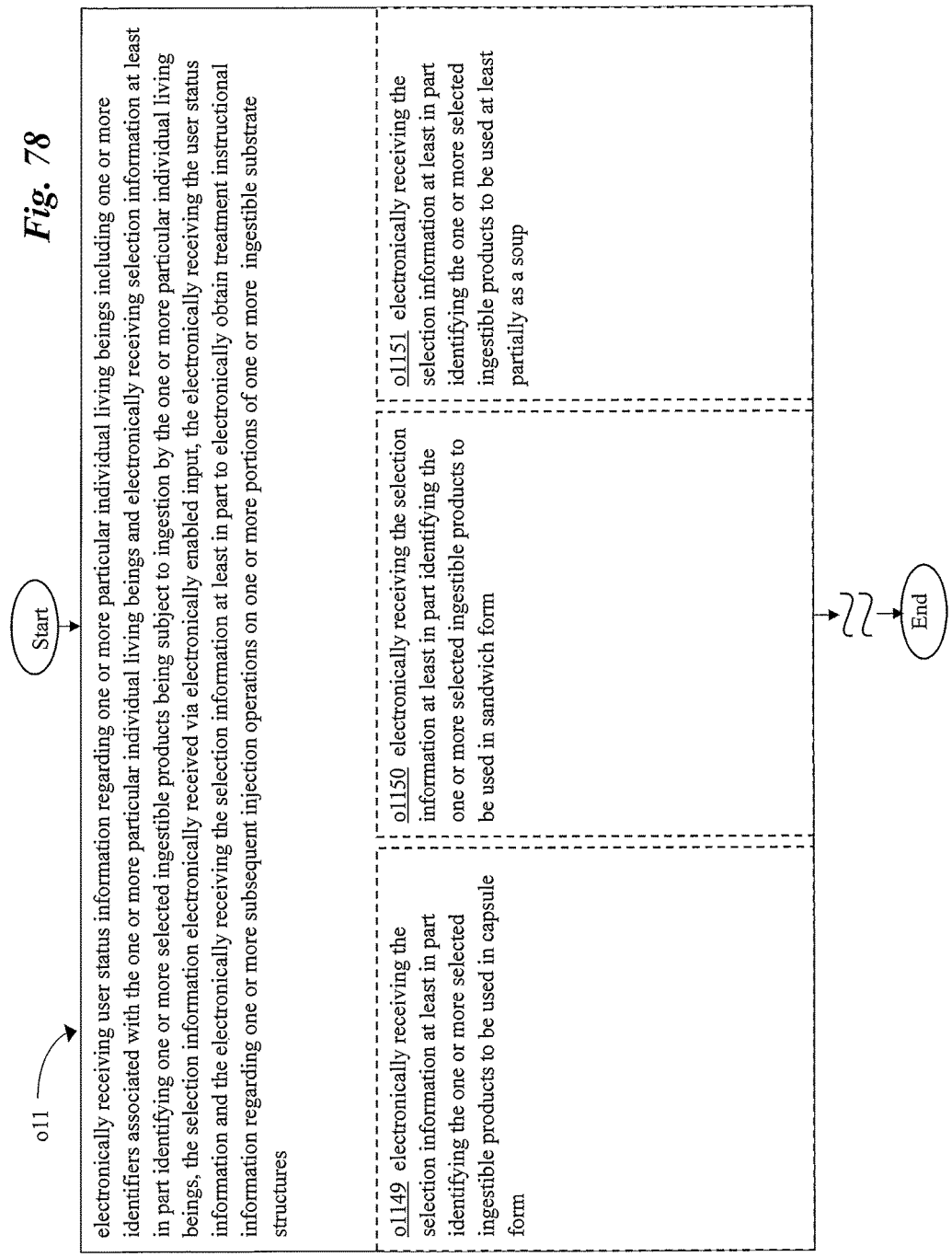
FIG. 78 is a high-level flowchart including exemplary implementations of operation O11 of FIG. 61.

In one or more implementations, as shown in FIG. 78, operation o11 includes an operation o1149 for electronically receiving the selection information at least in part identifying the one or more selected ingestible products to be used in capsule form. Origination of an illustratively derived receiving information capsule component group can be accomplished through skilled in the art design choice selection of one or more of the above depicted components from one or more of the above depicted subsystems shown in FIG. 30. Components from the receiving information capsule component group can be used in implementing execution of the one or more receiving information capsule instructions i1149 of FIG. 49, can be used in performance of the receiving information capsule electrical circuitry arrangement e1149 of FIG. 42, and/or can be used in otherwise fulfillment of the operation o1149. An exemplary non-transitory signal bearing medium version of the information storage subsystem s200 is depicted in FIG. 49 as bearing the one or more receiving information capsule instructions i1149 that when executed will direct performance of the operation o1149. Furthermore, the receiving information capsule electrical circuitry arrangement ("elec circ arrange") e1149, when activated, will perform the operation o1149. Also, the receiving information capsule module m1149, when executed and/or activated, will direct performance of and/or perform the operation o1149. For instance, in one or more exemplary implementations, the one or more receiving information capsule instructions i1149, when executed, direct performance of the operation o1149 in the illustrative depiction as follows, and/or the receiving information capsule electrical circuitry arrangement e1149, when activated, performs the operation o1149 in the illustrative depiction as follows, and/or the receiving information capsule module m1149, when executed and/or activated, directs performance of and/or performs the operation o1149 in the illustrative depiction as follows, and/or the operation o1149 is otherwise carried out in the illustrative depiction as follows: electronically receiving the selection information at least in part identifying the one or more selected ingestible products to be used in capsule form (e.g. including an implementation of the receiver component s528 is configured to electronically receive the selection information and engage with the processor component s102 to direct the material processing subsystem s700 to at least in part electronically generate the one or more selection menus electronically identifying at least in part the one or more selected ingestible products to be used in capsule form, such as through capsules via encapsulation, and/or etc.).

In one or more implementations, as shown in FIG. 78, operation o11 includes an operation o1150 for electronically receiving the selection information at least in part identifying the one or more selected ingestible products to be used in sandwich form. Origination of an illustratively derived receiving information sandwich component group can be accomplished through skilled in the art design choice selection of one or more of the above depicted components from one or more of the above depicted subsystems shown in FIG. 30. Components from the receiving information sandwich component group can be used in implementing execution of the one or more receiving information sandwich instructions i1150 of FIG. 49, can be used in performance of the receiving information sandwich electrical circuitry arrangement e1150 of FIG. 42, and/or can be used in otherwise fulfillment of the operation o1150. An exemplary non-transitory signal bearing medium version of the information storage subsystem s200 is depicted in FIG. 49 as bearing the one or more receiving information sandwich instructions i1150 that when executed will direct performance of the operation o1150. Furthermore, the receiving information sandwich electrical circuitry arrangement ("elec circ arrange") e1150, when activated, will perform the operation o1150. Also, the receiving information sandwich module m1150, when executed and/or activated, will direct performance of and/or perform the operation o1150. For instance, in one or more exemplary implementations, the one or more receiving information sandwich instructions i1150, when executed, direct performance of the operation o1150 in the illustrative depiction as follows, and/or the receiving information sandwich electrical circuitry arrangement e1150, when activated, performs the operation o1150 in the illustrative depiction as follows, and/or the receiving information sandwich module m1150, when executed and/or activated, directs performance of and/or performs the operation o1150 in the illustrative depiction as follows, and/or the operation o1150 is otherwise carried out in the illustrative depiction as follows: electronically receiving the selection information at least in part identifying the one or more selected ingestible products to be used in sandwich form (e.g. including an implementation of the receiver component s528 is configured to electronically receive the selection information and engage with the processor component s102 to at least in part electronically identify the one or more selected ingestible products in sandwich form such as a hamburger, and/or etc.).

In one or more implementations, as shown in FIG. 78, operation o11 includes an operation o1151 for electronically receiving the selection information at least in part identifying the one or more selected ingestible products to be used at least partially as a soup. Origination of an illustratively derived receiving information soup component group can be accomplished through skilled in the art design choice selection of one or more of the above depicted components from one or more of the above depicted subsystems shown in FIG. 30. Components from the receiving information soup component group can be used in implementing execution of the one or more receiving information soup instructions i1151 of FIG. 49, can be used in performance of the receiving information soup electrical circuitry arrangement e1151 of FIG. 42, and/or can be used in otherwise fulfillment of the operation o1151. An exemplary non-transitory signal bearing medium version of the information storage subsystem s200 is depicted in FIG. 49 as bearing the one or more receiving information soup instructions i1151 that when executed will direct performance of the operation o1151. Furthermore, the receiving information soup electrical circuitry arrangement ("elec circ arrange") e1151, when activated, will perform the operation o1151. Also, the receiving information soup module m1151, when executed and/or activated, will direct performance of and/or perform the operation o1151. For instance, in one or more exemplary implementations, the one or more receiving information soup instructions i1151, when executed, direct performance of the operation o1151 in the illustrative depiction as follows, and/or the receiving information soup electrical circuitry arrangement e1151, when activated, performs the operation o1151 in the illustrative depiction as follows, and/or the receiving information soup module m1151, when executed and/or activated, directs performance of and/or performs the operation o1151 in the illustrative depiction as follows, and/or the operation o1151 is otherwise carried out in the illustrative depiction as follows: electronically receiving the selection information at least in part identifying the one or more selected ingestible products to be used at least partially as a soup (e.g. including an implementation of the receiver component s528 is configured to electronically receive the selection information and engage with the processor component s102 to at least in part electronically identify the one or more selected ingestible products to be used as a soup such as tomato soup, and/or etc.).

Figure 79:
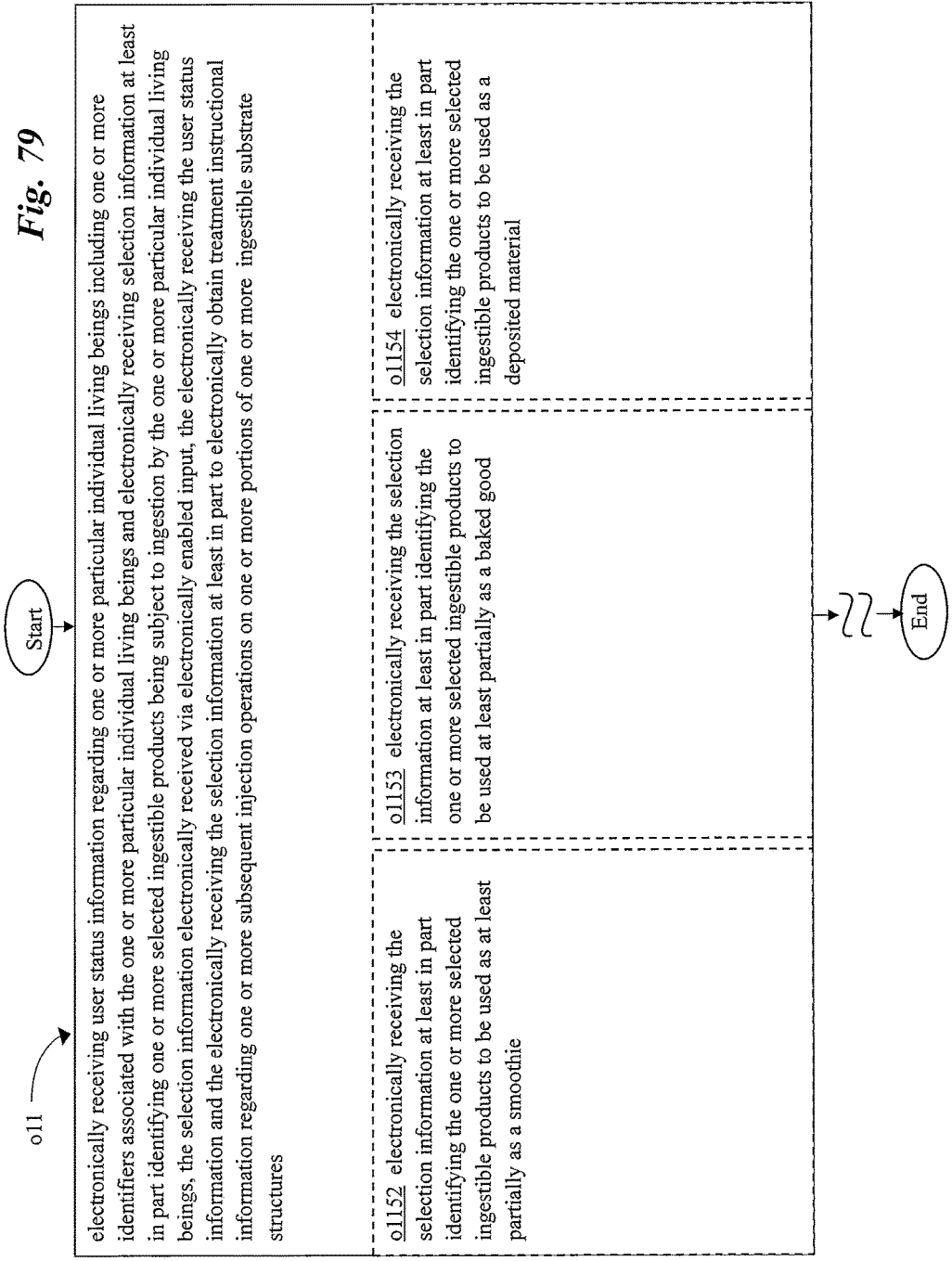
FIG. 79 is a high-level flowchart including exemplary implementations of operation O11 of FIG. 61.

In one or more implementations, as shown in FIG. 79, operation o11 includes an operation o1152 for electronically receiving the selection information at least in part identifying the one or more selected ingestible products to be used as at least partially as a smoothie. Origination of an illustratively derived receiving information smoothie component group can be accomplished through skilled in the art design choice selection of one or more of the above depicted components from one or more of the above depicted subsystems shown in FIG. 30. Components from the receiving information smoothie component group can be used in implementing execution of the one or more receiving information smoothie instructions i1152 of FIG. 49, can be used in performance of the receiving information smoothie electrical circuitry arrangement e1152 of FIG. 42, and/or can be used in otherwise fulfillment of the operation o1152. An exemplary non-transitory signal bearing medium version of the information storage subsystem s200 is depicted in FIG. 49 as bearing the one or more receiving information smoothie instructions i1152 that when executed will direct performance of the operation o1152. Furthermore, the receiving information smoothie electrical circuitry arrangement ("elec circ arrange") e1152, when activated, will perform the operation o1152. Also, the receiving information smoothie module m1152, when executed and/or activated, will direct performance of and/or perform the operation o1152. For instance, in one or more exemplary implementations, the one or more receiving information smoothie instructions i1152, when executed, direct performance of the operation o1152 in the illustrative depiction as follows, and/or the receiving information smoothie electrical circuitry arrangement e1152, when activated, performs the operation o1152 in the illustrative depiction as follows, and/or the receiving information smoothie module m1152, when executed and/or activated, directs performance of and/or performs the operation o1152 in the illustrative depiction as follows, and/or the operation o1152 is otherwise carried out in the illustrative depiction as follows: electronically receiving the selection information at least in part identifying the one or more selected ingestible products to be used as at least partially as a smoothie (e.g. including an implementation of the receiver component s528 is configured to electronically receive the selection information and engage with the processor component s102 to at least in part electronically identify the one or more selected ingestible products to be used a smoothie such as a fruit smoothie, and/or etc.).

In one or more implementations, as shown in FIG. 79, operation o11 includes an operation o1153 for electronically receiving the selection information at least in part identifying the one or more selected ingestible products to be used at least partially as a baked good. Origination of an illustratively derived receiving information baked component group can be accomplished through skilled in the art design choice selection of one or more of the above depicted components from one or more of the above depicted subsystems shown in FIG. 30. Components from the receiving information baked component group can be used in implementing execution of the one or more receiving information baked instructions i1153 of FIG. 49, can be used in performance of the receiving information baked electrical circuitry arrangement e1153 of FIG. 42, and/or can be used in otherwise fulfillment of the operation o1153. An exemplary non-transitory signal bearing medium version of the information storage subsystem s200 is depicted in FIG. 49 as bearing the one or more receiving information baked instructions i1153 that when executed will direct performance of the operation o1153. Furthermore, the receiving information baked electrical circuitry arrangement ("elec circ arrange") e1153, when activated, will perform the operation o1153. Also, the receiving information baked module m1153, when executed and/or activated, will direct performance of and/or perform the operation o1153. For instance, in one or more exemplary implementations, the one or more receiving information baked instructions i1153, when executed, direct performance of the operation o1153 in the illustrative depiction as follows, and/or the receiving information baked electrical circuitry arrangement e1153, when activated, performs the operation o1153 in the illustrative depiction as follows, and/or the receiving information baked module m1153, when executed and/or activated, directs performance of and/or performs the operation o1153 in the illustrative depiction as follows, and/or the operation o1153 is otherwise carried out in the illustrative depiction as follows: electronically receiving the selection information at least in part identifying the one or more selected ingestible products to be used at least partially as a baked good (e.g. including an implementation of the receiver component s528 is configured to electronically receive the selection information and engage with the processor component s102 to at least in part electronically identifying at least in part the one or more selected ingestible products to be used as a baked good such as a muffin, and/or etc.).

In one or more implementations, as shown in FIG. 79, operation o11 includes an operation o1154 for electronically receiving the selection information at least in part identifying the one or more selected ingestible products to be used as a deposited material. Origination of an illustratively derived receiving information deposited component group can be accomplished through skilled in the art design choice selection of one or more of the above depicted components from one or more of the above depicted subsystems shown in FIG. 30. Components from the receiving information deposited component group can be used in implementing execution of the one or more receiving information deposited instructions i1154 of FIG. 49, can be used in performance of the receiving information deposited electrical circuitry arrangement e1154 of FIG. 42, and/or can be used in otherwise fulfillment of the operation o1154. An exemplary non-transitory signal bearing medium version of the information storage subsystem s200 is depicted in FIG. 49 as bearing the one or more receiving information deposited instructions i1154 that when executed will direct performance of the operation o1154. Furthermore, the receiving information deposited electrical circuitry arrangement ("elec circ arrange") e1154, when activated, will perform the operation o1154. Also, the receiving information deposited module m1154, when executed and/or activated, will direct performance of and/or perform the operation o1154. For instance, in one or more exemplary implementations, the one or more receiving information deposited instructions i1154, when executed, direct performance of the operation o1154 in the illustrative depiction as follows, and/or the receiving information deposited electrical circuitry arrangement e1154, when activated, performs the operation o1154 in the illustrative depiction as follows, and/or the receiving information deposited module m1154, when executed and/or activated, directs performance of and/or performs the operation o1154 in the illustrative depiction as follows, and/or the operation o1154 is otherwise carried out in the illustrative depiction as follows: electronically receiving the selection information at least in part identifying the one or more selected ingestible products to be used as a deposited material (e.g. including an implementation of the receiver component s528 is configured to electronically receive the selection information and engage with the processor component s102 to direct the material processing subsystem s700 to at least in part electronically identify at least in part the one or more selected ingestible products to be used as a deposited material such as frosting on a multi-layered cake, and/or etc.).

Figure 80:
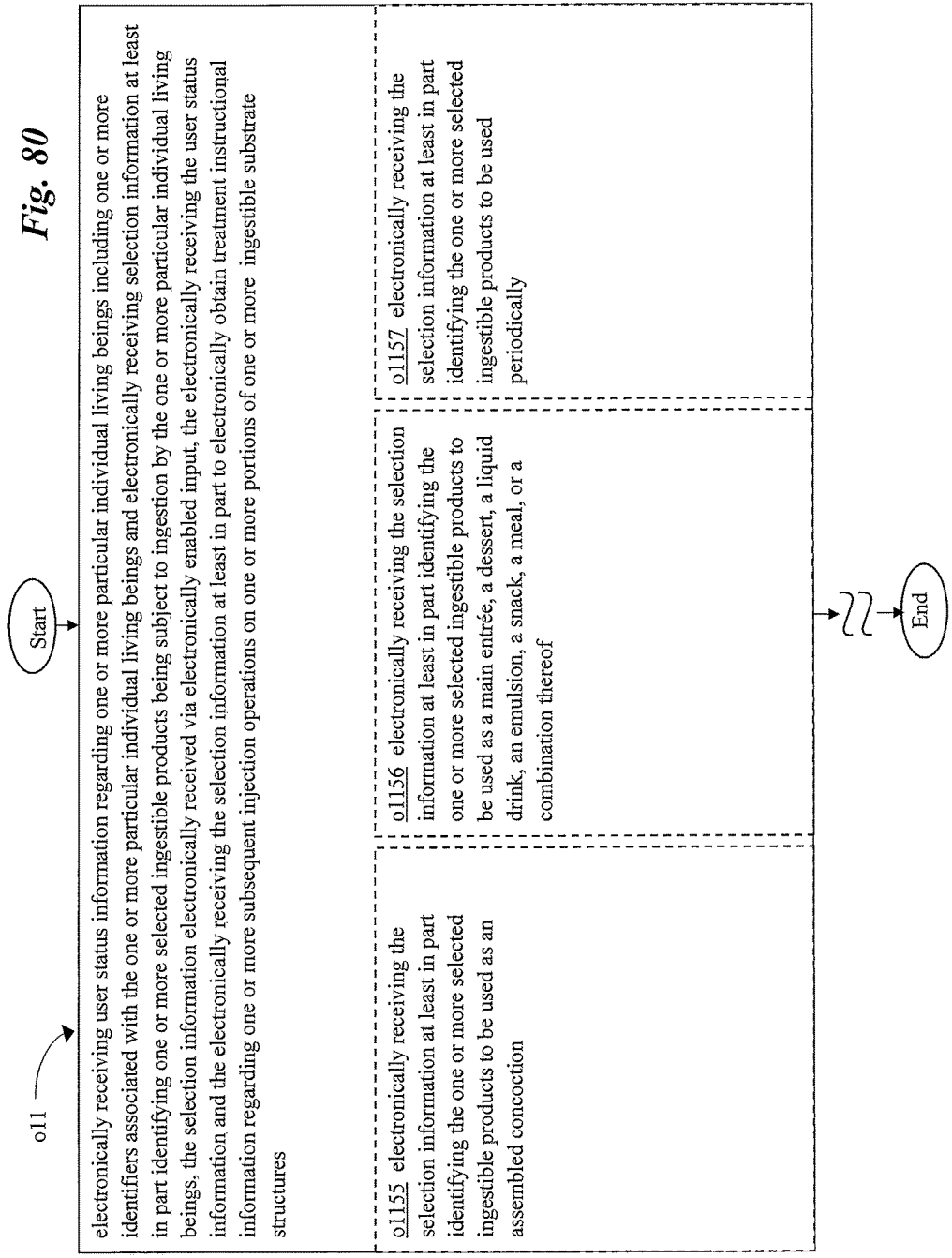
FIG. 80 is a high-level flowchart including exemplary implementations of operation O11 of FIG. 61.

In one or more implementations, as shown in FIG. 80, operation o11 includes an operation o1155 for electronically receiving the selection information at least in part identifying the one or more selected ingestible products to be used as an assembled concoction. Origination of an illustratively derived receiving information assembled component group can be accomplished through skilled in the art design choice selection of one or more of the above depicted components from one or more of the above depicted subsystems shown in FIG. 30. Components from the receiving information assembled component group can be used in implementing execution of the one or more receiving information assembled instructions i1155 of FIG. 49, can be used in performance of the receiving information assembled electrical circuitry arrangement e1155 of FIG. 42, and/or can be used in otherwise fulfillment of the operation o1155. An exemplary non-transitory signal bearing medium version of the information storage subsystem s200 is depicted in FIG. 49 as bearing the one or more receiving information assembled instructions i1155 that when executed will direct performance of the operation o1155. Furthermore, the receiving information assembled electrical circuitry arrangement ("elec circ arrange") e1155, when activated, will perform the operation o1155. Also, the receiving information assembled module m1155, when executed and/or activated, will direct performance of and/or perform the operation o1155. For instance, in one or more exemplary implementations, the one or more receiving information assembled instructions i1155, when executed, direct performance of the operation o1155 in the illustrative depiction as follows, and/or the receiving information assembled electrical circuitry arrangement e1155, when activated, performs the operation o1155 in the illustrative depiction as follows, and/or the receiving information assembled module m1155, when executed and/or activated, directs performance of and/or performs the operation o1155 in the illustrative depiction as follows, and/or the operation o1155 is otherwise carried out in the illustrative depiction as follows: electronically receiving the selection information at least in part identifying the one or more selected ingestible products to be used as an assembled concoction (e.g. including an implementation of the receiver component s528 is configured to electronically receive the selection information and engage with the processor component s102 to direct the material processing subsystem s700 to at least in part electronically identify at least the one or more selected ingestible products to be used as an assembled concoction such as a decorated confection, and/or etc.).

In one or more implementations, as shown in FIG. 80, operation o11 includes an operation o1156 for electronically receiving the selection information at least in part identifying the one or more selected ingestible products to be used as a main entrée, a dessert, a liquid drink, an emulsion, a snack, a meal, or a combination thereof. Origination of an illustratively derived receiving information uses component group can be accomplished through skilled in the art design choice selection of one or more of the above depicted components from one or more of the above depicted subsystems shown in FIG. 30. Components from the receiving information uses component group can be used in implementing execution of the one or more receiving information uses instructions i1156 of FIG. 49, can be used in performance of the receiving information uses electrical circuitry arrangement e1156 of FIG. 42, and/or can be used in otherwise fulfillment of the operation o1156. An exemplary non-transitory signal bearing medium version of the information storage subsystem s200 is depicted in FIG. 49 as bearing the one or more receiving information uses instructions i1156 that when executed will direct performance of the operation o1156. Furthermore, the receiving information uses electrical circuitry arrangement ("elec circ arrange") e1156, when activated, will perform the operation o1156. Also, the receiving information uses module m1156, when executed and/or activated, will direct performance of and/or perform the operation o1156. For instance, in one or more exemplary implementations, the one or more receiving information uses instructions i1156, when executed, direct performance of the operation o1156 in the illustrative depiction as follows, and/or the receiving information uses electrical circuitry arrangement e1156, when activated, performs the operation o1156 in the illustrative depiction as follows, and/or the receiving information uses module m1156, when executed and/or activated, directs performance of and/or performs the operation o1156 in the illustrative depiction as follows, and/or the operation o1156 is otherwise carried out in the illustrative depiction as follows: electronically receiving the selection information at least in part identifying the one or more selected ingestible products to be used as a main entrée, a dessert, a liquid drink, an emulsion, a snack, a meal, or a combination thereof (e.g. including an implementation of the receiver component s528 is configured to electronically receive the selection information and engage with the processor component s102 to at least in part electronically identify the one or more selected ingestible products to be used as a as a main entrée, a dessert, a liquid drink, an emulsion, a snack, a meal, or a combination thereof such as a steak dinner, and/or etc.).

In one or more implementations, as shown in FIG. 80, operation o11 includes an operation o1157 for electronically receiving the selection information at least in part identifying the one or more selected ingestible products to be used periodically. Origination of an illustratively derived receiving information periods component group can be accomplished through skilled in the art design choice selection of one or more of the above depicted components from one or more of the above depicted subsystems shown in FIG. 30. Components from the receiving information periods component group can be used in implementing execution of the one or more receiving information periods instructions i1157 of FIG. 49, can be used in performance of the receiving information periods electrical circuitry arrangement e1157 of FIG. 42, and/or can be used in otherwise fulfillment of the operation o1157. An exemplary non-transitory signal bearing medium version of the information storage subsystem s200 is depicted in FIG. 49 as bearing the one or more receiving information periods instructions i1157 that when executed will direct performance of the operation o1157. Furthermore, the receiving information periods electrical circuitry arrangement ("elec circ arrange") e1157, when activated, will perform the operation o1157. Also, the receiving information periods module m1157, when executed and/or activated, will direct performance of and/or perform the operation o1157. For instance, in one or more exemplary implementations, the one or more receiving information periods instructions i1157, when executed, direct performance of the operation o1157 in the illustrative depiction as follows, and/or the receiving information periods electrical circuitry arrangement e1157, when activated, performs the operation o1157 in the illustrative depiction as follows, and/or the receiving information periods module m1157, when executed and/or activated, directs performance of and/or performs the operation o1157 in the illustrative depiction as follows, and/or the operation o1157 is otherwise carried out in the illustrative depiction as follows: electronically receiving the selection information at least in part identifying the one or more selected ingestible products to be used periodically (e.g. including an implementation of the receiver component s528 is configured to electronically receive the selection information and engage with the processor component s102 to at least in part electronically identify the one or more selected ingestible products to be used periodically such as once a week, and/or etc.).

Figure 81:
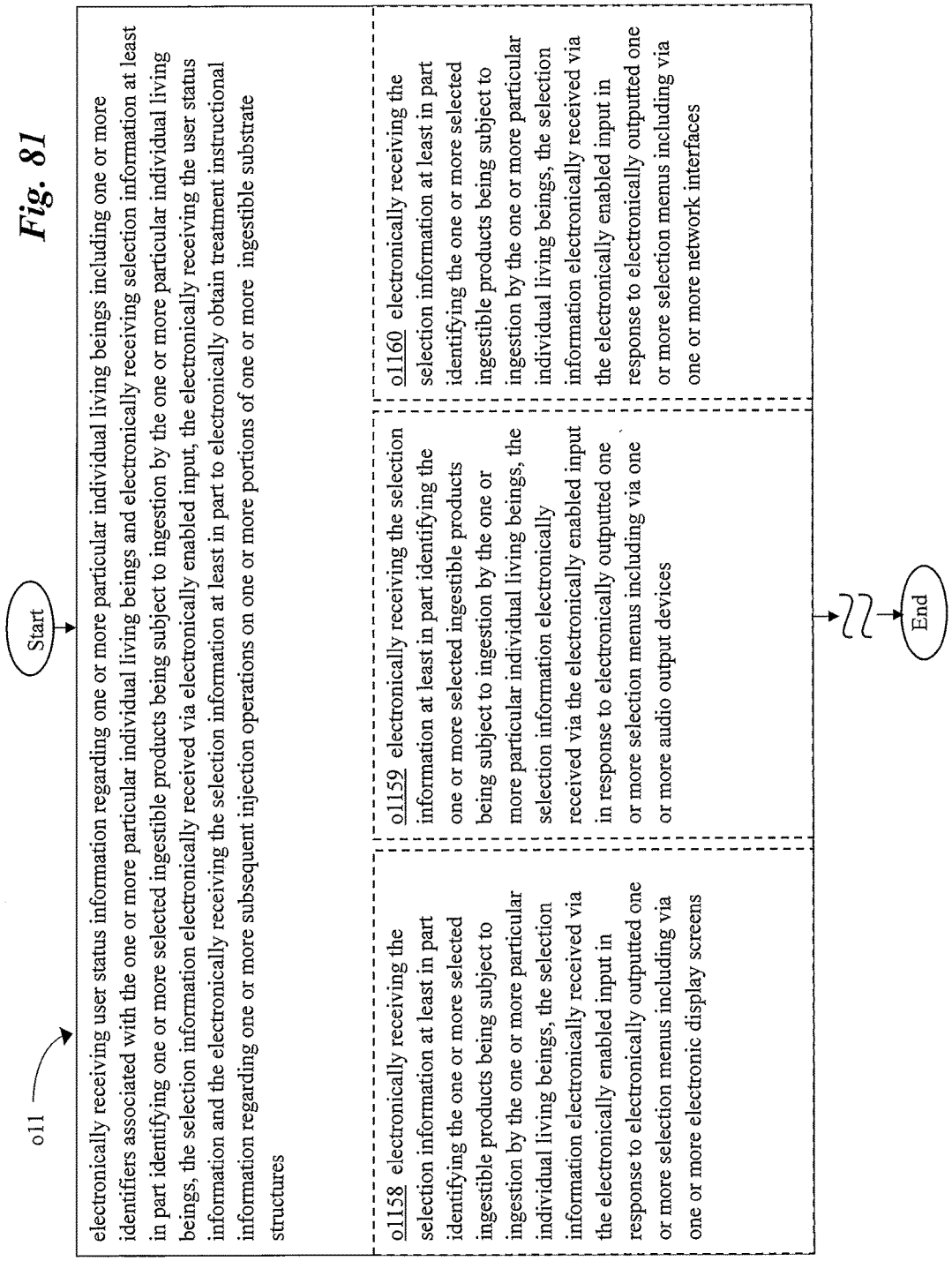
FIG. 81 is a high-level flowchart including exemplary implementations of operation O11 of FIG. 61.

In one or more implementations, as shown in FIG. 81, operation o11 includes an operation o1158 for electronically receiving the selection information at least in part identifying the one or more selected ingestible products being subject to ingestion by the one or more particular individual living beings, the selection information electronically received via the electronically enabled input in response to electronically outputted one or more selection menus including via one or more electronic display screens. Origination of an illustratively derived receiving information display component group can be accomplished through skilled in the art design choice selection of one or more of the above depicted components from one or more of the above depicted subsystems shown in FIG. 30. Components from the receiving information display component group can be used in implementing execution of the one or more receiving information display instructions i1158 of FIG. 49, can be used in performance of the receiving information display electrical circuitry arrangement e1158 of FIG. 42, and/or can be used in otherwise fulfillment of the operation o1158. An exemplary non-transitory signal bearing medium version of the information storage subsystem s200 is depicted in FIG. 49 as bearing the one or more receiving information display instructions i1158 that when executed will direct performance of the operation o1158. Furthermore, the receiving information display electrical circuitry arrangement ("elec circ arrange") e1158, when activated, will perform the operation o1158. Also, the receiving information display module m1158, when executed and/or activated, will direct performance of and/or perform the operation o1158. For instance, in one or more exemplary implementations, the one or more receiving information display instructions i1158, when executed, direct performance of the operation o1158 in the illustrative depiction as follows, and/or the receiving information display electrical circuitry arrangement e1158, when activated, performs the operation o1158 in the illustrative depiction as follows, and/or the receiving information display module m1158, when executed and/or activated, directs performance of and/or performs the operation o1158 in the illustrative depiction as follows, and/or the operation o1158 is otherwise carried out in the illustrative depiction as follows: electronically receiving the selection information at least in part identifying the one or more selected ingestible products being subject to ingestion by the one or more particular individual living beings, the selection information electronically received via the electronically enabled input in response to electronically outputted one or more selection menus including via one or more electronic display screens (e.g. including an implementation of the receiver component s528 is configured to electronically receive the selection information in a format for the processor component s102 to at least in part electronically output the one or more selection menus to be electronically outputted including via one or more display screens such as via graphical user interface (GUI) component s302, and/or etc.).

In one or more implementations, as shown in FIG. 81, operation o11 includes an operation o1159 for electronically receiving the selection information at least in part identifying the one or more selected ingestible products being subject to ingestion by the one or more particular individual living beings, the selection information electronically received via the electronically enabled input in response to electronically outputted one or more selection menus including via one or more audio output devices. Origination of an illustratively derived receiving information audio component group can be accomplished through skilled in the art design choice selection of one or more of the above depicted components from one or more of the above depicted subsystems shown in FIG. 30. Components from the receiving information audio component group can be used in implementing execution of the one or more receiving information audio instructions i1159 of FIG. 49, can be used in performance of the receiving information audio electrical circuitry arrangement e1159 of FIG. 42, and/or can be used in otherwise fulfillment of the operation o1159. An exemplary non-transitory signal bearing medium version of the information storage subsystem s200 is depicted in FIG. 49 as bearing the one or more receiving information audio instructions i1159 that when executed will direct performance of the operation o1159. Furthermore, the receiving information audio electrical circuitry arrangement ("elec circ arrange") e1159, when activated, will perform the operation o1159. Also, the receiving information audio module m1159, when executed and/or activated, will direct performance of and/or perform the operation o1159. For instance, in one or more exemplary implementations, the one or more receiving information audio instructions i1159, when executed, direct performance of the operation o1159 in the illustrative depiction as follows, and/or the receiving information audio electrical circuitry arrangement e1159, when activated, performs the operation o1159 in the illustrative depiction as follows, and/or the receiving information audio module m1159, when executed and/or activated, directs performance of and/or performs the operation o1159 in the illustrative depiction as follows, and/or the operation o1159 is otherwise carried out in the illustrative depiction as follows: electronically receiving the selection information at least in part identifying the one or more selected ingestible products being subject to ingestion by the one or more particular individual living beings, the selection information electronically received via the electronically enabled input in response to electronically outputted one or more selection menus including via one or more audio output devices (e.g. including an implementation of the receiver component s528 is configured to electronically receive the selection information in a format for the processor component s102 to at least in part electronically generate the one or more selection menus to be electronically outputted including via one or more audio output devices such as via audio in/out component s328, and/or etc.).

In one or more implementations, as shown in FIG. 81, operation o11 includes an operation o1160 for electronically receiving the selection information at least in part identifying the one or more selected ingestible products being subject to ingestion by the one or more particular individual living beings, the selection information electronically received via the electronically enabled input in response to electronically outputted one or more selection menus including via one or more network interfaces. Origination of an illustratively derived receiving information interface component group can be accomplished through skilled in the art design choice selection of one or more of the above depicted components from one or more of the above depicted subsystems shown in FIG. 30. Components from the receiving information interface component group can be used in implementing execution of the one or more receiving information interface instructions i1160 of FIG. 50, can be used in performance of the receiving information interface electrical circuitry arrangement e1160 of FIG. 43, and/or can be used in otherwise fulfillment of the operation o1160. An exemplary non-transitory signal bearing medium version of the information storage subsystem s200 is depicted in FIG. 50 as bearing the one or more receiving information interface instructions i1160 that when executed will direct performance of the operation o1160. Furthermore, the receiving information interface electrical circuitry arrangement ("elec circ arrange") e1160, when activated, will perform the operation o1160. Also, the receiving information interface module m1160, when executed and/or activated, will direct performance of and/or perform the operation o1160. For instance, in one or more exemplary implementations, the one or more receiving information interface instructions i1160, when executed, direct performance of the operation o1160 in the illustrative depiction as follows, and/or the receiving information interface electrical circuitry arrangement e1160, when activated, performs the operation o1160 in the illustrative depiction as follows, and/or the receiving information interface module m1160, when executed and/or activated, directs performance of and/or performs the operation o1160 in the illustrative depiction as follows, and/or the operation o1160 is otherwise carried out in the illustrative depiction as follows: electronically receiving the selection information at least in part identifying the one or more selected ingestible products being subject to ingestion by the one or more particular individual living beings, the selection information electronically received via the electronically enabled input in response to electronically outputted one or more selection menus including via one or more network interfaces (e.g. including an implementation of the receiver component s528 is configured to electronically receive the selection information in a format for the processor component s102 to at least in part electronically generate the one or more selection menus to be electronically outputted including via one or more network interfaces such as via wide area network component s516, and/or etc.).

Figure 82:
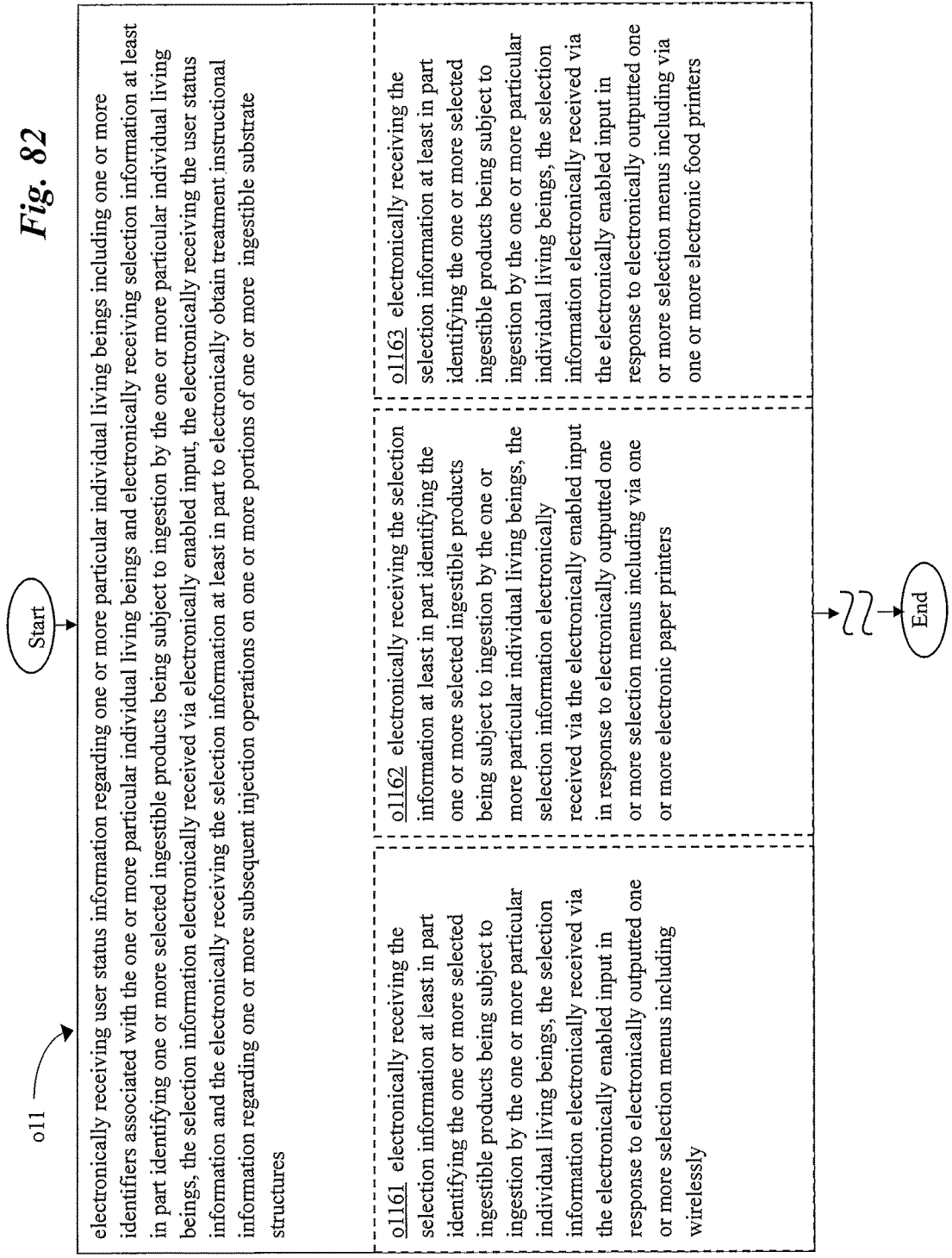
FIG. 82 is a high-level flowchart including exemplary implementations of operation O11 of FIG. 61.

In one or more implementations, as shown in FIG. 82, operation o11 includes an operation o1161 for electronically receiving the selection information at least in part identifying the one or more selected ingestible products being subject to ingestion by the one or more particular individual living beings, the selection information electronically received via the electronically enabled input in response to electronically outputted one or more selection menus including wirelessly. Origination of an illustratively derived receiving information wirelessly component group can be accomplished through skilled in the art design choice selection of one or more of the above depicted components from one or more of the above depicted subsystems shown in FIG. 30. Components from the receiving information wirelessly component group can be used in implementing execution of the one or more receiving information wirelessly instructions i1161 of FIG. 50, can be used in performance of the receiving information wirelessly electrical circuitry arrangement e1161 of FIG. 43, and/or can be used in otherwise fulfillment of the operation o1161. An exemplary non-transitory signal bearing medium version of the information storage subsystem s200 is depicted in FIG. 50 as bearing the one or more receiving information wirelessly instructions i1161 that when executed will direct performance of the operation o1161. Furthermore, the receiving information wirelessly electrical circuitry arrangement ("elec circ arrange") e1161, when activated, will perform the operation o1161. Also, the receiving information wirelessly module m1161, when executed and/or activated, will direct performance of and/or perform the operation o1161. For instance, in one or more exemplary implementations, the one or more receiving information wirelessly instructions i1161, when executed, direct performance of the operation o1161 in the illustrative depiction as follows, and/or the receiving information wirelessly electrical circuitry arrangement e1161, when activated, performs the operation o1161 in the illustrative depiction as follows, and/or the receiving information wirelessly module m1161, when executed and/or activated, directs performance of and/or performs the operation o1161 in the illustrative depiction as follows, and/or the operation o1161 is otherwise carried out in the illustrative depiction as follows: electronically receiving the selection information at least in part identifying the one or more selected ingestible products being subject to ingestion by the one or more particular individual living beings, the selection information electronically received via the electronically enabled input in response to electronically outputted one or more selection menus including wirelessly (e.g. including an implementation of the receiver component s528 is configured to electronically receive the selection information in a format for the processor component s102 to at least in part electronically generate the one or more selection menus to be electronically outputted including wirelessly such as via wireless network component s510, and/or etc.).

In one or more implementations, as shown in FIG. 82, operation o11 includes an operation o1162 for electronically receiving the selection information at least in part identifying the one or more selected ingestible products being subject to ingestion by the one or more particular individual living beings, the selection information electronically received via the electronically enabled input in response to electronically outputted one or more selection menus including via one or more electronic paper printers. Origination of an illustratively derived receiving information paper printer component group can be accomplished through skilled in the art design choice selection of one or more of the above depicted components from one or more of the above depicted subsystems shown in FIG. 30. Components from the receiving information paper printer component group can be used in implementing execution of the one or more receiving information paper printer instructions i1162 of FIG. 50, can be used in performance of the receiving information paper printer electrical circuitry arrangement e1162 of FIG. 43, and/or can be used in otherwise fulfillment of the operation o1162. An exemplary non-transitory signal bearing medium version of the information storage subsystem s200 is depicted in FIG. 50 as bearing the one or more receiving information paper printer instructions i1162 that when executed will direct performance of the operation o1162. Furthermore, the receiving information paper printer electrical circuitry arrangement ("elec circ arrange") e1162, when activated, will perform the operation o1162. Also, the receiving information paper printer module m1162, when executed and/or activated, will direct performance of and/or perform the operation o1162. For instance, in one or more exemplary implementations, the one or more receiving information paper printer instructions i1162, when executed, direct performance of the operation o1162 in the illustrative depiction as follows, and/or the receiving information paper printer electrical circuitry arrangement e1162, when activated, performs the operation o1162 in the illustrative depiction as follows, and/or the receiving information paper printer module m1162, when executed and/or activated, directs performance of and/or performs the operation o1162 in the illustrative depiction as follows, and/or the operation o1162 is otherwise carried out in the illustrative depiction as follows: electronically receiving the selection information at least in part identifying the one or more selected ingestible products being subject to ingestion by the one or more particular individual living beings, the selection information electronically received via electronically enabled input in response to electronically outputted one or more selection menus including via the one or more electronic paper printers (e.g. including an implementation of the receiver component s528 is configured to electronically receive the selection information in a format for the processor component s102 to at least in part electronically generate the one or more selection menus to be electronically outputted including via electronic paper printer such as via scanner component s338, and/or etc.).

In one or more implementations, as shown in FIG. 82, operation o11 includes an operation o1163 for electronically receiving the selection information at least in part identifying the one or more selected ingestible products being subject to ingestion by the one or more particular individual living beings, the selection information electronically received via the electronically enabled input in response to electronically outputted one or more selection menus including via one or more electronic food printers. Origination of an illustratively derived receiving information food printer component group can be accomplished through skilled in the art design choice selection of one or more of the above depicted components from one or more of the above depicted subsystems shown in FIG. 30. Components from the receiving information food printer component group can be used in implementing execution of the one or more receiving information food printer instructions i1163 of FIG. 50, can be used in performance of the receiving information food printer electrical circuitry arrangement e1163 of FIG. 43, and/or can be used in otherwise fulfillment of the operation o1163. An exemplary non-transitory signal bearing medium version of the information storage subsystem s200 is depicted in FIG. 50 as bearing the one or more receiving information food printer instructions i1163 that when executed will direct performance of the operation o1163. Furthermore, the receiving information food printer electrical circuitry arrangement ("elec circ arrange") e1163, when activated, will perform the operation o1163. Also, the receiving information food printer module m1163, when executed and/or activated, will direct performance of and/or perform the operation o1163. For instance, in one or more exemplary implementations, the one or more receiving information food printer instructions i1163, when executed, direct performance of the operation o1163 in the illustrative depiction as follows, and/or the receiving information food printer electrical circuitry arrangement e1163, when activated, performs the operation o1163 in the illustrative depiction as follows, and/or the receiving information food printer module m1163, when executed and/or activated, directs performance of and/or performs the operation o1163 in the illustrative depiction as follows, and/or the operation o1163 is otherwise carried out in the illustrative depiction as follows: electronically receiving the selection information at least in part identifying the one or more selected ingestible products being subject to ingestion by the one or more particular individual living beings, the selection information electronically received via electronically enabled input in response to electronically outputted one or more selection menus including via the one or more electronic food printers (e.g. including an implementation of the receiver component s528 is configured to electronically receive the user status information in a format for the processor component s102 to at least in part electronically generate the one or more selection menus to be electronically outputted including via electronic food printer such as via deposition component s740, and/or etc.).

Figure 83:
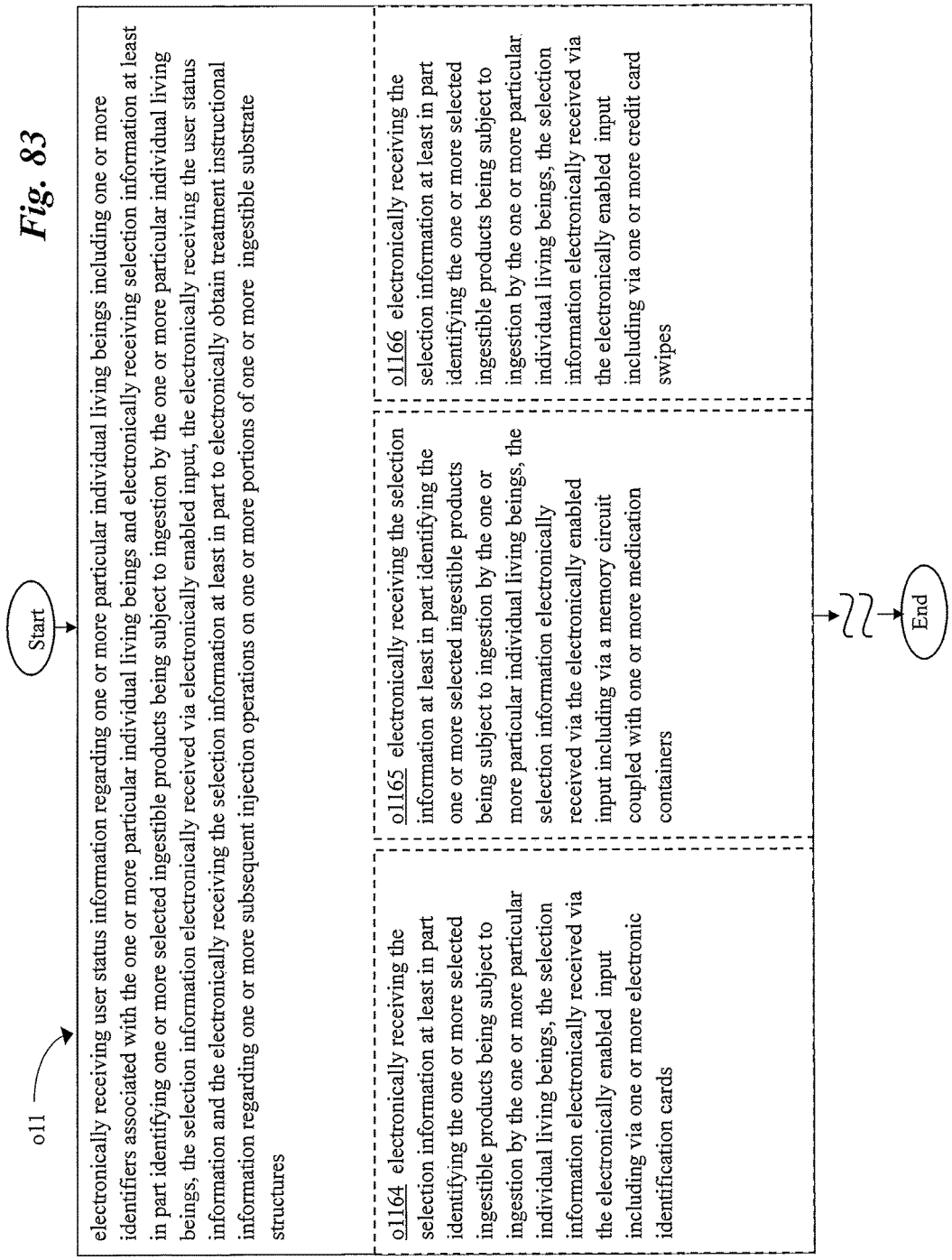
FIG. 83 is a high-level flowchart including exemplary implementations of operation O11 of FIG. 61.

In one or more implementations, as shown in FIG. 83, operation o11 includes an operation o1164 for electronically receiving the selection information at least in part identifying the one or more selected ingestible products being subject to ingestion by the one or more particular individual living beings, the selection information electronically received via the electronically enabled input including via one or more electronic identification cards. Origination of an illustratively derived receiving information ID card component group can be accomplished through skilled in the art design choice selection of one or more of the above depicted components from one or more of the above depicted subsystems shown in FIG. 30. Components from the receiving information ID card component group can be used in implementing execution of the one or more receiving information ID card instructions i1164 of FIG. 50, can be used in performance of the receiving information ID card electrical circuitry arrangement e1164 of FIG. 43, and/or can be used in otherwise fulfillment of the operation o1164. An exemplary non-transitory signal bearing medium version of the information storage subsystem s200 is depicted in FIG. 50 as bearing the one or more receiving information ID card instructions i1164 that when executed will direct performance of the operation o1164. Furthermore, the receiving information ID card electrical circuitry arrangement ("elec circ arrange") e1164, when activated, will perform the operation o1164. Also, the receiving information ID card module m1164, when executed and/or activated, will direct performance of and/or perform the operation o1164. For instance, in one or more exemplary implementations, the one or more receiving information ID card instructions i1164, when executed, direct performance of the operation o1164 in the illustrative depiction as follows, and/or the receiving information ID card electrical circuitry arrangement e1164, when activated, performs the operation o1164 in the illustrative depiction as follows, and/or the receiving information ID card module m1164, when executed and/or activated, directs performance of and/or performs the operation o1164 in the illustrative depiction as follows, and/or the operation o1164 is otherwise carried out in the illustrative depiction as follows: electronically receiving the selection information at least in part identifying the one or more selected ingestible products being subject to ingestion by the one or more particular individual living beings, the selection information electronically received via the electronically enabled input including via one or more electronic identification cards (e.g. including an implementation of the receiver component s528 is configured to electronically engage with a card having memory storage holding the selection information to be used by the processor component s102, and/or etc.).

In one or more implementations, as shown in FIG. 83, operation o11 includes an operation o1165 for electronically receiving the selection information at least in part identifying the one or more selected ingestible products being subject to ingestion by the one or more particular individual living beings, the selection information electronically received via the electronically enabled input including via a memory circuit coupled with one or more medication containers. Origination of an illustratively derived receiving information containers component group can be accomplished through skilled in the art design choice selection of one or more of the above depicted components from one or more of the above depicted subsystems shown in FIG. 30. Components from the receiving information containers component group can be used in implementing execution of the one or more receiving information containers instructions i1165 of FIG. 50, can be used in performance of the receiving information containers electrical circuitry arrangement e1165 of FIG. 43, and/or can be used in otherwise fulfillment of the operation o1165. An exemplary non-transitory signal bearing medium version of the information storage subsystem s200 is depicted in FIG. 50 as bearing the one or more receiving information containers instructions i1165 that when executed will direct performance of the operation o1165. Furthermore, the receiving information containers electrical circuitry arrangement ("elec circ arrange") e1165, when activated, will perform the operation o1165. Also, the receiving information containers module m1165, when executed and/or activated, will direct performance of and/or perform the operation o1165. For instance, in one or more exemplary implementations, the one or more receiving information containers instructions i1165, when executed, direct performance of the operation o1165 in the illustrative depiction as follows, and/or the receiving information containers electrical circuitry arrangement e1165, when activated, performs the operation o1165 in the illustrative depiction as follows, and/or the receiving information containers module m1165, when executed and/or activated, directs performance of and/or performs the operation o1165 in the illustrative depiction as follows, and/or the operation o1165 is otherwise carried out in the illustrative depiction as follows: electronically receiving the selection information at least in part identifying the one or more selected ingestible products being subject to ingestion by the one or more particular individual living beings, the selection information electronically received via the electronically enabled input including via a memory circuit coupled with one or more medication containers (e.g. including an implementation of the receiver component s528 is configured to electronically engage with a memory storage coupled with a medication container to receive the selection information via the electronically enabled input in electronic form to be used by the processor component s102, and/or etc.).

In one or more implementations, as shown in FIG. 83, operation o11 includes an operation o1166 for electronically receiving the selection information at least in part identifying the one or more selected ingestible products being subject to ingestion by the one or more particular individual living beings, the selection information electronically received via the electronically enabled input including via one or more credit card swipes. Origination of an illustratively derived receiving information credit component group can be accomplished through skilled in the art design choice selection of one or more of the above depicted components from one or more of the above depicted subsystems shown in FIG. 30. Components from the receiving information credit component group can be used in implementing execution of the one or more receiving information credit instructions i1166 of FIG. 50, can be used in performance of the receiving information credit electrical circuitry arrangement e1166 of FIG. 43, and/or can be used in otherwise fulfillment of the operation o1166. An exemplary non-transitory signal bearing medium version of the information storage subsystem s200 is depicted in FIG. 50 as bearing the one or more receiving information credit instructions i1166 that when executed will direct performance of the operation o1166. Furthermore, the receiving information credit electrical circuitry arrangement ("elec circ arrange") e1166, when activated, will perform the operation o1166. Also, the receiving information credit module m1166, when executed and/or activated, will direct performance of and/or perform the operation o1166. For instance, in one or more exemplary implementations, the one or more receiving information credit instructions i1166, when executed, direct performance of the operation o1166 in the illustrative depiction as follows, and/or the receiving information credit electrical circuitry arrangement e1166, when activated, performs the operation o1166 in the illustrative depiction as follows, and/or the receiving information credit module m1166, when executed and/or activated, directs performance of and/or performs the operation o1166 in the illustrative depiction as follows, and/or the operation o1166 is otherwise carried out in the illustrative depiction as follows: electronically receiving the selection information at least in part identifying the one or more selected ingestible products being subject to ingestion by the one or more particular individual living beings, the selection information electronically received via the electronically enabled input including via one or more credit card swipes (e.g. including an implementation of the receiver component s528 is configured to electronically engage with an electronic memory stripe integrated into a credit card to receive the selection information via electronically enabled input to be used by the processor component s102, and/or etc.).

Figure 84:
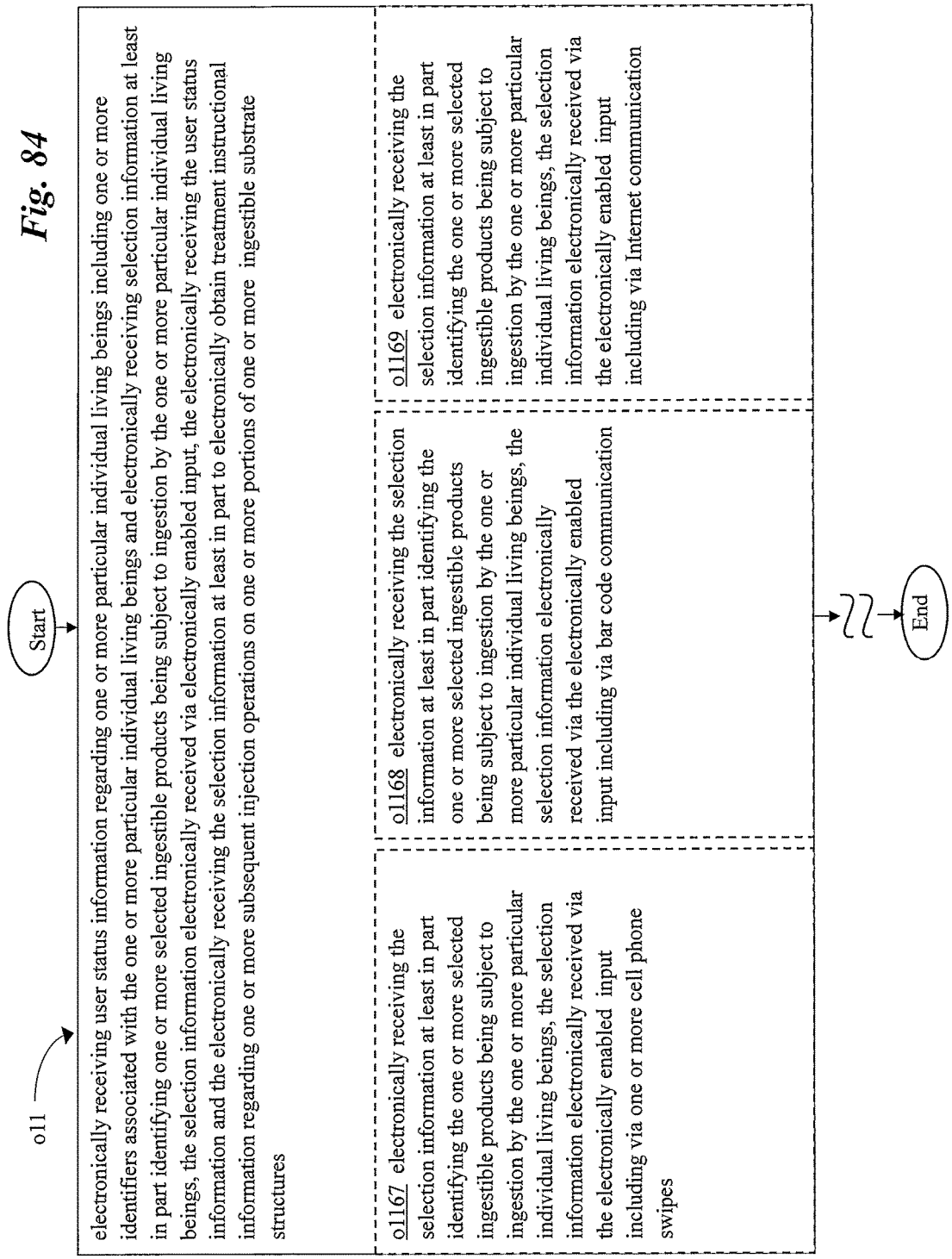
FIG. 84 is a high-level flowchart including exemplary implementations of operation O11 of FIG. 61.

In one or more implementations, as shown in FIG. 84, operation o11 includes an operation o1167 for electronically receiving the selection information at least in part identifying the one or more selected ingestible products being subject to ingestion by the one or more particular individual living beings, the selection information electronically received via the electronically enabled input including via one or more cell phone swipes. Origination of an illustratively derived receiving information cell component group can be accomplished through skilled in the art design choice selection of one or more of the above depicted components from one or more of the above depicted subsystems shown in FIG. 30. Components from the receiving information cell component group can be used in implementing execution of the one or more receiving information cell instructions i1167 of FIG. 50, can be used in performance of the receiving information cell electrical circuitry arrangement e1167 of FIG. 43, and/or can be used in otherwise fulfillment of the operation o1167. An exemplary non-transitory signal bearing medium version of the information storage subsystem s200 is depicted in FIG. 50 as bearing the one or more receiving information cell instructions i1167 that when executed will direct performance of the operation o1167. Furthermore, the receiving information cell electrical circuitry arrangement ("elec circ arrange") e1167, when activated, will perform the operation o1167. Also, the receiving information cell module m1167, when executed and/or activated, will direct performance of and/or perform the operation o1167. For instance, in one or more exemplary implementations, the one or more receiving information cell instructions i1167, when executed, direct performance of the operation o1167 in the illustrative depiction as follows, and/or the receiving information cell electrical circuitry arrangement e1167, when activated, performs the operation o1167 in the illustrative depiction as follows, and/or the receiving information cell module m1167, when executed and/or activated, directs performance of and/or performs the operation o1167 in the illustrative depiction as follows, and/or the operation o1167 is otherwise carried out in the illustrative depiction as follows: electronically receiving the selection information at least in part identifying the one or more selected ingestible products being subject to ingestion by the one or more particular individual living beings, the selection information electronically received via the electronically enabled input including via one or more cell phone swipes (e.g. including an implementation of the receiver component s528 is configured to electronically engage with an electronic memory component integrated into a cell phone to receive the selection information via electronically enabled input to be used by the processor component s102 to generate the one or more selection menus, and/or etc.).

In one or more implementations, as shown in FIG. 84, operation o11 includes an operation o1168 for electronically receiving the selection information at least in part identifying the one or more selected ingestible products being subject to ingestion by the one or more particular individual living beings, the selection information electronically received via the electronically enabled input including via bar code communication. Origination of an illustratively derived receiving information bar code component group can be accomplished through skilled in the art design choice selection of one or more of the above depicted components from one or more of the above depicted subsystems shown in FIG. 30. Components from the receiving information bar code component group can be used in implementing execution of the one or more receiving information bar code instructions i1168 of FIG. 50, can be used in performance of the receiving information bar code electrical circuitry arrangement e1168 of FIG. 43, and/or can be used in otherwise fulfillment of the operation o1168. An exemplary non-transitory signal bearing medium version of the information storage subsystem s200 is depicted in FIG. 50 as bearing the one or more receiving information bar code instructions i1168 that when executed will direct performance of the operation o1168. Furthermore, the receiving information bar code electrical circuitry arrangement ("elec circ arrange") e1168, when activated, will perform the operation o1168. Also, the receiving information bar code module m1168, when executed and/or activated, will direct performance of and/or perform the operation o1168. For instance, in one or more exemplary implementations, the one or more receiving information bar code instructions i1168, when executed, direct performance of the operation o1168 in the illustrative depiction as follows, and/or the receiving information bar code electrical circuitry arrangement e1168, when activated, performs the operation o1168 in the illustrative depiction as follows, and/or the receiving information bar code module m1168, when executed and/or activated, directs performance of and/or performs the operation o1168 in the illustrative depiction as follows, and/or the operation o1168 is otherwise carried out in the illustrative depiction as follows: electronically receiving the selection information at least in part identifying the one or more selected ingestible products being subject to ingestion by the one or more particular individual living beings, the selection information electronically received via the electronically enabled input including via bar code communication (e.g. including an implementation of the receiver component s528 is configured to electronically read a bar code label to receive the selection information via electronically enabled input to be used by the processor component s102, and/or etc.).

In one or more implementations, as shown in FIG. 84, operation o11 includes an operation o1169 for electronically receiving the selection information at least in part identifying the one or more selected ingestible products being subject to ingestion by the one or more particular individual living beings, the selection information electronically received via the electronically enabled input including via Internet communication. Origination of an illustratively derived receiving information Internet component group can be accomplished through skilled in the art design choice selection of one or more of the above depicted components from one or more of the above depicted subsystems shown in FIG. 30. Components from the receiving information Internet component group can be used in implementing execution of the one or more receiving information Internet instructions i1169 of FIG. 50, can be used in performance of the receiving information Internet electrical circuitry arrangement e1169 of FIG. 43, and/or can be used in otherwise fulfillment of the operation o1169. An exemplary non-transitory signal bearing medium version of the information storage subsystem s200 is depicted in FIG. 50 as bearing the one or more receiving information Internet instructions i1169 that when executed will direct performance of the operation o1169. Furthermore, the receiving information Internet electrical circuitry arrangement ("elec circ arrange") e1169, when activated, will perform the operation o1169. Also, the receiving information Internet module m1169, when executed and/or activated, will direct performance of and/or perform the operation o1169. For instance, in one or more exemplary implementations, the one or more receiving information Internet instructions i1169, when executed, direct performance of the operation o1169 in the illustrative depiction as follows, and/or the receiving information Internet electrical circuitry arrangement e1169, when activated, performs the operation o1169 in the illustrative depiction as follows, and/or the receiving information Internet module m1169, when executed and/or activated, directs performance of and/or performs the operation o1169 in the illustrative depiction as follows, and/or the operation o1169 is otherwise carried out in the illustrative depiction as follows: electronically receiving the selection information at least in part identifying the one or more selected ingestible products being subject to ingestion by the one or more particular individual living beings, the selection information electronically received via the electronically enabled input including via Internet communication (e.g. including an implementation of the receiver component s528 is configured to electronically receive the selection information through the internet network component s508 to be used by the processor component s102, and/or etc.).

Figure 85:
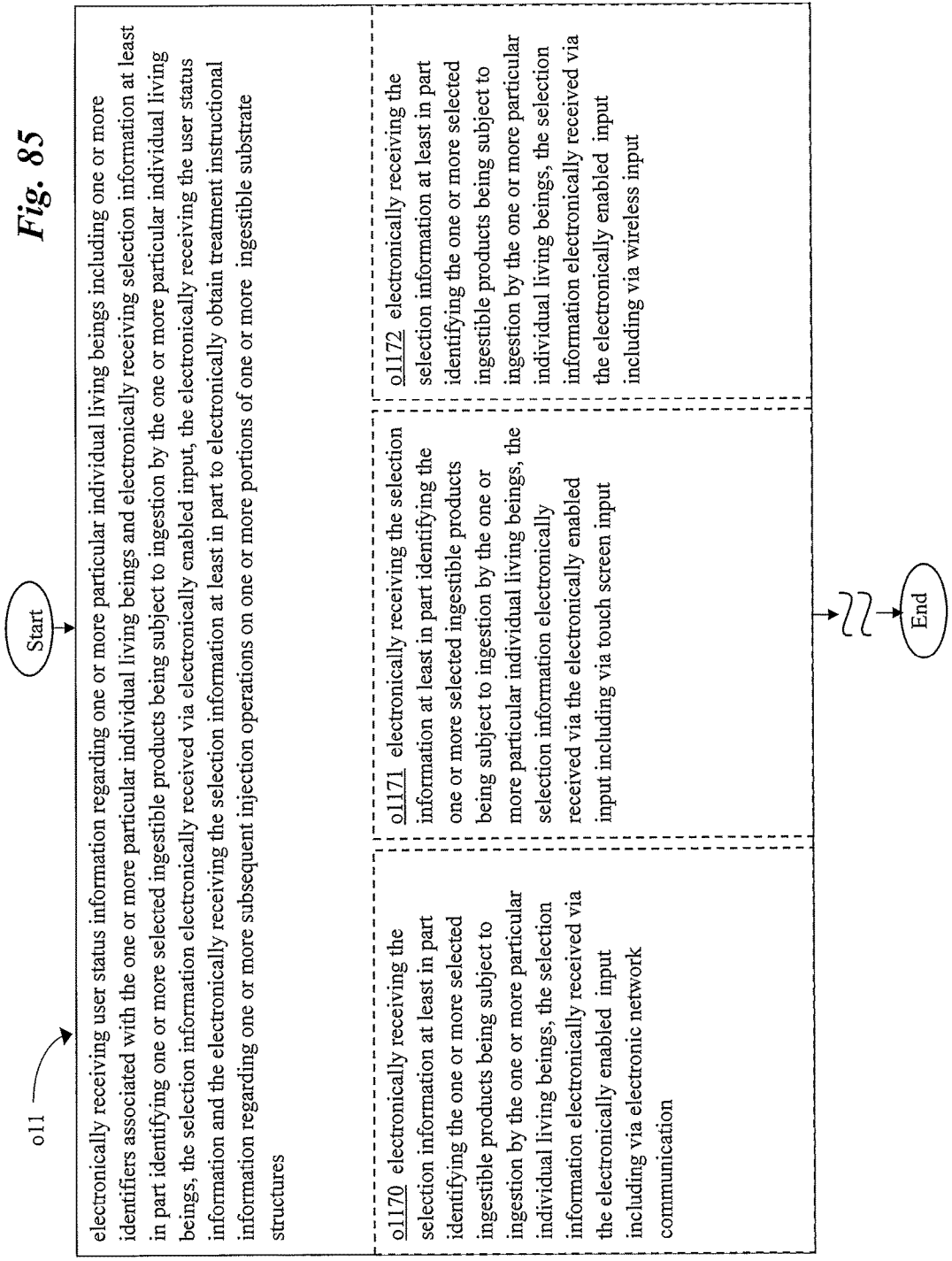
FIG. 85 is a high-level flowchart including exemplary implementations of operation O11 of FIG. 61.

In one or more implementations, as shown in FIG. 85, operation o11 includes an operation o1170 for electronically receiving the selection information at least in part identifying the one or more selected ingestible products being subject to ingestion by the one or more particular individual living beings, the selection information electronically received via the electronically enabled input including via electronic network communication. Origination of an illustratively derived receiving information network component group can be accomplished through skilled in the art design choice selection of one or more of the above depicted components from one or more of the above depicted subsystems shown in FIG. 30. Components from the receiving information network component group can be used in implementing execution of the one or more receiving information network instructions i1170 of FIG. 50, can be used in performance of the receiving information network electrical circuitry arrangement e1170 of FIG. 43, and/or can be used in otherwise fulfillment of the operation o1170. An exemplary non-transitory signal bearing medium version of the information storage subsystem s200 is depicted in FIG. 50 as bearing the one or more receiving information network instructions i1170 that when executed will direct performance of the operation o1170. Furthermore, the receiving information network electrical circuitry arrangement ("elec circ arrange") e1170, when activated, will perform the operation o1170. Also, the receiving information network module m1170, when executed and/or activated, will direct performance of and/or perform the operation o1170. For instance, in one or more exemplary implementations, the one or more receiving information network instructions i1170, when executed, direct performance of the operation o1170 in the illustrative depiction as follows, and/or the receiving information network electrical circuitry arrangement e1170, when activated, performs the operation o1170 in the illustrative depiction as follows, and/or the receiving information network module m1170, when executed and/or activated, directs performance of and/or performs the operation o1170 in the illustrative depiction as follows, and/or the operation o1170 is otherwise carried out in the illustrative depiction as follows: electronically receiving the selection information at least in part identifying the one or more selected ingestible products being subject to ingestion by the one or more particular individual living beings, the selection information electronically received via the electronically enabled input including via electronic network communication (e.g. including an implementation of the receiver component s528 is configured to electronically engage with the network cable component s502 to receive the selection information to be used by the processor component s102, and/or etc.).

In one or more implementations, as shown in FIG. 85, operation o11 includes an operation o1171 for electronically receiving the selection information at least in part identifying the one or more selected ingestible products being subject to ingestion by the one or more particular individual living beings, the selection information electronically received via the electronically enabled input including via touch screen input. Origination of an illustratively derived receiving information touch component group can be accomplished through skilled in the art design choice selection of one or more of the above depicted components from one or more of the above depicted subsystems shown in FIG. 30. Components from the receiving information touch component group can be used in implementing execution of the one or more receiving information touch instructions i1171 of FIG. 50, can be used in performance of the receiving information touch electrical circuitry arrangement e1171 of FIG. 43, and/or can be used in otherwise fulfillment of the operation o1171. An exemplary non-transitory signal bearing medium version of the information storage subsystem s200 is depicted in FIG. 50 as bearing the one or more receiving information touch instructions i1171 that when executed will direct performance of the operation o1171. Furthermore, the receiving information touch electrical circuitry arrangement ("elec circ arrange") e1171, when activated, will perform the operation o1171. Also, the receiving information touch module m1171, when executed and/or activated, will direct performance of and/or perform the operation o1171. For instance, in one or more exemplary implementations, the one or more receiving information touch instructions i1171, when executed, direct performance of the operation o1171 in the illustrative depiction as follows, and/or the receiving information touch electrical circuitry arrangement e1171, when activated, performs the operation o1171 in the illustrative depiction as follows, and/or the receiving information touch module m1171, when executed and/or activated, directs performance of and/or performs the operation o1171 in the illustrative depiction as follows, and/or the operation o1171 is otherwise carried out in the illustrative depiction as follows: electronically receiving the selection information at least in part identifying the one or more selected ingestible products being subject to ingestion by the one or more particular individual living beings, the selection information electronically received via the electronically enabled input including via touch screen input (e.g. including an implementation of the receiver component s528 is configured to electronically receive through the touch screen component s314 the selection information to be used by the processor component s102, and/or etc.).

In one or more implementations, as shown in FIG. 85, operation o11 includes an operation o1172 for electronically receiving the selection information at least in part identifying the one or more selected ingestible products being subject to ingestion by the one or more particular individual living beings, the selection information electronically received via the electronically enabled input including via wireless input. Origination of an illustratively derived receiving information wireless component group can be accomplished through skilled in the art design choice selection of one or more of the above depicted components from one or more of the above depicted subsystems shown in FIG. 30. Components from the receiving information wireless component group can be used in implementing execution of the one or more receiving information wireless instructions i1172 of FIG. 50, can be used in performance of the receiving information wireless electrical circuitry arrangement e1172 of FIG. 43, and/or can be used in otherwise fulfillment of the operation o1172. An exemplary non-transitory signal bearing medium version of the information storage subsystem s200 is depicted in FIG. 50 as bearing the one or more receiving information wireless instructions i1172 that when executed will direct performance of the operation o1172. Furthermore, the receiving information wireless electrical circuitry arrangement ("elec circ arrange") e1172, when activated, will perform the operation o1172. Also, the receiving information wireless module m1172, when executed and/or activated, will direct performance of and/or perform the operation o1172. For instance, in one or more exemplary implementations, the one or more receiving information wireless instructions i1172, when executed, direct performance of the operation o1172 in the illustrative depiction as follows, and/or the receiving information wireless electrical circuitry arrangement e1172, when activated, performs the operation o1172 in the illustrative depiction as follows, and/or the receiving information wireless module m1172, when executed and/or activated, directs performance of and/or performs the operation o1172 in the illustrative depiction as follows, and/or the operation o1172 is otherwise carried out in the illustrative depiction as follows: electronically receiving the selection information at least in part identifying the one or more selected ingestible products being subject to ingestion by the one or more particular individual living beings, the selection information electronically received via the electronically enabled input including via wireless input (e.g. including an implementation of the receiver component s528 is configured to electronically receive through the wireless network component s510 to receive the selection information to be used by the processor component s102, and/or etc.).

Figure 86:
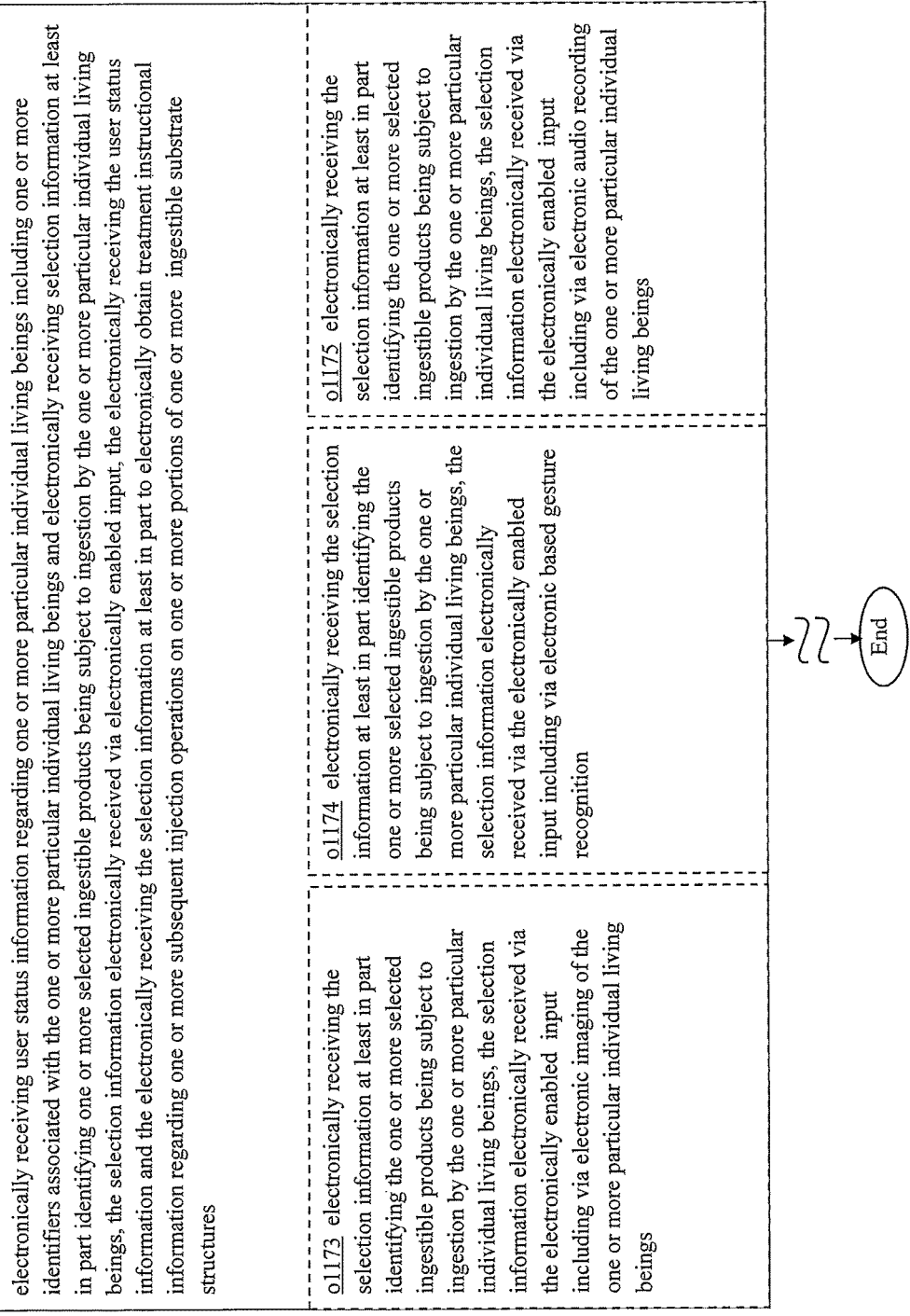
FIG. 86 is a high-level flowchart including exemplary implementations of operation O11 of FIG. 61.

In one or more implementations, as shown in FIG. 86, operation o11 includes an operation o1173 for electronically receiving the selection information at least in part identifying the one or more selected ingestible products being subject to ingestion by the one or more particular individual living beings, the selection information electronically received via the electronically enabled input including via electronic imaging of the one or more particular individual living beings. Origination of an illustratively derived receiving information imaging component group can be accomplished through skilled in the art design choice selection of one or more of the above depicted components from one or more of the above depicted subsystems shown in FIG. 30. Components from the receiving information imaging component group can be used in implementing execution of the one or more receiving information imaging instructions i1173 of FIG. 50, can be used in performance of the receiving information imaging electrical circuitry arrangement e1173 of FIG. 43, and/or can be used in otherwise fulfillment of the operation o1173. An exemplary non-transitory signal bearing medium version of the information storage subsystem s200 is depicted in FIG. 50 as bearing the one or more receiving information imaging instructions i1173 that when executed will direct performance of the operation o1173. Furthermore, the receiving information imaging electrical circuitry arrangement ("elec circ arrange") e1173, when activated, will perform the operation o1173. Also, the receiving information imaging module m1173, when executed and/or activated, will direct performance of and/or perform the operation o1173. For instance, in one or more exemplary implementations, the one or more receiving information imaging instructions i1173, when executed, direct performance of the operation o1173 in the illustrative depiction as follows, and/or the receiving information imaging electrical circuitry arrangement e1173, when activated, performs the operation o1173 in the illustrative depiction as follows, and/or the receiving information imaging module m1173, when executed and/or activated, directs performance of and/or performs the operation o1173 in the illustrative depiction as follows, and/or the operation o1173 is otherwise carried out in the illustrative depiction as follows: electronically receiving the selection information at least in part identifying the one or more selected ingestible products being subject to ingestion by the one or more particular individual living beings, the selection information electronically received via the electronically enabled input including via electronic imaging (e.g. including an implementation of the receiver component s528 is configured to electronically receive through the camera component s336 the selection information to be used by the processor component s102, and/or etc.) of the one or more particular individual living beings.

In one or more implementations, as shown in FIG. 86, operation o11 includes an operation o1174 for electronically receiving the selection information at least in part identifying the one or more selected ingestible products being subject to ingestion by the one or more particular individual living beings, the selection information electronically received via the electronically enabled input including via electronic based gesture recognition. Origination of an illustratively derived receiving information gesture component group can be accomplished through skilled in the art design choice selection of one or more of the above depicted components from one or more of the above depicted subsystems shown in FIG. 30. Components from the receiving information gesture component group can be used in implementing execution of the one or more receiving information gesture instructions i1174 of FIG. 50, can be used in performance of the receiving information gesture electrical circuitry arrangement e1174 of FIG. 43, and/or can be used in otherwise fulfillment of the operation o1174. An exemplary non-transitory signal bearing medium version of the information storage subsystem s200 is depicted in FIG. 50 as bearing the one or more receiving information gesture instructions i1174 that when executed will direct performance of the operation o1174. Furthermore, the receiving information gesture electrical circuitry arrangement ("elec circ arrange") e1174, when activated, will perform the operation o1174. Also, the receiving information gesture module m1174, when executed and/or activated, will direct performance of and/or perform the operation o1174. For instance, in one or more exemplary implementations, the one or more receiving information gesture instructions i1174, when executed, direct performance of the operation o1174 in the illustrative depiction as follows, and/or the receiving information gesture electrical circuitry arrangement e1174, when activated, performs the operation o1174 in the illustrative depiction as follows, and/or the receiving information gesture module m1174, when executed and/or activated, directs performance of and/or performs the operation o1174 in the illustrative depiction as follows, and/or the operation o1174 is otherwise carried out in the illustrative depiction as follows: electronically receiving the selection information at least in part identifying the one or more selected ingestible products being subject to ingestion by the one or more particular individual living beings, the selection information electronically received via the electronically enabled input including via electronic based gesture recognition (e.g. including an implementation of the receiver component s528 is configured to electronically engage with the optical sensing component s418 to receive the selection to be used by the processor component s102, and/or etc.).

In one or more implementations, as shown in FIG. 86, operation o11 includes an operation o1175 for electronically receiving the selection information at least in part identifying the one or more selected ingestible products being subject to ingestion by the one or more particular individual living beings, the selection information electronically received via the electronically enabled input including via electronic audio recording of the one or more particular individual living beings. Origination of an illustratively derived receiving information audio component group can be accomplished through skilled in the art design choice selection of one or more of the above depicted components from one or more of the above depicted subsystems shown in FIG. 30. Components from the receiving information audio component group can be used in implementing execution of the one or more receiving information audio instructions i1175 of FIG. 50, can be used in performance of the receiving information audio electrical circuitry arrangement e1175 of FIG. 43, and/or can be used in otherwise fulfillment of the operation o1175. An exemplary non-transitory signal bearing medium version of the information storage subsystem s200 is depicted in FIG. 50 as bearing the one or more receiving information audio instructions i1175 that when executed will direct performance of the operation o1175. Furthermore, the receiving information audio electrical circuitry arrangement ("elec circ arrange") e1175, when activated, will perform the operation o1175. Also, the receiving information audio module m1175, when executed and/or activated, will direct performance of and/or perform the operation o1175. For instance, in one or more exemplary implementations, the one or more receiving information audio instructions i1175, when executed, direct performance of the operation o1175 in the illustrative depiction as follows, and/or the receiving information audio electrical circuitry arrangement e1175, when activated, performs the operation o1175 in the illustrative depiction as follows, and/or the receiving information audio module m1175, when executed and/or activated, directs performance of and/or performs the operation o1175 in the illustrative depiction as follows, and/or the operation o1175 is otherwise carried out in the illustrative depiction as follows: electronically receiving the selection information at least in part identifying the one or more selected ingestible products being subject to ingestion by the one or more particular individual living beings, the selection information electronically received via the electronically enabled input including via electronic audio recording (e.g. including an implementation of the receiver component s528 is configured to electronically engage with the sound sensing component s420 to receive the selection information to be used by the processor component s102, and/or etc.) of the one or more particular individual living beings.

Figure 87:
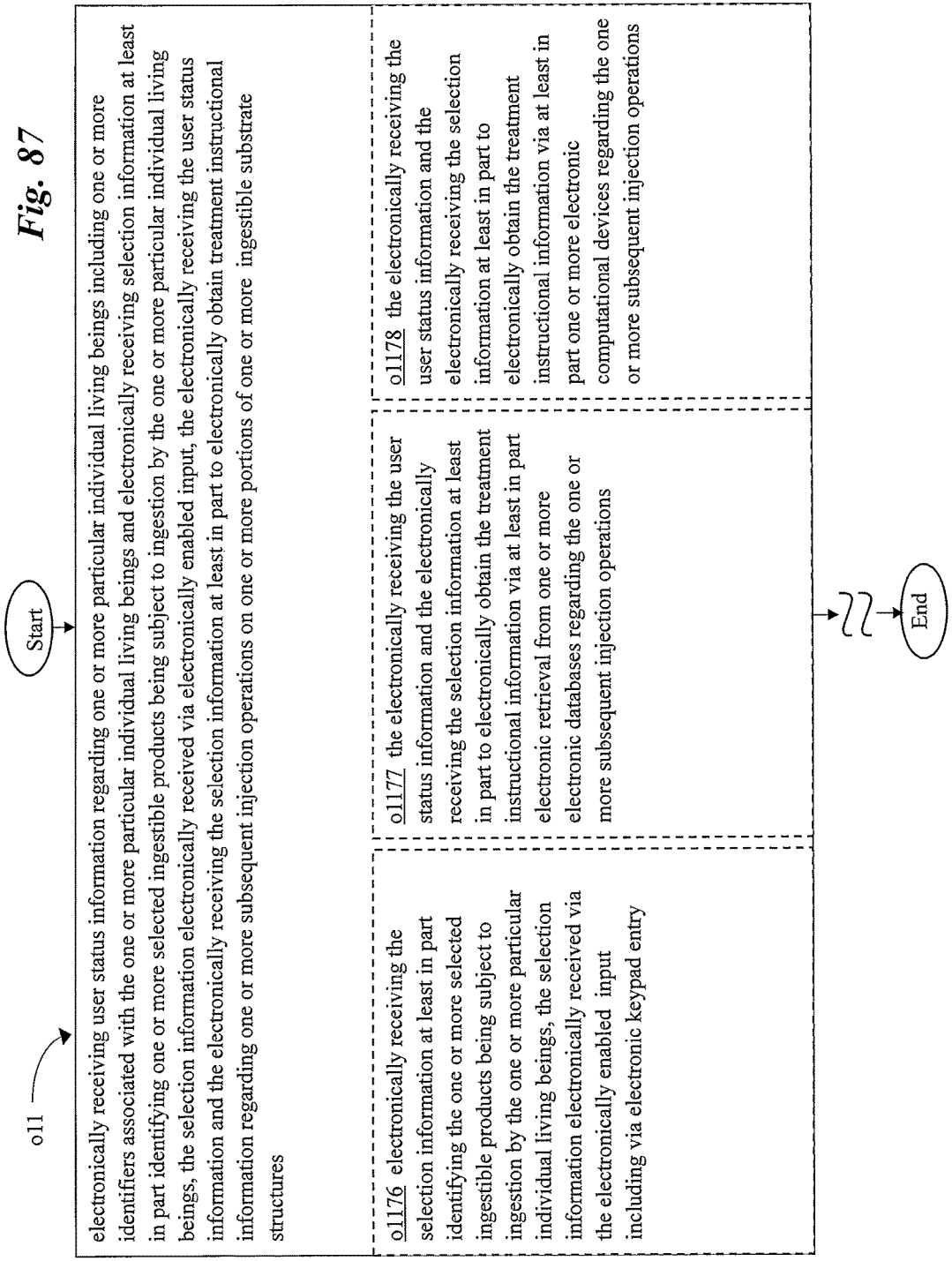
FIG. 87 is a high-level flowchart including exemplary implementations of operation O11 of FIG. 61.

In one or more implementations, as shown in FIG. 87, operation o11 includes an operation o1176 for electronically receiving the selection information at least in part identifying the one or more selected ingestible products being subject to ingestion by the one or more particular individual living beings, the selection information electronically received via the electronically enabled input including via electronic keypad entry. Origination of an illustratively derived receiving information keypad component group can be accomplished through skilled in the art design choice selection of one or more of the above depicted components from one or more of the above depicted subsystems shown in FIG. 30. Components from the receiving information keypad component group can be used in implementing execution of the one or more receiving information keypad instructions i1176 of FIG. 50, can be used in performance of the receiving information keypad electrical circuitry arrangement e1176 of FIG. 43, and/or can be used in otherwise fulfillment of the operation o1176. An exemplary non-transitory signal bearing medium version of the information storage subsystem s200 is depicted in FIG. 50 as bearing the one or more receiving information keypad instructions i1176 that when executed will direct performance of the operation o1176. Furthermore, the receiving information keypad electrical circuitry arrangement ("elec circ arrange") e1176, when activated, will perform the operation o1176. Also, the receiving information keypad module m1176, when executed and/or activated, will direct performance of and/or perform the operation o1176. For instance, in one or more exemplary implementations, the one or more receiving information keypad instructions i1176, when executed, direct performance of the operation o1176 in the illustrative depiction as follows, and/or the receiving information keypad electrical circuitry arrangement e1176, when activated, performs the operation o1176 in the illustrative depiction as follows, and/or the receiving information keypad module m1176, when executed and/or activated, directs performance of and/or performs the operation o1176 in the illustrative depiction as follows, and/or the operation o1176 is otherwise carried out in the illustrative depiction as follows: electronically receiving the selection information at least in part identifying the one or more selected ingestible products being subject to ingestion by the one or more particular individual living beings, the selection information electronically received via the electronically enabled input including via electronic keypad entry (e.g. including an implementation of the receiver component s528 is configured to electronically engage with the keypad component s308 to receive the selection information to be used by the processor component s102, and/or etc.).

In one or more implementations, as shown in FIG. 87, operation o11 includes an operation o1177 for the electronically receiving the user status information and the electronically receiving the selection information at least in part to electronically obtain the treatment instructional information via at least in part electronic retrieval from one or more electronic databases regarding the one or more subsequent injection operations. Origination of an illustratively derived obtain instructional database component group can be accomplished through skilled in the art design choice selection of one or more of the above depicted components from one or more of the above depicted subsystems shown in FIG. 30. Components from the obtain instructional database component group can be used in implementing execution of the one or more obtain instructional database instructions i1177 of FIG. 50, can be used in performance of the obtain instructional database electrical circuitry arrangement e1177 of FIG. 43, and/or can be used in otherwise fulfillment of the operation o1177. An exemplary non-transitory signal bearing medium version of the information storage subsystem s200 is depicted in FIG. 50 as bearing the one or more obtain instructional database instructions i1177 that when executed will direct performance of the operation o1177. Furthermore, the obtain instructional database electrical circuitry arrangement ("elec circ arrange") e1177, when activated, will perform the operation o1177. Also, the obtain instructional database module m1177, when executed and/or activated, will direct performance of and/or perform the operation o1177. For instance, in one or more exemplary implementations, the one or more obtain instructional database instructions i1177, when executed, direct performance of the operation o1177 in the illustrative depiction as follows, and/or the obtain instructional database electrical circuitry arrangement e1177, when activated, performs the operation o1177 in the illustrative depiction as follows, and/or the obtain instructional database module m1177, when executed and/or activated, directs performance of and/or performs the operation o1177 in the illustrative depiction as follows, and/or the operation o1177 is otherwise carried out in the illustrative depiction as follows: the electronically receiving the user status information and the electronically receiving the selection information at least in part to electronically obtain the treatment instructional information via at least in part electronic retrieval from one or more electronic databases (e.g. including an implementation of the receiver component s528 is configured to electronically engage with the electromagnetic sensing component s402 to receive the selection information to be used by the processor component s102, and/or etc.) regarding the one or more subsequent injection operations.

In one or more implementations, as shown in FIG. 87, operation o11 includes an operation o1178 for the electronically receiving the user status information and the electronically receiving the selection information at least in part to electronically obtain the treatment instructional information via at least in part one or more electronic computational devices regarding the one or more subsequent injection operations. Origination of an illustratively derived obtain instructional computational component group can be accomplished through skilled in the art design choice selection of one or more of the above depicted components from one or more of the above depicted subsystems shown in FIG. 30. Components from the obtain instructional computational component group can be used in implementing execution of the one or more obtain instructional computational instructions i1178 of FIG. 50, can be used in performance of the obtain instructional computational electrical circuitry arrangement e1178 of FIG. 43, and/or can be used in otherwise fulfillment of the operation o1178. An exemplary non-transitory signal bearing medium version of the information storage subsystem s200 is depicted in FIG. 50 as bearing the one or more obtain instructional computational instructions i1178 that when executed will direct performance of the operation o1178. Furthermore, the obtain instructional computational electrical circuitry arrangement ("elec circ arrange") e1178, when activated, will perform the operation o1178. Also, the obtain instructional computational module m1178, when executed and/or activated, will direct performance of and/or perform the operation o1178. For instance, in one or more exemplary implementations, the one or more obtain instructional computational instructions i1178, when executed, direct performance of the operation o1178 in the illustrative depiction as follows, and/or the obtain instructional computational electrical circuitry arrangement e1178, when activated, performs the operation o1178 in the illustrative depiction as follows, and/or the obtain instructional computational module m1178, when executed and/or activated, directs performance of and/or performs the operation o1178 in the illustrative depiction as follows, and/or the operation o1178 is otherwise carried out in the illustrative depiction as follows: the electronically receiving the user status information and the electronically receiving the selection information at least in part to electronically obtain the treatment instructional information via at least in part one or more electronic computational devices (e.g. including an implementation of the receiver component s528 is configured to electronically engage with the encrypted communication component s520 to receive the selection information to be used by the processor component s102, and/or etc.) regarding the one or more subsequent injection operations.

Figure 88:
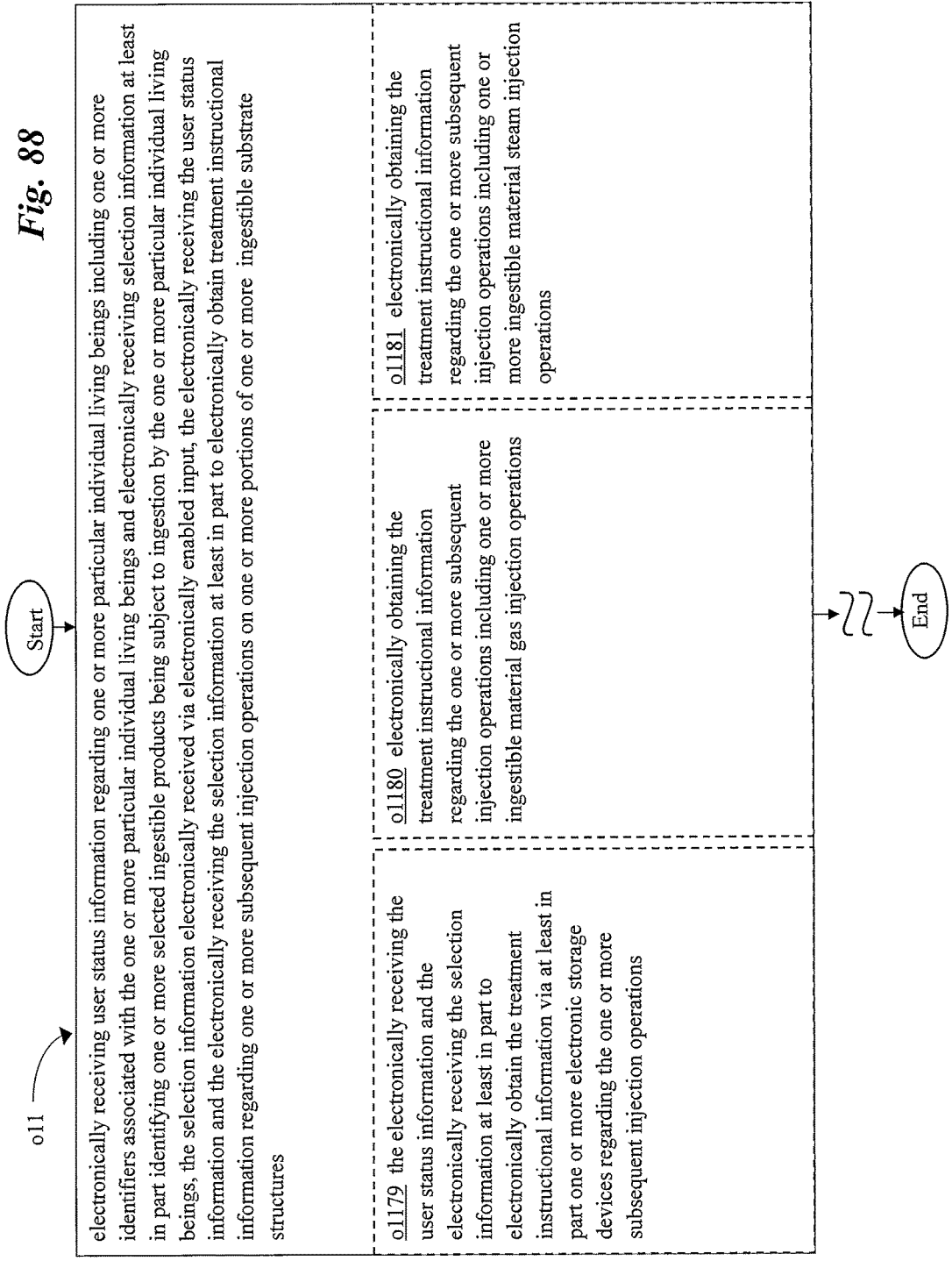
FIG. 88 is a high-level flowchart including exemplary implementations of operation O11 of FIG. 61.

In one or more implementations, as shown in FIG. 88, operation o11 includes an operation o1179 for the electronically receiving the user status information and the electronically receiving the selection information at least in part to electronically obtain the treatment instructional information via at least in part one or more electronic storage devices regarding the one or more subsequent injection operations. Origination of an illustratively derived obtain instructional storage component group can be accomplished through skilled in the art design choice selection of one or more of the above depicted components from one or more of the above depicted subsystems shown in FIG. 30. Components from the obtain instructional storage component group can be used in implementing execution of the one or more obtain instructional storage instructions i1179 of FIG. 50, can be used in performance of the obtain instructional storage electrical circuitry arrangement e1179 of FIG. 43, and/or can be used in otherwise fulfillment of the operation o1179. An exemplary non-transitory signal bearing medium version of the information storage subsystem s200 is depicted in FIG. 50 as bearing the one or more obtain instructional storage instructions i1179 that when executed will direct performance of the operation o1179. Furthermore, the obtain instructional storage electrical circuitry arrangement ("elec circ arrange") e1179, when activated, will perform the operation o1179. Also, the obtain instructional storage module m1179, when executed and/or activated, will direct performance of and/or perform the operation o1179. For instance, in one or more exemplary implementations, the one or more obtain instructional storage instructions i1179, when executed, direct performance of the operation o1179 in the illustrative depiction as follows, and/or the obtain instructional storage electrical circuitry arrangement e1179, when activated, performs the operation o1179 in the illustrative depiction as follows, and/or the obtain instructional storage module m1179, when executed and/or activated, directs performance of and/or performs the operation o1179 in the illustrative depiction as follows, and/or the operation o1179 is otherwise carried out in the illustrative depiction as follows: the electronically receiving the user status information and the electronically receiving the selection information at least in part to electronically obtain the treatment instructional information via at least in part one or more electronic storage devices (e.g. including an implementation of the receiver component s528 is configured to electronically engage with one or more components of the information storage subsystem s200, such as the server component s230, to receive the selection information to be used by the processor component s102, and/or etc.) regarding the one or more subsequent injection operations.

In one or more implementations, as shown in FIG. 88, operation o11 includes an operation o1180 for electronically obtaining the treatment instructional information regarding the one or more subsequent injection operations including one or more ingestible material gas injection operations. Origination of an illustratively derived obtain instructional gas component group can be accomplished through skilled in the art design choice selection of one or more of the above depicted components from one or more of the above depicted subsystems shown in FIG. 30. Components from the obtain instructional gas component group can be used in implementing execution of the one or more obtain instructional gas instructions i1180 of FIG. 51, can be used in performance of the obtain instructional gas electrical circuitry arrangement e1180 of FIG. 44, and/or can be used in otherwise fulfillment of the operation o1180. An exemplary non-transitory signal bearing medium version of the information storage subsystem s200 is depicted in FIG. 51 as bearing the one or more obtain instructional gas instructions i1180 that when executed will direct performance of the operation o1180. Furthermore, the obtain instructional gas electrical circuitry arrangement ("elec circ arrange") e1180, when activated, will perform the operation o1180. Also, the obtain instructional gas module m1180, when executed and/or activated, will direct performance of and/or perform the operation o1180. For instance, in one or more exemplary implementations, the one or more obtain instructional gas instructions i1180, when executed, direct performance of the operation o1180 in the illustrative depiction as follows, and/or the obtain instructional gas electrical circuitry arrangement e1180, when activated, performs the operation o1180 in the illustrative depiction as follows, and/or the obtain instructional gas module m1180, when executed and/or activated, directs performance of and/or performs the operation o1180 in the illustrative depiction as follows, and/or the operation o1180 is otherwise carried out in the illustrative depiction as follows: electronically obtaining the treatment instructional information regarding the one or more subsequent injection operations including one or more ingestible material gas injection operations (e.g. including one or more injection probes, needles, tubes, syringes, and/or etc. that are configured to pierce, penetrate, be inserted into, and/or etc. and/or pressurized, defined, directed, controlled, and/or etc. jets, streams, flows and/or etc. one or more portions of the one or more ingestible substrate structures, the one or more injection probes, needles, and/or etc. having channels, conduits, voids, chambers, passageways, and/or etc. sized, shaped, and/or etc. to introduce, deliver, inject, and/or etc. at least one or more gases such as carbon dioxide, helium, methane, nitrogen, oxygen, and/or etc. into, through, and/or etc. the one or more portions of the one or more ingestible substrate structures, and/or etc.).

In one or more implementations, as shown in FIG. 88, operation o11 includes an operation o1181 for electronically obtaining the treatment instructional information regarding the one or more subsequent injection operations including one or more ingestible material steam injection operations. Origination of an illustratively derived obtain instructional steam component group can be accomplished through skilled in the art design choice selection of one or more of the above depicted components from one or more of the above depicted subsystems shown in FIG. 30. Components from the obtain instructional steam component group can be used in implementing execution of the one or more obtain instructional steam instructions i1181 of FIG. 51, can be used in performance of the obtain instructional steam electrical circuitry arrangement e1181 of FIG. 44, and/or can be used in otherwise fulfillment of the operation o1181. An exemplary non-transitory signal bearing medium version of the information storage subsystem s200 is depicted in FIG. 51 as bearing the one or more obtain instructional steam instructions i1181 that when executed will direct performance of the operation o1181. Furthermore, the obtain instructional steam electrical circuitry arrangement ("elec circ arrange") e1181, when activated, will perform the operation o1181. Also, the obtain instructional steam module m1181, when executed and/or activated, will direct performance of and/or perform the operation o1181. For instance, in one or more exemplary implementations, the one or more obtain instructional steam instructions i1181, when executed, direct performance of the operation o1181 in the illustrative depiction as follows, and/or the obtain instructional steam electrical circuitry arrangement e1181, when activated, performs the operation o1181 in the illustrative depiction as follows, and/or the obtain instructional steam module m1181, when executed and/or activated, directs performance of and/or performs the operation o1181 in the illustrative depiction as follows, and/or the operation o1181 is otherwise carried out in the illustrative depiction as follows: electronically obtaining the treatment instructional information regarding the one or more subsequent injection operations including one or more ingestible material steam injection operations (e.g. including one or more injection probes, needles, tubes, syringes, and/or etc. that are configured to pierce, penetrate, be inserted into, and/or etc. one or more portions of the one or more ingestible substrate structures, the one or more injection probes, needles, and/or etc. having channels, conduits, voids, chambers, passageways, and/or etc. sized, shaped, and/or etc. and/or pressurized, defined, directed, controlled, and/or etc. jets, streams, flows and/or etc. to introduce, deliver, inject, and/or etc. at least steam such as wet steam, dry steam, high pressure steam, low pressure steam, adiabatic steam, and/or etc. into, through, and/or etc. the one or more portions of the one or more ingestible substrate structures, and/or etc.).

Figure 89:
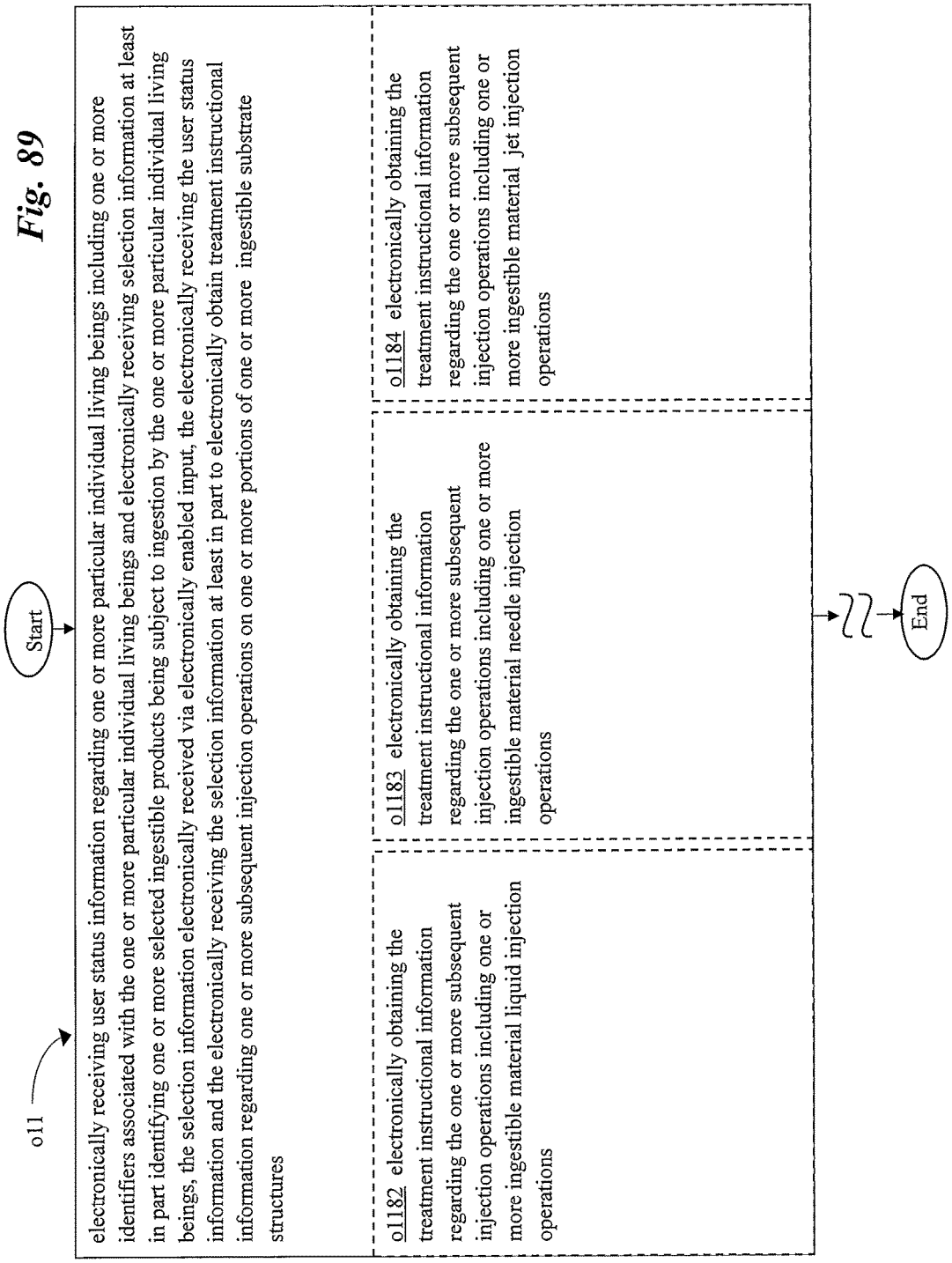
FIG. 89 is a high-level flowchart including exemplary implementations of operation O11 of FIG. 61.

In one or more implementations, as shown in FIG. 89, operation o11 includes an operation o1182 for electronically obtaining the treatment instructional information regarding the one or more subsequent injection operations including one or more ingestible material liquid injection operations. Origination of an illustratively derived obtain instructional liquid component group can be accomplished through skilled in the art design choice selection of one or more of the above depicted components from one or more of the above depicted subsystems shown in FIG. 30. Components from the obtain instructional liquid component group can be used in implementing execution of the one or more obtain instructional liquid instructions i1182 of FIG. 51, can be used in performance of the obtain instructional liquid electrical circuitry arrangement e1182 of FIG. 44, and/or can be used in otherwise fulfillment of the operation o1182. An exemplary non-transitory signal bearing medium version of the information storage subsystem s200 is depicted in FIG. 51 as bearing the one or more obtain instructional liquid instructions i1182 that when executed will direct performance of the operation o1182. Furthermore, the obtain instructional liquid electrical circuitry arrangement ("elec circ arrange") e1182, when activated, will perform the operation o1182. Also, the obtain instructional liquid module m1182, when executed and/or activated, will direct performance of and/or perform the operation o1182. For instance, in one or more exemplary implementations, the one or more obtain instructional liquid instructions i1182, when executed, direct performance of the operation o1182 in the illustrative depiction as follows, and/or the obtain instructional liquid electrical circuitry arrangement e1182, when activated, performs the operation o1182 in the illustrative depiction as follows, and/or the obtain instructional liquid module m1182, when executed and/or activated, directs performance of and/or performs the operation o1182 in the illustrative depiction as follows, and/or the operation o1182 is otherwise carried out in the illustrative depiction as follows: electronically obtaining the treatment instructional information regarding the one or more subsequent injection operations including one or more ingestible material liquid injection operations (e.g. including one or more injection probes, needles, tubes, syringes, and/or etc. that are configured to pierce, penetrate, be inserted into, and/or etc. one or more portions of the one or more ingestible substrate structures, the one or more injection probes, needles, and/or etc. having channels, conduits, voids, chambers, passageways, and/or etc. sized, shaped, and/or etc. and/or pressurized, defined, directed, controlled, and/or etc. jets, streams, flows and/or etc. to introduce, deliver, inject, and/or etc. at least one or more liquids such as one or more viscous liquids, one or more thinning liquids, one or more lubricating liquids, one or more colloidal liquids, one or more ionic liquids, one or more flavored liquids, one or more unflavored liquids, one or more heated liquids, one or more cooled liquids, and/or etc. into, through, and/or etc. the one or more portions of the one or more ingestible substrate structures, and/or etc.).

In one or more implementations, as shown in FIG. 89, operation o11 includes an operation o1183 for electronically obtaining the treatment instructional information regarding the one or more subsequent injection operations including one or more ingestible material needle injection operations. Origination of an illustratively derived obtain instructional needle component group can be accomplished through skilled in the art design choice selection of one or more of the above depicted components from one or more of the above depicted subsystems shown in FIG. 30. Components from the obtain instructional needle component group can be used in implementing execution of the one or more obtain instructional needle instructions i1183 of FIG. 51, can be used in performance of the obtain instructional needle electrical circuitry arrangement e1183 of FIG. 44, and/or can be used in otherwise fulfillment of the operation o1183. An exemplary non-transitory signal bearing medium version of the information storage subsystem s200 is depicted in FIG. 51 as bearing the one or more obtain instructional needle instructions i1183 that when executed will direct performance of the operation o1183. Furthermore, the obtain instructional needle electrical circuitry arrangement ("elec circ arrange") e1183, when activated, will perform the operation o1183. Also, the obtain instructional needle module m1183, when executed and/or activated, will direct performance of and/or perform the operation o1183. For instance, in one or more exemplary implementations, the one or more obtain instructional needle instructions i1183, when executed, direct performance of the operation o1183 in the illustrative depiction as follows, and/or the obtain instructional needle electrical circuitry arrangement e1183, when activated, performs the operation o1183 in the illustrative depiction as follows, and/or the obtain instructional needle module m1183, when executed and/or activated, directs performance of and/or performs the operation o1183 in the illustrative depiction as follows, and/or the operation o1183 is otherwise carried out in the illustrative depiction as follows: electronically obtaining the treatment instructional information regarding the one or more subsequent injection operations including one or more ingestible material needle injection operations (e.g. including one or more injection probes, needles, tubes, syringes, and/or etc. that are configured to pierce, penetrate, be inserted into, and/or etc. one or more portions of the one or more ingestible substrate structures, the one or more injection probes, needles, and/or etc. having channels, conduits, voids, chambers, passageways, and/or etc. sized, shaped, and/or etc. to introduce, deliver, inject, and/or etc. at least one or more liquids, gases, fluids, steam, and/or etc. such as one or more viscous liquids, one or more thinning liquids, one or more lubricating liquids, one or more colloidal liquids, one or more ionic liquids, one or more flavored liquids, one or more unflavored liquids, one or more heated liquids, one or more cooled liquids, and/or etc. into, through, and/or etc. the one or more portions of the one or more ingestible substrate structures, and/or etc.).

In one or more implementations, as shown in FIG. 89, operation o11 includes an operation o1184 for electronically obtaining the treatment instructional information regarding the one or more subsequent injection operations including one or more ingestible material jet injection operations. Origination of an illustratively derived obtain instructional jet component group can be accomplished through skilled in the art design choice selection of one or more of the above depicted components from one or more of the above depicted subsystems shown in FIG. 30. Components from the obtain instructional jet component group can be used in implementing execution of the one or more obtain instructional jet instructions i1184 of FIG. 51, can be used in performance of the obtain instructional jet electrical circuitry arrangement e1184 of FIG. 44, and/or can be used in otherwise fulfillment of the operation o1184. An exemplary non-transitory signal bearing medium version of the information storage subsystem s200 is depicted in FIG. 51 as bearing the one or more obtain instructional jet instructions i1184 that when executed will direct performance of the operation o1184. Furthermore, the obtain instructional jet electrical circuitry arrangement ("elec circ arrange") e1184, when activated, will perform the operation o1184. Also, the obtain instructional jet module m1184, when executed and/or activated, will direct performance of and/or perform the operation o1184. For instance, in one or more exemplary implementations, the one or more obtain instructional jet instructions i1184, when executed, direct performance of the operation o1184 in the illustrative depiction as follows, and/or the obtain instructional jet electrical circuitry arrangement e1184, when activated, performs the operation o1184 in the illustrative depiction as follows, and/or the obtain instructional jet module m1184, when executed and/or activated, directs performance of and/or performs the operation o1184 in the illustrative depiction as follows, and/or the operation o1184 is otherwise carried out in the illustrative depiction as follows: electronically obtaining the treatment instructional information regarding the one or more subsequent injection operations including one or more ingestible material jet injection operations (e.g. including one or more of pressurized, defined, directed, controlled, and/or etc. jets, streams, flows and/or etc. to introduce, deliver, inject, and/or etc. at least one or more liquids such as one or more viscous liquids, one or more thinning liquids, one or more lubricating liquids, one or more colloidal liquids, one or more ionic liquids, one or more flavored liquids, one or more unflavored liquids, one or more heated liquids, one or more cooled liquids, and/or etc. into, through, and/or etc. the one or more portions of the one or more ingestible substrate structures, and/or etc.).

Figure 90:
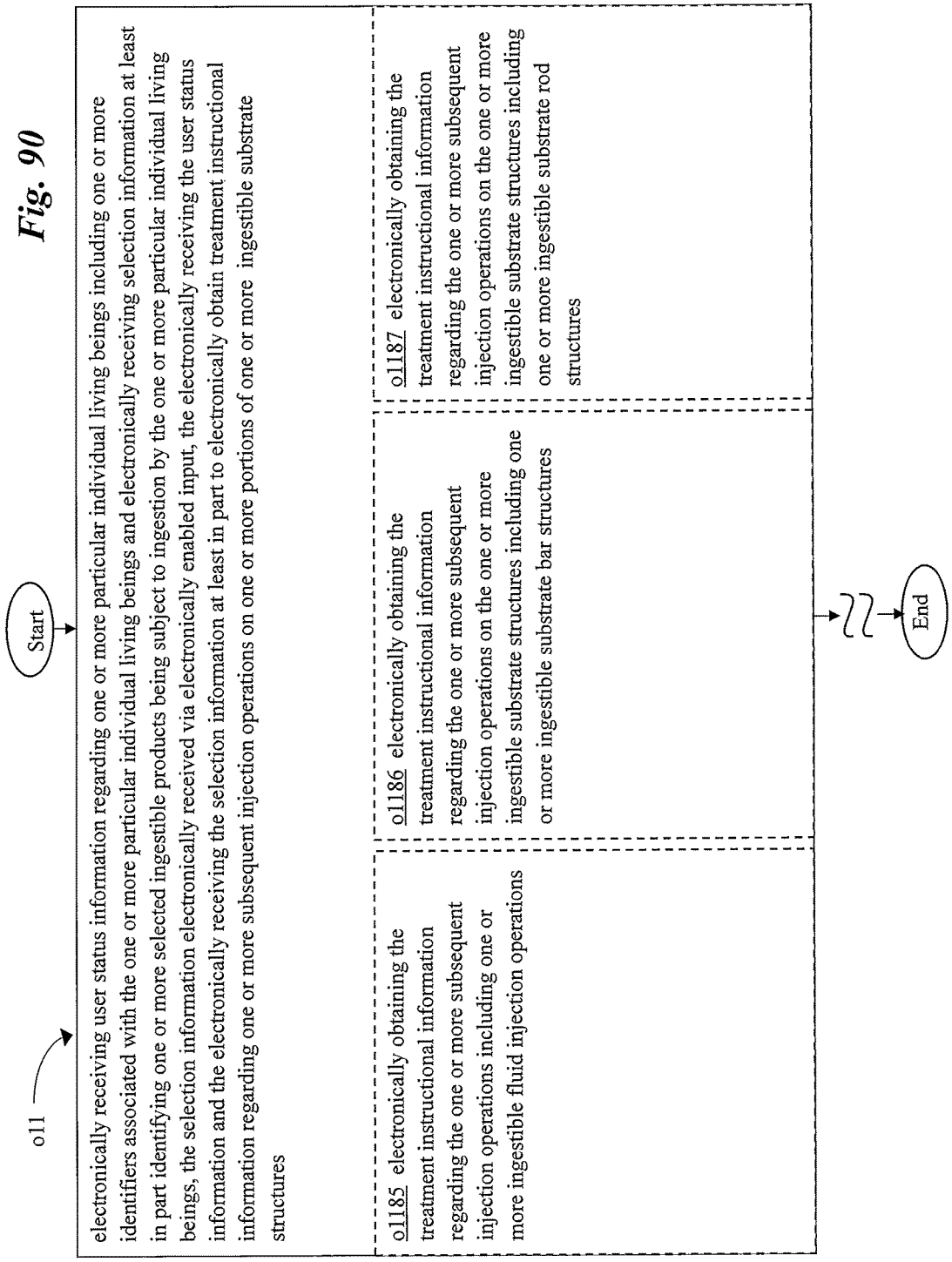
FIG. 90 is a high-level flowchart including exemplary implementations of operation O11 of FIG. 61.

In one or more implementations, as shown in FIG. 90, operation o11 includes an operation o1185 for electronically obtaining the treatment instructional information regarding the one or more subsequent injection operations including one or more ingestible fluid injection operations. Origination of an illustratively derived obtain instructional fluid component group can be accomplished through skilled in the art design choice selection of one or more of the above depicted components from one or more of the above depicted subsystems shown in FIG. 30. Components from the obtain instructional fluid component group can be used in implementing execution of the one or more obtain instructional fluid instructions i1185 of FIG. 51, can be used in performance of the obtain instructional fluid electrical circuitry arrangement e1185 of FIG. 44, and/or can be used in otherwise fulfillment of the operation o1185. An exemplary non-transitory signal bearing medium version of the information storage subsystem s200 is depicted in FIG. 51 as bearing the one or more obtain instructional fluid instructions i1185 that when executed will direct performance of the operation o1185. Furthermore, the obtain instructional fluid electrical circuitry arrangement ("elec circ arrange") e1185, when activated, will perform the operation o1185. Also, the obtain instructional fluid module m1185, when executed and/or activated, will direct performance of and/or perform the operation o1185. For instance, in one or more exemplary implementations, the one or more obtain instructional fluid instructions i1185, when executed, direct performance of the operation o1185 in the illustrative depiction as follows, and/or the obtain instructional fluid electrical circuitry arrangement e1185, when activated, performs the operation o1185 in the illustrative depiction as follows, and/or the obtain instructional fluid module m1185, when executed and/or activated, directs performance of and/or performs the operation o1185 in the illustrative depiction as follows, and/or the operation o1185 is otherwise carried out in the illustrative depiction as follows: electronically obtaining the treatment instructional information regarding the one or more subsequent injection operations including one or more ingestible material fluid injection operations (e.g. including one or more injection probes, needles, tubes, syringes, and/or etc. that are configured to pierce, penetrate, be inserted into, and/or etc. one or more portions of the one or more ingestible substrate structures, the one or more injection probes, needles, and/or etc. having channels, conduits, voids, chambers, passageways, and/or etc. sized, shaped, and/or etc. to introduce, deliver, inject, and/or etc. at least one or more fluids such as one or more viscous fluids, one or more thinning fluids, one or more lubricating fluids, one or more colloidal fluids, one or more ionic fluids, one or more flavored fluids, one or more unflavored fluids, one or more heated fluids, one or more cooled fluids, and/or etc. into, through, and/or etc. the one or more portions of the one or more ingestible substrate structures, and/or etc.).

In one or more implementations, as shown in FIG. 90, operation o11 includes an operation o1186 for electronically obtaining the treatment instructional information regarding the one or more subsequent injection operations on the one or more ingestible substrate structures including one or more ingestible substrate bar structures. Origination of an illustratively derived obtain instructional bar component group can be accomplished through skilled in the art design choice selection of one or more of the above depicted components from one or more of the above depicted subsystems shown in FIG. 30. Components from the obtain instructional bar component group can be used in implementing execution of the one or more obtain instructional bar instructions i1186 of FIG. 51, can be used in performance of the obtain instructional bar electrical circuitry arrangement e1186 of FIG. 44, and/or can be used in otherwise fulfillment of the operation o1186. An exemplary non-transitory signal bearing medium version of the information storage subsystem s200 is depicted in FIG. 51 as bearing the one or more obtain instructional bar instructions i1186 that when executed will direct performance of the operation o1186. Furthermore, the obtain instructional bar electrical circuitry arrangement ("elec circ arrange") e1186, when activated, will perform the operation o1186. Also, the obtain instructional bar module m1186, when executed and/or activated, will direct performance of and/or perform the operation o1186. For instance, in one or more exemplary implementations, the one or more obtain instructional bar instructions i1186, when executed, direct performance of the operation o1186 in the illustrative depiction as follows, and/or the obtain instructional bar electrical circuitry arrangement e1186, when activated, performs the operation o1186 in the illustrative depiction as follows, and/or the obtain instructional bar module m1186, when executed and/or activated, directs performance of and/or performs the operation o1186 in the illustrative depiction as follows, and/or the operation o1186 is otherwise carried out in the illustrative depiction as follows: electronically obtaining the treatment instructional information regarding the one or more subsequent injection operations on the one or more ingestible substrate structures including one or more ingestible substrate bar structures (e.g. including rectangular shaped bars, and/or etc.).

In one or more implementations, as shown in FIG. 90, operation o11 includes an operation o1187 for electronically obtaining the treatment instructional information regarding the one or more subsequent injection operations on the one or more ingestible substrate structures including one or more ingestible substrate rod structures. Origination of an illustratively derived obtain instructional rod component group can be accomplished through skilled in the art design choice selection of one or more of the above depicted components from one or more of the above depicted subsystems shown in FIG. 30. Components from the obtain instructional rod component group can be used in implementing execution of the one or more obtain instructional rod instructions i1187 of FIG. 51, can be used in performance of the obtain instructional rod electrical circuitry arrangement e1187 of FIG. 44, and/or can be used in otherwise fulfillment of the operation o1187. An exemplary non-transitory signal bearing medium version of the information storage subsystem s200 is depicted in FIG. 51 as bearing the one or more obtain instructional rod instructions i1187 that when executed will direct performance of the operation o1187. Furthermore, the obtain instructional rod electrical circuitry arrangement ("elec circ arrange") e1187, when activated, will perform the operation o1187. Also, the obtain instructional rod module m1187, when executed and/or activated, will direct performance of and/or perform the operation o1187. For instance, in one or more exemplary implementations, the one or more obtain instructional rod instructions i1187, when executed, direct performance of the operation o1187 in the illustrative depiction as follows, and/or the obtain instructional rod electrical circuitry arrangement e1187, when activated, performs the operation o1187 in the illustrative depiction as follows, and/or the obtain instructional rod module m1187, when executed and/or activated, directs performance of and/or performs the operation o1187 in the illustrative depiction as follows, and/or the operation o1187 is otherwise carried out in the illustrative depiction as follows: electronically obtaining the treatment instructional information regarding the one or more subsequent injection operations on the one or more ingestible substrate structures including one or more ingestible substrate rod structures (e.g. including pretzel sticks, and/or etc.).

Figure 91:
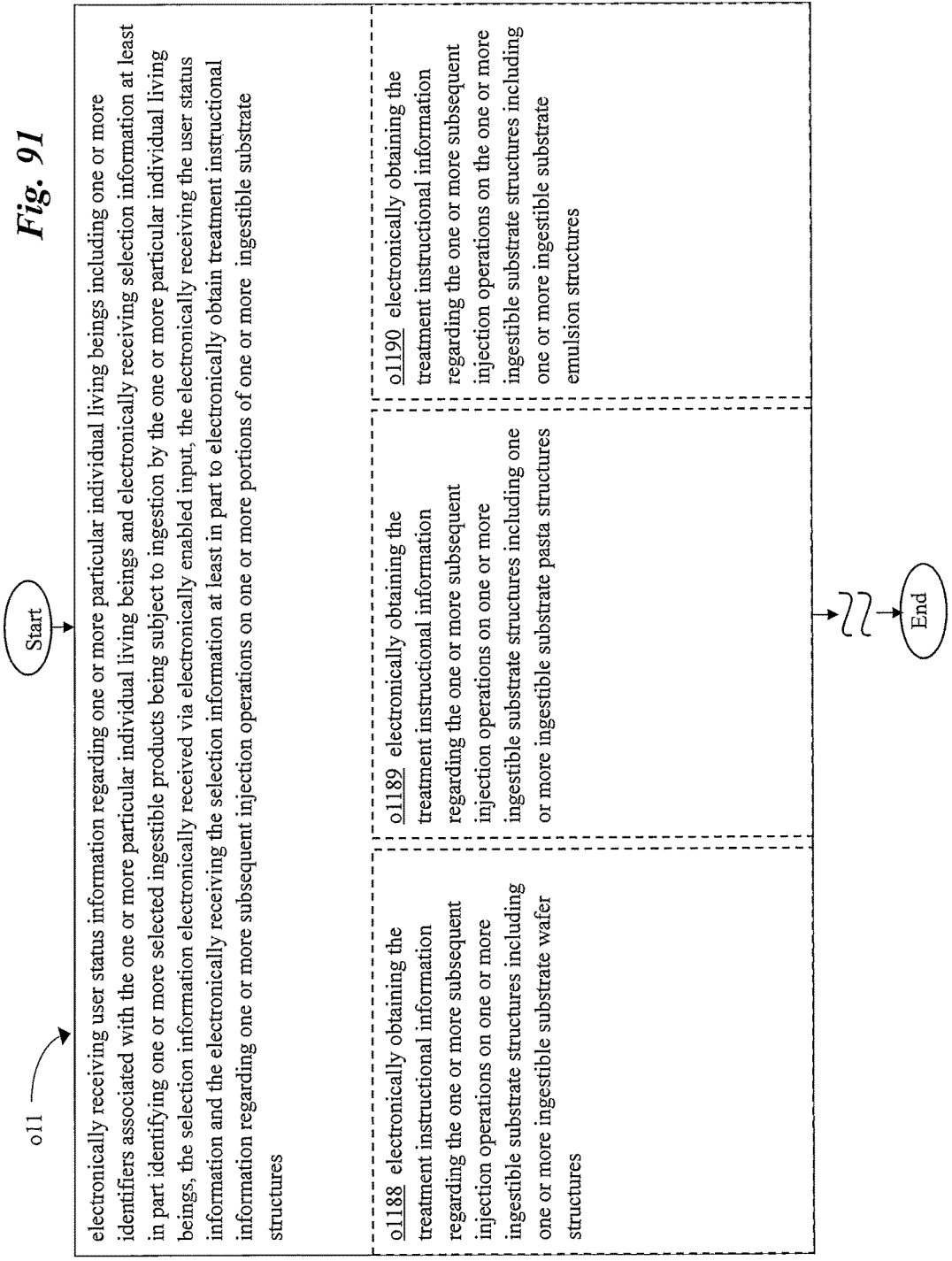
FIG. 91 is a high-level flowchart including exemplary implementations of operation O11 of FIG. 61.

In one or more implementations, as shown in FIG. 91, operation o11 includes an operation o1188 for electronically obtaining the treatment instructional information regarding the one or more subsequent injection operations on one or more ingestible substrate structures including one or more ingestible substrate wafer structures. Origination of an illustratively derived obtain instructional wafer component group can be accomplished through skilled in the art design choice selection of one or more of the above depicted components from one or more of the above depicted subsystems shown in FIG. 30. Components from the obtain instructional wafer component group can be used in implementing execution of the one or more obtain instructional wafer instructions i1188 of FIG. 51, can be used in performance of the obtain instructional wafer electrical circuitry arrangement e1188 of FIG. 44, and/or can be used in otherwise fulfillment of the operation o1188. An exemplary non-transitory signal bearing medium version of the information storage subsystem s200 is depicted in FIG. 51 as bearing the one or more obtain instructional wafer instructions i1188 that when executed will direct performance of the operation o1188. Furthermore, the obtain instructional wafer electrical circuitry arrangement ("elec circ arrange") e1188, when activated, will perform the operation o1188. Also, the obtain instructional wafer module m1188, when executed and/or activated, will direct performance of and/or perform the operation o1188. For instance, in one or more exemplary implementations, the one or more obtain instructional wafer instructions i1188, when executed, direct performance of the operation o1188 in the illustrative depiction as follows, and/or the obtain instructional wafer electrical circuitry arrangement e1188, when activated, performs the operation o1188 in the illustrative depiction as follows, and/or the obtain instructional wafer module m1188, when executed and/or activated, directs performance of and/or performs the operation o1188 in the illustrative depiction as follows, and/or the operation o1188 is otherwise carried out in the illustrative depiction as follows: electronically obtaining the treatment instructional information regarding the one or more subsequent injection operations on one or more ingestible substrate structures including one or more ingestible substrate wafer structures (e.g. including cookie textured structures, and/or etc.).

In one or more implementations, as shown in FIG. 91, operation o11 includes an operation o1189 for electronically obtaining the treatment instructional information regarding the one or more subsequent injection operations on one or more ingestible substrate structures including one or more ingestible substrate pasta structures. Origination of an illustratively derived obtain instructional pasta component group can be accomplished through skilled in the art design choice selection of one or more of the above depicted components from one or more of the above depicted subsystems shown in FIG. 30. Components from the obtain instructional pasta component group can be used in implementing execution of the one or more obtain instructional pasta instructions i1189 of FIG. 51, can be used in performance of the obtain instructional pasta electrical circuitry arrangement e1189 of FIG. 44, and/or can be used in otherwise fulfillment of the operation o1189. An exemplary non-transitory signal bearing medium version of the information storage subsystem s200 is depicted in FIG. 51 as bearing the one or more obtain instructional pasta instructions i1189 that when executed will direct performance of the operation o1189. Furthermore, the obtain instructional pasta electrical circuitry arrangement ("elec circ arrange") e1189, when activated, will perform the operation o1189. Also, the obtain instructional pasta module m1189, when executed and/or activated, will direct performance of and/or perform the operation o1189. For instance, in one or more exemplary implementations, the one or more obtain instructional pasta instructions i1189, when executed, direct performance of the operation o1189 in the illustrative depiction as follows, and/or the obtain instructional pasta electrical circuitry arrangement e1189, when activated, performs the operation o1189 in the illustrative depiction as follows, and/or the obtain instructional pasta module m1189, when executed and/or activated, directs performance of and/or performs the operation o1189 in the illustrative depiction as follows, and/or the operation o1189 is otherwise carried out in the illustrative depiction as follows: electronically obtaining the treatment instructional information regarding the one or more subsequent injection operations on one or more ingestible substrate structures including one or more ingestible substrate pasta structures (e.g. including noodle structures, and/or etc.).

In one or more implementations, as shown in FIG. 91, operation o11 includes an operation o1190 for electronically obtaining the treatment instructional information regarding the one or more subsequent injection operations on the one or more ingestible substrate structures including one or more ingestible substrate emulsion structures. Origination of an illustratively derived obtain instructional emulsion component group can be accomplished through skilled in the art design choice selection of one or more of the above depicted components from one or more of the above depicted subsystems shown in FIG. 30. Components from the obtain instructional emulsion component group can be used in implementing execution of the one or more obtain instructional emulsion instructions i1190 of FIG. 51, can be used in performance of the obtain instructional emulsion electrical circuitry arrangement e1190 of FIG. 44, and/or can be used in otherwise fulfillment of the operation o1190. An exemplary non-transitory signal bearing medium version of the information storage subsystem s200 is depicted in FIG. 51 as bearing the one or more obtain instructional emulsion instructions i1190 that when executed will direct performance of the operation o1190. Furthermore, the obtain instructional emulsion electrical circuitry arrangement ("elec circ arrange") e1190, when activated, will perform the operation o1190. Also, the obtain instructional emulsion module m1190, when executed and/or activated, will direct performance of and/or perform the operation o1190. For instance, in one or more exemplary implementations, the one or more obtain instructional emulsion instructions i1190, when executed, direct performance of the operation o1190 in the illustrative depiction as follows, and/or the obtain instructional emulsion electrical circuitry arrangement e1190, when activated, performs the operation o1190 in the illustrative depiction as follows, and/or the obtain instructional emulsion module m1190, when executed and/or activated, directs performance of and/or performs the operation o1190 in the illustrative depiction as follows, and/or the operation o1190 is otherwise carried out in the illustrative depiction as follows: electronically obtaining the treatment instructional information regarding the one or more subsequent injection operations on the one or more ingestible substrate structures including one or more ingestible substrate emulsion structures (e.g. including a substrate incorporating oil and vinegar, and/or etc.).

Figure 92:
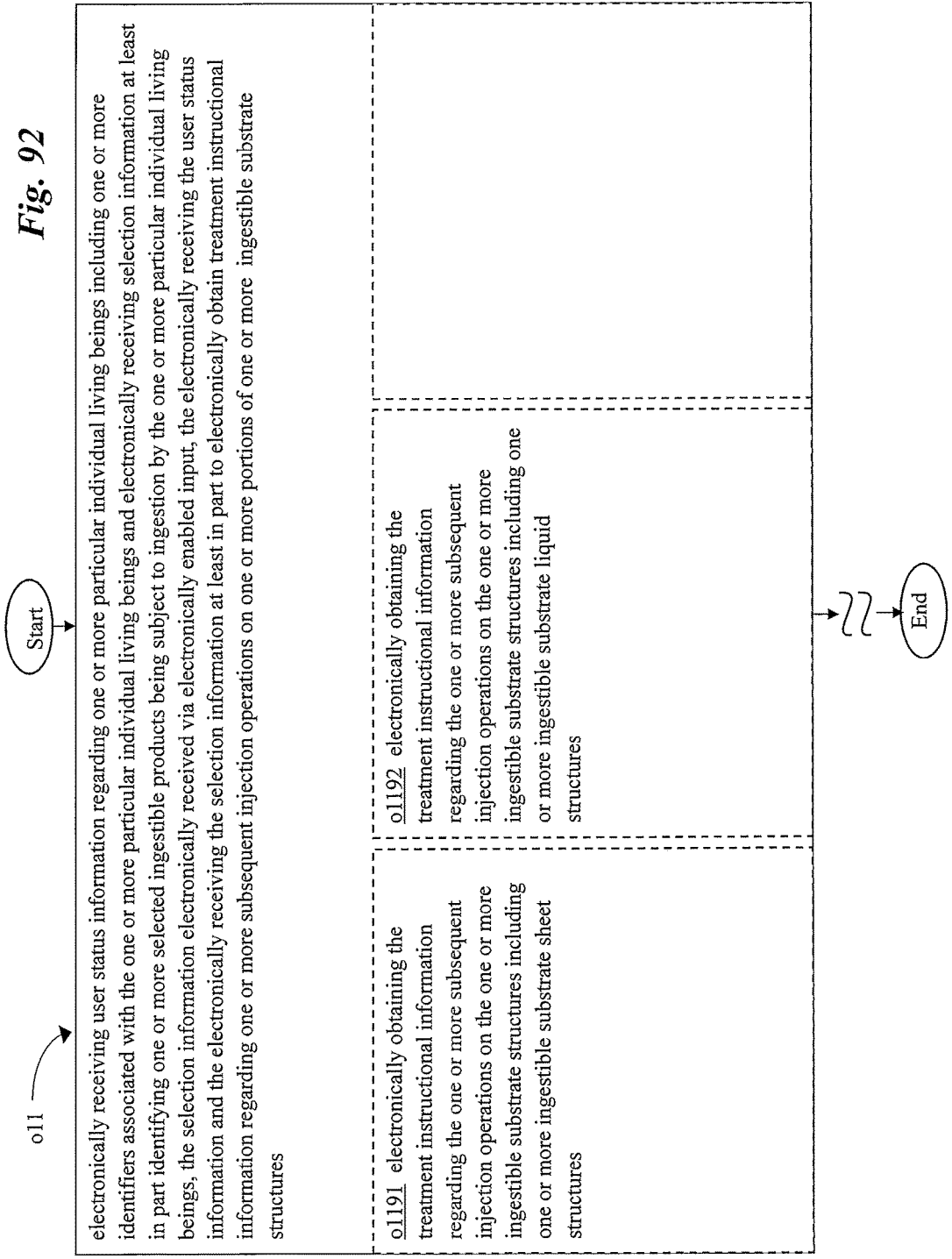
FIG. 92 is a high-level flowchart including exemplary implementations of operation O11 of FIG. 61.

In one or more implementations, as shown in FIG. 92, operation o11 includes an operation o1191 for electronically obtaining the treatment instructional information regarding the one or more subsequent injection operations on the one or more ingestible substrate structures including one or more ingestible substrate sheet structures. Origination of an illustratively derived obtain instructional sheet component group can be accomplished through skilled in the art design choice selection of one or more of the above depicted components from one or more of the above depicted subsystems shown in FIG. 30. Components from the obtain instructional sheet component group can be used in implementing execution of the one or more obtain instructional sheet instructions i1191 of FIG. 51, can be used in performance of the obtain instructional sheet electrical circuitry arrangement e1191 of FIG. 44, and/or can be used in otherwise fulfillment of the operation o1191. An exemplary non-transitory signal bearing medium version of the information storage subsystem s200 is depicted in FIG. 51 as bearing the one or more obtain instructional sheet instructions i1191 that when executed will direct performance of the operation o1191. Furthermore, the obtain instructional sheet electrical circuitry arrangement ("elec circ arrange") e1191, when activated, will perform the operation o1191. Also, the obtain instructional sheet module m1191, when executed and/or activated, will direct performance of and/or perform the operation o1191. For instance, in one or more exemplary implementations, the one or more obtain instructional sheet instructions i1191, when executed, direct performance of the operation o1191 in the illustrative depiction as follows, and/or the obtain instructional sheet electrical circuitry arrangement e1191, when activated, performs the operation o1191 in the illustrative depiction as follows, and/or the obtain instructional sheet module m1191, when executed and/or activated, directs performance of and/or performs the operation o1191 in the illustrative depiction as follows, and/or the operation o1191 is otherwise carried out in the illustrative depiction as follows: electronically obtaining the treatment instructional information regarding the one or more subsequent injection operations on the one or more ingestible substrate structures including one or more ingestible substrate sheet structures (e.g. including cake layers, and/or etc.).

In one or more implementations, as shown in FIG. 92, operation o11 includes an operation o1192 for electronically obtaining the treatment instructional information regarding the one or more subsequent injection operations on the one or more ingestible substrate structures including one or more ingestible substrate liquid structures. Origination of an illustratively derived obtain instructional liquid component group can be accomplished through skilled in the art design choice selection of one or more of the above depicted components from one or more of the above depicted subsystems shown in FIG. 30. Components from the obtain instructional liquid component group can be used in implementing execution of the one or more obtain instructional liquid instructions i1192 of FIG. 51, can be used in performance of the obtain instructional liquid electrical circuitry arrangement e1192 of FIG. 44, and/or can be used in otherwise fulfillment of the operation o1192. An exemplary non-transitory signal bearing medium version of the information storage subsystem s200 is depicted in FIG. 51 as bearing the one or more obtain instructional liquid instructions i1192 that when executed will direct performance of the operation o1192. Furthermore, the obtain instructional liquid electrical circuitry arrangement ("elec circ arrange") e1192, when activated, will perform the operation o1192. Also, the obtain instructional liquid module m1192, when executed and/or activated, will direct performance of and/or perform the operation o1192. For instance, in one or more exemplary implementations, the one or more obtain instructional liquid instructions i1192, when executed, direct performance of the operation o1192 in the illustrative depiction as follows, and/or the obtain instructional liquid electrical circuitry arrangement e1192, when activated, performs the operation o1192 in the illustrative depiction as follows, and/or the obtain instructional liquid module m1192, when executed and/or activated, directs performance of and/or performs the operation o1192 in the illustrative depiction as follows, and/or the operation o1192 is otherwise carried out in the illustrative depiction as follows: electronically obtaining the treatment instructional information regarding the one or more subsequent injection operations on the one or more ingestible substrate structures including one or more ingestible substrate liquid structures (e.g. including smoothie ingredients, and/or etc.).

As shown in FIG. 61, the operational flow o10 proceeds to operation o12 for electronically directing control of at least partial treatment of the one or more portions of the one or more ingestible substrate structures according to the treatment instructional information regarding the one or more subsequent injection operations including at least one or more injections of one or more materials into the one or more portions of the one or more ingestible substrate structures to form at least in part the one or more selected ingestible products subsequent to and based at least in part upon the electronically receiving the user status information regarding the one or more particular individual living beings and the electronically receiving the selection information at least in part identifying the one or more selected ingestible products. An exemplary version of a non-transitory signal bearing medium of information storage subsystem s200 is depicted as bearing one or more controlling treatment instructions i12 that when executed will direct performance of the operation o12. In an implementation, the one or more controlling treatment instructions i12 when executed direct electronically directing control (e.g. including the microprocessor component s102 can direct control, and/or etc.) of at least partial treatment (e.g. including injection treatment, and/or etc.) of the one or more portions of the one or more ingestible substrate structures (e.g. including rods, pasta, wafers, and/or etc.) according to the treatment instructional information (e.g. including treatment steps, and/or etc.) regarding the one or more subsequent injection operations (e.g. including injection gas, liquid, steam, fluid, and/or etc.) including at least one or more injections (e.g. including needle, jet, and/or etc.) of one or more materials (e.g. carbohydrates, fats, proteins, non-nutritive, flavors, colors, extracts, concentrates, and/or etc.) into the one or more portions of the one or more ingestible substrate structures (e.g. including cones, semi-spheres, rectangles, girders, and/or etc.) to form (e.g. including assemble fabricate, layer, make, and/or etc.) at least in part the one or more selected ingestible products (e.g. including snacks, meals, sandwiches, smoothies, and/or etc.) subsequent to and based at least in part upon the electronically receiving (e.g. including through wireless, network, direct electrical connection, packets, and/or etc.) the user status information (e.g. including identification, memberships, and/or etc.) regarding the one or more particular individual living beings (e.g. including children, adults, retired, and/or etc.) and the electronically receiving (e.g. including wired reception, and/or etc.) the selection information (e.g. including meal selection, and/or etc.) at least in part identifying (e.g. including titles, names, serial numbers, and/or etc.) the one or more selected ingestible products (e.g. including full meals, European dishes, Asian dishes, Mexican dishes, South American dishes, American dishes, and/or etc.). Furthermore, the controlling treatment electrical circuitry arrangement e12 when activated will perform the operation o12. Also, the controlling treatment module m12, when executed and/or activated, will direct performance of and/or perform the operation o12. In an implementation, the controlling treatment electrical circuitry arrangement e12, when activated performs the operation o12 in the illustrative depiction as follows, and/or the controlling treatment module m12, when executed and/or activated, directs performance of and/or performs electronically directing control (e.g. including the microprocessor component s102 can direct control, and/or etc.) of at least partial treatment (e.g. including injection treatment, and/or etc.) of the one or more portions of the one or more ingestible substrate structures (e.g. including rods, pasta, wafers, and/or etc.) according to the treatment instructional information (e.g. including treatment steps, and/or etc.) regarding the one or more subsequent injection operations (e.g. including injection gas, liquid, steam, fluid, and/or etc.) including at least one or more injections (e.g. including needle, jet, and/or etc.) of one or more materials (e.g. carbohydrates, fats, proteins, non-nutritive, flavors, colors, extracts, concentrates, and/or etc.) into the one or more portions of the one or more ingestible substrate structures (e.g. including cones, semi-spheres, rectangles, girders, and/or etc.) to form (e.g. including assemble fabricate, layer, make, and/or etc.) at least in part the one or more selected ingestible products (e.g. including snacks, meals, sandwiches, smoothies, and/or etc.) subsequent to and based at least in part upon the electronically receiving (e.g. including through wireless, network, direct electrical connection, packets, and/or etc.) the user status information (e.g. including identification, memberships, and/or etc.) regarding the one or more particular individual living beings (e.g. including children, adults, retired, and/or etc.) and the electronically receiving (e.g. including wired reception, and/or etc.) the selection information (e.g. including meal selection, and/or etc.) at least in part identifying (e.g. including titles, names, serial numbers, and/or etc.) the one or more selected ingestible products (e.g. including full meals, European dishes, Asian dishes, Mexican dishes, South American dishes, American dishes, and/or etc.). In an implementation, the electronically directing control of at least partial treatment of the one or more portions of the one or more ingestible substrate structures according to the treatment instructional information regarding the one or more subsequent injection operations including at least one or more injections of one or more materials into the one or more portions of the one or more ingestible substrate structures to form at least in part the one or more selected ingestible products subsequent to and based at least in part upon the electronically receiving the user status information regarding the one or more particular individual living beings and the electronically receiving the selection information at least in part identifying the one or more selected ingestible products is carried out by electronically directing control (e.g. including the microprocessor component s102 can direct control, and/or etc.) of at least partial treatment (e.g. including injection treatment, and/or etc.) of the one or more portions of the one or more ingestible substrate structures (e.g. including rods, pasta, wafers, and/or etc.) according to the treatment instructional information (e.g. including treatment steps, and/or etc.) regarding the one or more subsequent injection operations (e.g. including injection gas, liquid, steam, fluid, and/or etc.) including at least one or more injections (e.g. including needle, jet, and/or etc.) of one or more materials (e.g. carbohydrates, fats, proteins, non-nutritive, flavors, colors, extracts, concentrates, and/or etc.) into the one or more portions of the one or more ingestible substrate structures (e.g. including cones, semi-spheres, rectangles, girders, and/or etc.) to form (e.g. including assemble fabricate, layer, make, and/or etc.) at least in part the one or more selected ingestible products (e.g. including snacks, meals, sandwiches, smoothies, and/or etc.) subsequent to and based at least in part upon the electronically receiving (e.g. including through wireless, network, direct electrical connection, packets, and/or etc.) the user status information (e.g. including identification, memberships, and/or etc.) regarding the one or more particular individual living beings (e.g. including children, adults, retired, and/or etc.) and the electronically receiving (e.g. including wired reception, and/or etc.) the selection information (e.g. including meal selection, and/or etc.) at least in part identifying (e.g. including titles, names, serial numbers, and/or etc.) the one or more selected ingestible products (e.g. including full meals, European dishes, Asian dishes, Mexican dishes, South American dishes, American dishes, and/or etc.).

In one or more implementations, as shown in FIG. 93, operation o12 includes an operation o1201 for electronically directing control of the at least partial treatment of the one or more ingestible substrate structures according to the treatment instructional information regarding the one or more subsequent injection operations via at least in part one or more directly connected electrical circuits. Origination of an illustratively derived direct treatment circuits component group can be accomplished through skilled in the art design choice selection of one or more of the above depicted components from one or more of the above depicted subsystems shown in FIG. 30. Components from the direct treatment circuits component group can be used in implementing execution of the one or more direct treatment circuits instructions i1201 of FIG. 52, can be used in performance of the direct treatment circuits electrical circuitry arrangement e1201 of FIG. 45, and/or can be used in otherwise fulfillment of the operation o1201. An exemplary non-transitory signal bearing medium version of the information storage subsystem s200 is depicted in FIG. 52 as bearing the one or more direct treatment circuits instructions i1201 that when executed will direct performance of the operation o1201. Furthermore, the direct treatment circuits electrical circuitry arrangement ("elec circ arrange") e1201, when activated, will perform the operation o1201. Also, the direct treatment circuits module m1201, when executed and/or activated, will direct performance of and/or perform the operation o1201. For instance, in one or more exemplary implementations, the one or more direct treatment circuits instructions i1201, when executed, direct performance of the operation o1201 in the illustrative depiction as follows, and/or the direct treatment circuits electrical circuitry arrangement e1201, when activated, performs the operation o1201 in the illustrative depiction as follows, and/or the direct treatment circuits module m1201, when executed and/or activated, directs performance of and/or performs the operation o1201 in the illustrative depiction as follows, and/or the operation o1201 is otherwise carried out in the illustrative depiction as follows: electronically directing control of the at least partial treatment of the one or more ingestible substrate structures according to the treatment instructional information regarding the one or more subsequent injection operations via at least in part one or more directly connected electrical circuits (e.g. including an implementation of the processor component s102 is configured to electronically receive directing control through receiver component s528 electrically connected with the material processing subsystem 700 for treatment of the one or more ingestible products, and/or etc.).

In one or more implementations, as shown in FIG. 93, operation o12 includes an operation o1202 for electronically directing control of the at least partial treatment of the one or more ingestible substrate structures according to the treatment instructional information regarding the one or more subsequent injection operations via at least in part electronic computer network communication. Origination of an illustratively derived direct treatment network component group can be accomplished through skilled in the art design choice selection of one or more of the above depicted components from one or more of the above depicted subsystems shown in FIG. 30. Components from the direct treatment network component group can be used in implementing execution of the one or more direct treatment network instructions i1202 of FIG. 52, can be used in performance of the direct treatment network electrical circuitry arrangement e1202 of FIG. 45, and/or can be used in otherwise fulfillment of the operation o1202. An exemplary non-transitory signal bearing medium version of the information storage subsystem s200 is depicted in FIG. 52 as bearing the one or more direct treatment network instructions i1202 that when executed will direct performance of the operation o1202. Furthermore, the direct treatment network electrical circuitry arrangement ("elec circ arrange") e1202, when activated, will perform the operation o1202. Also, the direct treatment network module m1202, when executed and/or activated, will direct performance of and/or perform the operation o1202. For instance, in one or more exemplary implementations, the one or more direct treatment network instructions i1202, when executed, direct performance of the operation o1202 in the illustrative depiction as follows, and/or the direct treatment network electrical circuitry arrangement e1202, when activated, performs the operation o1202 in the illustrative depiction as follows, and/or the direct treatment network module m1202, when executed and/or activated, directs performance of and/or performs the operation o1202 in the illustrative depiction as follows, and/or the operation o1202 is otherwise carried out in the illustrative depiction as follows: electronically directing control of the at least partial treatment of the one or more ingestible substrate structures according to the treatment instructional information regarding the one or more subsequent injection operations via at least in part electronic computer network communication (e.g. including an implementation of the processor component s102 is configured to electronically receive directing control through internet network components s508 to control the material processing subsystem 700 for treatment of the one or more ingestible products, and/or etc.).

In one or more implementations, as shown in FIG. 93, operation o12 includes an operation o1203 for electronically directing control of the at least partial treatment of the one or more ingestible substrate structures through electronic circuitry located substantially adjacent to electronic circuitry for the electronically receiving the user status information and the electronically receiving the selection information. Origination of an illustratively derived direct treatment adjacent component group can be accomplished through skilled in the art design choice selection of one or more of the above depicted components from one or more of the above depicted subsystems shown in FIG. 30. Components from the direct treatment adjacent component group can be used in implementing execution of the one or more direct treatment adjacent instructions i1203 of FIG. 52, can be used in performance of the direct treatment adjacent electrical circuitry arrangement e1203 of FIG. 45, and/or can be used in otherwise fulfillment of the operation o1203. An exemplary non-transitory signal bearing medium version of the information storage subsystem s200 is depicted in FIG. 52 as bearing the one or more direct treatment adjacent instructions i1203 that when executed will direct performance of the operation o1203. Furthermore, the direct treatment adjacent electrical circuitry arrangement ("elec circ arrange") e1203, when activated, will perform the operation o1203. Also, the direct treatment adjacent module m1203, when executed and/or activated, will direct performance of and/or perform the operation o1203. For instance, in one or more exemplary implementations, the one or more direct treatment adjacent instructions i1203, when executed, direct performance of the operation o1203 in the illustrative depiction as follows, and/or the direct treatment adjacent electrical circuitry arrangement e1203, when activated, performs the operation o1203 in the illustrative depiction as follows, and/or the direct treatment adjacent module m1203, when executed and/or activated, directs performance of and/or performs the operation o1203 in the illustrative depiction as follows, and/or the operation o1203 is otherwise carried out in the illustrative depiction as follows: electronically directing control of the at least partial treatment of the one or more ingestible substrate structures through electronic circuitry (e.g. including a first electronic component of processing subsystem s100 such as the processor component s102, and/or etc.) located substantially adjacent to electronic circuitry (e.g. including a second electronic component of the processing subsystem s100 such as the CPU component s104, and/or etc.) for the electronically receiving the user status information and the electronically receiving the selection information.

In one or more implementations, as shown in FIG. 94, operation o12 includes an operation o1204 for electronically directing control of the one or more injections of the one or more materials as one or more color modification materials into the one or more portions of the one or more ingestible substrate structures to modify one or more color properties of the one or more portions of the one or more ingestible substrate structures to form at least in part the one or more selected ingestible products. Origination of an illustratively derived direct modify color component group can be accomplished through skilled in the art design choice selection of one or more of the above depicted components from one or more of the above depicted subsystems shown in FIG. 30. Components from the direct modify color component group can be used in implementing execution of the one or more direct modify color instructions i1204 of FIG. 52, can be used in performance of the direct modify color electrical circuitry arrangement e1204 of FIG. 45, and/or can be used in otherwise fulfillment of the operation o1204. An exemplary non-transitory signal bearing medium version of the information storage subsystem s200 is depicted in FIG. 52 as bearing the one or more direct modify color instructions i1204 that when executed will direct performance of the operation o1204. Furthermore, the direct modify color electrical circuitry arrangement ("elec circ arrange") e1204, when activated, will perform the operation o1204. Also, the direct modify color module m1204, when executed and/or activated, will direct performance of and/or perform the operation o1204. For instance, in one or more exemplary implementations, the one or more direct modify color instructions i1204, when executed, direct performance of the operation o1204 in the illustrative depiction as follows, and/or the direct modify color electrical circuitry arrangement e1204, when activated, performs the operation o1204 in the illustrative depiction as follows, and/or the direct modify color module m1204, when executed and/or activated, directs performance of and/or performs the operation o1204 in the illustrative depiction as follows, and/or the operation o1204 is otherwise carried out in the illustrative depiction as follows: electronically directing control of the one or more injections of the one or more materials as one or more color modification materials into the one or more portions of the one or more ingestible substrate structures to modify (e.g. including replace, and/or etc.) one or more color properties (e.g. including increase intensity of existing surface color, and/or etc.) of the one or more portions of the one or more ingestible substrate structures to form at least in part the one or more selected ingestible products.

In one or more implementations, as shown in FIG. 94, operation o12 includes an operation o1205 for electronically directing control of the one or more injections of the one or more materials as one or more surface texture modification materials into the one or more portions of the one or more ingestible substrate structures to modify one or more surface texture properties of the one or more portions of the one or more ingestible substrate structures to form at least in part the one or more selected ingestible products. Origination of an illustratively derived direct modify surface component group can be accomplished through skilled in the art design choice selection of one or more of the above depicted components from one or more of the above depicted subsystems shown in FIG. 30. Components from the direct modify surface component group can be used in implementing execution of the one or more direct modify surface instructions i1205 of FIG. 52, can be used in performance of the direct modify surface electrical circuitry arrangement e1205 of FIG. 45, and/or can be used in otherwise fulfillment of the operation o1205. An exemplary non-transitory signal bearing medium version of the information storage subsystem s200 is depicted in FIG. 52 as bearing the one or more direct modify surface instructions i1205 that when executed will direct performance of the operation o1205. Furthermore, the direct modify surface electrical circuitry arrangement ("elec circ arrange") e1205, when activated, will perform the operation o1205. Also, the direct modify surface module m1205, when executed and/or activated, will direct performance of and/or perform the operation o1205. For instance, in one or more exemplary implementations, the one or more direct modify surface instructions i1205, when executed, direct performance of the operation o1205 in the illustrative depiction as follows, and/or the direct modify surface electrical circuitry arrangement e1205, when activated, performs the operation o1205 in the illustrative depiction as follows, and/or the direct modify surface module m1205, when executed and/or activated, directs performance of and/or performs the operation o1205 in the illustrative depiction as follows, and/or the operation o1205 is otherwise carried out in the illustrative depiction as follows: electronically directing control of the one or more injections of the one or more materials as one or more surface texture modification materials (e.g. including one or more liquids, and/or etc.) into the one or more portions of the one or more ingestible substrate structures to modify (e.g. including create indentations, and/or etc.) one or more surface texture properties (e.g. including surface integrity, and/or etc.) of the one or more portions of the one or more ingestible substrate structures to form at least in part the one or more selected ingestible products.

In one or more implementations, as shown in FIG. 94, operation o12 includes an operation o1206 for electronically directing control of the one or more injections of the one or more materials as one or more oral sensation modification materials into the one or more portions of the one or more ingestible substrate structures to modify one or more oral sensation properties of the one or more portions of the one or more ingestible substrate structures to form at least in part the one or more selected ingestible products. Origination of an illustratively derived direct modify oral component group can be accomplished through skilled in the art design choice selection of one or more of the above depicted components from one or more of the above depicted subsystems shown in FIG. 30. Components from the direct modify oral component group can be used in implementing execution of the one or more direct modify oral instructions i1206 of FIG. 52, can be used in performance of the direct modify oral electrical circuitry arrangement e1206 of FIG. 45, and/or can be used in otherwise fulfillment of the operation o1206. An exemplary non-transitory signal bearing medium version of the information storage subsystem s200 is depicted in FIG. 52 as bearing the one or more direct modify oral instructions i1206 that when executed will direct performance of the operation o1206. Furthermore, the direct modify oral electrical circuitry arrangement ("elec circ arrange") e1206, when activated, will perform the operation o1206. Also, the direct modify oral module m1206, when executed and/or activated, will direct performance of and/or perform the operation o1206. For instance, in one or more exemplary implementations, the one or more direct modify oral instructions i1206, when executed, direct performance of the operation o1206 in the illustrative depiction as follows, and/or the direct modify oral electrical circuitry arrangement e1206, when activated, performs the operation o1206 in the illustrative depiction as follows, and/or the direct modify oral module m1206, when executed and/or activated, directs performance of and/or performs the operation o1206 in the illustrative depiction as follows, and/or the operation o1206 is otherwise carried out in the illustrative depiction as follows: electronically directing control of the one or more injections of the one or more materials as one or more oral sensation modification materials (e.g. including flavored gels, and/or etc.) into the one or more portions of the one or more ingestible substrate structures to modify (e.g. including enhancement, and/or etc.) one or more oral sensation properties (e.g. including adding mint-based flavors, and/or etc.) of the one or more portions of the one or more ingestible substrate structures to form at least in part the one or more selected ingestible products.

In one or more implementations, as shown in FIG. 95, operation o12 includes an operation o1207 for electronically directing control of the one or more injections of the one or more materials as one or more sound modification materials into the one or more portions of the one or more ingestible substrate structures to modify one or more sound properties of the one or more portions of the one or more ingestible substrate structures to form at least in part the one or more selected ingestible product. Origination of an illustratively derived direct modify sound component group can be accomplished through skilled in the art design choice selection of one or more of the above depicted components from one or more of the above depicted subsystems shown in FIG. 30. Components from the direct modify sound component group can be used in implementing execution of the one or more direct modify sound instructions i1207 of FIG. 52, can be used in performance of the direct modify sound electrical circuitry arrangement e1207 of FIG. 45, and/or can be used in otherwise fulfillment of the operation o1207. An exemplary non-transitory signal bearing medium version of the information storage subsystem s200 is depicted in FIG. 52 as bearing the one or more direct modify sound instructions i1207 that when executed will direct performance of the operation o1207. Furthermore, the direct modify sound electrical circuitry arrangement ("elec circ arrange") e1207, when activated, will perform the operation o1207. Also, the direct modify sound module m1207, when executed and/or activated, will direct performance of and/or perform the operation o1207. For instance, in one or more exemplary implementations, the one or more direct modify sound instructions i1207, when executed, direct performance of the operation o1207 in the illustrative depiction as follows, and/or the direct modify sound electrical circuitry arrangement e1207, when activated, performs the operation o1207 in the illustrative depiction as follows, and/or the direct modify sound module m1207, when executed and/or activated, directs performance of and/or performs the operation o1207 in the illustrative depiction as follows, and/or the operation o1207 is otherwise carried out in the illustrative depiction as follows: electronically directing control of the one or more injections of the one or more materials as one or more sound modification materials (e.g. including one or more powders, and/or etc.) into the one or more portions of the one or more ingestible substrate structures to modify (e.g. including reducing decibel levels, and/or etc.) one or more sound properties (e.g. including decibel levels when substrate is bitten into, and/or etc.) of the one or more portions of the one or more ingestible substrate structures to form at least in part the one or more selected ingestible products.

In one or more implementations, as shown in FIG. 95, operation o12 includes an operation o1208 for electronically directing control of the one or more injections of the one or more materials as one or more structural texture modification materials into the one or more portions of the one or more ingestible substrate structures to modify one or more structural texture properties of the one or more portions of the one or more ingestible substrate structures to form at least in part the one or more selected ingestible products. Origination of an illustratively derived direct modify structural component group can be accomplished through skilled in the art design choice selection of one or more of the above depicted components from one or more of the above depicted subsystems shown in FIG. 30. Components from the direct modify structural component group can be used in implementing execution of the one or more direct modify structural instructions i1208 of FIG. 52, can be used in performance of the direct modify structural electrical circuitry arrangement e1208 of FIG. 45, and/or can be used in otherwise fulfillment of the operation o1208. An exemplary non-transitory signal bearing medium version of the information storage subsystem s200 is depicted in FIG. 52 as bearing the one or more direct modify structural instructions i1208 that when executed will direct performance of the operation o1208. Furthermore, the direct modify structural electrical circuitry arrangement ("elec circ arrange") e1208, when activated, will perform the operation o1208. Also, the direct modify structural module m1208, when executed and/or activated, will direct performance of and/or perform the operation o1208. For instance, in one or more exemplary implementations, the one or more direct modify structural instructions i1208, when executed, direct performance of the operation o1208 in the illustrative depiction as follows, and/or the direct modify structural electrical circuitry arrangement e1208, when activated, performs the operation o1208 in the illustrative depiction as follows, and/or the direct modify structural module m1208, when executed and/or activated, directs performance of and/or performs the operation o1208 in the illustrative depiction as follows, and/or the operation o1208 is otherwise carried out in the illustrative depiction as follows: electronically directing control of the one or more injections of the one or more materials as one or more structural texture modification materials (e.g. including liquid binders, and/or etc.) into the one or more portions of the one or more ingestible substrate structures to modify (e.g. including strengthening, and/or etc.) one or more structural texture properties (e.g. including rigidity, and/or etc.) of the one or more portions of the one or more ingestible substrate structures to form at least in part the one or more selected ingestible products.

In one or more implementations, as shown in FIG. 95, operation o12 includes an operation o1209 for electronically directing control of the one or more injections of the one or more materials as one or more olfactory modification materials into the one or more portions of the one or more ingestible substrate structures to modify one or more olfactory properties of the one or more portions of the one or more ingestible substrate structures to form at least in part the one or more selected ingestible products. Origination of an illustratively derived direct modify olfactory component group can be accomplished through skilled in the art design choice selection of one or more of the above depicted components from one or more of the above depicted subsystems shown in FIG. 30. Components from the direct modify olfactory component group can be used in implementing execution of the one or more direct modify olfactory instructions i1209 of FIG. 52, can be used in performance of the direct modify olfactory electrical circuitry arrangement e1209 of FIG. 45, and/or can be used in otherwise fulfillment of the operation o1209. An exemplary non-transitory signal bearing medium version of the information storage subsystem s200 is depicted in FIG. 52 as bearing the one or more direct modify olfactory instructions i1209 that when executed will direct performance of the operation o1209. Furthermore, the direct modify olfactory electrical circuitry arrangement ("elec circ arrange") e1209, when activated, will perform the operation o1209. Also, the direct modify olfactory module m1209, when executed and/or activated, will direct performance of and/or perform the operation o1209. For instance, in one or more exemplary implementations, the one or more direct modify olfactory instructions i1209, when executed, direct performance of the operation o1209 in the illustrative depiction as follows, and/or the direct modify olfactory electrical circuitry arrangement e1209, when activated, performs the operation o1209 in the illustrative depiction as follows, and/or the direct modify olfactory module m1209, when executed and/or activated, directs performance of and/or performs the operation o1209 in the illustrative depiction as follows, and/or the operation o1209 is otherwise carried out in the illustrative depiction as follows: electronically directing control of the one or more injections of the one or more materials as one or more olfactory modification materials (e.g. including one or more food extracts, and/or etc.) into the one or more portions of the one or more ingestible substrate structures to modify (e.g. including adding scents, and/or etc.) one or more olfactory properties (e.g. including smell of the substrate, and/or etc.) of the one or more portions of the one or more ingestible substrate structures to form at least in part the one or more selected ingestible products.

Figure 96:
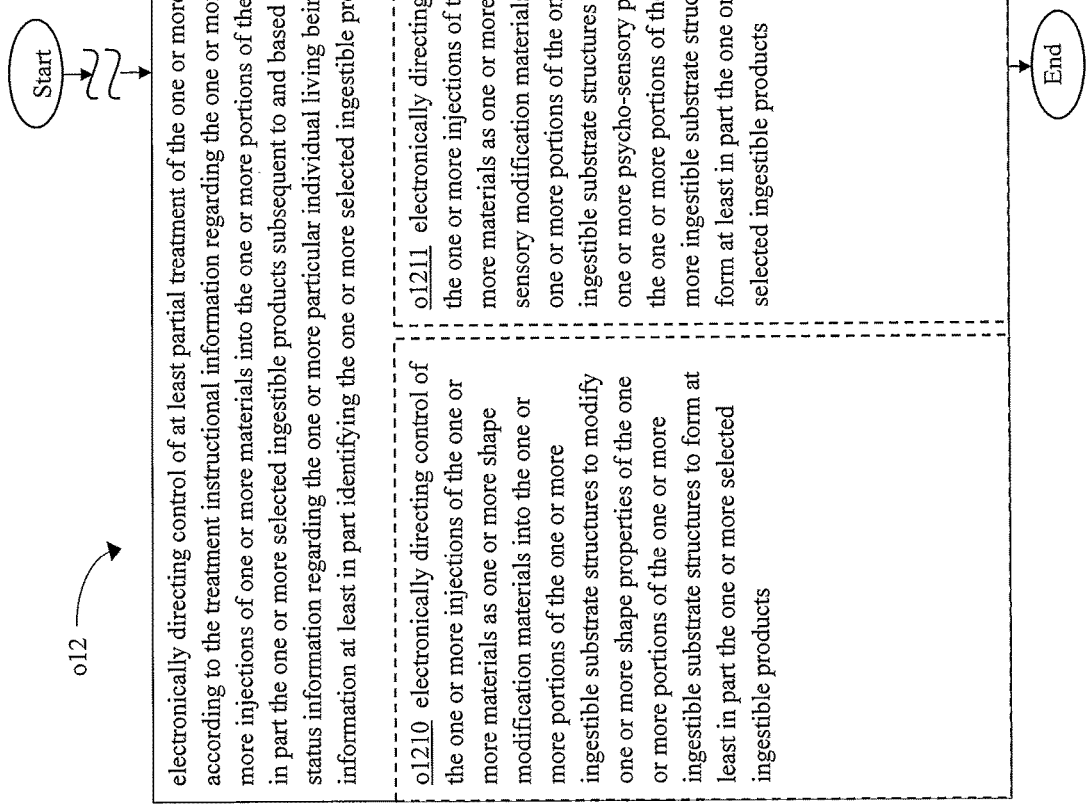
FIG. 96 is a high-level flowchart including exemplary implementations of operation O12 of FIG. 61.

In one or more implementations, as shown in FIG. 96, operation o12 includes an operation o1210 for electronically directing control of the one or more injections of the one or more materials as one or more shape modification materials into the one or more portions of the one or more ingestible substrate structures to modify one or more shape properties of the one or more portions of the one or more ingestible substrate structures to form at least in part the one or more selected ingestible products. Origination of an illustratively derived direct modify shape component group can be accomplished through skilled in the art design choice selection of one or more of the above depicted components from one or more of the above depicted subsystems shown in FIG. 30. Components from the direct modify shape component group can be used in implementing execution of the one or more direct modify shape instructions i1210 of FIG. 52, can be used in performance of the direct modify shape electrical circuitry arrangement e1210 of FIG. 45, and/or can be used in otherwise fulfillment of the operation o1210. An exemplary non-transitory signal bearing medium version of the information storage subsystem s200 is depicted in FIG. 52 as bearing the one or more direct modify shape instructions i1210 that when executed will direct performance of the operation o1210. Furthermore, the direct modify shape electrical circuitry arrangement ("elec circ arrange") e1210, when activated, will perform the operation o1210. Also, the direct modify shape module m1210, when executed and/or activated, will direct performance of and/or perform the operation o1210. For instance, in one or more exemplary implementations, the one or more direct modify shape instructions i1210, when executed, direct performance of the operation o1210 in the illustrative depiction as follows, and/or the direct modify shape electrical circuitry arrangement e1210, when activated, performs the operation o1210 in the illustrative depiction as follows, and/or the direct modify shape module m1210, when executed and/or activated, directs performance of and/or performs the operation o1210 in the illustrative depiction as follows, and/or the operation o1210 is otherwise carried out in the illustrative depiction as follows: electronically directing control of the one or more injections of the one or more materials as one or more shape modification materials (e.g. including dissolving agents, and/or etc.) into the one or more portions of the one or more ingestible substrate structures to modify (e.g. including eliminate portions of the substrate, and/or etc.) one or more shape properties (e.g. including changing a rectangularly configured substrate to irregularly configured substrate, and/or etc.) of the one or more portions of the one or more ingestible substrate structures to form at least in part the one or more selected ingestible products.

In one or more implementations, as shown in FIG. 96, operation o12 includes an operation o1211 for electronically directing control of the one or more injections of the one or more materials as one or more psycho-sensory modification materials into the one or more portions of the one or more ingestible substrate structures to modify one or more psycho-sensory properties of the one or more portions of the one or more ingestible substrate structures to form at least in part the one or more selected ingestible products. Origination of an illustratively derived direct modify psycho-sensory component group can be accomplished through skilled in the art design choice selection of one or more of the above depicted components from one or more of the above depicted subsystems shown in FIG. 30. Components from the direct modify psycho-sensory component group can be used in implementing execution of the one or more direct modify psycho-sensory instructions i1211 of FIG. 52, can be used in performance of the direct modify psycho-sensory electrical circuitry arrangement e1211 of FIG. 45, and/or can be used in otherwise fulfillment of the operation o1211. An exemplary non-transitory signal bearing medium version of the information storage subsystem s200 is depicted in FIG. 52 as bearing the one or more direct modify psycho-sensory instructions i1211 that when executed will direct performance of the operation o1211. Furthermore, the direct modify psycho-sensory electrical circuitry arrangement ("elec circ arrange") e1211, when activated, will perform the operation o1211. Also, the direct modify psycho-sensory module m1211, when executed and/or activated, will direct performance of and/or perform the operation o1211. For instance, in one or more exemplary implementations, the one or more direct modify psycho-sensory instructions i1211, when executed, direct performance of the operation o1211 in the illustrative depiction as follows, and/or the direct modify psycho-sensory electrical circuitry arrangement e1211, when activated, performs the operation o1211 in the illustrative depiction as follows, and/or the direct modify psycho-sensory module m1211, when executed and/or activated, directs performance of and/or performs the operation o1211 in the illustrative depiction as follows, and/or the operation o1211 is otherwise carried out in the illustrative depiction as follows: electronically directing control of the one or more injections of the one or more materials as one or more psycho-sensory modification materials (e.g. including colored and scented liquids, and/or etc.) into the one or more portions of the one or more ingestible substrate structures to modify (e.g. including adding perceived sensory output associated with a selected ingestible product, and/or etc.) one or more psycho-sensory properties (e.g. including perceived flavor as influenced by a combination of color and scent, and/or etc.) of the one or more portions of the one or more ingestible substrate structures to form at least in part the one or more selected ingestible products.

In one or more implementations, as shown in FIG. 96, operation o12 includes an operation o1212 for electronically directing control of the one or more injections of the one or more materials as one or more acidic materials into the one or more portions of the one or more ingestible substrate structures to modify one or more properties of the one or more portions of the one or more ingestible substrate structures to form at least in part the one or more selected ingestible products. Origination of an illustratively derived direct modify acidic component group can be accomplished through skilled in the art design choice selection of one or more of the above depicted components from one or more of the above depicted subsystems shown in FIG. 30. Components from the direct modify acidic component group can be used in implementing execution of the one or more direct modify acidic instructions i1212 of FIG. 52, can be used in performance of the direct modify acidic electrical circuitry arrangement e1212 of FIG. 45, and/or can be used in otherwise fulfillment of the operation o1212. An exemplary non-transitory signal bearing medium version of the information storage subsystem s200 is depicted in FIG. 52 as bearing the one or more direct modify acidic instructions i1212 that when executed will direct performance of the operation o1212. Furthermore, the direct modify acidic electrical circuitry arrangement ("elec circ arrange") e1212, when activated, will perform the operation o1212. Also, the direct modify acidic module m1212, when executed and/or activated, will direct performance of and/or perform the operation o1212. For instance, in one or more exemplary implementations, the one or more direct modify acidic instructions i1212, when executed, direct performance of the operation o1212 in the illustrative depiction as follows, and/or the direct modify acidic electrical circuitry arrangement e1212, when activated, performs the operation o1212 in the illustrative depiction as follows, and/or the direct modify acidic module m1212, when executed and/or activated, directs performance of and/or performs the operation o1212 in the illustrative depiction as follows, and/or the operation o1212 is otherwise carried out in the illustrative depiction as follows: electronically directing control of the one or more injections of the one or more materials as one or more acidic materials (e.g. including acetic acid, and/or etc.) into the one or more portions of the one or more ingestible substrate structures to modify (e.g. including intensify, and/or etc.) one or more properties (e.g. including flavors, and/or etc.) of the one or more portions of the one or more ingestible substrate structures to form at least in part the one or more selected ingestible products.

Figure 97:
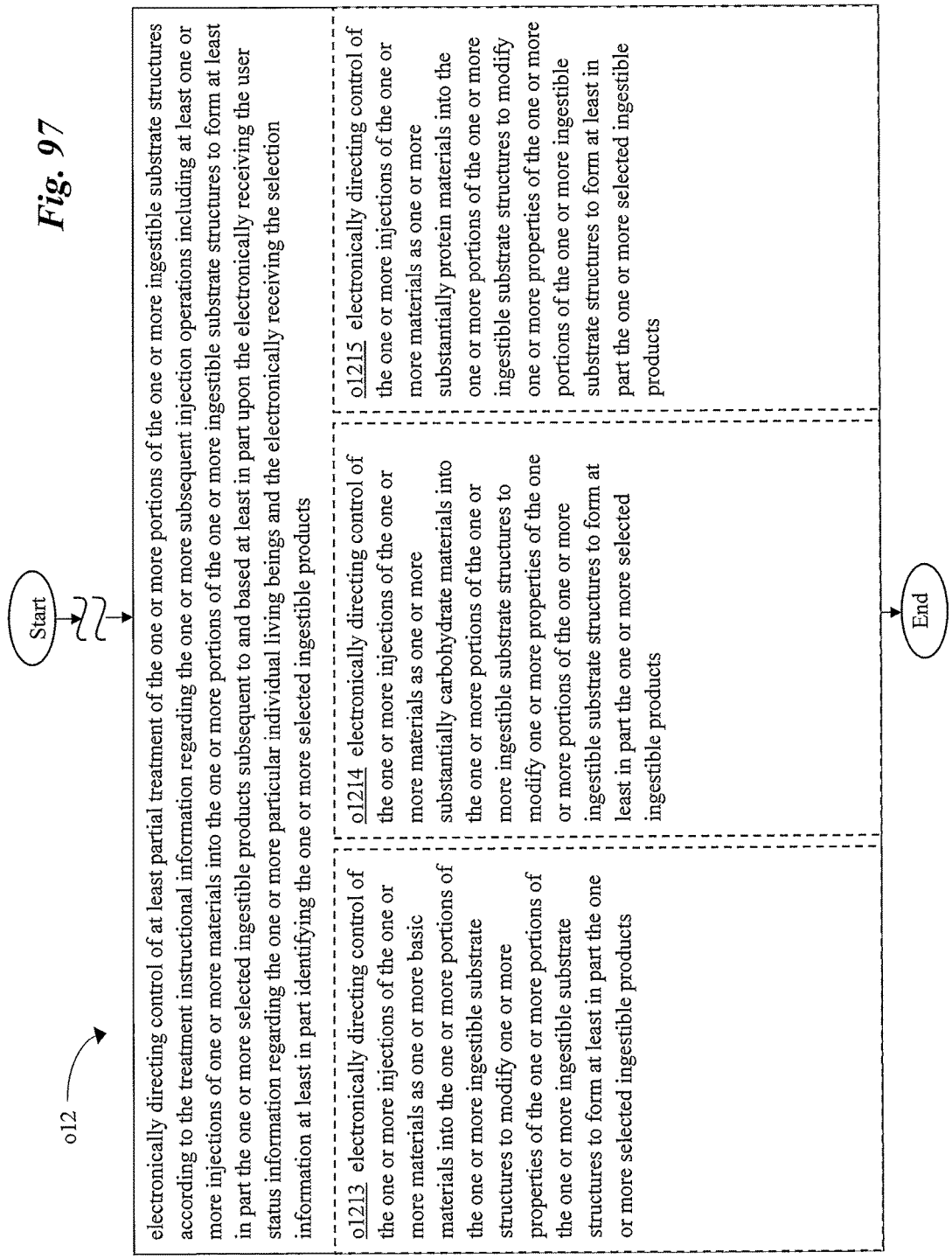
FIG. 97 is a high-level flowchart including exemplary implementations of operation O12 of FIG. 61.

In one or more implementations, as shown in FIG. 97, operation o12 includes an operation o1213 for electronically directing control of the one or more injections of the one or more materials as one or more basic materials into the one or more portions of the one or more ingestible substrate structures to modify one or more properties of the one or more portions of the one or more ingestible substrate structures to form at least in part the one or more selected ingestible products. Origination of an illustratively derived direct modify basic component group can be accomplished through skilled in the art design choice selection of one or more of the above depicted components from one or more of the above depicted subsystems shown in FIG. 30. Components from the direct modify basic component group can be used in implementing execution of the one or more direct modify basic instructions i1213 of FIG. 52, can be used in performance of the direct modify basic electrical circuitry arrangement e1213 of FIG. 45, and/or can be used in otherwise fulfillment of the operation o1213. An exemplary non-transitory signal bearing medium version of the information storage subsystem s200 is depicted in FIG. 52 as bearing the one or more direct modify basic instructions i1213 that when executed will direct performance of the operation o1213. Furthermore, the direct modify basic electrical circuitry arrangement ("elec circ arrange") e1213, when activated, will perform the operation o1213. Also, the direct modify basic module m1213, when executed and/or activated, will direct performance of and/or perform the operation o1213. For instance, in one or more exemplary implementations, the one or more direct modify basic instructions i1213, when executed, direct performance of the operation o1213 in the illustrative depiction as follows, and/or the direct modify basic electrical circuitry arrangement e1213, when activated, performs the operation o1213 in the illustrative depiction as follows, and/or the direct modify basic module m1213, when executed and/or activated, directs performance of and/or performs the operation o1213 in the illustrative depiction as follows, and/or the operation o1213 is otherwise carried out in the illustrative depiction as follows: electronically directing control of the one or more injections of the one or more materials as one or more basic materials (e.g. including sodium bicarbonate, and/or etc.) into the one or more portions of the one or more ingestible substrate structures to modify (e.g. including reactivity to oxidizing compounds, and/or etc.) one or more properties (e.g. including surface color, and/or etc.) of the one or more portions of the one or more ingestible substrate structures to form at least in part the one or more selected ingestible products.

In one or more implementations, as shown in FIG. 97, operation o12 includes an operation o1214 for electronically directing control of the one or more injections of the one or more materials as one or more substantially carbohydrate materials into the one or more portions of the one or more ingestible substrate structures to modify one or more properties of the one or more portions of the one or more ingestible substrate structures to form at least in part the one or more selected ingestible products. Origination of an illustratively derived direct modify carbohydrate component group can be accomplished through skilled in the art design choice selection of one or more of the above depicted components from one or more of the above depicted subsystems shown in FIG. 30. Components from the direct modify carbohydrate component group can be used in implementing execution of the one or more direct modify carbohydrate instructions i1214 of FIG. 52, can be used in performance of the direct modify carbohydrate electrical circuitry arrangement e1214 of FIG. 45, and/or can be used in otherwise fulfillment of the operation o1214. An exemplary non-transitory signal bearing medium version of the information storage subsystem s200 is depicted in FIG. 52 as bearing the one or more direct modify carbohydrate instructions i1214 that when executed will direct performance of the operation o1214. Furthermore, the direct modify carbohydrate electrical circuitry arrangement ("elec circ arrange") e1214, when activated, will perform the operation o1214. Also, the direct modify carbohydrate module m1214, when executed and/or activated, will direct performance of and/or perform the operation o1214. For instance, in one or more exemplary implementations, the one or more direct modify carbohydrate instructions i1214, when executed, direct performance of the operation o1214 in the illustrative depiction as follows, and/or the direct modify carbohydrate electrical circuitry arrangement e1214, when activated, performs the operation o1214 in the illustrative depiction as follows, and/or the direct modify carbohydrate module m1214, when executed and/or activated, directs performance of and/or performs the operation o1214 in the illustrative depiction as follows, and/or the operation o1214 is otherwise carried out in the illustrative depiction as follows: electronically directing control of the one or more injections of the one or more materials as one or more substantially carbohydrate materials (e.g. including sugars, and/or etc.) into the one or more portions of the one or more ingestible substrate structures to modify (e.g. change surface composition, and/or etc.) one or more properties (e.g. including flavor, and/or etc.) of the one or more portions of the one or more ingestible substrate structures to form at least in part the one or more selected ingestible products.

In one or more implementations, as shown in FIG. 97, operation o12 includes an operation o1215 for electronically directing control of the one or more injections of the one or more materials as one or more substantially protein materials into the one or more portions of the one or more ingestible substrate structures to modify one or more properties of the one or more portions of the one or more ingestible substrate structures to form at least in part the one or more selected ingestible products. Origination of an illustratively derived direct modify protein component group can be accomplished through skilled in the art design choice selection of one or more of the above depicted components from one or more of the above depicted subsystems shown in FIG. 30. Components from the direct modify protein component group can be used in implementing execution of the one or more direct modify protein instructions i1215 of FIG. 52, can be used in performance of the direct modify protein electrical circuitry arrangement e1215 of FIG. 45, and/or can be used in otherwise fulfillment of the operation o1215. An exemplary non-transitory signal bearing medium version of the information storage subsystem s200 is depicted in FIG. 52 as bearing the one or more direct modify protein instructions i1215 that when executed will direct performance of the operation o1215. Furthermore, the direct modify protein electrical circuitry arrangement ("elec circ arrange") e1215, when activated, will perform the operation o1215. Also, the direct modify protein module m1215, when executed and/or activated, will direct performance of and/or perform the operation o1215. For instance, in one or more exemplary implementations, the one or more direct modify protein instructions i1215, when executed, direct performance of the operation o1215 in the illustrative depiction as follows, and/or the direct modify protein electrical circuitry arrangement e1215, when activated, performs the operation o1215 in the illustrative depiction as follows, and/or the direct modify protein module m1215, when executed and/or activated, directs performance of and/or performs the operation o1215 in the illustrative depiction as follows, and/or the operation o1215 is otherwise carried out in the illustrative depiction as follows: electronically directing control of the one or more injections of the one or more materials as one or more substantially protein materials (e.g. including whey powder, and/or etc.) into the one or more portions of the one or more ingestible substrate structures to modify (e.g. including add to the surface composition, and/or etc.) one or more properties (e.g. including increase protein content, and/or etc.) of the one or more portions of the one or more ingestible substrate structures to form at least in part the one or more selected ingestible products.

Figure 98:
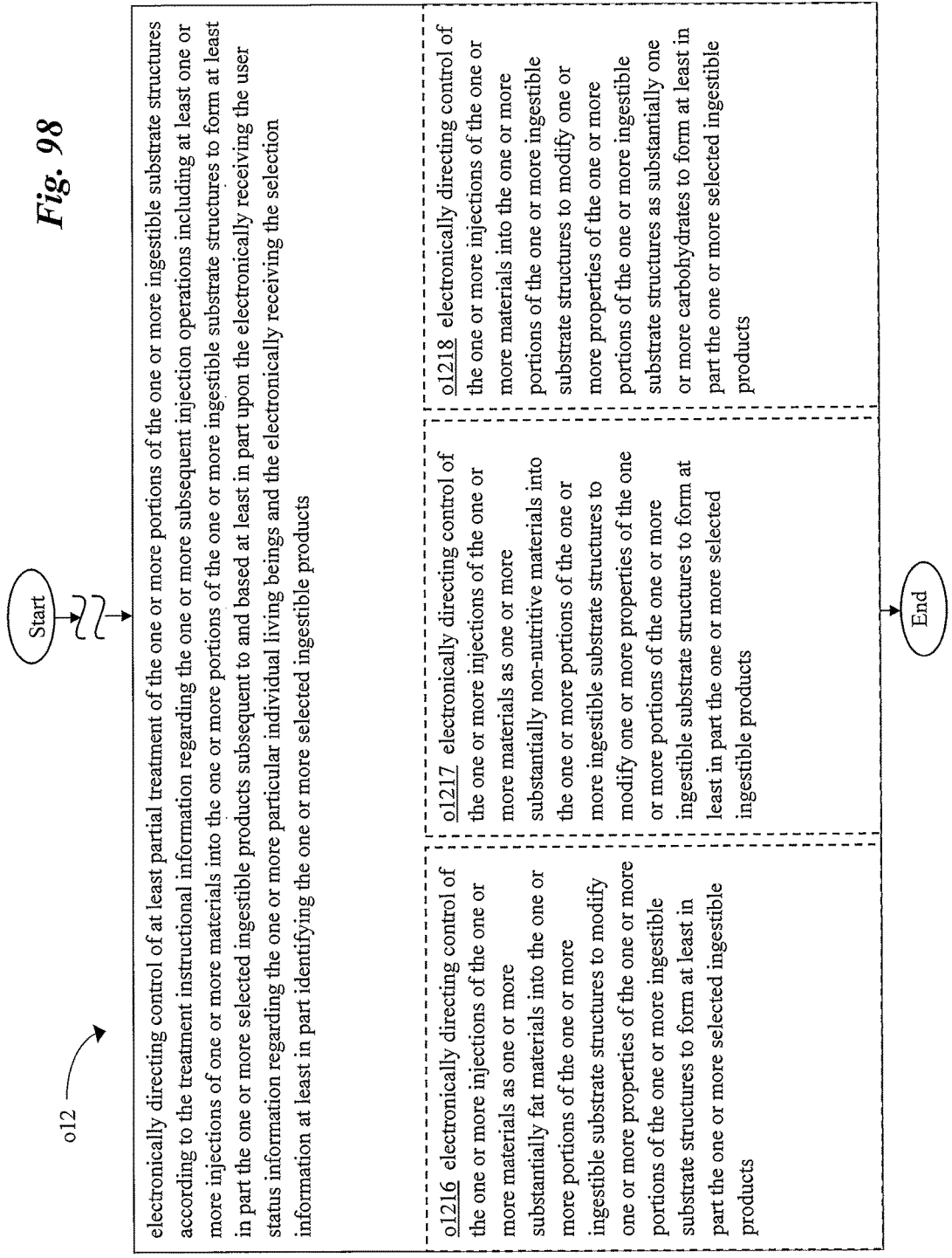
FIG. 98 is a high-level flowchart including exemplary implementations of operation O12 of FIG. 61.

In one or more implementations, as shown in FIG. 98, operation o12 includes an operation o1216 for electronically directing control of the one or more injections of the one or more materials as one or more substantially fat materials into the one or more portions of the one or more ingestible substrate structures to modify one or more properties of the one or more portions of the one or more ingestible substrate structures to form at least in part the one or more selected ingestible products. Origination of an illustratively derived direct modify fat component group can be accomplished through skilled in the art design choice selection of one or more of the above depicted components from one or more of the above depicted subsystems shown in FIG. 30. Components from the direct modify fat component group can be used in implementing execution of the one or more direct modify fat instructions i1216 of FIG. 52, can be used in performance of the direct modify fat electrical circuitry arrangement e1216 of FIG. 45, and/or can be used in otherwise fulfillment of the operation o1216. An exemplary non-transitory signal bearing medium version of the information storage subsystem s200 is depicted in FIG. 52 as bearing the one or more direct modify fat instructions i1216 that when executed will direct performance of the operation o1216. Furthermore, the direct modify fat electrical circuitry arrangement ("elec circ arrange") e1216, when activated, will perform the operation o1216. Also, the direct modify fat module m1216, when executed and/or activated, will direct performance of and/or perform the operation o1216. For instance, in one or more exemplary implementations, the one or more direct modify fat instructions i1216, when executed, direct performance of the operation o1216 in the illustrative depiction as follows, and/or the direct modify fat electrical circuitry arrangement e1216, when activated, performs the operation o1216 in the illustrative depiction as follows, and/or the direct modify fat module m1216, when executed and/or activated, directs performance of and/or performs the operation o1216 in the illustrative depiction as follows, and/or the operation o1216 is otherwise carried out in the illustrative depiction as follows: electronically directing control of the one or more injections of the one or more materials as one or more substantially fat materials (e.g. including refined vegetable oil, and/or etc.) into the one or more portions of the one or more ingestible substrate structures to modify (e.g. including increase fat content of structure, and/or etc.) one or more properties (e.g. including calorie content, and/or etc.) of the one or more portions of the one or more ingestible substrate structures to form at least in part the one or more selected ingestible products.

In one or more implementations, as shown in FIG. 98, operation o12 includes an operation o1217 for electronically directing control of the one or more injections of the one or more materials as one or more substantially non-nutritive materials into the one or more portions of the one or more ingestible substrate structures to modify one or more properties of the one or more portions of the one or more ingestible substrate structures to form at least in part the one or more selected ingestible products. Origination of an illustratively derived direct modify non-nutritive component group can be accomplished through skilled in the art design choice selection of one or more of the above depicted components from one or more of the above depicted subsystems shown in FIG. 30. Components from the direct modify non-nutritive component group can be used in implementing execution of the one or more direct modify non-nutritive instructions i1217 of FIG. 52, can be used in performance of the direct modify non-nutritive electrical circuitry arrangement e1217 of FIG. 45, and/or can be used in otherwise fulfillment of the operation o1217. An exemplary non-transitory signal bearing medium version of the information storage subsystem s200 is depicted in FIG. 52 as bearing the one or more direct modify non-nutritive instructions i1217 that when executed will direct performance of the operation o1217. Furthermore, the direct modify non-nutritive electrical circuitry arrangement ("elec circ arrange") e1217, when activated, will perform the operation o1217. Also, the direct modify non-nutritive module m1217, when executed and/or activated, will direct performance of and/or perform the operation o1217. For instance, in one or more exemplary implementations, the one or more direct modify non-nutritive instructions i1217, when executed, direct performance of the operation o1217 in the illustrative depiction as follows, and/or the direct modify non-nutritive electrical circuitry arrangement e1217, when activated, performs the operation o1217 in the illustrative depiction as follows, and/or the direct modify non-nutritive module m1217, when executed and/or activated, directs performance of and/or performs the operation o1217 in the illustrative depiction as follows, and/or the operation o1217 is otherwise carried out in the illustrative depiction as follows: electronically directing control of the one or more injections of the one or more materials as one or more substantially non-nutritive materials (e.g. including a bulking agent powder, and/or etc.) into the one or more portions of the one or more ingestible substrate structures to modify (e.g. including increasing volume, and/or etc.) one or more properties (e.g. including size and structural texture, and/or etc.) of the one or more portions of the one or more ingestible substrate structures to form at least in part the one or more selected ingestible products.

In one or more implementations, as shown in FIG. 98, operation o12 includes an operation o1218 for electronically directing control of the one or more injections of the one or more materials into the one or more portions of the one or more ingestible substrate structures to modify one or more properties of the one or more portions of the one or more ingestible substrate structures as substantially one or more carbohydrates to form at least in part the one or more selected ingestible products. Origination of an illustratively derived direct substrate carbohydrate component group can be accomplished through skilled in the art design choice selection of one or more of the above depicted components from one or more of the above depicted subsystems shown in FIG. 30. Components from the direct substrate carbohydrate component group can be used in implementing execution of the one or more direct substrate carbohydrate instructions i1218 of FIG. 52, can be used in performance of the direct substrate carbohydrate electrical circuitry arrangement e1218 of FIG. 45, and/or can be used in otherwise fulfillment of the operation o1218. An exemplary non-transitory signal bearing medium version of the information storage subsystem s200 is depicted in FIG. 52 as bearing the one or more direct substrate carbohydrate instructions i1218 that when executed will direct performance of the operation o1218. Furthermore, the direct substrate carbohydrate electrical circuitry arrangement ("elec circ arrange") e1218, when activated, will perform the operation o1218. Also, the direct substrate carbohydrate module m1218, when executed and/or activated, will direct performance of and/or perform the operation o1218. For instance, in one or more exemplary implementations, the one or more direct substrate carbohydrate instructions i1218, when executed, direct performance of the operation o1218 in the illustrative depiction as follows, and/or the direct substrate carbohydrate electrical circuitry arrangement e1218, when activated, performs the operation o1218 in the illustrative depiction as follows, and/or the direct substrate carbohydrate module m1218, when executed and/or activated, directs performance of and/or performs the operation o1218 in the illustrative depiction as follows, and/or the operation o1218 is otherwise carried out in the illustrative depiction as follows: electronically directing control of the one or more injections of the one or more materials into the one or more portions of the one or more ingestible substrate structures to modify (e.g. including changing, and/or etc.) one or more properties (e.g. including flavor, and/or etc.) of the one or more portions of the one or more ingestible substrate structures as substantially one or more carbohydrates (e.g. including rice starch, and/or etc.) to form at least in part the one or more selected ingestible products.

Figure 99:
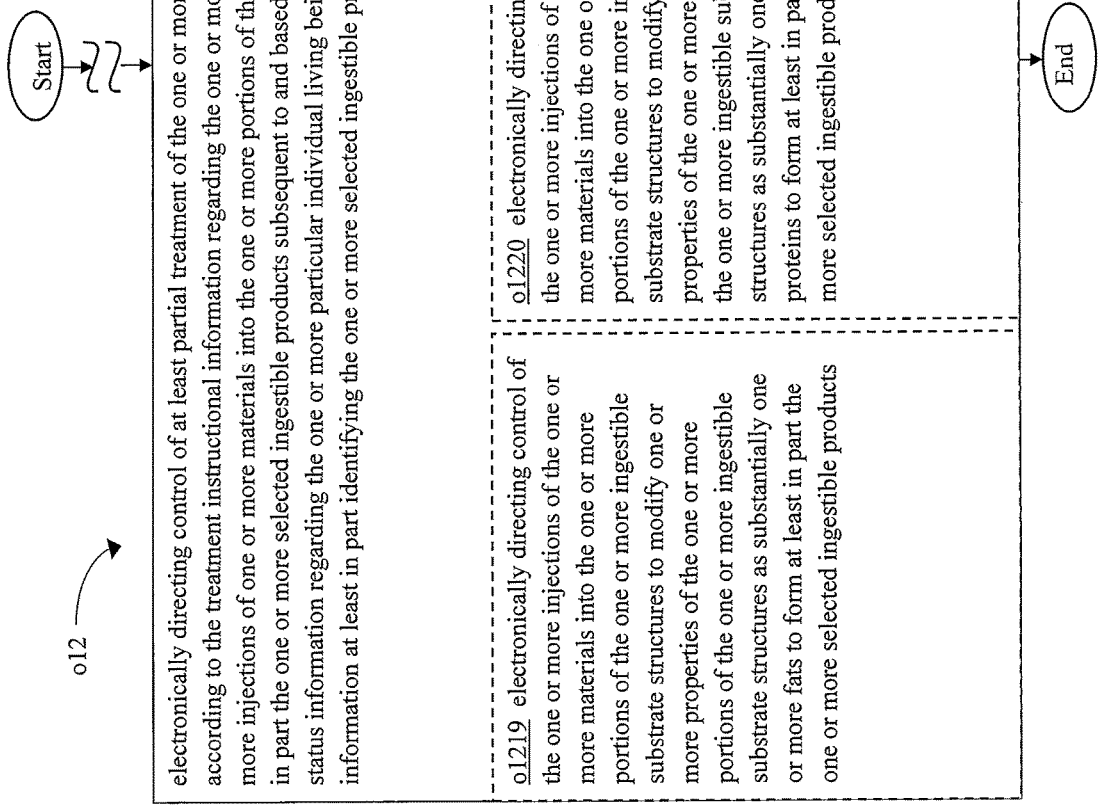
FIG. 99 is a high-level flowchart including exemplary implementations of operation O12 of FIG. 61.

In one or more implementations, as shown in FIG. 99, operation o12 includes an operation o1219 for electronically directing control of the one or more injections of the one or more materials into the one or more portions of the one or more ingestible substrate structures to modify one or more properties of the one or more portions of the one or more ingestible substrate structures as substantially one or more fats to form at least in part the one or more selected ingestible products. Origination of an illustratively derived direct substrate fat component group can be accomplished through skilled in the art design choice selection of one or more of the above depicted components from one or more of the above depicted subsystems shown in FIG. 30. Components from the direct substrate fat component group can be used in implementing execution of the one or more direct substrate fat instructions i1219 of FIG. 52, can be used in performance of the direct substrate fat electrical circuitry arrangement e1219 of FIG. 45, and/or can be used in otherwise fulfillment of the operation o1219. An exemplary non-transitory signal bearing medium version of the information storage subsystem s200 is depicted in FIG. 52 as bearing the one or more direct substrate fat instructions i1219 that when executed will direct performance of the operation o1219. Furthermore, the direct substrate fat electrical circuitry arrangement ("elec circ arrange") e1219, when activated, will perform the operation o1219. Also, the direct substrate fat module m1219, when executed and/or activated, will direct performance of and/or perform the operation o1219. For instance, in one or more exemplary implementations, the one or more direct substrate fat instructions i1219, when executed, direct performance of the operation o1219 in the illustrative depiction as follows, and/or the direct substrate fat electrical circuitry arrangement e1219, when activated, performs the operation o1219 in the illustrative depiction as follows, and/or the direct substrate fat module m1219, when executed and/or activated, directs performance of and/or performs the operation o1219 in the illustrative depiction as follows, and/or the operation o1219 is otherwise carried out in the illustrative depiction as follows: electronically directing control of the one or more injections of the one or more materials into the one or more portions of the one or more ingestible substrate structures to modify (e.g. including darken, and/or etc.) one or more properties (e.g. including substrate color, and/or etc.) of the one or more portions of the one or more ingestible substrate structures as substantially one or more fats (e.g. including coconut oil, and/or etc.) to form at least in part the one or more selected ingestible products.

Figure 53:
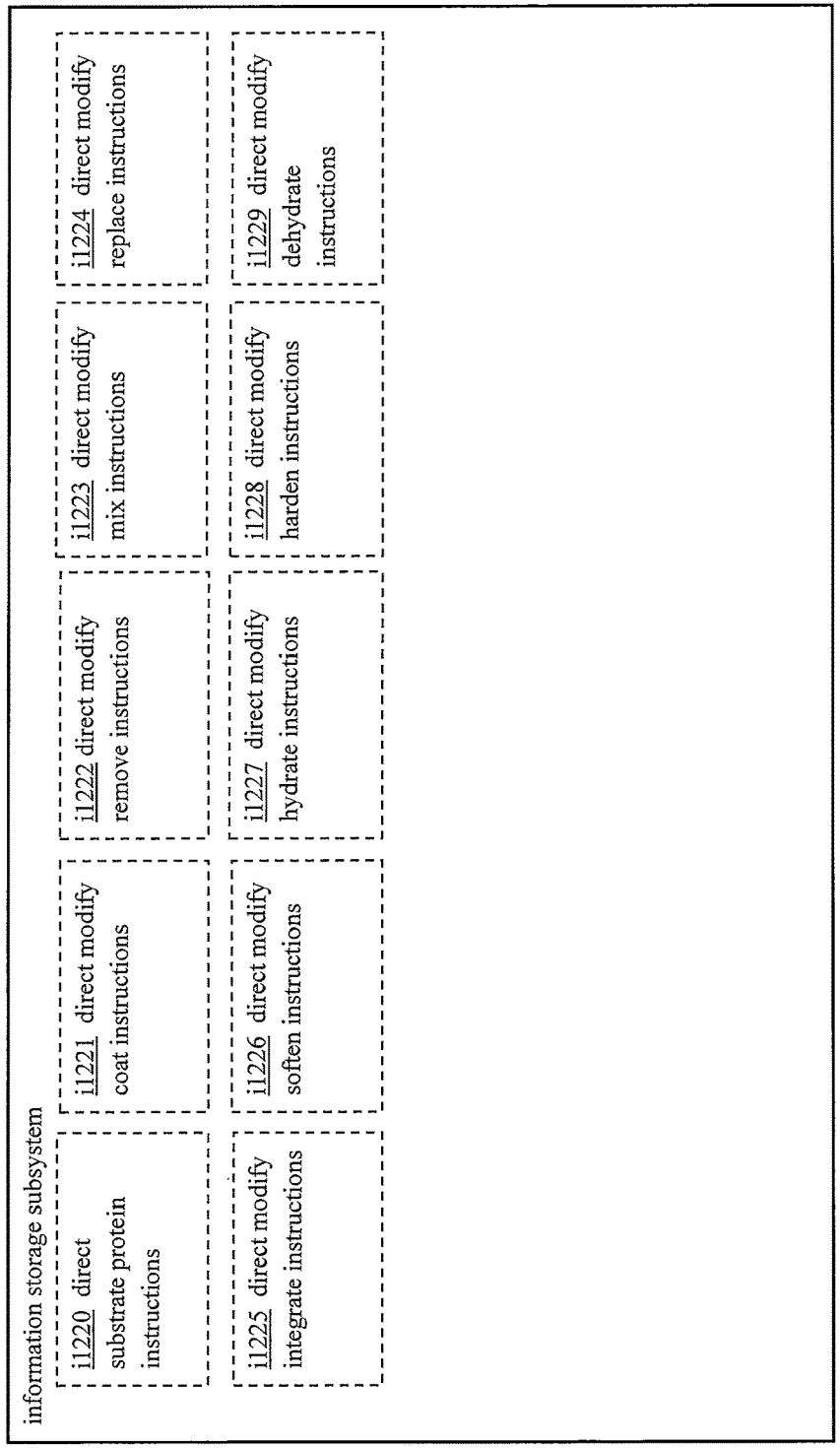
FIG. 53 is a block diagram depicting one or more exemplary instructions of the information storage subsystem s200 of the ingestible product preparation system 10 of FIG. 1.

In one or more implementations, as shown in FIG. 99, operation o12 includes an operation o1220 for electronically directing control of the one or more injections of the one or more materials into the one or more portions of the one or more ingestible substrate structures to modify one or more properties of the one or more portions of the one or more ingestible substrate structures as substantially one or more proteins to form at least in part the one or more selected ingestible products. Origination of an illustratively derived direct substrate protein component group can be accomplished through skilled in the art design choice selection of one or more of the above depicted components from one or more of the above depicted subsystems shown in FIG. 30. Components from the direct substrate protein component group can be used in implementing execution of the one or more direct substrate protein instructions i1220 of FIG. 53, can be used in performance of the direct substrate protein electrical circuitry arrangement e1220 of FIG. 46, and/or can be used in otherwise fulfillment of the operation o1220. An exemplary non-transitory signal bearing medium version of the information storage subsystem s200 is depicted in FIG. 53 as bearing the one or more direct substrate protein instructions i1220 that when executed will direct performance of the operation o1220. Furthermore, the direct substrate protein electrical circuitry arrangement ("elec circ arrange") e1220, when activated, will perform the operation o1220. Also, the direct substrate protein module m1220, when executed and/or activated, will direct performance of and/or perform the operation o1220. For instance, in one or more exemplary implementations, the one or more direct substrate protein instructions i1220, when executed, direct performance of the operation o1220 in the illustrative depiction as follows, and/or the direct substrate protein electrical circuitry arrangement e1220, when activated, performs the operation o1220 in the illustrative depiction as follows, and/or the direct substrate protein module m1220, when executed and/or activated, directs performance of and/or performs the operation o1220 in the illustrative depiction as follows, and/or the operation o1220 is otherwise carried out in the illustrative depiction as follows: electronically directing control of the one or more injections of the one or more materials into the one or more portions of the one or more ingestible substrate structures to modify (e.g. including increase, and/or etc.) one or more properties (e.g. including protein content, and/or etc.) of the one or more portions of the one or more ingestible substrate structures as substantially one or more proteins (e.g. including peanut butter, and/or etc.) to form at least in part the one or more selected ingestible products.

In one or more implementations, as shown in FIG. 99, operation o12 includes an operation o1221 for electronically directing control of the one or more injections of the one or more materials into the one or more portions of the one or more ingestible substrate structures to modify one or more properties of the one or more portions of the one or more ingestible substrate structures by at least partially internally coating the one or more portions of the one or more ingestible substrate structures to form at least in part the one or more selected ingestible products. Origination of an illustratively derived direct modify coat component group can be accomplished through skilled in the art design choice selection of one or more of the above depicted components from one or more of the above depicted subsystems shown in FIG. 30. Components from the direct modify coat component group can be used in implementing execution of the one or more direct modify coat instructions i1221 of FIG. 53, can be used in performance of the direct modify coat electrical circuitry arrangement e1221 of FIG. 46, and/or can be used in otherwise fulfillment of the operation o1221. An exemplary non-transitory signal bearing medium version of the information storage subsystem s200 is depicted in FIG. 53 as bearing the one or more direct modify coat instructions i1221 that when executed will direct performance of the operation o1221. Furthermore, the direct modify coat electrical circuitry arrangement ("elec circ arrange") e1221, when activated, will perform the operation o1221. Also, the direct modify coat module m1221, when executed and/or activated, will direct performance of and/or perform the operation o1221. For instance, in one or more exemplary implementations, the one or more direct modify coat instructions i1221, when executed, direct performance of the operation o1221 in the illustrative depiction as follows, and/or the direct modify coat electrical circuitry arrangement e1221, when activated, performs the operation o1221 in the illustrative depiction as follows, and/or the direct modify coat module m1221, when executed and/or activated, directs performance of and/or performs the operation o1221 in the illustrative depiction as follows, and/or the operation o1221 is otherwise carried out in the illustrative depiction as follows: electronically directing control of the one or more injections of the one or more materials into the one or more portions of the one or more ingestible substrate structures to modify (e.g. including changing, and/or etc.) one or more properties (e.g. including flavor, and/or etc.) of the one or more portions of the one or more ingestible substrate structures by at least partially internally coating (e.g. depositing through injection an internally spreading material to coat pockets, passageways, and/or etc.) the one or more portions of the one or more ingestible substrate structures to form at least in part the one or more selected ingestible products.

Figure 100:
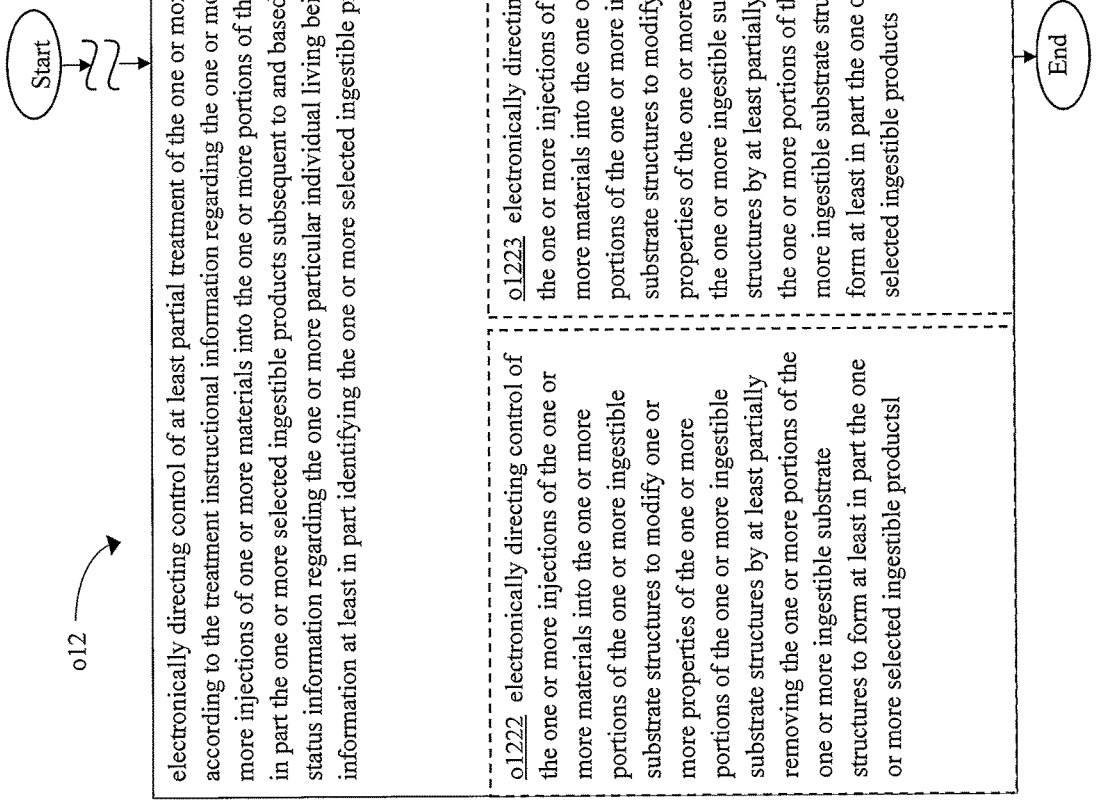
FIG. 100 is a high-level flowchart including exemplary implementations of operation O12 of FIG. 61.

In one or more implementations, as shown in FIG. 100, operation o12 includes an operation o1222 for electronically directing control of the one or more injections of the one or more materials into the one or more portions of the one or more ingestible substrate structures to modify one or more properties of the one or more portions of the one or more ingestible substrate structures by at least partially removing the one or more portions of the one or more ingestible substrate structures to form at least in part the one or more selected ingestible products. Origination of an illustratively derived direct modify remove component group can be accomplished through skilled in the art design choice selection of one or more of the above depicted components from one or more of the above depicted subsystems shown in FIG. 30. Components from the direct modify remove component group can be used in implementing execution of the one or more direct modify remove instructions i1222 of FIG. 53, can be used in performance of the direct modify remove electrical circuitry arrangement e1222 of FIG. 46, and/or can be used in otherwise fulfillment of the operation o1222. An exemplary non-transitory signal bearing medium version of the information storage subsystem s200 is depicted in FIG. 53 as bearing the one or more direct modify remove instructions i1222 that when executed will direct performance of the operation o1222. Furthermore, the direct modify remove electrical circuitry arrangement ("elec circ arrange") e1222, when activated, will perform the operation o1222. Also, the direct modify remove module m1222, when executed and/or activated, will direct performance of and/or perform the operation o1222. For instance, in one or more exemplary implementations, the one or more direct modify remove instructions i1222, when executed, direct performance of the operation o1222 in the illustrative depiction as follows, and/or the direct modify remove electrical circuitry arrangement e1222, when activated, performs the operation o1222 in the illustrative depiction as follows, and/or the direct modify remove module m1222, when executed and/or activated, directs performance of and/or performs the operation o1222 in the illustrative depiction as follows, and/or the operation o1222 is otherwise carried out in the illustrative depiction as follows: electronically directing control of the one or more injections of the one or more materials into the one or more portions of the one or more ingestible substrate structures to modify (e.g. including removing, and/or etc.) one or more properties (e.g. including shape, and/or etc.) of the one or more portions of the one or more ingestible substrate structures by at least partially removing (e.g. including reactive chemicals through injection with the substrate, and/or etc.) the one or more portions of the one or more ingestible substrate structures to form at least in part the one or more selected ingestible products.

In one or more implementations, as shown in FIG. 100, operation o12 includes an operation o1223 for electronically directing control of the one or more injections of the one or more materials into the one or more portions of the one or more ingestible substrate structures to modify one or more properties of the one or more portions of the one or more ingestible substrate structures by at least partially mixing with the one or more portions of the one or more ingestible substrate structures to form at least in part the one or more selected ingestible products. Origination of an illustratively derived direct modify mix component group can be accomplished through skilled in the art design choice selection of one or more of the above depicted components from one or more of the above depicted subsystems shown in FIG. 30. Components from the direct modify mix component group can be used in implementing execution of the one or more direct modify mix instructions i1223 of FIG. 53, can be used in performance of the direct modify mix electrical circuitry arrangement e1223 of FIG. 46, and/or can be used in otherwise fulfillment of the operation o1223. An exemplary non-transitory signal bearing medium version of the information storage subsystem s200 is depicted in FIG. 53 as bearing the one or more direct modify mix instructions i1223 that when executed will direct performance of the operation o1223. Furthermore, the direct modify mix electrical circuitry arrangement ("elec circ arrange") e1223, when activated, will perform the operation o1223. Also, the direct modify mix module m1223, when executed and/or activated, will direct performance of and/or perform the operation o1223. For instance, in one or more exemplary implementations, the one or more direct modify mix instructions i1223, when executed, direct performance of the operation o1223 in the illustrative depiction as follows, and/or the direct modify mix electrical circuitry arrangement e1223, when activated, performs the operation o1223 in the illustrative depiction as follows, and/or the direct modify mix module m1223, when executed and/or activated, directs performance of and/or performs the operation o1223 in the illustrative depiction as follows, and/or the operation o1223 is otherwise carried out in the illustrative depiction as follows: electronically directing control of the one or more injections of the one or more materials into the one or more portions of the one or more ingestible substrate structures to modify (e.g. including increasing, and/or etc.) one or more properties (e.g. including flavor, and/or etc.) of the one or more portions of the one or more ingestible substrate structures by at least partially mixing (e.g. including mixing through injection one or more added flavors, and/or etc.) with the one or more portions of the one or more ingestible substrate structures to form at least in part the one or more selected ingestible products.

In one or more implementations, as shown in FIG. 100, operation o12 includes an operation o1224 for electronically directing control of the one or more injections of the one or more materials into the one or more portions of the one or more ingestible substrate structures to modify one or more properties of the one or more portions of the one or more ingestible substrate structures by at least partially replacing the one or more portions of the one or more ingestible substrate structures to form at least in part the one or more selected ingestible products. Origination of an illustratively derived direct modify replace component group can be accomplished through skilled in the art design choice selection of one or more of the above depicted components from one or more of the above depicted subsystems shown in FIG. 30. Components from the direct modify replace component group can be used in implementing execution of the one or more direct modify replace instructions i1224 of FIG. 53, can be used in performance of the direct modify replace electrical circuitry arrangement e1224 of FIG. 46, and/or can be used in otherwise fulfillment of the operation o1224. An exemplary non-transitory signal bearing medium version of the information storage subsystem s200 is depicted in FIG. 53 as bearing the one or more direct modify replace instructions i1224 that when executed will direct performance of the operation o1224. Furthermore, the direct modify replace electrical circuitry arrangement ("elec circ arrange") e1224, when activated, will perform the operation o1224. Also, the direct modify replace module m1224, when executed and/or activated, will direct performance of and/or perform the operation o1224. For instance, in one or more exemplary implementations, the one or more direct modify replace instructions i1224, when executed, direct performance of the operation o1224 in the illustrative depiction as follows, and/or the direct modify replace electrical circuitry arrangement e1224, when activated, performs the operation o1224 in the illustrative depiction as follows, and/or the direct modify replace module m1224, when executed and/or activated, directs performance of and/or performs the operation o1224 in the illustrative depiction as follows, and/or the operation o1224 is otherwise carried out in the illustrative depiction as follows: electronically directing control of the one or more injections of the one or more materials into the one or more portions of the one or more ingestible substrate structures to modify (e.g. including decreasing, and/or etc.) one or more properties (e.g. including structural texture, and/or etc.) of the one or more portions of the one or more ingestible substrate structures by at least partially replacing (e.g. including substituting through injection softer ingestible materials in portion of the substrate, and/or etc.) the one or more portions of the one or more ingestible substrate structures to form at least in part the one or more selected ingestible products.

Figure 101:
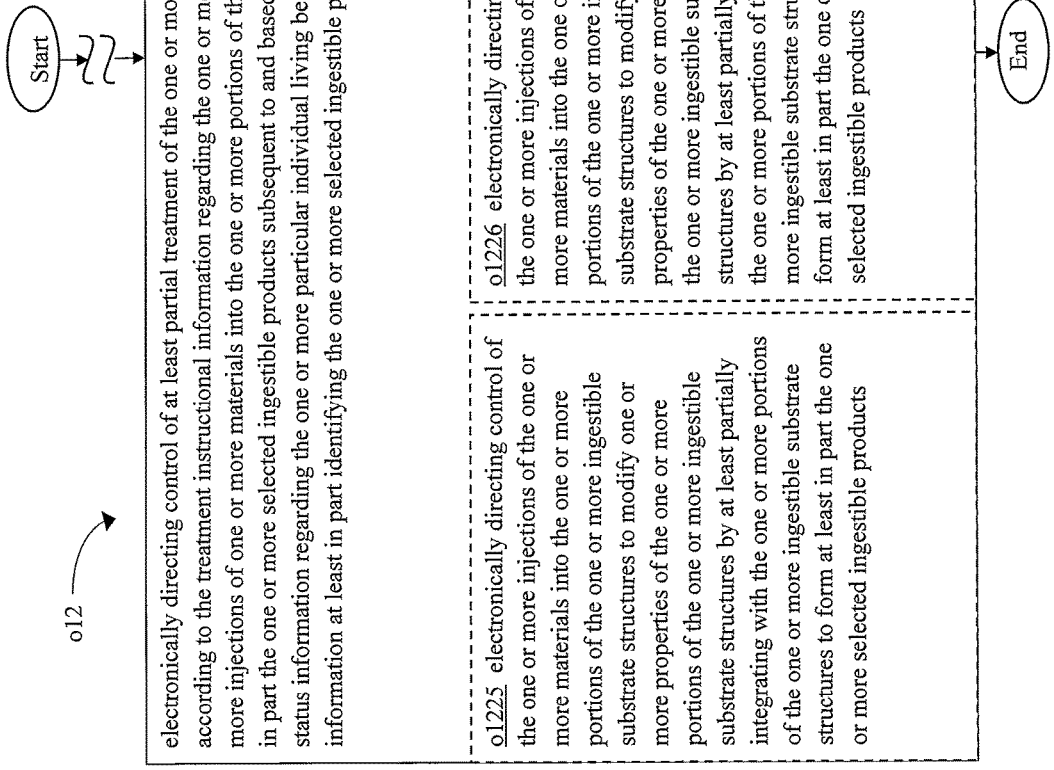
FIG. 101 is a high-level flowchart including exemplary implementations of operation O12 of FIG. 61.

In one or more implementations, as shown in FIG. 101, operation o12 includes an operation o1225 for electronically directing control of the one or more injections of the one or more materials into the one or more portions of the one or more ingestible substrate structures to modify one or more properties of the one or more portions of the one or more ingestible substrate structures by at least partially integrating with the one or more portions of the one or more ingestible substrate structures to form at least in part the one or more selected ingestible products. Origination of an illustratively derived direct modify integrate component group can be accomplished through skilled in the art design choice selection of one or more of the above depicted components from one or more of the above depicted subsystems shown in FIG. 30. Components from the direct modify integrate component group can be used in implementing execution of the one or more direct modify integrate instructions i1225 of FIG. 53, can be used in performance of the direct modify integrate electrical circuitry arrangement e1225 of FIG. 46, and/or can be used in otherwise fulfillment of the operation o1225. An exemplary non-transitory signal bearing medium version of the information storage subsystem s200 is depicted in FIG. 53 as bearing the one or more direct modify integrate instructions i1225 that when executed will direct performance of the operation o1225. Furthermore, the direct modify integrate electrical circuitry arrangement ("elec circ arrange") e1225, when activated, will perform the operation o1225. Also, the direct modify integrate module m1225, when executed and/or activated, will direct performance of and/or perform the operation o1225. For instance, in one or more exemplary implementations, the one or more direct modify integrate instructions i1225, when executed, direct performance of the operation o1225 in the illustrative depiction as follows, and/or the direct modify integrate electrical circuitry arrangement e1225, when activated, performs the operation o1225 in the illustrative depiction as follows, and/or the direct modify integrate module m1225, when executed and/or activated, directs performance of and/or performs the operation o1225 in the illustrative depiction as follows, and/or the operation o1225 is otherwise carried out in the illustrative depiction as follows: electronically directing control of the one or more injections of the one or more materials into the one or more portions of the one or more ingestible substrate structures to modify (e.g. including changing, and/or etc.) one or more properties (e.g. including substrate color, and/or etc.) of the one or more portions of the one or more ingestible substrate structures by at least partially integrating (e.g. including combining added ingredients to the substrate structure to change color, and/or etc.) with the one or more portions of the one or more ingestible substrate structures to form at least in part the one or more selected ingestible products.

In one or more implementations, as shown in FIG. 101, operation o12 includes an operation o1226 for electronically directing control of the one or more injections of the one or more materials into the one or more portions of the one or more ingestible substrate structures to modify one or more properties of the one or more portions of the one or more ingestible substrate structures by at least partially softening the one or more portions of the one or more ingestible substrate structures to form at least in part the one or more selected ingestible products. Origination of an illustratively derived direct modify soften component group can be accomplished through skilled in the art design choice selection of one or more of the above depicted components from one or more of the above depicted subsystems shown in FIG. 30. Components from the direct modify soften component group can be used in implementing execution of the one or more direct modify soften instructions i1226 of FIG. 53, can be used in performance of the direct modify soften electrical circuitry arrangement e1226 of FIG. 46, and/or can be used in otherwise fulfillment of the operation o1226. An exemplary non-transitory signal bearing medium version of the information storage subsystem s200 is depicted in FIG. 53 as bearing the one or more direct modify soften instructions i1226 that when executed will direct performance of the operation o1226. Furthermore, the direct modify soften electrical circuitry arrangement ("elec circ arrange") e1226, when activated, will perform the operation o1226. Also, the direct modify soften module m1226, when executed and/or activated, will direct performance of and/or perform the operation o1226. For instance, in one or more exemplary implementations, the one or more direct modify soften instructions i1226, when executed, direct performance of the operation o1226 in the illustrative depiction as follows, and/or the direct modify soften electrical circuitry arrangement e1226, when activated, performs the operation o1226 in the illustrative depiction as follows, and/or the direct modify soften module m1226, when executed and/or activated, directs performance of and/or performs the operation o1226 in the illustrative depiction as follows, and/or the operation o1226 is otherwise carried out in the illustrative depiction as follows: electronically directing control of the one or more injections of the one or more materials into the one or more portions of the one or more ingestible substrate structures to modify (e.g. including changing, and/or etc.) one or more properties (e.g. including structural texture, and/or etc.) of the one or more portions of the one or more ingestible substrate structures by at least partially softening (e.g. including introducing ingestible gel into the substrate structure, and/or etc.) the one or more portions of the one or more ingestible substrate structures to form at least in part the one or more selected ingestible products.

In one or more implementations, as shown in FIG. 101, operation o12 includes an operation o1227 for electronically directing control of the one or more injections of the one or more materials into the one or more portions of the one or more ingestible substrate structures to modify one or more properties of the one or more portions of the one or more ingestible substrate structures by at least partially hydrating the one or more portions of the one or more ingestible substrate structures to form at least in part the one or more selected ingestible products. Origination of an illustratively derived direct modify hydrate component group can be accomplished through skilled in the art design choice selection of one or more of the above depicted components from one or more of the above depicted subsystems shown in FIG. 30. Components from the direct modify hydrate component group can be used in implementing execution of the one or more direct modify hydrate instructions i1227 of FIG. 53, can be used in performance of the direct modify hydrate electrical circuitry arrangement e1227 of FIG. 46, and/or can be used in otherwise fulfillment of the operation o1227. An exemplary non-transitory signal bearing medium version of the information storage subsystem s200 is depicted in FIG. 53 as bearing the one or more direct modify hydrate instructions i1227 that when executed will direct performance of the operation o1227. Furthermore, the direct modify hydrate electrical circuitry arrangement ("elec circ arrange") e1227, when activated, will perform the operation o1227. Also, the direct modify hydrate module m1227, when executed and/or activated, will direct performance of and/or perform the operation o1227. For instance, in one or more exemplary implementations, the one or more direct modify hydrate instructions i1227, when executed, direct performance of the operation o1227 in the illustrative depiction as follows, and/or the direct modify hydrate electrical circuitry arrangement e1227, when activated, performs the operation o1227 in the illustrative depiction as follows, and/or the direct modify hydrate module m1227, when executed and/or activated, directs performance of and/or performs the operation o1227 in the illustrative depiction as follows, and/or the operation o1227 is otherwise carried out in the illustrative depiction as follows: electronically directing control of the one or more injections of the one or more materials into the one or more portions of the one or more ingestible substrate structures to modify (e.g. including decreasing, and/or etc.) one or more properties (e.g. including structural texture including rigidity, and/or etc.) of the one or more portions of the one or more ingestible substrate structures by at least partially hydrating (e.g. including exposing portion of substrate to water injection, and/or etc.) the one or more portions of the one or more ingestible substrate structures to form at least in part the one or more selected ingestible products.

In one or more implementations, as shown in FIG. 102, operation o12 includes an operation o1228 for electronically directing control of the one or more injections of the one or more materials into the one or more portions of the one or more ingestible substrate structures to modify one or more properties of the one or more portions of the one or more ingestible substrate structures by at least partially hardening the one or more portions of the one or more ingestible substrate structures to form at least in part the one or more selected ingestible products. Origination of an illustratively derived direct modify harden component group can be accomplished through skilled in the art design choice selection of one or more of the above depicted components from one or more of the above depicted subsystems shown in FIG. 30. Components from the direct modify harden component group can be used in implementing execution of the one or more direct modify harden instructions i1228 of FIG. 53, can be used in performance of the direct modify harden electrical circuitry arrangement e1228 of FIG. 46, and/or can be used in otherwise fulfillment of the operation o1228. An exemplary non-transitory signal bearing medium version of the information storage subsystem s200 is depicted in FIG. 53 as bearing the one or more direct modify harden instructions i1228 that when executed will direct performance of the operation o1228. Furthermore, the direct modify harden electrical circuitry arrangement ("elec circ arrange") e1228, when activated, will perform the operation o1228. Also, the direct modify harden module m1228, when executed and/or activated, will direct performance of and/or perform the operation o1228. For instance, in one or more exemplary implementations, the one or more direct modify harden instructions i1228, when executed, direct performance of the operation o1228 in the illustrative depiction as follows, and/or the direct modify harden electrical circuitry arrangement e1228, when activated, performs the operation o1228 in the illustrative depiction as follows, and/or the direct modify harden module m1228, when executed and/or activated, directs performance of and/or performs the operation o1228 in the illustrative depiction as follows, and/or the operation o1228 is otherwise carried out in the illustrative depiction as follows: electronically directing control of the one or more injections of the one or more materials into the one or more portions of the one or more ingestible substrate structures to modify (e.g. including changing, and/or etc.) one or more properties (e.g. including structural texture, and/or etc.) of the one or more portions of the one or more ingestible substrate structures by at least partially hardening (e.g. including depositing hardening agent on surface to penetrate substrate, and/or etc.) the one or more portions of the one or more ingestible substrate structures to form at least in part the one or more selected ingestible products.

In one or more implementations, as shown in FIG. 102, operation o12 includes an operation o1229 for electronically directing control of the one or more injections of the one or more materials into the one or more portions of the one or more ingestible substrate structures to modify one or more properties of the one or more portions of the one or more ingestible substrate structures by at least partially dehydrating the one or more portions of the one or more ingestible substrate structures to form at least in part the one or more selected ingestible products. Origination of an illustratively derived direct modify dehydrate component group can be accomplished through skilled in the art design choice selection of one or more of the above depicted components from one or more of the above depicted subsystems shown in FIG. 30. Components from the direct modify dehydrate component group can be used in implementing execution of the one or more direct modify dehydrate instructions i1229 of FIG. 53, can be used in performance of the direct modify dehydrate electrical circuitry arrangement e1229 of FIG. 46, and/or can be used in otherwise fulfillment of the operation o1229. An exemplary non-transitory signal bearing medium version of the information storage subsystem s200 is depicted in FIG. 53 as bearing the one or more direct modify dehydrate instructions i1229 that when executed will direct performance of the operation o1229. Furthermore, the direct modify dehydrate electrical circuitry arrangement ("elec circ arrange") e1229, when activated, will perform the operation o1229. Also, the direct modify dehydrate module m1229, when executed and/or activated, will direct performance of and/or perform the operation o1229. For instance, in one or more exemplary implementations, the one or more direct modify dehydrate instructions i1229, when executed, direct performance of the operation o1229 in the illustrative depiction as follows, and/or the direct modify dehydrate electrical circuitry arrangement e1229, when activated, performs the operation o1229 in the illustrative depiction as follows, and/or the direct modify dehydrate module m1229, when executed and/or activated, directs performance of and/or performs the operation o1229 in the illustrative depiction as follows, and/or the operation o1229 is otherwise carried out in the illustrative depiction as follows: electronically directing control of the one or more injections of the one or more materials into the one or more portions of the one or more ingestible substrate structures to modify (e.g. including increasing, and/or etc.) one or more properties (e.g. including structural texture, and/or etc.) of the one or more portions of the one or more ingestible substrate structures by at least partially dehydrating (e.g. including depositing dehydrating agents such as calcium carbonate on surface, and/or etc.) the one or more portions of the one or more ingestible substrate structures to form at least in part the one or more selected ingestible products.

The one or more instructions discussed herein may be, for example, computer executable and/or logic-implemented instructions. In some implementations, signal-bearing medium as articles of manufacture may store the one or more instructions. In some implementations, the signal bearing medium may include a computer-readable medium. In some implementations, the signal-bearing medium may include a recordable medium. In some implementations, the signal-bearing medium may include a communication medium.

Those having skill in the art will recognize that the state of the art has progressed to the point where there is little distinction left between hardware and software implementations of aspects of systems; the use of hardware or software is generally (but not always, in that in certain contexts the choice between hardware an d software can become significant) a design choice representing cost vs. efficiency tradeoffs. Those having skill in the art will appreciate that there are various vehicles by which processes and/or systems and/or other technologies described herein can be effected (e.g., hardware, software, and/or firmware in one or more machines or articles of manufacture), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation that is implemented in one or more machines or articles of manufacture; or, yet again alternatively, the implementer may opt for some combination of hardware, software, and/or firmware in one or more machines or articles of manufacture (limited to patentable subject matter under 35 USC 101). Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware in one or more machines or articles of manufacture.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof (limited to patentable subject matter under 35 U.S.C. 101). In one embodiment, several portions of the subject matter described herein may be implemented via Application Specific Integrated Circuitry (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuitry, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure (limited to patentable subject matter under 35 USC 101). In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various aspects described herein which can be implemented, individually and/or collectively, by a wide range of hardware, software, firmware, or any combination thereof (limited to patentable subject matter under 35 U.S.C. 101) can be viewed as being composed of various types of "electrical circuitry" including "electrical circuitry arrangements." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those having skill in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.).

In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The claims, description, and drawings of this application may describe one or more of the instant technologies in operational/functional language, for example as a set of operations to be performed by a computer. Such operational/functional description in most instances would be understood by one skilled the art as specifically-configured hardware (e.g., because a general purpose computer in effect becomes a special purpose computer once it is programmed to perform particular functions pursuant to instructions from program software).

Importantly, although the operational/functional descriptions described herein are understandable by the human mind, they are not abstract ideas of the operations/functions divorced from computational implementation of those operations/functions. Rather, the operations/functions represent a specification for the massively complex computational machines or other means. As discussed in detail below, the operational/functional language must be read in its proper technological context, i.e., as concrete specifications for physical implementations.

The logical operations/functions described herein are a distillation of machine specifications or other physical mechanisms specified by the operations/functions such that the otherwise inscrutable machine specifications may be comprehensible to the human mind. The distillation also allows one of skill in the art to adapt the operational/functional description of the technology across many different specific vendors' hardware configurations or platforms, without being limited to specific vendors' hardware configurations or platforms.

Some of the present technical description (e.g., detailed description, drawings, claims, etc.) may be set forth in terms of logical operations/functions. As described in more detail in the following paragraphs, these logical operations/functions are not representations of abstract ideas, but rather representative of static or sequenced specifications of various hardware elements. Differently stated, unless context dictates otherwise, the logical operations/functions will be understood by those of skill in the art to be representative of static or sequenced specifications of various hardware elements. This is true because tools available to one of skill in the art to implement technical disclosures set forth in operational/functional formats—tools in the form of a high-level programming language (e.g., C, java, visual basic), etc.), or tools in the form of Very high speed Hardware Description Language ("VHDL," which is a language that uses text to describe logic circuits)—are generators of static or sequenced specifications of various hardware configurations. This fact is sometimes obscured by the broad term "software," but, as shown by the following explanation, those skilled in the art understand that what is termed "software" is a shorthand for a massively complex inter-chaining/specification of ordered-matter elements. The term "ordered-matter elements" may refer to physical components of computation, such as assemblies of electronic logic gates, molecular computing logic constituents, quantum computing mechanisms, etc.

For example, a high-level programming language is a programming language with strong abstraction, e.g., multiple levels of abstraction, from the details of the sequential organizations, states, inputs, outputs, etc., of the machines that a high-level programming language actually specifies. See, e.g., Wikipedia, *High-level programming language*, http://en.wikipedia.org/wiki/High-level_programming_language (as of Jun. 5, 2012, 21:00 GMT). In order to facilitate human comprehension, in many instances, high-level programming languages resemble or even share symbols with natural languages. See, e.g., Wikipedia, *Natural language*, http://en.wikipedia.org/wiki/Natural_language (as of Jun. 5, 2012, 21:00 GMT).

It has been argued that because high-level programming languages use strong abstraction (e.g., that they may resemble or share symbols with natural languages), they are therefore a "purely mental construct." (e.g., that "software"—a computer program or computer programming—is somehow an ineffable mental construct, because at a high level of abstraction, it can be conceived and understood in the human mind). This argument has been used to characterize technical description in the form of functions/operations as somehow "abstract ideas." In fact, in technological arts (e.g., the information and communication technologies) this is not true.

The fact that high-level programming languages use strong abstraction to facilitate human understanding should not be taken as an indication that what is expressed is an abstract idea. In fact, those skilled in the art understand that just the opposite is true. If a high-level programming language is the tool used to implement a technical disclosure in the form of functions/operations, those skilled in the art will recognize that, far from being abstract, imprecise, "fuzzy," or "mental" in any significant semantic sense, such a tool is instead a near incomprehensibly precise sequential specification of specific computational machines—the parts of which are built up by activating/selecting such parts from typically more general computational machines over time (e.g., clocked time). This fact is sometimes obscured by the superficial similarities between high-level programming languages and natural languages. These superficial similarities also may cause a glossing over of the fact that high-level programming language implementations ultimately perform valuable work by creating/controlling many different computational machines.

The many different computational machines that a high-level programming language specifies are almost unimaginably complex. At base, the hardware used in the computational machines typically consists of some type of ordered matter (e.g., traditional electronic devices (e.g., transistors), deoxyribonucleic acid (DNA), quantum devices, mechanical switches, optics, fluidics, pneumatics, optical devices (e.g., optical interference devices), molecules, etc.) that are arranged to form logic gates. Logic gates are typically physical devices that may be electrically, mechanically, chemically, or otherwise driven to change physical state in order to create a physical reality of Boolean logic.

Logic gates may be arranged to form logic circuits, which are typically physical devices that may be electrically, mechanically, chemically, or otherwise driven to create a physical reality of certain logical functions. Types of logic circuits include such devices as multiplexers, registers, arithmetic logic units (ALUs), computer memory, etc., each type of which may be combined to form yet other types of physical devices, such as a central processing unit (CPU)—the best known of which is the microprocessor. A modern microprocessor will often contain more than one hundred million logic gates in its many logic circuits (and often more than a billion transistors). See, e.g., Wikipedia, *Logic gates*, http://en.wikipedia.org/wiki/Logic_gates (as of Jun. 5, 2012, 21:03 GMT).

The logic circuits forming the microprocessor are arranged to provide a microarchitecture that will carry out the instructions defined by that microprocessor's defined Instruction Set Architecture. The Instruction Set Architecture is the part of the microprocessor architecture related to programming, including the native data types, instructions, registers, addressing modes, memory architecture, interrupt and exception handling, and external Input/Output. See, e.g., Wikipedia, *Computer architecture*, http://en.wikipedia.org/wiki/Computer_architecture (as of Jun. 5, 2012, 21:03 GMT).

The Instruction Set Architecture includes a specification of the machine language that can be used by programmers to use/control the microprocessor. Since the machine language instructions are such that they may be executed directly by the microprocessor, typically they consist of strings of binary digits, or bits. For example, a typical machine language instruction might be many bits long (e.g., 32, 64, or 128 bit strings are currently common). A typical machine language instruction might take the form "11110000101011110000111100111111" (a 32 bit instruction).

It is significant here that, although the machine language instructions are written as sequences of binary digits, in actuality those binary digits specify physical reality. For example, if certain semiconductors are used to make the operations of Boolean logic a physical reality, the apparently mathematical bits "1" and "0" in a machine language instruction actually constitute a shorthand that specifies the application of specific voltages to specific wires. For example, in some semiconductor technologies, the binary number "1" (e.g., logical "1") in a machine language instruction specifies around +5 volts applied to a specific "wire" (e.g., metallic traces on a printed circuit board) and the binary number "0" (e.g., logical "0") in a machine language instruction specifies around −5 volts applied to a specific "wire." In addition to specifying voltages of the machines' configuration, such machine language instructions also select out and activate specific groupings of logic gates from the millions of logic gates of the more general machine. Thus, far from abstract mathematical expressions, machine language instruction programs, even though written as a string of zeros and ones, specify many, many constructed physical machines or physical machine states.

Machine language is typically incomprehensible by most humans (e.g., the above example was just ONE instruction, and some personal computers execute more than two billion instructions every second). See, e.g., Wikipedia, *Instructions per second*, http://en.wikipedia.org/wiki/Instructions_per_second (as of Jun. 5, 2012, 21:04 GMT).

Thus, programs written in machine language—which may be tens of millions of machine language instructions long—are incomprehensible. In view of this, early assembly languages were developed that used mnemonic codes to refer to machine language instructions, rather than using the machine language instructions' numeric values directly (e.g., for performing a multiplication operation, programmers coded the abbreviation "mult," which represents the binary number "011000" in MIPS machine code). While assembly languages were initially a great aid to humans controlling the microprocessors to perform work, in time the complexity of the work that needed to be done by the humans outstripped the ability of humans to control the microprocessors using merely assembly languages.

At this point, it was noted that the same tasks needed to be done over and over, and the machine language necessary to do those repetitive tasks was the same. In view of this, compilers were created. A compiler is a device that takes a statement that is more comprehensible to a human than either machine or assembly language, such as "add 2+2 and output the result," and translates that human understandable statement into a complicated, tedious, and immense machine language code (e.g., millions of 32, 64, or 128 bit length strings). Compilers thus translate high-level programming language into machine language.

This compiled machine language, as described above, is then used as the technical specification which sequentially constructs and causes the interoperation of many different computational machines such that humanly useful, tangible, and concrete work is done. For example, as indicated above, such machine language—the compiled version of the higher-level language—functions as a technical specification which selects out hardware logic gates, specifies voltage levels, voltage transition timings, etc., such that the humanly useful work is accomplished by the hardware.

Thus, a functional/operational technical description, when viewed by one of skill in the art, is far from an abstract idea. Rather, such a functional/operational technical description, when understood through the tools available in the art such as those just described, is instead understood to be a humanly understandable representation of a hardware specification, the complexity and specificity of which far exceeds the comprehension of most any one human. With this in mind, those skilled in the art will understand that any such operational/functional technical descriptions—in view of the disclosures herein and the knowledge of those skilled in the art—may be understood as operations made into physical reality by (a) one or more interchained physical machines, (b) interchained logic gates configured to create one or more physical machine(s) representative of sequential/combinatorial logic(s), (c) interchained ordered matter making up logic gates (e.g., interchained electronic devices (e.g., transistors), DNA, quantum devices, mechanical switches, optics, fluidics, pneumatics, molecules, etc.) that create physical reality representative of logic(s), or (d) virtually any combination of the foregoing. Indeed, any physical object which has a stable, measurable, and changeable state may be used to construct a machine based on the above technical description. Charles Babbage, for example, constructed the first computer out of wood and powered by cranking a handle.

Thus, far from being understood as an abstract idea, those skilled in the art will recognize a functional/operational technical description as a humanly-understandable representation of one or more almost unimaginably complex and time sequenced hardware instantiations. The fact that functional/operational technical descriptions might lend themselves readily to high-level computing languages (or high-level block diagrams for that matter) that share some words, structures, phrases, etc. with natural language simply cannot be taken as an indication that such functional/operational technical descriptions are abstract ideas, or mere expressions of abstract ideas. In fact, as outlined herein, in the technological arts this is simply not true. When viewed through the tools available to those of skill in the art, such functional/operational technical descriptions are seen as specifying hardware configurations of almost unimaginable complexity.

As outlined above, the reason for the use of functional/operational technical descriptions is at least twofold. First, the use of functional/operational technical descriptions allows near-infinitely complex machines and machine operations arising from interchained hardware elements to be described in a manner that the human mind can process (e.g., by mimicking natural language and logical narrative flow). Second, the use of functional/operational technical descriptions assists the person of skill in the art in understanding the described subject matter by providing a description that is more or less independent of any specific vendor's piece(s) of hardware.

The use of functional/operational technical descriptions assists the person of skill in the art in understanding the described subject matter since, as is evident from the above discussion, one could easily, although not quickly, transcribe the technical descriptions set forth in this document as trillions of ones and zeroes, billions of single lines of assembly-level machine code, millions of logic gates, thousands of gate arrays, or any number of intermediate levels of abstractions. However, if any such low-level technical descriptions were to replace the present technical description, a person of skill in the art could encounter undue difficulty in implementing the disclosure, because such a low-level technical description would likely add complexity without a corresponding benefit (e.g., by describing the subject matter utilizing the conventions of one or more vendor-specific pieces of hardware). Thus, the use of functional/operational technical descriptions assists those of skill in the art by separating the technical descriptions from the conventions of any vendor-specific piece of hardware.

In view of the foregoing, the logical operations/functions set forth in the present technical description are representative of static or sequenced specifications of various ordered-matter elements, in order that such specifications may be comprehensible to the human mind and adaptable to create many various hardware configurations. The logical operations/functions disclosed herein should be treated as such, and should not be disparagingly characterized as abstract ideas merely because the specifications they represent are presented in a manner that one of skill in the art can readily understand and apply in a manner independent of a specific vendor's hardware implementation.

What is claimed is:

1. A system, comprising:
   circuitry configured for receiving user status information regarding one or more particular individual living beings, the user status information regarding the one or more particular individual living beings including at least one or more identifiers associated with the one or more particular individual living beings;
   circuitry configured for receiving selection information at least in part identifying one or more selected ingestible products;
   circuitry configured for obtaining treatment instructional information, the treatment instructional information obtained via at least in part one or more electronic storage devices and regarding one or more subsequent injection operations on one or more ingestible substrate structures, based at least in part upon the circuitry configured for receiving the user status information regarding the one or more particular individual living beings and based at least in part upon the circuitry configured for receiving the selection information at least in part identifying the one or more selected ingestible products; and
   circuitry configured for directing control of one or more injections of at least one of methane or hydrogen into the one or more ingestible substrate structures to form at least in part the one or more selected ingestible products based at least in part upon the circuitry configured for obtaining the treatment instructional information.

2. The system of claim 1, wherein circuitry configured for obtaining treatment instructional information, the treatment instructional information obtained via at least in part one or more electronic storage devices and regarding one or more subsequent injection operations on one or more ingestible substrate structures, based at least in part upon the circuitry configured for receiving the user status information regarding the one or more particular individual living beings and based at least in part upon the circuitry configured for receiving the selection information at least in part identifying the one or more selected ingestible products comprises:
   circuitry configured for obtaining treatment instructional information via at least in part one or more electronic storage devices and regarding one or more subsequent gas injection operations on one or more ingestible substrate structures.

3. The system of claim 1, wherein circuitry configured for obtaining treatment instructional information, the treatment instructional information obtained via at least in part one or more electronic storage devices and regarding one or more subsequent injection operations on one or more ingestible substrate structures, based at least in part upon the circuitry configured for receiving the user status information regarding the one or more particular individual living beings and based at least in part upon the circuitry configured for receiving the selection information at least in part identifying the one or more selected ingestible products comprises:
 circuitry configured for obtaining the treatment instructional information regarding the one or more subsequent injection operations on one or more ingestible substrate wafer structures.

4. The system of claim 1, wherein circuitry configured for obtaining treatment instructional information, the treatment instructional information obtained via at least in part one or more electronic storage devices and regarding one or more subsequent injection operations on one or more ingestible substrate structures, based at least in part upon the circuitry configured for receiving the user status information regarding the one or more particular individual living beings and based at least in part upon the circuitry configured for receiving the selection information at least in part identifying the one or more selected ingestible products comprises:
 circuitry configured for obtaining the treatment instructional information regarding the one or more subsequent injection operations on one or more ingestible substrate pasta structures.

5. The system of claim 1, wherein circuitry configured for obtaining treatment instructional information, the treatment instructional information obtained via at least in part one or more electronic storage devices and regarding one or more subsequent injection operations on one or more ingestible substrate structures, based at least in part upon the circuitry configured for receiving the user status information regarding the one or more particular individual living beings and based at least in part upon the circuitry configured for receiving the selection information at least in part identifying the one or more selected ingestible products comprises:
 circuitry configured for obtaining the treatment instructional information regarding the one or more subsequent injection operations on one or more ingestible substrate emulsion structures.

6. The system of claim 1, wherein circuitry configured for obtaining treatment instructional information, the treatment instructional information obtained via at least in part one or more electronic storage devices and regarding one or more subsequent injection operations on one or more ingestible substrate structures, based at least in part upon the circuitry configured for receiving the user status information regarding the one or more particular individual living beings and based at least in part upon the circuitry configured for receiving the selection information at least in part identifying the one or more selected ingestible products comprises:
 circuitry configured for obtaining the treatment instructional information regarding the one or more subsequent injection operations on one or more ingestible substrate sheet structures.

7. The system of claim 1, wherein circuitry configured for obtaining treatment instructional information, the treatment instructional information obtained via at least in part one or more electronic storage devices and regarding one or more subsequent injection operations on one or more ingestible substrate structures, based at least in part upon the circuitry configured for receiving the user status information regarding the one or more particular individual living beings and based at least in part upon the circuitry configured for receiving the selection information at least in part identifying the one or more selected ingestible products comprises:
 circuitry configured for obtaining the treatment instructional information regarding the one or more subsequent injection operations on the one or more ingestible substrate structures including one or more ingestible substrate liquid structures.

8. The system of claim 1, wherein circuitry configured for directing control of one or more injections of at least one of methane or hydrogen into the one or more ingestible substrate structures to form at least in part the one or more selected ingestible products based at least in part upon the circuitry configured for obtaining the treatment instructional information comprises:
 circuitry configured for directing control of one or more injections via at least in part one or more directly connected electrical circuits.

9. The system of claim 1, wherein circuitry configured for directing control of one or more injections of at least one of methane or hydrogen into the one or more ingestible substrate structures to form at least in part the one or more selected ingestible products based at least in part upon the circuitry configured for obtaining the treatment instructional information comprises:
 circuitry configured for directing control of the one or more injections via at least in part electronic computer network communication.

10. The system of claim 1, wherein circuitry configured for directing control of one or more injections of at least one of methane or hydrogen into the one or more ingestible substrate structures to form at least in part the one or more selected ingestible products based at least in part upon the circuitry configured for obtaining the treatment instructional information comprises:
 circuitry configured for directing control of the one or more injections color properties of the one or more ingestible substrate structures to form at least in part the one or more selected ingestible products.

11. The system of claim 1, wherein circuitry configured for directing control of one or more injections of at least one of methane or hydrogen into the one or more ingestible substrate structures to form at least in part the one or more selected ingestible products based at least in part upon the circuitry configured for obtaining the treatment instructional information comprises:
 circuitry configured for directing control of the one or more injections to modify one or more surface texture properties of the one or more ingestible substrate structures to form at least in part the one or more selected ingestible products.

12. The system of claim 1, wherein circuitry configured for directing control of one or more injections of at least one of methane or hydrogen into the one or more ingestible substrate structures to form at least in part the one or more selected ingestible products based at least in part upon the circuitry configured for obtaining the treatment instructional information comprises:
 circuitry configured for directing control of the one or more injections to modify one or more oral sensation properties of the one or more ingestible substrate structures to form at least in part the one or more selected ingestible products.

13. The system of claim 1, wherein circuitry configured for directing control of one or more injections of at least one of methane or hydrogen into the one or more ingestible substrate structures to form at least in part the one or more selected ingestible products based at least in part upon the circuitry configured for obtaining the treatment instructional information comprises:
 circuitry configured for directing control of the one or more injections to modify one or more sound properties of the one or more ingestible substrate structures to form at least in part the one or more selected ingestible product.

14. The system of claim 1, wherein circuitry configured for directing control of one or more injections of at least one of methane or hydrogen into the one or more ingestible substrate structures to form at least in part the one or more selected ingestible products based at least in part upon the circuitry configured for obtaining the treatment instructional information comprises:
 circuitry configured for directing control of the one or more injections to modify one or more structural texture properties of the one or more ingestible substrate structures to form at least in part the one or more selected ingestible products.

15. The system of claim 1, wherein circuitry configured for directing control of one or more injections of at least one of methane or hydrogen into the one or more ingestible substrate structures to form at least in part the one or more selected ingestible products based at least in part upon the circuitry configured for obtaining the treatment instructional information comprises:
 circuitry configured for directing control of the one or more injections to modify one or more olfactory properties of the one or more ingestible substrate structures to form at least in part the one or more selected ingestible products.

16. The system of claim 1, wherein circuitry configured for directing control of one or more injections of at least one of methane or hydrogen into the one or more ingestible substrate structures to form at least in part the one or more selected ingestible products based at least in part upon the circuitry configured for obtaining the treatment instructional information comprises:
 circuitry configured for directing control of the one or more injections to modify one or more shape properties of the one or more ingestible substrate structures to form at least in part the one or more selected ingestible products.

17. The system of claim 1, wherein circuitry configured for directing control of one or more injections of at least one of methane or hydrogen into the one or more ingestible substrate structures to form at least in part the one or more selected ingestible products based at least in part upon the circuitry configured for obtaining the treatment instructional information comprises:
 circuitry configured for directing control of the one or more injections to modify one or more psycho-sensory properties of the one or more ingestible substrate structures to form at least in part the one or more selected ingestible products.

18. The system of claim 1, wherein circuitry configured for directing control of one or more injections of at least one of methane or hydrogen into the one or more ingestible substrate structures to form at least in part the one or more selected ingestible products based at least in part upon the circuitry configured for obtaining the treatment instructional information comprises:
 circuitry configured for directing control of the one or more injections to modify one or more properties of the one or more ingestible substrate structures to form at least in part the one or more selected ingestible products.

19. The system of claim 1, wherein circuitry configured for directing control of one or more injections of at least one of methane or hydrogen into the one or more ingestible substrate structures to form at least in part the one or more selected ingestible products based at least in part upon the circuitry configured for obtaining the treatment instructional information comprises:
 circuitry configured for directing control of the one or more injections of at least one of methane or hydrogen into one or more gas jets provided as one or more structures for at least in part heating one or more ingestible substrates to form at least in part the one or more selected ingestible products.

20. The system of claim 1, wherein circuitry configured for directing control of one or more injections of at least one of methane or hydrogen into the one or more ingestible substrate structures to form at least in part the one or more selected ingestible products based at least in part upon the circuitry configured for obtaining the treatment instructional information comprises:
 circuitry configured for directing control of the one or more injections of at least one of methane or hydrogen into one or more substantially carbohydrate portions of the one or more ingestible substrate structures to form at least in part the one or more selected ingestible products.

21. The system of claim 1, wherein circuitry configured for directing control of one or more injections of at least one of methane or hydrogen into the one or more ingestible substrate structures to form at least in part the one or more selected ingestible products based at least in part upon the circuitry configured for obtaining the treatment instructional information comprises:
 circuitry configured for directing control of the one or more injections of at least one of methane or hydrogen one or more portions of at least one substance in which the one or more ingestible substrate structures will be prepared, including at least partial hydrogenation of the at least one substance in which the one or more ingestible substrate structures will be prepared, previous to preparation of the one or more selected ingestible products.

22. The system of claim 1, wherein circuitry configured for directing control of one or more injections of at least one of methane or hydrogen into the one or more ingestible substrate structures to form at least in part the one or more selected ingestible products based at least in part upon the circuitry configured for obtaining the treatment instructional information comprises:
 circuitry configured for directing control of the one or more injections of at least one of methane or hydrogen into one or more substantially fat portions of the one or more ingestible substrate structures to form at least in part the one or more selected ingestible products.

23. The system of claim 1, wherein circuitry configured for directing control of one or more injections of at least one of methane or hydrogen into the one or more ingestible substrate structures to form at least in part the one or more selected ingestible products based at least in part upon the circuitry configured for obtaining the treatment instructional information comprises:

circuitry configured for directing control of the one or more injections of at least some hydrogen into at least some water to form at least in part at least one portion of hydrogen water as the one or more selected ingestible products.

24. The system of claim 1, wherein circuitry configured for directing control of one or more injections of at least one of methane or hydrogen into the one or more ingestible substrate structures to form at least in part the one or more selected ingestible products based at least in part upon the circuitry configured for obtaining the treatment instructional information comprises:
 circuitry configured for directing control of the one or more injections of at least one of methane or hydrogen into the one or more ingestible substrate structures to modify one or more properties of the one or more ingestible substrate structures as substantially one or more carbohydrates to form at least in part the one or more selected ingestible products.

25. The system of claim 1, wherein circuitry configured for directing control of one or more injections of at least one of methane or hydrogen into the one or more ingestible substrate structures to form at least in part the one or more selected ingestible products based at least in part upon the circuitry configured for obtaining the treatment instructional information comprises:
 circuitry configured for directing control of the one or more injections of at least one of methane or hydrogen into the one or more ingestible substrate structures to modify one or more properties of the one or more ingestible substrate structures as substantially one or more fats to form at least in part the one or more selected ingestible products.

26. The system of claim 1, wherein circuitry configured for directing control of one or more injections of at least one of methane or hydrogen into the one or more ingestible substrate structures to form at least in part the one or more selected ingestible products based at least in part upon the circuitry configured for obtaining the treatment instructional information comprises:
 circuitry configured for directing control of the one or more injections of at least one of methane or hydrogen into the one or more ingestible substrate structures to modify one or more properties of the one or more ingestible substrate structures as substantially one or more proteins to form at least in part the one or more selected ingestible products.

27. The system of claim 1, wherein circuitry configured for directing control of one or more injections of at least one of methane or hydrogen into the one or more ingestible substrate structures to form at least in part the one or more selected ingestible products based at least in part upon the circuitry configured for obtaining the treatment instructional information comprises:
 circuitry configured for directing control of the one or more injections of at least one of methane or hydrogen into the one or more ingestible substrate structures to modify one or more properties of the one or more ingestible substrate structures by at least partially internally coating at least one portion of the one or more ingestible substrate structures to form at least in part the one or more selected ingestible products.

28. The system of claim 1, wherein circuitry configured for directing control of one or more injections of at least one of methane or hydrogen into the one or more ingestible substrate structures to form at least in part the one or more selected ingestible products based at least in part upon the circuitry configured for obtaining the treatment instructional information comprises:
 circuitry configured for directing control of the one or more injections of at least one of methane or hydrogen into the one or more ingestible substrate structures to modify one or more properties of the one or more ingestible substrate structures by at least partially removing at least one portion of the one or more ingestible substrate structures to form at least in part the one or more selected ingestible products.

29. The system of claim 1, wherein circuitry configured for directing control of one or more injections of at least one of methane or hydrogen into the one or more ingestible substrate structures to form at least in part the one or more selected ingestible products based at least in part upon the circuitry configured for obtaining the treatment instructional information comprises:
 circuitry configured for directing control of the one or more injections of at least one of methane or hydrogen into the one or more ingestible substrate structures to modify one or more properties of the one or more ingestible substrate structures by at least partially mixing with at least one portion of the one or more ingestible substrate structures to form at least in part the one or more selected ingestible products.

30. The system of claim 1, wherein circuitry configured for directing control of one or more injections of at least one of methane or hydrogen into the one or more ingestible substrate structures to form at least in part the one or more selected ingestible products based at least in part upon the circuitry configured for obtaining the treatment instructional information comprises:
 circuitry configured for directing control of the one or more injections of at least one of methane or hydrogen into the one or more ingestible substrate structures to modify one or more properties of the one or more ingestible substrate structures by at least partially replacing at least one portion of the one or more ingestible substrate structures to form at least in part the one or more selected ingestible products.

31. The system of claim 1, wherein circuitry configured for directing control of one or more injections of at least one of methane or hydrogen into the one or more ingestible substrate structures to form at least in part the one or more selected ingestible products based at least in part upon the circuitry configured for obtaining the treatment instructional information comprises:
 circuitry configured for directing control of the one or more injections of at least one of methane or hydrogen into the one or more ingestible substrate structures to modify one or more properties of the one or more ingestible substrate structures by at least partially integrating with at least one portion of the one or more ingestible substrate structures to form at least in part the one or more selected ingestible products.

32. The system of claim 1, wherein circuitry configured for directing control of one or more injections of at least one of methane or hydrogen into the one or more ingestible substrate structures to form at least in part the one or more selected ingestible products based at least in part upon the circuitry configured for obtaining the treatment instructional information comprises:
 circuitry configured for directing control of the one or more injections of at least one of methane or hydrogen into the one or more ingestible substrate structures to modify one or more properties of the one or more ingestible substrate structures by at least partially softening at least one portion of the one or more ingestible substrate structures to form at least in part the one or more selected ingestible products.

33. The system of claim 1, wherein circuitry configured for directing control of one or more injections of at least one of methane or hydrogen into the one or more ingestible substrate structures to form at least in part the one or more selected ingestible products based at least in part upon the circuitry configured for obtaining the treatment instructional information comprises:
circuitry configured for directing control of the one or more injections of at least one of methane or hydrogen into the one or more ingestible substrate structures to modify one or more properties of the one or more ingestible substrate structures by at least partially hydrogenating at least one portion of the one or more ingestible substrate structures to form at least in part the one or more selected ingestible products.

34. The system of claim 1, wherein circuitry configured for directing control of one or more injections of at least one of methane or hydrogen into the one or more ingestible substrate structures to form at least in part the one or more selected ingestible products based at least in part upon the circuitry configured for obtaining the treatment instructional information comprises:
circuitry configured for directing control of the one or more injections of at least one of methane or hydrogen into the one or more ingestible substrate structures to modify one or more properties of the one or more ingestible substrate structures by at least partially hardening at least one portion of the one or more ingestible substrate structures to form at least in part the one or more selected ingestible products.

35. The system of claim 1, wherein
circuitry configured for directing control of one or more injections of at least one of methane or hydrogen into the one or more ingestible substrate structures to form at least in part the one or more selected ingestible products based at least in part upon the circuitry configured for obtaining the treatment instructional information comprises:
circuitry configured for directing control of the one or more injections of at least one of methane or hydrogen into the one or more ingestible substrate structures to modify one or more properties of the one or more ingestible substrate structures by at least partially dehydrating at least one portion of the one or more ingestible substrate structures to form at least in part the one or more selected ingestible products.

36. A method, comprising:
receiving user status information regarding one or more particular individual living beings, the user status information regarding the one or more particular individual living beings including at least one or more identifiers associated with the one or more particular individual living beings;
receiving selection information at least in part identifying one or more selected ingestible products;
obtaining treatment instructional information, the treatment instructional information obtained via at least in part one or more electronic storage devices and regarding one or more subsequent injection operations on one or more ingestible substrate structures, based at least in part upon the receiving the user status information regarding the one or more particular individual living beings and based at least in part upon the receiving the selection information at least in part identifying the one or more selected ingestible products; and
directing control of one or more injections of at least one of methane or hydrogen into the one or more ingestible substrate structures to form at least in part the one or more selected ingestible products based at least in part upon the obtaining the treatment instructional information,
wherein at least one of the receiving, obtaining, or directing is at least partially implemented using at least one processing device.

37. The system of claim 1, wherein circuitry configured for directing control of one or more injections of at least one of methane or hydrogen into the one or more ingestible substrate structures to form at least in part the one or more selected ingestible products based at least in part upon the circuitry configured for obtaining the treatment instructional information comprises:
circuitry configured for directing control of one or more gas injections of at least one of methane or hydrogen into the one or more ingestible substrate structures to form at least in part the one or more selected ingestible products based at least in part upon the circuitry configured for obtaining the treatment instructional information.

38. The system of claim 37, wherein circuitry configured for directing control of one or more gas injections of at least one of methane or hydrogen into the one or more ingestible substrate structures to form at least in part the one or more selected ingestible products based at least in part upon the circuitry configured for obtaining the treatment instructional information comprises:
circuitry configured for directing control of one or more gas injections via one or more operations of piercing into the one or more ingestible substrate structures.

39. The system of claim 37, wherein circuitry configured for directing control of one or more gas injections of at least one of methane or hydrogen into the one or more ingestible substrate structures to form at least in part the one or more selected ingestible products based at least in part upon the circuitry configured for obtaining the treatment instructional information comprises:
circuitry configured for directing control of one or more gas injections via one or more channels in the one or more ingestible substrate structures.

40. The system of claim 37, wherein circuitry configured for directing control of one or more gas injections of at least one of methane or hydrogen into the one or more ingestible substrate structures to form at least in part the one or more selected ingestible products based at least in part upon the circuitry configured for obtaining the treatment instructional information comprises:
circuitry configured for directing control of one or more gas injections into one or more containers including at least one or more ingestible materials as the one or more ingestible substrate structures.

41. The system of claim 37, wherein circuitry configured for directing control of one or more gas injections of at least one of methane or hydrogen into the one or more ingestible substrate structures to form at least in part the one or more selected ingestible products based at least in part upon the circuitry configured for obtaining the treatment instructional information comprises:
circuitry configured for directing control of one or more gas injections via at least one of one or more injection probes, one or more injection needles, one or more injection tubes, or one or more injection syringes into the one or more ingestible substrate structures.

42. The system of claim 2, wherein circuitry configured for obtaining treatment instructional information, the treatment instructions information obtained via at least in part one or more electronic storage devices and regarding one or more subsequent injection operations on one or more ingestible substrate structures, based at least in part upon the circuitry configured for receiving the user status information regarding the one or more particular individual living beings and based at least in part upon the circuitry configured for receiving the selection information at least in part identifying the one or more selected ingestible products comprises:

circuitry configured for obtaining treatment instructional information regarding one or more subsequent steam injection operations on one or more ingestible substrate structures.

43. The system of claim 42, wherein circuitry configured for obtaining treatment instructional information regarding one or more subsequent steam injection operations on one or more ingestible substrate structures comprises:

circuitry configured for obtaining treatment instructional information regarding one or more subsequent steam injection operations on one or more ingestible substrate structures, the one or more subsequent steam injection operations including at least one operation of obtaining one or more liquids, at least one operation of heating the one or more liquids to obtain one or more steam portions, and at least one operation of injecting the one or more steam portions into the one or more ingestible substrate structures.

44. The system of claim 1, wherein circuitry configured for receiving user status information regarding one or more particular individual living beings, the user status information regarding the one or more particular individual living beings including at least one or more identifiers associated with the one or more particular individual living beings comprises:

circuitry configured for receiving user status information regarding one or more particular individual living beings including at least one or more identifiers associated with the one or more particular individual living beings and one or more preferences of the one or more particular individual living beings for preparation of ingestible products by steaming.

45. The system of claim 1, wherein circuitry configured for receiving selection information at least in part identifying one or more selected ingestible products comprises:

circuitry configured for receiving selection information at least in part identifying one or more selected ingestible products capable of preparation by steaming.

46. The system of claim 1, wherein circuitry configured for receiving selection information at least in part identifying one or more selected ingestible products comprises:

circuitry configured for receiving selection information at least in part identifying one or more selected ingestible products in response to one or more selection menus outputted via at least one electronic display and identifying one or more candidate ingestible products and one or more preparation methods, including at least steaming, available for preparation of the one or more candidate ingestible products.

47. A system, comprising:

at least one computing device; and one or more instructions which, when executed by the at least one computing device, configure the at least one computing device to perform one or more operations, including at least:

receiving user status information regarding one or more particular individual living beings, the user status information regarding the one or more particular individual living beings including at least one or more identifiers associated with the one or more particular individual living beings;

receiving selection information at least in part identifying one or more selected ingestible products;

obtaining treatment instructional information, the treatment instructional information obtained via at least in part one or more electronic storage devices and regarding one or more subsequent injection operations on one or more ingestible substrate structures, based at least in part upon the receiving the user status information regarding the one or more particular individual living beings and based at least in part upon the receiving the selection information at least in part identifying the one or more selected ingestible products; and directing control of one or more injections of at least one of methane or hydrogen into the one or more ingestible substrate structures to form at least in part the one or more selected ingestible products based at least in part upon the obtaining the treatment instructional information.

\* \* \* \* \*